(12) United States Patent
Chubb et al.

(10) Patent No.: US 7,592,362 B2
(45) Date of Patent: Sep. 22, 2009

(54) SUBSTITUTED IMIDAZOLES

(75) Inventors: Nathan Anthony Logan Chubb, Sandwich (GB); Mark Roger Cox, Sandwich (GB); Jerome Sebastien Dauvergne, Sandwich (GB); Richard Andrew Ewin, Sandwich (GB); Christelle Lauret, Sandwich (GB)

(73) Assignee: Pfizer Limited, Sandwich, Kent (GB)

( * ) Notice: Subject to any disclaimer, the term of this patent is extended or adjusted under 35 U.S.C. 154(b) by 6 days.

(21) Appl. No.: 11/619,735

(22) Filed: Jan. 4, 2007

(65) Prior Publication Data
US 2007/0167506 A1 Jul. 19, 2007

Related U.S. Application Data

(60) Provisional application No. 60/760,765, filed on Jan. 19, 2006.

(51) Int. Cl.
*A61K 31/4164* (2006.01)
*A01N 43/50* (2006.01)
*C07D 233/54* (2006.01)

(52) U.S. Cl. .................................. 514/396; 548/346.1
(58) Field of Classification Search .............. 548/300.1, 548/335.1, 343.1, 343.5, 346.1; 514/396
See application file for complete search history.

(56) References Cited

U.S. PATENT DOCUMENTS

| 4,678,775 | A | | 7/1987 | Nathanson |
| 5,017,596 | A | * | 5/1991 | Colombo et al. ............ 514/406 |
| 5,646,153 | A | | 7/1997 | Spada et al. |
| 6,103,733 | A | | 8/2000 | Bachmann et al. |
| 2005/0222135 | A1 | | 10/2005 | Buschmann et al. |
| 2006/0178404 | A1 | | 8/2006 | Bowles |
| 2007/0155717 | A1 | | 7/2007 | Allegretti et al. |
| 2007/0167506 | A1 | | 7/2007 | Chubb et al. |
| 2007/0197621 | A1 | | 8/2007 | Galley et al. |

FOREIGN PATENT DOCUMENTS

| DE | 103 04 374 | 8/2004 |
| FR | 2 681 322 | 3/1993 |
| JP | 7-243054 | 9/1995 |
| WO | WO 99/28300 | 6/1999 |
| WO | WO 01/00686 | 1/2001 |
| WO | 01/94318 | 12/2001 |
| WO | WO 03/092374 | 11/2003 |
| WO | WO 2004/103959 | 12/2004 |
| WO | WO 2005/007188 | 1/2005 |

OTHER PUBLICATIONS

Stella, Valentino J, Expert Opinion of Therapeutic Patents, Prodrugs as therapeutics, 2004 14(3): 277-280.*
Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
Patani, George A. Bioisosterism: A rational approach in drug design. Chem. Rev. 96 (1996) 3147-3176.*
Miller, Duane D. Synthesis and α2-Adrenoceptor Effects of Substituted Catecholimidazoline and Catecholimidazole Analogues in Human Platelets. Journal of Medicinal Chemistry. 33 (1990) 1138-1144.*
Huh, Dal H. A novel synthetic method for 2-arylmethyl substituted imidazolines and imidazoles from 2 aryl-1,1-dibromoethenes. Tetrahedron 60 (2004) 9857-9862.*
PCT International Search Report, PCT/IB2007/000071.
Torregrosa et al., "Isoprene-catalyzed lithiation of imidazole: synthesis of 2-(hydroxyalkyl)- and 2-(aminoalkyl) imidazoles", Tetrahedron, 61:11148-11155, 2005.
Nardi et al., "Research Research on durene derivatives. Note I—hypertensive activity of 2-(2,3,5,6-tetramethylbenzyl) imidazoline and related compounds", Farmaco, Ed. Sci., 34(9):789-801, 1979.

* cited by examiner

*Primary Examiner*—Kamal A Saeed
*Assistant Examiner*—Samantha L Shterengarts
(74) *Attorney, Agent, or Firm*—Austin W. Zhang; Lucy X. Yang; Paul M. Misiak

(57) ABSTRACT

This invention relates to a range of alpha substituted 2-benzyl substituted imidazole compounds and pharmaceutically acceptable salts and solvates thereof, to compositions comprising such compounds, processes for their synthesis and their use as parasiticides.

3 Claims, No Drawings

SUBSTITUTED IMIDAZOLES

This invention relates to imidazoles having parasiticidal properties. The compounds of interest are substituted imidazoles and, more particularly, the invention relates to alpha substituted 2-benzyl imidazoles.

There is a need for improved antiparasitic agents for use with mammals, including humans and animals, and in particular there is a need for improved insecticides and acaricides. Furthermore there is a need for improved topical products with convenient administration and which contain one or more of such antiparasitic agents which can be used to effectively treat ectoparasites, such as insects and acarids, and particularly aracids such as mites and ticks. Such products would be particularly useful for the treatment of companion animals, such as cats, dogs and horses, and livestock, such as cattle. There is equally a need for agents to control parasitic infestations in animal hosts other than mammals, including insects such as bees, which are susceptible to parasites such as varroa mites.

The compounds currently available for insecticidal and acaricidal treatment of companion animals and livestock do not always demonstrate good activity, good speed of action, or a long duration of action. Most treatments contain hazardous chemicals that can have serious consequences when either used too often or when used in excess of recommended quantities. Many products have toxic side effects and some are lethal to cats when accidentally ingested. They are not always suitable for use as a topical or spot-on formulation and some topical and spot-on formulations are disadvantaged by common side effects in animals and owners. Persons applying these insecticidal and acaricidal agents are advised to limit their exposure to the chemicals by wearing gloves and avoiding inhalation of the chemical vapours. Pet collars and tags have been utilised to overcome some problems, but these are susceptible to chewing and therefore are disadvantageous since the compound may be accidentally orally ingested. Thus, treatments currently achieve varying degrees of success depending on a variety of factors including toxicity and the method of administration. In some cases toxicity may be attributed to their non-selective activity at various receptors. In addition it has recently been shown that some current agents are becoming ineffective as the parasites develop resistance.

The present invention overcomes one or more of the various disadvantages of, or improves upon, the properties of existing compounds. In particular the present invention develops some new alpha substituted 2-benzyl imidazoles which demonstrate such properties.

Heterocyclic derivatives have been disclosed in the prior art as having insecticidal and acaricidal activity against agricultural pests, for example International patent application publication no. WO 03/092374.

Generic disclosures also exist in the prior art of heterocyclic derivatives which optionally encompass alpha substituted 2-benzyl imidazoles. For example, international patent application publication no. WO 2005/007188 describes a generic structure, which optionally encompasses alpha substituted 2-benzyl imidazoles for the inhibition of the hatching of an ectoparasite egg; international patent application publication no. WO 2004/103959 describes a generic structure which optionally encompasses alpha substituted 2-benzyl imidazoles for use as antibacterial agents; international patent applications publication nos WO 01/00586 and WO 99/28300 both describe a generic structure which optionally encompasses alpha substituted 2-benzyl imidazoles and discloses their adrenergic activity; and U.S. Pat. No. 6,103,733 describes a generic structure which optionally encompasses alpha substituted 2-benzyl imidazoles for increasing blood serum and HDL cholesterol levels. However, none of this prior art exemplifies any alpha substituted 2-benzyl imidazoles, nor does the prior art indicate that such compounds would be useful against a spectrum of parasites relevant to companion animals and livestock or against the range of ectoparasite lifecycle stages.

Thus, it is an aim of the present invention to overcome one or more of the various disadvantages of, or improve on the properties of, known compounds. In particular it is an aim of the invention to develop some new alpha substituted 2-benzyl substituted imidazoles. It is a further aim that such new compounds have the same or improved activity when compared to the prior art compounds against parasites. It is another aim of the present invention to develop compounds which have a similar or decreased toxicity profile when compared to the prior art compounds. It is yet another aim to develop compounds which demonstrate selectivity for the octopaminergic receptor, a known invertebrate neurotransmitter, over the ubiquitous animal adrenergic receptor. Furthermore, it is an aim of the invention to reduce the exposure of both humans and animals to the treatment by developing compounds which can be dosed as a low volume spot-on or topical application. The compounds of the present invention have especially good ability to control arthropods as shown by the results of tests demonstrating their potency and efficacy. In particular, the compounds of the present invention are active against ticks and they are able to prevent ticks from attaching to, and feeding from, the host animal. It is yet another aim of the present invention to provide compounds which have good speed of action when compared to those of the prior art and hence an improved efficacy against the transmission of tick borne diseases.

It is also desirable that the compounds of the present invention should have one or more of the same or improved duration of action, an improved pharmacokinetic profile, improved safety, improved persistence, improved solubility or other improved physicochemical and formulation properties such as good spreading after topical application compared to those of the prior art.

Thus, according to the present invention, there is provided a compound of formula (I):

Formula (I)

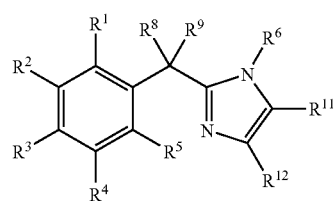

wherein:
$R^1$, $R^2$, $R^3$, $R^4$, $R^5$ are independently selected from the group consisting of hydrogen, cyano, nitro, halo, hydroxy, $C_{1-4}$ alkyl optionally substituted by one or more hydroxy groups, $C_{3-6}$ cycloalkyl optionally substituted by one or more $C_{1-4}$ alkyl or halo groups, $C_{1-4}$ alkoxy, $C_{1-4}$ haloalkyl, $C_{1-4}$ haloalkoxy, phenyl, amino, $NR^xR^y$, and $S(O)_nR^{10}$;
$R^6$ is selected from the group consisting of hydrogen, —$C_{0-2}$alkylene$R^7$, —$C_{1-2}$alkyleneO$R^7$, —$C_{0-2}$alkyleneC(O)$R^7$, —$C_{1-2}$alkyleneOC(O)$R^7$, —$C_{1-2}$alkyleneOC(O)O$R^7$, —$C_{0-2}$alkyleneC(O)O$R^7$, —$C_{1-2}$alkyleneN(H)C(O)$R^7$, —$C_{1-2}$alkyleneN($R^7$)C(O)$R^7$, —$C_{0-2}$alkyleneC(O)NH$R^7$, —$C_{0-2}$alkyleneC(O)N$R^{15}R^{16}$, —$C_{1-2}$alkyleneNHC(O)N$R^{15}R^{16}$, —$C_{1-2}$alkyleneN$R^7$C(O)N$R^{15}R^{16}$, —$C_{1-2}$alkyleneOC(O)NH$R^7$, —$C_{1-2}$alkyleneOC(O)N$R^{15}R^{16}$, —$C_{0-2}$alkyleneCH=N($R^7$), —$C_{1-2}$alkyleneP(=O)(N$R^{15}R^{16}$)(N$R^{15}R^{16}$), —$C_{0-2}$alkyleneSi($R^7$)$_3$, and —$C_{0-2}$alkyleneS(O)$_nR^{10}$;

where the $C_{0-2}$alkylene or $C_{1-2}$alkylene of $R^6$ may, where chemically possible, optionally be substituted by one or more substituents selected from the group consisting of $C_{1-6}$ alkyl, $C_{3-6}$ cycloalkyl, $C_{1-4}$ alkylene($C_{3-6}$ cycloalkyl), $C_{0-6}$ alkylenephenyl, which $C_{0-2}$alkylene or $C_{1-2}$alkylene substituent may in turn be optionally further substituted, where chemically possible, by one or more substituents selected from the group consisting of hydrogen, cyano, nitro, halo, formyl, oxo, hydroxy, C(O)OH, $C_{1-4}$ alkyl, $C_{1-4}$ alkylene$C_{3-6}$ cycloalkyl, $C_{1-4}$ alkoxy, $C_{1-4}$ alkylene$C_{1-4}$ alkyoxy, —C(O)O$C_{1-4}$ alkyl, $C_{1-4}$ haloalkyl, $C_{1-4}$ haloalkoxy, amino, $C_{1-4}$ alkylamino, $C_{1-4}$ dialkylamino, and S(O)$_nR^{10}$;

where each $R^7$, $R^{15}$ and $R^{16}$, where chemically possible, is independently selected from the group consisting of hydrogen, $C_{1-8}$ alkyl, $C_{2-6}$ alkenyl, $C_{2-6}$ alkynyl, $C_{3-8}$ cycloalkyl, $C_{1-4}$ alkylene($C_{3-6}$ cycloalkyl), $C_{1-4}$ alkylene$C_{1-4}$ alkoxy, $C_{1-6}$ haloalkyl, $C_{0-6}$ alkylenephenyl, $C_{0-6}$ alkylenenaphthyl, $C_{0-6}$ alkylene(tetrahydronaphthyl), and $C_{0-2}$ alkylene(Het), where Het is selected from oxetanyl, tetrahydropyranyl, piperidinyl, morpholinyl, furyl, pyridyl, benzofuranyl, benzothiazolyl, indolyl, 2,3-benzodioxolyl, 2,3-dihydro-1,4-benzodioxinyl, indolyl and 1,5-naphthyridinyl;

or $R^{15}$ and $R^{16}$ together with the nitrogen to which they are attached may form a three to seven-membered saturated or unsaturated heterocyclic ring optionally containing one or more further N, O or S atoms or SO$_2$ groups;

where each of the above $R^7$, $R^{15}$ or $R^{16}$ groups may independently include one or more optional substituents where chemically possible selected from hydrogen, cyano, nitro, halo, formyl, oxo, hydroxy, C(O)OH, $C_{1-4}$ alkyl, $C_{2-4}$ alkenyl, $C_{2-4}$ alkynyl, $C_{3-6}$ cycloalkyl, $C_{1-4}$ alkylene$C_{3-6}$ cycloalkyl, $C_{1-4}$ alkoxy, $C_{1-4}$ alkylene$C_{1-4}$ alkyoxy, $C_{1-4}$ alkoxy$C_{1-4}$ alkoxy, $C_{1-4}$ alkanoyl, —C(O)O$C_{1-4}$ alkyl, $C_{1-4}$ haloalkyl, $C_{3-6}$ halocycloalkyl, $C_{1-4}$ haloalkoxy, $C_{1-4}$ haloalkanoyl, —C(O)O$C_{1-4}$ haloalkyl, phenyl, 4-halophenyl, 4-alkoxyphenyl, 2-cyanophenyl, phenoxy, 4-halophenoxy, benzyloxy, 4-halobenzyloxy, benzoyl, pyrazolyl, triazolyl, 2-halo-4-pyrimidinyl, 2-phenylethyl, amino, $C_{1-4}$ alkylamino, $C_{1-4}$ dialkylamino, C(O)N($C_{1-4}$ alkyl)$_2$, N($C_{1-4}$ alkylene)C(O)($C_{1-4}$ alkyl) and S(O)$_nR^{10}$;

$R^8$ and $R^9$ are independently selected from the group consisting of hydrogen, $C_{1-4}$ alkyl, $C_{1-4}$ alkoxy, $C_{1-4}$ haloalkyl, $C_{1-4}$ haloalkoxy and $C_{0-4}$ alkylenephenyl but with the proviso that $R^8$ and $R^9$ are not both hydrogen;

where each of $R^8$ and $R^9$ may independently include one or more optional substituents where chemically possible selected from hydrogen, cyano, halo, hydroxy, $C_{1-4}$ alkyl, $C_{3-6}$ cycloalkyl, $C_{1-4}$ alkoxy, —C(O)O$C_{1-4}$ alkyl, $C_{1-4}$ haloalkyl, $C_{1-4}$ haloalkoxy, and S(O)$_nR^{10}$;

or $R^8$ and $R^9$ together with the carbon to which they are attached may form a three to six membered carbocyclic, saturated ring, which ring is optionally substituted with one or more substituents selected from the group consisting of halo, $C_{1-2}$ alkyl, $C_{1-2}$ alkoxy, $C_{1-2}$ haloalkyl, $C_{1-2}$ haloalkoxy;

$R^{11}$ and $R^{12}$ are independently selected from the group consisting of hydrogen, halo, cyano, $C_{1-4}$ alkyl, $C_{1-4}$ alkoxy, $C_{1-4}$ haloalkyl, and $C_{1-4}$ haloalkoxy;

where $R^x$ and $R^y$ are independently selected from hydrogen, $C_{1-4}$ alkyl, $C_{1-4}$ haloalkyl, and S(O)$_nR^{10}$;

each n is independently 0, 1 or 2;

and each $R^{10}$ is independently hydrogen, hydroxy, $C_{1-4}$ alkyl, $C_{1-4}$ haloalkyl, 4-halophenyl, amino, $C_{1-6}$ alkyl amino and di $C_{1-6}$ alkyl amino;

or a pharmaceutically acceptable salt or a prodrug thereof.

In particular, there is provided a compound of formula (I):

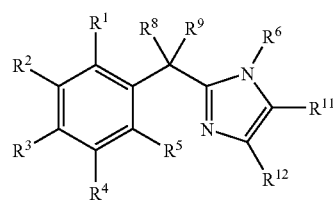

Formula (I)

wherein:

$R^1$, $R^2$, $R^3$, $R^4$, $R^5$ are independently selected from the group consisting of hydrogen, cyano, nitro, halo, hydroxy, $C_{1-4}$ alkyl, $C_{3-6}$ cycloalkyl, $C_{1-4}$ alkoxy, $C_{1-4}$ haloalkyl, $C_{1-4}$ haloalkoxy, amino, N$R^xR^y$, and S(O)$_nR^1$;

$R^6$ is selected from the group consisting of hydrogen, —$C_{0-2}$alkylene$R^7$, —$C_{1-2}$alkyleneO$R^7$, —$C_{0-2}$alkyleneC(O)$R^7$, —$C_{1-2}$alkyleneOC(O)$R^7$, —$C_{1-2}$alkyleneOC(O)O$R^7$, —$C_{0-2}$alkyleneC(O)O$R^7$, —$C_{1-2}$alkyleneN(H)C(O)$R^7$, —$C_{1-2}$alkyleneN($R^7$)C(O)$R^7$, —$C_{0-2}$alkyleneC(O)NH$R^7$, —$C_{0-2}$alkyleneC(O)N$R^{15}R^{16}$, —$C_{1-2}$alkyleneNHC(O)N$R^{15}R^{16}$, —$C_{1-2}$alkyleneN$R^7$C(O)N$R^{15}R^{16}$, —$C_{1-2}$alkyleneOC(O)NH$R^7$, —$C_{1-2}$alkyleneOC(O)N$R^{15}R^{16}$, —$C_{0-2}$alkyleneCH=N($R^7$), —$C_{1-2}$alkyleneP(=O)(N$R^{15}R^{16}$)(N$R^{15}R^{16}$), —$C_{0-2}$alkyleneSi($R^7$)$_3$, and —$C_{0-2}$alkyleneS(O)$_nR^{10}$;

where the $C_{0-2}$alkylene or $C_{1-2}$alkylene of $R^6$ may, where chemically possible, optionally be substituted by one or more substituents selected from the group consisting of $C_{1-6}$ alkyl, $C_{3-6}$ cycloalkyl, $C_{1-4}$ alkylene($C_{3-6}$ cycloalkyl), $C_{0-6}$ alkylenephenyl, which $C_{0-2}$alkylene or $C_{1-2}$alkylene substituent may in turn be optionally further substituted, where chemically possible, by one or more substituents selected from the group consisting of hydrogen, cyano, nitro, halo, formyl, oxo, hydroxy, C(O)OH, $C_{1-4}$ alkyl, $C_{1-4}$ alkylene$C_{3-6}$ cycloalkyl, $C_{1-4}$ alkoxy, $C_{1-4}$ alkylene$C_{1-4}$ alkyoxy, —C(O)O$C_{1-4}$ alkyl, $C_{1-4}$ haloalkyl, $C_{1-4}$ haloalkoxy, amino, $C_{1-4}$ alkylamino, $C_{1-4}$ dialkylamino, and S(O)$_nR^{10}$;

where each $R^7$, $R^{15}$ and $R^{16}$, where chemically possible, is independently selected from the group consisting of hydrogen, $C_{1-8}$ alkyl, $C_{2-6}$ alkenyl, $C_{2-6}$ alkynyl, $C_{3-8}$ cycloalkyl, $C_{1-4}$ alkylene($C_{3-6}$ cycloalkyl), $C_{1-4}$ alkylene$C_{1-4}$ alkoxy, $C_{1-6}$ haloalkyl, $C_{0-6}$ alkylenephenyl;

or $R^{15}$ and $R^{15}$ together with the nitrogen to which they are attached may form a three to seven-membered saturated or unsaturated heterocyclic ring optionally containing one or more further N, O or S atoms;

where each of the above $R^7$, $R^{15}$ or $R^{16}$ groups may independently include one or more optional substituents where chemically possible selected from hydrogen, cyano, nitro, halo, formyl, oxo, hydroxy, C(O)OH, $C_{1-4}$ alkyl, $C_{2-4}$ alkenyl, $C_{2-4}$ alkynyl, $C_{3-6}$ cycloalkyl, $C_{1-4}$ alkylene$C_{3-6}$ cycloalkyl, $C_{1-4}$ alkoxy, $C_{1-4}$ alkylene$C_{1-4}$ alkyoxy, $C_{1-4}$ alkanoyl, —C(O)O$C_{1-4}$ alkyl, $C_{1-4}$ haloalkyl, $C_{3-6}$ halocycloalkyl, $C_{1-4}$ haloalkoxy, $C_{1-4}$ haloalkanoyl, —C(O)

$OC_{1-4}$ haloalkyl, phenyl, 4-halophenyl, 4-alkoxyphenyl, amino, $C_{1-4}$ alkylamino, $C_{1-4}$ dialkylamino, $C(O)N(C_{1-4}$ alkyl$)_2$, $N(C_{1-4}$ alkylene$)C(O)(C_{1-4}$ alkyl) and $S(O)_nR^{10}$;

$R^8$ and $R^9$ are independently selected from the group consisting of hydrogen, $C_{1-4}$ alkyl, $C_{1-4}$ alkoxy, $C_{1-4}$ haloalkyl, $C_{1-4}$ haloalkoxy and $C_{0-4}$ alkylenephenyl but with the proviso that $R^8$ and $R^9$ are not both hydrogen;

where each of $R^8$ and $R^9$ may independently include one or more optional substituents where chemically possible selected from hydrogen, cyano, halo, hydroxy, $C_{1-4}$ alkyl, $C_{3-6}$ cycloalkyl, $C_{1-4}$ alkoxy, —$C(O)OC_{1-4}$ alkyl, $C_{1-4}$ haloalkyl, $C_{1-4}$ haloalkoxy, and $S(O)_nR^{10}$;

or $R^8$ and $R^9$ together with the carbon to which they are attached may form a three to six membered carbocyclic, saturated ring, which ring is optionally substituted with one or more substituents selected from the group consisting of halo, $C_{1-2}$ alkyl, $C_{1-2}$ alkoxy, $C_{1-2}$ haloalkyl, $C_{1-2}$ haloalkoxy;

$R^{11}$ and $R^{12}$ are independently selected from the group consisting of hydrogen, halo, cyano, $C_{1-4}$ alkyl, $C_{1-4}$ alkoxy, $C_{1-4}$ haloalkyl, and $C_{1-4}$ haloalkoxy;

where $R^x$ and $R^y$ are independently selected from hydrogen, $C_{1-4}$ alkyl, $C_{1-4}$ haloalkyl, and $S(O)_nR^{10}$;

each n is independently 0, 1 or 2;

and each $R^{10}$ is independently hydrogen, hydroxy, $C_{1-4}$ alkyl, $C_{1-4}$ haloalkyl, amino, $C_{1-6}$ alkyl amino and di $C_{1-6}$ alkyl amino;

or a pharmaceutically acceptable salt or a prodrug thereof.

In the definition of $R^1$, $R^2$, $R^3$, $R^4$ and $R^5$, "$C_{1-4}$ alkyl optionally substituted by one or more hydroxy groups" means an alkyl group with between one and four carbon atoms, which may be unsubstituted or may be substituted at any available position with a hydroxy group. For reasons of chemical stability, it is preferred that no carbon atom should be substituted with more than one hydroxy group. Accordingly, alkyl groups with up to four hydroxy substituents are foreseen. Preferred are alkyl groups with no more than two hydroxy substituents. Examples include hydroxymethyl, 1-hydroxyethyl, 2-hydroxyethyl, 1,2-dihydroxyethyl and 2,3-dihydroxypropyl.

In the definition of $R^1$, $R^2$, $R^3$, $R^4$ and $R^5$, "$C_{3-6}$ cycloalkyl optionally substituted by one or more $C_{1-4}$ alkyl or halo groups" means a cycloalkyl group with between three and six carbon atoms in the ring, which may be unsubstituted or may be substituted at any available position with an alkyl group of between one and four carbon atoms or a halogen atom. In the case of alkyl substituents, it is preferred that not more than four such substituents be present, and more preferred that not more than two such substituents be present. Examples include 1-methylcyclopropyl, 2,5-dimethylcyclopentyl and 4-tert-butylcyclohexyl. In the case of halo substituents, any degree of substitution up to complete substitution is foreseen. In the case of cyclohexyl therefore, up to eleven halo substituents may be present. While each halo group may be independently selected, it may be preferred to have all halo substituents the same. Preferably the halo is chloro or fluoro. Geminal disubstitution at any methylene position may be preferred ver monosubstitution. Examples include 2,2-dichlorocyclopropyl and perfluorocyclohexyl. Substitution with both alkyl and halo groups is also foreseen. An example is 2,2-difluoro-1-methylcyclobutyl.

Preferably, each of $R^1$, $R^2$, $R^3$, $R^4$, $R^5$ are independently selected from hydrogen, halo eg chloro or fluoro, $C_{1-4}$ alkyl eg methyl or ethyl, $C_{3-4}$ cycloalkyl eg cyclopropyl, $C_{1-4}$ alkoxy eg methoxy or ethoxy, $C_{1-4}$ haloalkyl eg trifluoromethyl, trifluoroethyl, $C_{1-4}$ haloalkoxy eg trifluoromethoxy or trifluoroethoxy, and $S(O)_nR^{10}$ where n is 0 and $R^{10}$ is preferably selected from $C_{1-4}$ alkyl such as methyl or ethyl or $C_{1-4}$ haloalkyl such as trifluoromethyl or trifluoroethyl to form for example trifluoromethylthio or trifluoroethylthio. More preferably each of $R^1$, $R^2$, $R^3$, $R^4$, $R^5$ are independently selected from hydrogen, halo eg chloro, $C_{1-4}$ alkyl eg methyl or ethyl, $C_{1-4}$ alkoxy eg methoxy or ethoxy, and $C_{1-4}$ haloalkyl eg trifluoromethyl, trifluoroethyl. Most preferably each of $R^1$, $R^2$, $R^3$, $R^4$, $R^5$ are independently selected from hydrogen, and $C_{1-4}$ alkyl eg methyl or ethyl.

Most preferably two of $R^1$, $R^2$, $R^3$, $R^4$, and $R^5$ are independently selected from $C_{1-4}$ alkyl eg methyl or ethyl, preferably methyl, and three of $R^1$, $R^2$, $R^3$, $R^4$, and $R^5$ are H. Even more preferably $R^1$ and $R^2$ are selected from $C_{1-4}$ alkyl eg methyl or ethyl, preferably methyl, and $R^3$, $R^4$ and $R^5$ are H.

Further suitable compounds include those where at least one of $R^1$, $R^2$, $R^3$, $R^4$, and $R^5$ is independently selected from $C_{1-4}$ haloalkyl eg trifluoromethyl, trifluoroethyl, preferably trifluoromethyl, with the others of $R^1$, $R^2$, $R^3$, $R^4$, and $R^5$ being H. Preferably $R^2$ is $C_{1-4}$ haloalkyl eg trifluoromethyl, trifluoroethyl preferably trifluoroethyl, with the others of $R^1$, $R^3$, $R^4$, and $R^5$ being H.

Other suitable compounds include those where at least one of $R^1$, $R^2$, $R^3$, $R^4$, and $R^5$ is independently selected from $C_{1-4}$ alkoxy eg methoxy or ethoxy preferably methoxy, with the others of $R^1$, $R^2$, $R^3$, $R^4$, and $R^5$ being H. Preferably $R^2$ and $R^3$ are selected from $C_{1-4}$ alkoxy eg methoxy or ethoxy preferably methoxy, and $R^1$, $R^4$ and $R^5$ are H.

Other suitable compounds include those where at least one of $R^1$, $R^2$, $R^3$, $R^4$, and $R^5$ is independently selected from halo eg chloro or fluoro, with the others of $R^1$, $R^2$, $R^3$, $R^4$, and $R^5$ being H.

Other suitable compounds include those where at least one of $R^1$, $R^2$, $R^3$, $R^4$, and $R^5$ is independently selected from halo eg chloro or fluoro, and another one of $R^1$, $R^2$, $R^3$, $R^4$, and $R^5$ is independently selected from $C_{1-4}$ alkyl eg methyl or ethyl, with the others of $R^1$, $R^2$, $R^3$, $R^4$, and $R^5$ being H.

Most preferred compounds are those where $R^1$ and $R^2$ are methyl and $R^3$, $R^4$, and $R^5$ are hydrogen.

Preferably $R^6$ is selected from the group consisting of hydrogen; —$C_{0-2}$alkylene$R^7$; —$C_{1-2}$alkyleneO$R^7$; —$C_{1-2}$alkyleneOC(O)$R^7$; —$C_{1-2}$alkyleneOC(O)O$R^7$; —$C_{0-2}$alkyleneC(O)$R^7$; —$C_{1-2}$alkyleneOC(O)NH$R^7$; —$C_{1-2}$alkyleneOC(O)N$R^{15}R^{16}$; and —$C_{0-2}$alkyleneS(O)$_nR^{10}$. More preferably $R^6$ is selected from the group consisting of hydrogen; —$C_{0-2}$alkylene$R^7$; —$C_{1-2}$alkyleneO$R^7$; —$C_{1-2}$alkyleneOC(O)$R^7$; —$C_{1-2}$alkyleneOC(O)O$R^7$; and —$C_{0-2}$alkyleneC(O)O$R^7$. Even more preferably $R^5$ is selected from the group consisting of hydrogen; —$C_{0-2}$alkylene$R^7$; —$C_{1-2}$ alkyleneOC(O)$R^7$ and —$C_{0-2}$alkyleneC(O)O$R^7$. Most preferably $R^6$ is hydrogen.

Preferably $R^7$, $R^{15}$ and $R^{16}$ are, where chemically possible, independently selected from the group consisting of hydrogen; $C_{1-8}$ alkyl for example methyl, ethyl, n-propyl, isopropyl, butyl, isobutyl, tert-butyl, n-pentyl, n-hexyl; $C_{3-8}$ cycloalkyl for example cyclopropyl, cyclobutyl, cyclopentyl, cyclohexyl; $C_{1-4}$ alkylene($C_{3-6}$ cycloalkyl) for example cyclopropylmethyl, cyclopropylethyl, cyclobutylmethyl, cyclobutylethyl, cyclopentylmethyl, cyclopentylethyl, cyclohexylmethyl, cyclohexylethyl; $C_{1-6}$ haloalkyl for example fluoromethyl, trifluoromethyl, chloromethyl, fluoroethyl, chloroethyl, trifluoroethyl and trifluoropropyl; and $C_{0-6}$ alkylphenyl for example phenyl, phenylmethyl and phenylethyl. More preferably $R^7$, $R^{15}$ and $R^{16}$ are, where chemically possible, independently selected from the group consisting of hydrogen; $C_{1-6}$ alkyl for example methyl, ethyl, n-propyl, isopropyl, butyl, tert-butyl, n-pentyl, n-hexyl; $C_{1-4}$ alkylene ($C_{3-6}$ cycloalkyl) for example cyclopropylmethyl, cyclopropylethyl, cyclobutylmethyl, cyclobutylethyl, cyclopentylmethyl, cyclopentylethyl, cyclohexylmethyl, cyclohexylethyl. Even more preferably $R^7$, $R^{15}$ and $R^{16}$ are, where chemically possible, independently selected from the group consisting of hydrogen and $C_{1-4}$ alkyl for example methyl, ethyl, propyl, isopropyl, n-butyl and tert-butyl.

Further suitable compounds include those where $R^7$, $R^{15}$ and $R^{16}$ are, where chemically possible, optionally substituted with one or more substituents selected from the group consisting of halo for example fluoro or chloro, $C_{1-4}$ alkyl for example methyl or ethyl preferably methyl, $C_{3-6}$ cycloalkyl, for example cyclopropyl, cyclobutyl or cyclopentyl preferably cyclopentyl, $C_{1-4}$ alkoxy for example methoxy or ethoxy, $C_{1-4}$ haloalkyl for example fluoromethyl, chloromethyl, trifluoromethyl, fluoroethyl, chloroethyl or trifluoroethyl, preferably trifluoroethyl or trifluoromethyl, and $S(O)_nR^{10}$ for example methylsulphonyl or dimethyl amido sulphonyl. Examples of $R^7$, $R^{15}$ and $R^{16}$ groups which have then been so substituted include for example branched alkyl groups such as 2-methylbutyl, 3-methylbutyl, substituted sulphonyl groups such as methylsulphonylmethyl, methylsulphonylethyl, dimethylamidosulphonylmethyl and dimethylamidosulphonylethyl and substituted phenyl groups such as 4-chlorophenyl, 4-nitrophenyl, 4-fluorophenyl, 4-methoxyphenyl, 2,4-dichlorophenyl, 4-chlorophenylmethyl, 4-nitrophenylmethyl, 4-fluorophenylmethyl, 4-methoxyphenyl methyl, 2,4-dichlorophenylmethyl, 4-chlorophenylethyl, 4-nitro phenyl ethyl, 4-fluorophenylethyl, 4-methoxyphenylethyl, and 2,4-dichlorophenylethyl.

Suitably when $R^{15}$ and $R^{16}$ together with the nitrogen to which they are attached form a three to seven-membered saturated or unsaturated heterocyclic ring optionally containing one or more further N, O or S atoms it is preferred that the ring is a five or six membered ring, is saturated and comprises one further heteroatom selected from N, O or S. Suitable examples of such rings include pyrrolidinyl, pyrazolidinyl, imidazolinyl, thiazolidinyl, isoxazolidinyl, piperidinyl, piperazinyl, morpholinyl, or thiomorpholinyl. Preferred rings include pyrrolidinyl, thiazolidinyl, morpholinyl, or thiomorpholinyl. Such rings may optionally be further substituted with one or more groups, preferably selected from the group consisting of oxo, C(O)OH, halo for example fluoro or chloro, and $C_{1-4}$ alkyl for example methyl or ethyl preferably methyl. For example any heterocyclic sulphur atoms may be optionally substituted with one or more oxo groups to form for example 1,1-dioxothiazolidinyl or 1,1-dioxothiomorpholinyl substitutents.

Suitable compounds include those where, when the $R^6$ group comprises a one carbon alkylene moiety, that said alkylene moiety is optionally substituted with one or two substituents. Further suitable compounds also include those where, when the $R^6$ group comprises a two carbon alkylene moiety, that said alkylene moiety is optionally substituted with one, two, three or four substituents which may be independently orientated on either the alpha or beta carbon positions with respect to the imidazole nitrogen to which the $R^6$ substitutent is bound.

Suitably when the $C_{0-2}$alkylene or $C_{1-2}$alkylene of $R^6$ is substituted with one or more substitutents it is preferred that such substituents are independently selected from the group consisting of hydrogen; $C_{1-4}$ alkyl for example methyl or ethyl; $C_{3-6}$ cycloalkyl for example cyclopropyl; $C_{1-4}$ alkyleneC$_{3-6}$ cycloalkyl for example cyclopropylmethyl or cyclopropylethyl; $C_{1-4}$ alkoxy for example methoxy or ethoxy; $C_{1-4}$ alkyleneC$_{1-4}$ alkyoxy for example methoxy methyl, methoxy ethyl, ethoxy methyl or ethoxy ethyl; $C_{1-4}$ haloalkyl for example fluromethyl, trifluromethyl, fluroethyl or 1,1,1-trifluoroethyl; phenyl, benzyl and 4-trifluoromethylbenzyl. More preferably such substituents are independently chosen from the group consisting of hydrogen; $C_{1-4}$ alkyl for example methyl or ethyl; $C_{3-6}$ cycloalkyl for example cyclopropyl; $C_{1-4}$ alkyleneC$_{3-6}$ cycloalkyl for example cyclopropylmethyl or cyclopropylethyl; $C_{1-4}$ haloalkyl for example fluromethyl, trifluromethyl, fluroethyl or 1,1,1-trifluoroethyl; and phenyl.

Suitable compounds include those where $R^6$ is selected from the group consisting of —C$_{0-2}$alkyleneR$^7$, preferably where $R^6$ is CH$_2$R$^7$, and where $R^7$ is selected from the group consisting of $C_{1-8}$ alkyl for example methyl, ethyl, n-propyl, isopropyl, butyl, tert-butyl; $C_{3-8}$ cycloalkyl for example cyclopropyl, cyclobutyl, cyclopentyl; $C_{1-6}$ haloalkyl for example trifluoromethyl, and trifluoroethyl; and C$_{0-6}$ alkylenephenyl for example phenyl which is optionally substituted to form for example 4-methoxy phenyl, 4-trifluoromethylphenyl. Further suitable compounds also include those where $R^6$ is selected from the group consisting of —C$_{0-2}$ alkyleneR$^7$, preferably where $R^6$ does not comprise an additional alkylene moiety (ie is CoalkyleneR$^7$)$^7$, and where $R^7$ is selected from the group consisting of $C_{1-8}$ alkyl for example methyl, ethyl, n-propyl, isopropyl, butyl, tert-butyl, preferably methyl and ethyl; $C_{3-8}$ cycloalkyl for example cyclopropyl, cyclobutyl, cyclopentyl, preferably cyclopropyl; $C_{1-6}$ haloalkyl for example trifluoromethyl, and trifluoroethyl; and C$_{0-6}$ alkylenephenyl for example phenyl which is optionally substituted to form for example 4-methoxy phenyl, 4-trifluoromethylphenyl.

A further group of suitable compounds include those where $R^6$ is selected from the group consisting of —C$_{1-2}$ alkyleneOR$^7$, preferably where $R^6$ is CH$_2$OR$^7$, and where $R^7$ is selected from the group consisting of $C_{1-8}$ alkyl for example methyl, ethyl, n-propyl, isopropyl, butyl, tert-butyl. Examples of such so substituted $R^6$ groups include methoxymethyl, ethoxymethyl, methoxyethyl, ethoxyethyl, propoxymethyl, propoxyethyl, isopropoxyethyl, butoxymethyl, sec-butoxyoxymethyl, isobutoxymethyl, tert-butoxymethyl, butoxyethyl, sec-butoxyoxyethyl, isobutoxyethyl, tert-butoxyethyl, pentyloxymethyl, pentyloxyethyl, hexyloxymethyl, hexyloxyethyl.

A still further group of suitable compounds include those where $R^6$ is selected from the group consisting of —C$_{1-2}$ alkyleneOC(O)R$^7$, preferably where $R^6$ is CH$_2$OC(O)R$^7$, and where $R^7$ is $C_{1-8}$ alkyl for example methyl, ethyl, n-propyl, isopropyl, butyl, tert-butyl, which $R^7$ in turn may be optionally further substituted. Examples of such so substituted $R^6$ groups include acetyloxymethyl, acetyloxyethyl, propionyloxymethyl, propionyloxyethyl, butyryloxymethyl, butyryloxyethyl, isobutyryloxymethyl, isobutyryloxyethyl, pentanoyloxymethyl, pentanoyloxyethyl, 2-methylbutyryloxymethyl, 2-methylbutyryloxyethyl, 3-methylbutyryloxymethyl, 3-methylbutyrylcarbonyloxy)ethyl, 2,2-dimethylpropionyloxymethyl, 2,2-dimethylpropionyloxyethyl hexanoyloxymethyl, hexanoyloxyethyl, heptanoyloxymethyl, heptanoyloxyethyl. Further suitable examples of compounds where $R^6$ is selected from the group consisting of —C$_{1-2}$alkyleneOC(O)R$^7$, preferably where $R^6$ is CH$_2$OC(O) R$^7$, also include those where $R^7$ is $C_{1-4}$ alkylene(C$_{3-6}$ cycloalkyl) for example cyclopropylmethyl, cyclopropylethyl, cyclobutylmethyl, cyclobutylethyl, cyclopentylmethyl, cyclopentylethyl, cyclopentylpropyl, cyclohexylmethyl, and cyclcohexylethyl. Examples of such so substituted $R^6$ groups include cyclopropylacetyloxymethyl, cyclopropylpropionyloxymethyl, cyclobutylacetyloxymethyl, cyclobutylpropionyloxymethyl, cyclopentylacetyloxymethyl, cyclopentylpropionyloxymethyl, cyclopentylbutyryloxymethyl, cyclohexylacetyloxymethyl, and cyclcohexylpropionyloxymethyl, cyclopropylacetyloxyethyl, cyclopropylpropionyloxyethyl, cyclobutylacetyloxyethyl, cyclobutylpropionyloxyethyl, cyclopentylacetyloxyethyl, cyclopentylpropionyloxyethyl, cyclopentylbutyryloxyethyl, cyclohexylacetyloxyethyl, and cyclcohexylpropionyloxyethyl. Preferably $R^6$ is 3-cyclopentylpropionyloxymethyl. It is preferred that in such compounds $R^7$ is preferably $C_{1-8}$ alkyl, more preferably ethyl or tert-butyl, and most preferably tert-butyl.

A yet further group of suitable compounds include those where $R^6$ is selected from the group consisting of —$C_{1-2}$alkyleneOC(O)OR$^7$, preferably where $R^6$ is $CH_2OC(O)OR^7$, and where $R^7$ is $C_{1-8}$ alkyl for example methyl, ethyl, n-propyl, isopropyl, butyl, tert-butyl, which may in turn be optionally further substituted. Examples of such so substituted $R^6$ groups include methoxycarbonyloxymethyl, methoxycarbonyloxyethyl, ethoxycarbonyloxymethyl, ethoxycarbonyloxyethyl, propoxycarbonyloxymethyl, propoxycarbonyloxyethyl, isopropoxycarbonyloxymethyl, isopropoxycarbonyloxyethyl, butoxycarbonyloxymethyl, butoxycarbonyloxyethyl, isobutoxycarbonyloxymethyl, isobutoxycarbonyloxyethyl, pentyloxycarbonyloxymethyl, pentyloxycarbonyloxyethyl, 2-methylbutoxycarbonyloxymethyl, 2-methylbutoxycarbonyloxyethyl, 3-methylbutoxycarbonyloxymethyl, 3-methylbutoxycarbonyloxyethyl, 2,2-dimethylpropoxycarbonyloxymethyl, 2,2-dimethylpropoxycarbonyloxyethyl, hexyloxycarbonyloxymethyl, hexyloxycarbonyloxyethyl. Further suitable examples of compounds where $R^6$ is selected from the group consisting of —$C_{1-2}$alkyleneOC(O)OR$^7$, preferably where $R^6$ is $CH_2OC(O)OR^7$, also include those where $R^7$ is selected from the group consisting of $C_{3-6}$ cycloalkyl for example cyclopropyl, cyclobutyl, cyclopentyl or cyclohexyl; $C_{1-4}$ alkylene($C_{3-6}$ cycloalkyl) for example cyclopropylmethyl, cyclopropylethyl, cyclobutylmethyl, cyclobutylethyl, cyclopentylmethyl, cyclopentylethyl, cyclohexylmethyl, cyclohexylethyl; $C_{1-6}$ haloalkyl for example trifluoromethyl, and 2,2,2-trifluoroethyl; and $C_{0-6}$ alkylphenyl for example phenyl which is optionally further substituted to form for example 4-methoxyphenyl, 4-trifluoromethylphenyl-4-methoxybenzyl. Examples of such so substituted $R^6$ groups include cyclopropyloxycarbonyloxymethyl, cyclobutyloxycarbonyloxymethyl, cyclopentyloxycarbonyloxymethyl or cyclohexyloxycarbonyloxymethyl cyclopropyloxycarbonyloxyethyl, cyclobutyloxycarbonyloxyethyl, cyclopentyloxycarbonyloxyethyl or cyclohexyloxycarbonyloxyethyl; $C_{1-4}$ alkylene($C_{3-6}$ cycloalkyl) for example cyclopropylmethyloxycarbonyloxymethyl, cyclopropylethyloxycarbonyloxymethyl, cyclobutylmethyloxycarbonyloxymethyl, cyclobutylethyloxycarbonyloxymethyl, cyclopentylmethyloxycarbonyloxymethyl, cyclopentylethyloxycarbonyloxymethyl, cyclohexylmethyloxycarbonyloxymethyl, cyclohexylethyloxycarbonyloxymethyl, cyclopropylmethyloxycarbonyloxyethyl, cyclopropylethyloxycarbonyloxyethyl, cyclobutylmethyloxycarbonyloxyethyl, cyclobutylethyloxycarbonyloxyethyl, cyclopentylmethyloxycarbonyloxyethyl, cyclopentylethyloxycarbonyloxyethyl, cyclohexylmethyloxycarbonyloxyethyl, cyclohexylethyloxycarbonyloxyethyl; $C_{1-6}$ haloalkyl for example trifluoromethyloxycarbonyloxymethyl, and 2,2,2-trifluoroethyloxycarbonyloxymethyl, trifluoromethyloxycarbonyloxyethyl, and 2,2,2-trifluoroethyloxycarbonyloxyethyl; and $C_{0-6}$ alkylphenyl for example phenyloxycarbonyloxymethyl which is optionally further substituted to form for example 4-methoxyphenyloxycarbonyloxymethyl, 4-trifluoromethylphenyloxycarbonyloxymethyl, 4-methoxybenzyloxycarbonyloxymethyl.

A still yet further group of suitable compounds include those where $R^6$ is selected from the group consisting of —$C_{0-2}$alkyleneC(O)OR$^7$, preferably where $R^6$ is C(O)OR$^7$, and where $R^7$ is $C_{1-8}$ alkyl for example methyl, ethyl, n-propyl, isopropyl, butyl, tert-butyl, which may in turn be optionally further substituted. Examples of such so substituted $R^6$ groups include methoxycarbonyl, methoxycarbonylmethyl, methoxycarbonylethyl, ethoxycarbonyl, ethoxycarbonylmethyl, ethoxycarbonylethyl, propoxycarbonyl, propoxycarbonylmethyl, propoxycarbonylethyl, isopropoxycarbonyl, isopropoxycarbonylmethyl, isopropoxycarbonylethyl, butoxycarbonyl, butoxycarbonylmethyl, butoxycarbonylethyl, isobutoxycarbonyl, isobutoxycarbonylmethyl, isobutoxycarbonylethyl, pentyloxycarbonyl, pentyloxycarbonylmethyl, pentyloxycarbonylethyl, 2-methylbutoxycarbonyl, 2-methylbutoxycarbonylmethyl, 2-methylbutoxycarbonylethyl, 3-methylbutoxycarbonyl, 3-methylbutoxycarbonylmethyl, 3-methylbutoxycarbonylethyl, 2,2-dimethylpropoxycarbonyl, 2,2-dimethylpropoxycarbonylmethyl, 2,2-dimethylpropoxycarbonylethyl, hexyloxycarbonyl, hexyloxycarbonylmethyl, hexyloxycarbonylethyl. Further suitable examples of compounds include those where $R^6$ is selected from the group consisting of —$C_{0-2}$alkyleneC(O) OR$^7$, preferably where $R^6$ is C(O)OR$^7$, also include those where $R^7$ is selected from the group consisting of $C_{0-6}$ alkylphenyl for example phenyl which in turn is optionally substituted to form for example 4-methoxy phenyl, 4-trifluoromethyl phenyl. Examples of such so substituted $R^6$ groups include phenyloxycarbonyl, phenyloxycarbonylmethyl, phenyloxycarbonylethyl.

An even further group of suitable compounds include those where $R^6$ is selected from the group consisting of —$C_{1-2}$alkyleneOC(O)NHR$^7$, preferably where $R^6$ is $CH_2OC(O)NHR^7$, and where $R^7$ is selected from the group consisting of $C_{1-8}$ alkyl for example methyl, ethyl, n-propyl, isopropyl, butyl, tert-butyl; $C_{3-6}$ cycloalkyl for example cyclopropyl, cyclobutyl, cyclopentyl or cyclohexyl; $C_{1-6}$ haloalkyl for example trifluoromethyl, and trifluoroethyl; and $C_{0-6}$ alkylphenyl for example phenyl, phenylmethyl or phenylethyl which $C_{0-6}$ alkylphenyl is optionally substituted to form for example 4-methoxyphenyl, 4-trifluoromethylphenyl, 2,4-dichlorophenyl, 4-methoxyphenylmethyl, 4-trifluoromethylphenylmethyl, 2,4-dichlorophenylmethyl, 4-methoxyphenylethyl, 4-trifluoromethylphenylethyl, or 2,4-dichlorophenylethyl.

Preferred are those compounds where $R^6$ is selected from the group consisting of hydrogen, —$C_{0-2}$alkyleneR$^7$ and —$C_{1-2}$alkyleneOC(O)R$^7$ and where $R^7$ is selected from the group consisting of $C_{1-8}$ alkyl. Even more preferred compounds are those where $R^6$ is hydrogen.

Preferably, each $R^8$ and $R^9$ are independently selected from the group consisting of hydrogen; $C_{1-4}$ alkyl eg methyl or ethyl, preferably methyl; $C_{1-4}$ haloalkyl for example trifluoromethyl, trichloromethyl, trichloroethyl or trifluoroethyl, preferably trifluoromethyl; $C_{1-4}$ alkoxy for example methoxy or ethoxy, preferably methoxy; and $C_{0-4}$ alkylenephenyl for example phenyl, phenylmethyl or phenylethyl, but with the proviso that $R^8$ and $R^9$ are not both hydrogen. More preferably each $R^8$ and $R^9$ are independently selected from the group consisting of hydrogen and $C_{1-4}$ alkyl eg methyl or ethyl, preferably methyl but again with the proviso that $R^8$ and $R^9$ are not both hydrogen. Most preferably $R^8$ is methyl and $R^9$ is hydrogen.

Suitably when either one or more of $R^8$ or $R^9$ are phenyl, the phenyl group is optionally substituted with one or more substitutents selected from the group consisting of fluoro, chloro, methoxy or trifluoromethyl.

Suitably when $R^8$ and $R^9$ together with the carbon to which they are attached may form a three to six membered carbocyclic, saturated ring it is preferred that the ring is a three membered ring.

Preferably each of $R^{11}$ and $R^{12}$ are independently selected from the group consisting of hydrogen, $C_{1-2}$ alkyl eg methyl or ethyl, preferably methyl, and $C_{1-2}$ alkoxy for example methoxy or ethoxy, preferably methoxy. More preferably at least one of $R^{11}$ and $R^{12}$ is hydrogen. Most preferably both of $R^{11}$ and $R^{12}$ are hydrogen.

A further group of suitable compounds of the present invention are those of formula (LV) where: each of $R^1$, $R^2$, $R^3$, $R^4$, $R^5$ are independently selected from hydrogen and $C_{1-4}$ alkyl eg methyl or ethyl, preferably methyl;

each $R^8$ and $R^9$ are independently selected from the group consisting of hydrogen and $C_{1-4}$ alkyl eg methyl or ethyl, preferably methyl; and each $R^{11}$ and $R^{12}$ are hydrogen or a pharmaceutically acceptable salt or a prodrug thereof. Preferably, in compounds of formula (LV): $R^1$, $R^2$ and $R^8$ are selected from $C_{1-4}$ alkyl eg methyl or ethyl, preferably methyl, $R^3$, $R^4$, $R^5$ and $R^9$ are H.

It will be understood that throughout the application all references to formula (I) apply equally to compounds of the formula (LV).

Furthermore, it will be understood that all the suitable groups and preferences applied to $R^1$-$R^{12}$, $R^a$, $R^b$ and n for formula (I) apply equally to compounds of the formula (LV).

A further group of preferred compounds are the compounds of formula (XXXX)

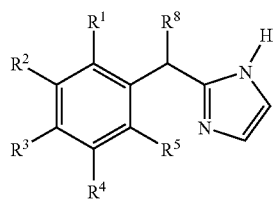

Formula (XXXX)

wherein $R^1$ to $R^5$ are selected from hydrogen, halo, $C_{1-4}$ alkyl, $C_{1-4}$ haloalkyl and CN, and $R^8$ is $C_{1-3}$ alkyl. Preferably, at least two of $R^1$ to $R^5$ are hydrogen, and more preferably at least three of $R^1$ to $R^5$ are hydrogen. Preferably, the groups from $R^1$ to $R^5$ that are not hydrogen are selected from chloro, fluoro, methyl, ethyl, difluoromethyl and trifluoromethyl, and more preferably from fluoro, chloro and methyl. Preferably $R^8$ is methyl or ethyl, and more preferably $R^8$ is methyl.

A further group of preferred compounds are the compounds of formula (XXXXI)

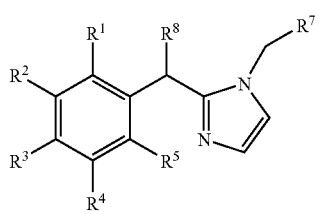

Formula (XXXXI)

wherein $R^1$ to $R^5$ are selected from hydrogen, halo, $C_{1-4}$ alkyl, $C_{1-4}$ haloalkyl and CN, $R^7$ is phenyl optionally substituted by one or more groups selected from cyano, nitro, halo, formyl, hydroxy, C(O)OH, $C_{1-4}$ alkyl, $C_{2-4}$ alkenyl, $C_{2-4}$ alkynyl, $C_{3-6}$ cycloalkyl, $C_{1-4}$ alkylene$C_{3-6}$ cycloalkyl, $C_{1-4}$ alkoxy, —C(O)O$C_{1-4}$ alkyl, $C_{1-4}$ haloalkyl, $C_{1-4}$ haloalkoxy, pyrazolyl, triazolyl, amino, $C_{1-4}$ alkylamino, and $C_{1-4}$ dialkylamino, and $R^8$ is $C_{1-3}$ alkyl. Preferably, at least two of $R^1$ to $R^5$ are hydrogen, and more preferably at least three of $R^1$ to $R^5$ are hydrogen. Preferably, the groups from $R^1$ to $R^5$ that are not hydrogen are selected from chloro, fluoro, methyl, ethyl, difluoromethyl and trifluoromethyl, and more preferably from fluoro, chloro and methyl. Preferably $R^7$ is phenyl optionally substituted by one or two groups selected from cyano, chloro, fluoro, hydroxy, $C_{1-3}$ alkyl, $C_{1-3}$ alkoxy and $C_{1-2}$ haloalkyl. Preferably $R^8$ is methyl or ethyl, and more preferably $R^8$ is methyl.

A further group of preferred compounds are the compounds of formula (XXXXII)

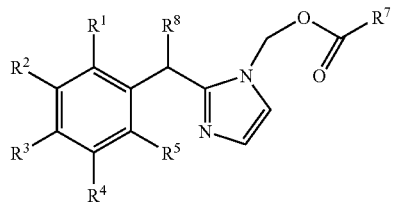

Formula (XXXXII)

wherein $R^1$ to $R^5$ are selected from hydrogen, halo, $C_{1-4}$ alkyl, $C_{1-4}$ haloalkyl and CN, $R^7$ is selected from $C_{1-3}$alkylenephenyl optionally substituted by on the phenyl ring by one or more groups selected from cyano, halo, hydroxy, C(O)OH, $C_{1-4}$ alkyl, $C_{3-6}$ cycloalkyl, $C_{1-4}$ alkylene$C_{3-6}$ cycloalkyl, $C_{1-4}$ alkoxy, —C(O)O$C_{1-4}$ alkyl, $C_{1-4}$ haloalkyl, and $C_{1-4}$ haloalkoxy, $C_{1-8}$ alkyl optionally substituted by one or two $C_{1-4}$ alkoxy groups, $C_{3-6}$ cycloalkyl, $C_{1-3}$alkylene$C_{3-6}$cycloalkyl, and $C_{1-6}$ haloalkyl, and $R^3$ is $C_{1-3}$ alkyl. Preferably, at least two of $R^1$ to $R^5$ are hydrogen, and more preferably at least three of $R^1$ to $R^5$ are hydrogen. Preferably, the groups from $R^1$ to $R^5$ that are not hydrogen are selected from chloro, fluoro, methyl, ethyl, difluoromethyl and trifluoromethyl, and more preferably from fluoro, chloro and methyl. Preferably $R^7$ is $C_{1-8}$alkyl or $C_{1-6}$haloalkyl. Preferably $R^8$ is methyl or ethyl, and more preferably $R^8$ is methyl.

A further group of preferred compounds are the compounds of formula (XXXXIII)

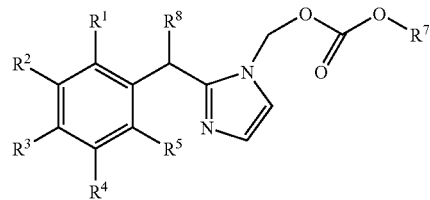

Formula (XXXXIII)

wherein $R^1$ to $R^5$ are selected from hydrogen, halo, $C_{1-4}$ alkyl, $C_{1-4}$ haloalkyl and CN, $R^7$ is selected from $C_{1-3}$alkylenephenyl optionally substituted by on the phenyl ring by one or more groups selected from cyano, halo, hydroxy, C(O)OH, $C_{1-4}$ alkyl, $C_{3-6}$ cycloalkyl, $C_{1-4}$ alkylene$C_{3-6}$ cycloalkyl, $C_{1-4}$ alkoxy, —C(O)O$C_{1-4}$ alkyl, $C_{1-4}$ haloalkyl, and $C_{1-4}$ haloalkoxy, $C_{1-8}$ alkyl optionally substituted by one or two $C_{1-4}$ alkoxy groups, $C_{3-6}$ cycloalkyl, $C_{1-3}$alkylene$C_{3-6}$cycloalkyl, and $C_{1-6}$ haloalkyl, and $R^8$ is $C_{1-3}$ alkyl.

Preferably, at least two of $R^1$ to $R^5$ are hydrogen, and more preferably at least three of $R^1$ to $R^5$ are hydrogen. Preferably, the groups from $R^1$ to $R^5$ that are not hydrogen are selected from chloro, fluoro, methyl, ethyl, difluoromethyl and trifluoromethyl, and more preferably from fluoro, chloro and methyl. Preferably $R^7$ is $C_{1-8}$alkyl or $C_{1-6}$haloalkyl. Preferably $R^8$ is methyl or ethyl, and more preferably $R^8$ is methyl.

A further group of preferred compounds are the compounds of formula (XXXXIV)

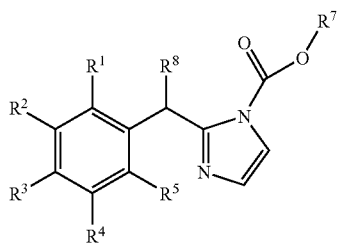

Formula (XXXXIV)

wherein $R^1$ to $R^5$ are selected from hydrogen, halo, $C_{1-4}$ alkyl, $C_{1-4}$ haloalkyl and CN, $R^7$ is selected from $C_{1-3}$alkylenephenyl optionally substituted by on the phenyl ring by one or more groups selected from cyano, halo, hydroxy, C(O)OH, $C_{1-4}$ alkyl, $C_{3-6}$ cycloalkyl, $C_{1-4}$ alkylene$C_{3-6}$ cycloalkyl, $C_{1-4}$ alkoxy, —C(O)O$C_{1-4}$ alkyl, $C_{1-4}$ haloalkyl, and $C_{1-4}$ haloalkoxy, $C_{1-8}$ alkyl optionally substituted by one or two $C_{1-4}$ alkoxy groups, $C_{3-6}$ cycloalkyl, $C_{1-3}$alkylene$C_{3-6}$cycloalkyl, and $C_{1-6}$ haloalkyl, and $R^8$ is $C_{1-3}$ alkyl. Preferably, at least two of $R^1$ to $R^5$ are hydrogen, and more preferably at least three of $R^1$ to $R^5$ are hydrogen. Preferably, the groups from $R^1$ to $R^5$ that are not hydrogen are selected from chloro, fluoro, methyl, ethyl, difluoromethyl and trifluoromethyl, and more preferably from fluoro, chloro and methyl. Preferably $R^7$ is $C_{1-8}$alkyl or $C_{1-6}$haloalkyl, and more preferably $R^7$ is isobutyl. Preferably $R^8$ is methyl or ethyl, and more preferably $R^8$ is methyl.

Preferred individual compounds of the invention are selected from the compounds of the Examples described herein.

More preferred individual compounds of the invention are selected from:
2-[(2,3-dimethylphenyl)(methoxy)methyl]-1H-imidazole;
2-[1-(2,5-dimethylphenyl)ethyl]-1H-imidazole;
2-[1-(2,4-dimethylphenyl)ethyl]-1H-imidazole;
2-[1-(3,4-dimethylphenyl)ethyl]-1H-imidazole;
2-{1-[2-(trifluoromethyl)phenyl]ethyl}-1H-imidazole;
(2,3-dimethylphenyl)(1H-imidazol-2-yl)methanol;
2-[1-(2,3-dimethylphenyl)ethyl]-1H-imidazole;
{2-[1-(2,3-dimethylphenyl)ethyl]-1H-imidazol-1-yl}methyl pivalate;
{2-[1-(2,3-dimethylphenyl)ethyl]-1H-imidazol-1-yl}methyl propionate;
{2-[1-(2,3-dimethylphenyl)ethyl]-1H-imidazol-1-yl}methyl 3-methylbutanoate;
{2-[1-(2,3-dimethylphenyl)ethyl]-1H-imidazol-1-yl}methyl butyrate;
{2-[1-(2,3-dimethylphenyl)ethyl]-1H-imidazol-1-yl}methyl 3-cyclopentylpropanoate;
{2-[1-(2,3-dimethylphenyl)ethyl]-1H-imidazol-1-yl}methyl heptanoate;
{2-[1-(2,3-dimethylphenyl)ethyl]-1H-imidazol-1-yl}methyl pentanoate
2-[1-(4-chloro-3-methylphenyl)ethyl]-1H-imidazole
2-[1-(3,5-dimethylphenyl)ethyl]-1H-imidazole
1-benzyl-2-[1-(2,3-dimethylphenyl)ethyl]-1H-imidazole
{2-[1-(2,3-dimethylphenyl)ethyl]-1H-imidazol-1-yl}methyl 4-methoxybenzyl carbonate
1-(cyclopropylmethyl)-2-[1-(2,3-dimethylphenyl)ethyl]-1H-imidazole
2-[1-(2,3-dimethylphenyl)ethyl]-1-methyl-1H-imidazole
cyclopropylmethyl {2-[1-(2,3-dimethylphenyl)ethyl]-1H-imidazol-1-yl}methyl carbonate
{2-[1-(2,3-dimethylphenyl)ethyl]-1H-imidazol-1-yl}methyl 3-methylbutyl carbonate
{2-[1-(2,3-dimethylphenyl)ethyl]-1H-imidazol-1-yl}methyl isopropyl carbonate
cyclobutyl {2-[1-(2,3-dimethylphenyl)ethyl]-1H-imidazol-1-yl}methyl carbonate
{2-[1-(2,3-dimethylphenyl)ethyl]-1H-imidazol-1-yl}methyl 2,2,2-trifluoroethyl carbonate
2-[1-(2,3-dimethylphenyl)ethyl]-1-ethyl-1H-imidazole
2-[1-(2,3-dimethylphenyl)ethyl]-1-(4-methoxybenzyl)-1H-imidazole
2-[1-(2,3-dimethylphenyl)ethyl]-1-(methoxymethyl)-1H-imidazole
2-[1-(2,3-dimethylphenyl)ethyl]-1-[4-(trifluoromethyl)benzyl]-1H-imidazole
4-fluorophenyl 2-[1-(2,3-dimethylphenyl)ethyl]-1H-imidazole-1-carboxylate
isobutyl 2-[1-(2,3-dimethylphenyl)ethyl]-1H-imidazole-1-carboxylate
isopropyl 2-[1-(2,3-dimethylphenyl)ethyl]-1H-imidazole-1-carboxylate
2-[1-(3-methylphenyl)ethyl]-1H-imidazole or a pharmaceutically acceptable salt or prodrug thereof.

More preferred individual compounds of the present invention are selected from:
2-[1-(2,3-dimethylphenyl)ethyl]-1H-imidazole;
2-[(1S)-1-(2,3-dimethylphenyl)ethyl]-1H-imidazole;
2-[(1R)-1-(2,3-dimethylphenyl)ethyl]-1H-imidazole;
{2-[1-(2,3-dimethylphenyl)ethyl]-1H-imidazol-1-yl}methyl pivalate;
{2-[(1S)-1-(2,3-dimethylphenyl)ethyl]-1H-imidazol-1-yl}methylpivalate;
{2-[(1R)-1-(2,3-dimethylphenyl)ethyl]-1H-imidazol-1-yl}methylpivalate;
{2-[1-(2,3-dimethylphenyl)ethyl]-1H-imidazol-1-yl}methyl propionate;
{2-[1-(2,3-dimethylphenyl)ethyl]-1H-imidazol-1-yl}methyl 3-methylbutanoate;
{2-[1-(2,3-dimethylphenyl)ethyl]-1H-imidazol-1-yl}methyl butyrate;
{2-[1-(2,3-dimethylphenyl)ethyl]-1H-imidazol-1-yl}methyl 3-cyclopentylpropanoate;
{2-[1-(2,3-dimethylphenyl)ethyl]-1H-imidazol-1-yl}methyl heptanoate;
{2-[1-(2,3-dimethylphenyl)ethyl]-1H-imidazol-1-yl}methyl pentanoate
2-{1-[2-(trifluoromethyl)phenyl]ethyl}-1H-imidazole;
2-[1-(2,5-dimethylphenyl)ethyl]-1H-imidazole
2-[1-(4-chloro-3-methylphenyl)ethyl]-1H-imidazole
2-[1-(3,5-dimethylphenyl)ethyl]-1H-imidazole
1-benzyl-2-[1-(2,3-dimethylphenyl)ethyl]-1H-imidazole {2-[1-(2,3-dimethylphenyl)ethyl]-1H-imidazol-1-yl}methyl 4-methoxybenzyl carbonate
1-(cyclopropylmethyl)-2-[1-(2,3-dimethylphenyl)ethyl]-1H-imidazole
2-[1-(2,3-dimethylphenyl)ethyl]-1-methyl-1H-imidazole
cyclopropylmethyl {2-[1-(2,3-dimethylphenyl)ethyl]-1H-imidazol-1-yl}methyl carbonate
{2-[1-(2,3-dimethylphenyl)ethyl]-1H-imidazol-1-yl}methyl 3-methylbutyl carbonate
{2-[1-(2,3-dimethylphenyl)ethyl]-1H-imidazol-1-yl}methyl isopropyl carbonate
cyclobutyl {2-[1-(2,3-dimethylphenyl)ethyl]-1H-imidazol-1-yl}methyl carbonate
{2-[1-(2,3-dimethylphenyl)ethyl]-1H-imidazol-1-yl}methyl 2,2,2-trifluoroethyl carbonate
2-[1-(2,3-dimethylphenyl)ethyl]-1-ethyl-1H-imidazole
2-[1-(2,3-dimethylphenyl)ethyl]-1-(4-methoxybenzyl)-1H-imidazole
2-[1-(2,3-dimethylphenyl)ethyl]-1-(methoxymethyl)-1H-imidazole
2-[1-(2,3-dimethylphenyl)ethyl]-1-[4-(trifluoromethyl)benzyl]-1H-imidazole
4-fluorophenyl 2-[1-(2,3-dimethylphenyl)ethyl]-1H-imidazole-1-carboxylate
isobutyl 2-[1-(2,3-dimethylphenyl)ethyl]-1H-imidazole-1-carboxylate
isopropyl 2-[1-(2,3-dimethylphenyl)ethyl]-1H-imidazole-1-carboxylate
2-[1-(3-methylphenyl)ethyl]-1H-imidazole or a pharmaceutically acceptable salt or prodrug thereof.

Even more preferred compounds of the present invention are 2-[1-(2,3-dimethylphenyl)ethyl]-1H-imidazole, and {2-[1-(2,3-dimethylphenyl)ethyl]-1H-imidazol-1-yl}methyl pivalate, or a pharmaceutically acceptable salt or prodrug thereof.

The most preferred compound of the present invention is 2-[1-(2,3-dimethylphenyl)ethyl]-1H-imidazole, or a pharmaceutically acceptable salt or prodrug thereof.

Included within the scope of the present invention are all stereoisomers such as enantiomers and diastereomers, all geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

It is to be understood that compounds of formula (I) may contain one or more asymmetric carbon atoms, thus compounds of the invention can exist as two or more stereoisomers. In particular it will be understood that when $R^8$ and $R^9$ are different substitutents a stereocentre exists at the carbon atom to which they are attached—the benzylic carbon. Suitable compounds for use in this invention include those where the absolute stereochemistry at the benzylic carbon has the "S configuration". Further suitable compounds for use in this invention include those where the absolute stereochemistry at the benzylic carbon has the "R configuration". Such stereoisomers can be resolved and identified by one skilled in the art using known techniques.

The present invention includes the individual stereoisomers of the compounds of formula (I) together with mixtures thereof. Preferred compounds of formula (I) include those of formula (IA) and formula (IB) which possess the stereochemistry shown below.

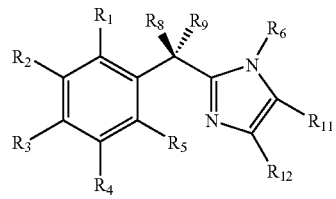

Formula (IA)

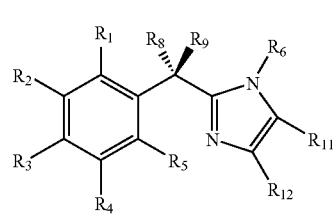

Formula (IB)

It will be understood that throughout the application all references to formula (I) apply equally to compounds of the formulae (IA) and (IB).

Furthermore, it will be understood that all the suitable groups and preferences applied to $R^1$-$R^{12}$, $R^a$, $R^b$ and n for formula (I) apply equally to compounds of the formulae (IA) and (IB).

In one particular embodiment of the invention preferred compounds are those of the formula (IA).

In one particular embodiment of the invention preferred compounds are those of the formula (IB).

Preferred compounds of the present invention include 2-[(1S)-1-(2,3-dimethylphenyl)ethyl]-1H-imidazole, 2-[(1R)-1-(2,3-dimethylphenyl)ethyl]-1H-imidazole, {2-[(1S)-1-(2,3-dimethylphenyl)ethyl]-1H-imidazol-1-yl}methylpivalate, {2-[(1R)-1-(2,3-dimethylphenyl)ethyl]-1H-imidazol-1-yl}methylpivalate or a pharmaceutically acceptable salt or prodrug thereof.

Even more preferred compounds of the present invention are 2-[(1S)-1-(2,3-dimethylphenyl)ethyl]-1H-imidazole, 2-[(1R)-1-(2,3-dimethylphenyl)ethyl]-1H-imidazole, or a pharmaceutically acceptable salt or prodrug thereof with the formulae shown below.

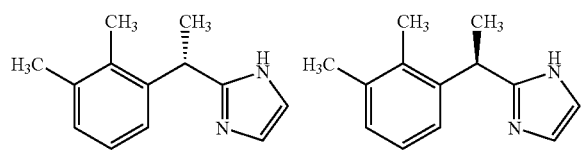

Most preferred is 2-[(1S)-1-(2,3-dimethylphenyl)ethyl]-1H-imidazole.

Geometric isomers may be separated by conventional techniques well known to those skilled in the art, for example, chromatography and fractional crystallisation.

Conventional techniques for the preparation/isolation of individual enantiomers include chiral synthesis from a suitable optically pure precursor, stereoselective synthesis from a prochiral precursor or resolution of the racemate (or the racemate of a salt or derivative) using, for example, fractional crystallization or chiral high pressure liquid chromatography (HPLC). Reference is made herein to "Enantiomers, Racemates and Resolutions" J. Jacques and A. Collet, published by Wiley, NY, 1981; and "Handbook of Chiral Chemicals" chapter 8, Eds D. Ager and M. Dekker, ISBN:0-8247-1058-4.

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluant affords the enriched mixture.

Stereoisomeric conglomerates may be separated by conventional techniques known to those skilled in the art—see, for example, "Stereochemistry of Organic Compounds" by E L Eliel (Wiley, New York, 1994).

In the compounds according to formula (I) the term 'halo' means a group selected from fluoro, chloro, bromo or iodo.

Alkyl, alkylene, alkenyl, alkynyl and alkoxy groups, containing the requisite number of carbon atoms, can be unbranched or branched. Examples of alkyl include methyl, ethyl, n-propyl, i-propyl, n-butyl, i-butyl, s-butyl and t-butyl. Examples of alkoxy include methoxy, ethoxy, n-propoxy, i-propoxy, n-butoxy, i-butoxy, s-butoxy and t-butoxy. Examples of alkylene include —$CH_2$—, —$CH(CH_3)$— and —$C_2H_4$—. Examples of cycloalkyl include cyclopropyl, cyclobutyl, cyclopentyl, cyclohexyl and cycloheptyl.

For the avoidance of doubt, it will be understood that throughout the application all references to pharmaceutically acceptable compounds includes references to veterinarily acceptable compounds or agriculturally acceptable compounds. Furthermore it will be understood that throughout the application all references to pharmaceutical activity includes references to veterinary activity or agricultural activity.

Pharmaceutically acceptable salts of the compounds of formula (I) include the acid addition and base salts thereof. Suitable acid addition salts are formed from acids, which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

The pharmaceutically, veterinarily and agriculturally acceptable acid addition salts of certain of the compounds of formula (I) may also be prepared in a conventional manner. For example, a solution of a free base may be treated with the appropriate acid, either neat or in a suitable solvent, and the resulting salt isolated either by filtration or by evaporation under reduced pressure of the reaction solvent. For a review on suitable salts, see "Handbook of Pharmaceutical Salts: Properties, Selection, and Use" by Stahl and Wermuth (Wiley-VCH, Weinheim, Germany, 2002).

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water. Pharmaceutically acceptable solvates in accordance with the invention include those wherein the solvent of crystallization may be isotopically substituted, e.g. $D_2O$, $d_6$-acetone, $d_6$-DMSO.

Hereinafter and throughout the application all references to compounds of formula (I) include references to salts, solvates and complexes thereof and to solvates and complexes of salts thereof.

As stated, the invention includes all polymorphs of the compounds of formula (I) as hereinbefore defined.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Within the scope of the invention are so-called 'prodrugs' of the compounds of formula (I). Thus certain derivatives of compounds of formula (I) which may have little or no pharmacological activity themselves can, when administered into or onto the body of an animal, be converted by the host or parasite into compounds of formula (I) having the desired activity, for example, by hydrolytic or enzymatic cleavage.

Such derivatives are referred to as 'prodrugs'. It will be appreciated that certain compounds of formula (I) may themselves act as pro-drugs of other compounds of formula (I). Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H Bundgaard (Elsevier, 1985).

Some examples of prodrugs in accordance with the invention include:

(i) where the compound of formula (I) contains a carboxylic acid functionality (—COOH), an ester thereof, for example, replacement of the hydrogen with ($C_1$-$C_8$)alkyl;

(ii) where the compound of formula (I) contains an alcohol functionality (—OH), an ether thereof, for example, replacement of the hydrogen with ($C_1$-$C_6$)alkanoyloxymethyl; and (iii) where the compound of formula (I) contains a primary or secondary amino functionality (—$NH_2$ or —NHR where R≠H), an amide thereof, for example, replacement of one or both hydrogens with ($C_1$-$C_{10}$)alkanoyl.

Prodrugs in accordance with the invention can, for example, be produced by reacting compounds of formula (I) wherein $R^6$ is H with certain moieties known to those skilled in the art as 'pro-drug moieties' as described, for example, in "Design of Prodrugs" by H Bundgaard (Elsevier, 1985); "Design and application of prodrugs," Textbook of Drug Design and Discovery, (3 Edition), 2002, 410-458, (Taylor and Francis Ltd., London); and references therein. Examples of substituents include: alkyl amines, aryl amines, amides, ureas, carbamates, carbonates, imines, enamines, imides, sulfenamides, and sulfonamides. The hydrocarbon portion of these groups contain $C_{1-6}$ alkyl, phenyl, heteroaryl such as pyridyl, $C_{2-6}$ alkenyl, and $C_{3-8}$ cycloalkyl; wherein each of the above groups may include one or more optional substituents where chemically possible independently selected from: halo; hydroxy; $C_{1-6}$ alkyl, $C_{1-6}$ haloalkyl and $C_{1-6}$ alkoxy.

Further examples of replacement groups in accordance with the foregoing example and examples of other prodrug types may be found in the aforementioned references.

A prodrug that is administered to a test animal and metabolized by the host according to the invention can be readily identified by sampling a body fluid for a compound of formula (I).

Finally, certain compounds of formula (I) may themselves act as prodrugs of other compounds of formula (I).

In a further aspect, the present invention provides processes for the preparation of a compound of formula (I), or a pharmaceutically, veterinarily or agriculturally acceptable salt thereof, or a pharmaceutically, veterinarily or agriculturally acceptable solvate (including hydrate) of either entity, as illustrated below.

The following processes are illustrative of the general synthetic procedures which may be adopted in order to obtain the compounds of the invention.

It will be apparent to those skilled in the art that sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc (1999), and references therein. Thus, when one or more of $R^1$, $R^2$, $R^3$, $R^4$, $R^5$, $R^6$, $R^7$, $R^8$, $R^9$, $R^{10}$, $R^{11}$ $R^{12}$, $R^{15}$ and $R^{16}$ contain reactive functional groups then additional protection may be provided according to standard procedures during the synthesis of compounds of formula (I). In the processes described below, for all synthetic precursors used in the synthesis of compounds of formula (I), the definitions of $R^1$, $R^2$, $R^3$, $R^4$, $R^5$, $R^6$, $R^7$, $R^8$, $R^9$, $R^{10}$ $R^{11}$ $R^{12}$, $R^{15}$ and $R^{16}$, wherein $R^1$, $R^2$, $R^3$, $R^4$, $R^5$, $R^6$, $R^7$, $R^8$, $R^9$, $R^{10}$, $R^{11}$ $R^{12}$, $R^{15}$ and $R^{16}$, are as defined for formula (I), are intended to optionally include suitably protected variants, $P^1$, $P^2$, $P^3$, $P^4$, $P^5$, $P^6$, $P^7$, $P^8$, $P^9$, $P^{10}$ $P^{11}$ $P^{12}$, $P^{15}$ and $P^{16}$. Such suitable protecting groups for these functionalities are described in the references listed below and the use of these protecting groups where needed is specifically intended to fall within the scope of the processes described in the present invention for producing compounds of formula (I) and its precursors. When suitable protecting groups are used, then these will need to be removed to yield compounds of formula (I). Deprotection can be effected according to standard procedures including those described in the references listed below. When $R^6$ is a protecting group it is preferred that it is chosen from benzyl, p-methoxybenzyl, diethoxymethyl, allyl and trityl.

Compounds of formula (I) may be obtained from other compounds of formula (I) by standard procedures such as electrophilic or nucleophilic substitution, organometallic catalysed cross coupling reactions and functional group interconversions known to those skilled in the art. For example, compounds of formula (I) in which one or more of $R^1$, $R^2$, $R^3$, $R^4$ and $R^5$ are $CO_2R^c$ wherein $R^c$=alkyl, may be transformed into compounds of formula (I) in which one or more of $R^1$, $R^2$, $R^3$, $R^4$ and $R^5$ are $CO_2R^d$ wherein $R^d$=$NH_2$ upon treatment with ammonium hydroxide at 85° C. for 2 h. Similarly compounds of formula (I) wherein one or more of $R^1$, $R^2$, $R^3$, $R^4$ and $R^5$ are $CO_2R$ wherein R=$NH_2$ upon treatment with a dehydrating agent such as thionyl chloride at low temperatures in an anhydrous solvent such as N,N-dimethylformamide produce the corresponding nitrile compound.

Compounds of formula (I), wherein $R^8$ is $C_1$-$C_4$ alkyl, $R^9$, $R^{11}$ and $R^{12}$ are hydrogen and $R^6$ is hydrogen or alkyl and $R^1$, $R^2$, $R^3$, $R^4$ and $R^5$ are as defined previously

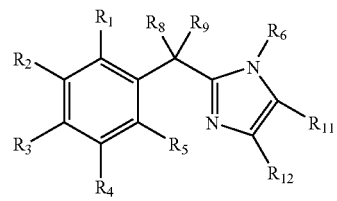

Formula (I)

may be synthesised from compounds of formula (II) using standard hydrogenation procedures. For example, compounds of formula (II) wherein $R^a$ is hydrogen, and $R^b$ is hydrogen or alkyl may be reduced to compounds of formula (I) in a suitable protic solvent such as methanol or propan-2-ol under a hydrogen atmosphere at temperatures up to 60° C. and elevated pressure up to 300 psi in the presence of 10% palladium on carbon or Freiborg activated 10% palladium on carbon for up to 72 h.

Compounds of formula (I) in which one or more of $R^1$, $R^2$, $R^3$, $R^4$ and $R^5$ are optionally halo, and the remainder of $R^1$, $R^2$, $R^3$, $R^4$ and $R^5$ are as previously defined, may be accessed from compounds of formula (II) in which one or more of $R^1$, $R^2$, $R^3$, $R^4$ and $R^5$ are optionally halo by hydrogenation procedures. Thus, compounds of formula (II) may be reduced to give compounds of formula (I) under a hydrogen atmosphere at temperatures up to 60° C. and elevated pressure up to 200 psi in the presence of 10% palladium on carbon and a chelating agent such as zinc bromide in a standard protic solvent such as methanol or propan-2-ol.

Alternatively, compounds of formula (I) may be obtained from compounds of formula (II) by transfer hydrogenation conditions. For example, ammonium formate or formic acid or ammonium formate in the presence of formic acid may be used to generate an in situ source of hydrogen which when in the presence of a hydrogenation catalyst such as 10% palladium on carbon in an alcoholic solvent such as propan-2-ol, for 2-3 hours at temperatures up to 80° C. can be used to effect the transformation of compounds of formula (II) to compounds of formula (I). Optionally reactions using formic acid as the hydrogen source may be performed without alcoholic solvents.

Stereoselective hydrogenations may be performed to yield a preferred stereoisomer using chiral catalysts, in accordance with standard organic chemistry textbooks or literature precedent. For example there are many known homogeneous and heterogeneous catalytic methods using transition metals such as palladium, rhodium and ruthenium. One particularly preferred catalyst is bis(norbornadiene)rhodium(I) tetrafluoroborate. Enantiopure ligands that have been utilised to effect enantioselective hydrogenations have been referenced in the literature and illustrative examples of homochiral ligands include phospholanes such as Duphos and its analogues, ferrocenyl ligands such as Josiphos, 1-[(R)-2-diphenylphosphino)ferrocenyl]ethyldi-tert-butylphosphine, biphenyl ligands such as (+/−)-2,2′-Bis(diphenylphosphino)-1,1′-binaphthalene (BINAP) and miscellaneous ligands such as Prophos, Diamp, Bicp, Monophos. References providing details of enantioselective hydrogenations include Y. Yamanori, T. Imamoto, Reviews on Heteroatom Chemistry, 1999, 20, 227; T. Clark, C. Landis, Tetrahedron: Asymmetry, 2004, 15, 14, 2123; H. Blaser, Topics in Catalysis, 2002, 19, 1, 3; H. Blaser et al, Synthetic Methods of organometallic and inorganic chemistry, 2002, 10, 78; Pure and Applied Chemistry, 1999, 71, 8, 1531; Pure and Applied Chemistry, 1998, 70, 8, 1477; U. Berens et al, Speciality Chemicals, 2000, 20, 6, 210; M. T. Reetz, Pure and Applied Chemistry, 1999, 71, 8, 1503; D. J. Bayston et al, Speciality Chemicals, 1998, 18, 5, 224; C. Saluzzo and M. Lemaire, Advanced Synthesis and Catalysis, 2002, 344, 9, 915; H. Kumobayashi, Synlett, 2001, (Spec Issue) 1055.

Thus, enantiomerically enriched compounds of formula (I) may be obtained from achiral compounds of formula (II) by stereoselective hydrogenation. For example, compounds of formula (II) wherein $R^a$ is hydrogen, and $R^b$ is hydrogen or alkyl may be reduced to compounds of formula (I) in a suitable protic solvent such as methanol under a hydrogen atmosphere at ambient temperatures and elevated pressure up to 60 psi in the presence of a rhodium catalyst such as bis(norbornadiene)rhodium(I) tetrafluoroborate and chiral ligand such as 1-[(R)-2-diphenylphosphino)ferrocenyl]ethyldi-tert-butylphosphine to give optically enriched compounds of formula (I).

Chiral resolution can be utilised to enhance the enantiomeric purity of compounds of formula (I). For example, an acid salt can be enantioselectively formed upon addition of an enantiomerically pure chiral acid such as di-p-toluoyl-L-tartaric acid in a suitable protic solvent such as methanol. Using this process one enantiomer preferentially forms a crystalline salt which can be removed by filtration whereas the other enantiomer remains in the mother liquor. Upon separately basifying the salt and mother liquor with a suitable base such as sodium hydroxide (1N), the enantiomers are resolved to give separated optically enriched compounds of formula (I).

Alternatively, racemic compounds of formula (I) may be resolved using chiral HPLC procedures, known to those skilled in the art, to give enantiomerically pure compounds of formula (I).

Compounds of formula (II) wherein $R^6$ is a protecting group such as benzyl or substituted benzyl e.g. p-methoxybenzyl, may be deprotected and reduced under hydrogenation conditions to give compounds of formula (I) wherein $R^6$ is hydrogen.

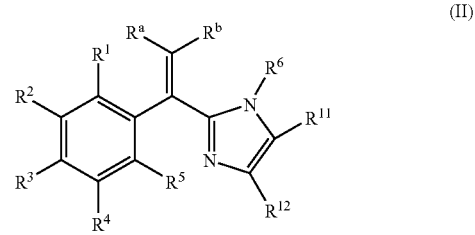

Imidazole ring formation can also be utilised to access compounds of formula (I), other synthetic methods are precedented in textbooks and the literature. One illustrative example is from desirably substituted phenylacetonitrile reactants, for example a compound such as 2-(2,3-dimethylphenyl)propanenitrile may be reacted with an appropriately substituted ethylenediamine for example, the p-toluenesulfonic acid salt of ethylenediamine at elevated temperatures ranging from 140°-180° C. to form the compound of formula (I) wherein $R^1$, $R^2$ and $R^8$ are methyl and $R^3$, $R^4$, $R^5$, $R^6$ and $R^9$, $R^{11}$ and $R^{12}$ are hydrogen.

Another example of imidazole ring formation is from the reaction of suitably 2-substituted 2-aryl-1,1-dibromoethenes and an appropriately substituted ethylenediamine at room temperature to give the intermediate 2-substituted 2-arylmethylimidazoline. Standard oxidation procedures such as Swern oxidation can transform the intermediate 2-substituted 2-arylmethylimidazoline into compounds of formula (I).

Compounds of formula (II) may be prepared by Wittig chemistry by the reaction of a compound of formula (X) with the appropriate alkylphosphonium salt-derived phosphorus ylid. For example treatment of a methyltriphenylphosphonium halide with a strong base in a suitable solvent, followed by the addition of (X), will produce a compound of formula (II) wherein both $R^a$ and $R^b$ are hydrogen. Preferably the base reagent is a solution of n-butyllithium in hexane, the solvent is ether or tetrahydrofuran and the reaction is conducted at from about room temperature to about 35° C.

Compounds of formula (II) may undergo functional group interconversion into other compounds of formula (II). For example, wherein one or more of $R^1$, $R^2$, $R^3$, $R^4$ and $R^5$ are bromo or iodo, and $R^6$ is protected with a suitable protecting group such as benzyl, palladium catalysed coupling reactions such as Stille, Heck and Suzuki coupling reactions may be effected. For example, treatment of such organohalide compounds of formula (II) with a suitable boronic acid such as an alkyl or aryl boronic acid, in an inert solvent such as toluene, in the presence of a suitable base such as potassium phosphate, a suitable phosphine ligand such as tricyclohexylphosphine and palladium acetate under an inert atmosphere at elevated temperatures up to 120° C. for up to 18 h provides the corresponding alkylated or arylated compound of formula (II). Similarly, compounds of formula (II) wherein one or more of $R^1$, $R^2$, $R^3$, $R^4$ and $R^5$ are bromo or iodo, and $R^6$ is protected with a suitable protecting group such as benzyl, may undergo transmetallation reaction with a palladium catalyst such as [1,1-bis(diphenylphosphino)ferrocene]palladium (II) chloride followed by cross coupling with a suitable boronic anhydride such as trialkylboroxine under an inert atmosphere, in the presence of a mild base such as sodium carbonate and a suitable inert solvent such as dioxane and water at elevated temperatures up to 120° C. Alternatively, compounds of formula (II) wherein one or more of $R^1$, $R^2$, $R^3$, $R^4$ and $R^5$ are bromo or iodo, and $R^6$ is protected with a suitable protecting group such as benzyl, may undergo nucleophilic substitution reactions. For example, nitrile compounds may be formed upon treatment of such a halo compound of formula (II) in a polar solvent such as N,N-dimethylacetamide with a cyanide source such as copper cyanide at temperatures up to 150° C. for 3 days to give the corresponding compound of formula (II) wherein one or more of $R^1$, $R^2$, $R^3$, $R^4$ and $R^5$ are cyano, and $R^6$ is protected with a suitable protecting group such as benzyl. Nitrile compounds of formula (II) may also be formed from the corresponding halo compound of formula (II) upon treatment with a cyanide source such as sodium cyanide in the presence of a suitable transmetallating agent such as nickel bromide in a polar solvent such as N-methylpyrrolidinone and heating in a 150 W microwave at up to 150° C. for 5 min. Nitrile compounds of formula (II) may also be formed from the corresponding halo compound of formula (II) from the reaction of a suitable cyanide source such as potassium hexacyanoferrate, a transmetallating agent such as copper iodide, a salt such as potassium iodide, and a coordinating agent such as dimethylethylenediamine in a polar solvent such as N-methylpyrrolidinone under an inert atmosphere at elevated temperatures up to 140° C. for up to 60 hours.

Compounds of formula (II) may be prepared from compounds of formula (III) by standard dehydration conditions, optionally $R^6$ may be a suitable protecting group e.g. benzyl, or substituted benzyl.

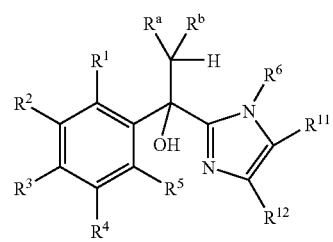
(III)

Thus, dehydration may be effected under acidic conditions. For example compounds of formula (III) may be treated with an inorganic acid such as hydrochloric acid (4-6N) or concentrated sulphuric acid, for up to 72 h, optionally in an organic miscible solvent such as acetonitrile, optionally at elevated temperatures up to 60° C. Alternatively, dehydration may result from heating compounds of formula (III) at reflux with an organic acid such as trifluoroacetic acid or p-toluenesulphonic acid in an aprotic solvent such as toluene. Otherwise, compounds of formula (III) may be dehydrated using Eaton's reagent, typically stirring at room temperature for several hours neat or in a polar solvent such as methanol. Dehydration may also be effected by treating a compound of formula (III) with thionyl chloride in a polar solvent such as acetonitrile.

Compounds of formula (III) may be used to directly access compounds of formula (I) upon treatment with Pearlman's catalyst in a suitable protic solvent such as methanol under a hydrogen atmosphere, in cases wherein $R^6$ is a benzylic protecting group a deprotected compound of formula (I) will be obtained wherein $R^6$ is hydrogen. Alternatively, compounds of formula (III) wherein $R^6$ is a protecting group such as benzyl may be deprotected, dehydrated and reduced simultaneously by hydrogenation under acidic conditions. For example, upon treatment of compounds of formula (III) with a hydrogen source such as ammonium formate in the presence of an acid such as formic acid and 10% palladium on carbon, optionally for up to 72 h, compounds of formula (I) wherein $R^6$ is hydrogen are obtained.

Compounds of formula (II) may be obtained by dehydrohalogenation procedures, known to the skilled man, from compounds of formula (III) for example by standard chlorination followed by dehydrochlorination procedures.

Alternatively, compounds of formula (II) can be obtained by transition metal catalysed cross-coupling reactions by utilizing methods known in the literature. For these reactions, it may be necessary to protect the basic imidazole, optionally $R^6$ may include a suitable protecting group such as diethoxymethyl. Thus, suitably protected organozincates such as compounds of formula (V), wherein X is halo for example chloro or bromo, can be coupled with suitably substituted styrenes such as compounds of formula (IV) wherein Y is a group suitable for transmetallation such as OTf, Cl, Br or I in the presence of a palladium catalyst such as $Pd(PPh_3)_3$.

Standard deprotection of compounds of formula (II) wherein $R^6$ is a suitable protecting group provides compounds of formula (II) in which $R^6$ is hydrogen. For example, when $R^6$ is diethoxymethyl treatment with an organic acid such as trifluoroacetic acid or an inorganic acid such as hydrochloric acid provides compound (II) wherein $R^6$ is hydrogen. Similarly, deprotection of compounds of formula (II) wherein $R^6$ is a benzyl moiety protecting group may easily be effected by hydrogenation.

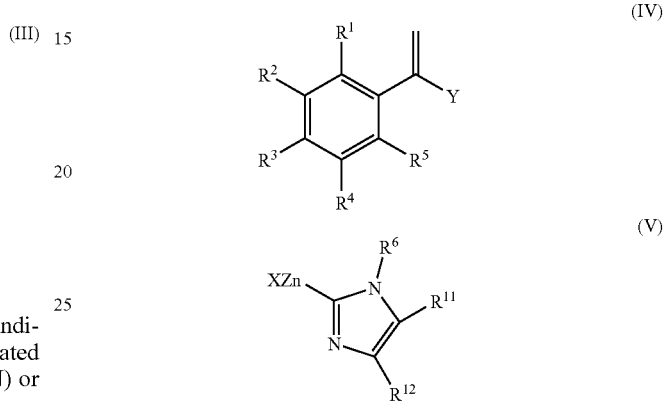

Compounds of formula (III) wherein $R^6$ is a protecting group can be formed by 1,2-addition of a suitably protected organometallic compound (VI) to the corresponding ketone (VII) where chemically feasible for example wherein $R^1$, $R^2$, $R^3$, $R^4$ and $R^5$ may be chosen independently from alkyl, chloro, and $R^a$ and $R^b$ may be chosen from alkyl.

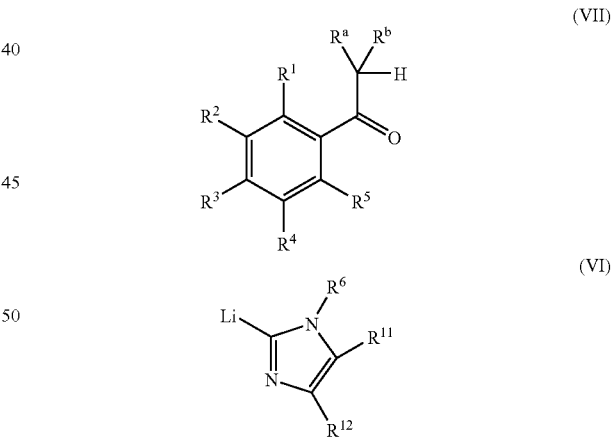

For example, compound (VI) may be reacted with ketone (VII) in an aprotic solvent such as tetrahydrofuran at temperatures typically ranging from −80 to 0° C. to give compounds of formula (III), which can be readily deprotected to give a compound of formula (III) wherein $R^6$ is H if desired.

Alternative organometallic chemistry may be utilized to yield a compound of formula (III), wherein $R^6$ is a suitable protecting group such as benzyl, when an organometallic compound of formula (VIII), wherein X may be a halo e.g. chloro or bromo, is added to a ketone of formula (IX) wherein $R^6$ is a protecting group.

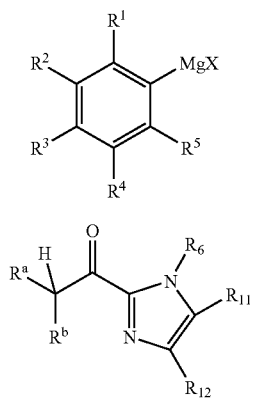

(VIII)

(IX)

Similarly, compounds of formula (III) wherein $R^6$ is optionally a suitable protecting group such as benzyl may also be accessed by organometallic addition to a protected ketone (X), suitable organometallic reagents include Grignard reagents and organolithium reagents. For example, a Grignard reagent such as methylmagnesium chloride may be added to a solution of compound (X) in an anhydrous, aprotic solvent such as tetrahydrofuran, toluene or diethyl ether at −10°-0° C. for up to 4 h to provide compounds of formula (III) wherein $R^a$ and $R^b$ are H.

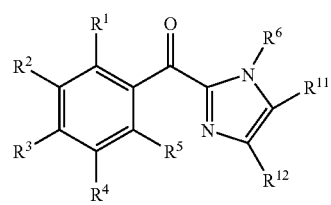

(X)

Compounds of formula (III) wherein $R^6$ is a protecting group such as benzyl may be deprotected using standard hydrogenation conditions such as 10% palladium on carbon in a protic solvent at elevated pressure and temperature to give deprotected compounds of formula (III) wherein $R^6$ is hydrogen. Deprotecting compounds of formula (III) in a stepwise manner, before dehydration to produce compounds of formula (II), allows compounds of formula (II) to be stereoselectively reduced to give compounds of formula (I) if desired.

Compounds of formula (IV), (V), (VI), (VII), (VIII), and (IX) may readily be accessed by utilisation of literature methods or simple modifications thereof as would be routinely employed by a skilled man. For example, compounds of formula (V) can be prepared by stirring a 1-protected imidazole with n-butyllithium at reduced temperature, typically −60 to −20° C. followed by the addition of zinc chloride and allowing to warm to room temperature.

For example, compound (VI) may be obtained in situ by treatment of a protected imidazole reactant, with an organolithium reagent such as n-butyllithium in an aprotic solvent such as tetrahydrofuran at reduced temperatures typically ranging from −80 to 0° C. Suitable protecting groups include diethoxymethyl.

For example, compounds of formula (IX) may be synthesised by acylating a suitably substituted imidazole using acid chlorides. Thus, heating for several hours a suitable acid chloride with a 1-protected imidazole in the presence of a mild base such as triethylamine provides compounds of formula (IX).

Compounds of formula (VII) may be accessed in a number of ways. Some methods utilise simple precursors as detailed below.

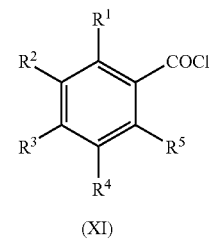

(XI)

SOCl$_2$ ↗ ↘ $R^aR^bHCMgBr$, Fe(acac)$_3$

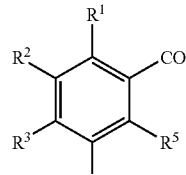

(XII)  $R^aR^bHCLi$  (VII)

($R^aR^bHCCO)_2O$ or $R^aR^bHCCONMe_2$ or $R^aR^bHCCOCl$ ↗

↑ $R^aR^bHCMgBr$

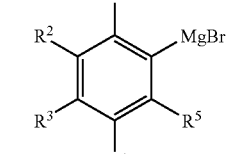 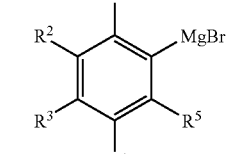

(XIII)  (XIV)

Compounds of formula (VII) may be prepared by the addition of a chelating agent such as Fe(acac)$_3$ and a Grignard reagent such as methylmagnesium bromide to a suitably substituted acid chloride (XI) at reduced temperatures, typically −20° C. in a suitable aprotic solvent. Acid chlorides (XI) may be prepared by the reaction of the corresponding benzoic acid (XII) with thionyl chloride or oxalyl chloride, at elevated temperatures, typically 100° C. for several hours.

Compounds of formula (VII) may also be prepared by reaction of an acid anhydride such as acetic anhydride, with a phenyl Grignard reactant (XIII) in an aprotic solvent. Alternatively, amides, or acid chlorides may be used in place of the acid anhydride. Compounds of formula (XIII) may be formed in situ by reacting a suitable bromobenzene derivative with magnesium turnings in an anhydrous, aprotic solvent such as tetrahydrofuran.

Similarly, compounds of formula (VII) may be prepared by reacting a Grignard reactant e.g. methylmagnesium bromide with an amide e.g. a suitably substituted benzoylmorpholine (XIV) at reflux in a suitable solvent such as tetrahydrofuran.

Compounds of formula (VII) may also be obtained from reaction of a suitable benzoic acid (XII) with an organolithium reactant, for example methyllithium, at reduced temperatures in an anhydrous aprotic solvent such as tetrahydrofuran.

Compounds of formula (VII) may be obtained by Friedel Crafts acylation of suitably functionalized phenyl moieties. For example, a functionalized phenyl reactant can be treated with a Lewis acid such as aluminium chloride, in the presence of a suitable acylating agent such as acetyl chloride, in an aprotic solvent such as dichloromethane at room temperature for up to 18 h to give the desired compounds of formula (VII).

Alternatively compounds of formula (VII) may by obtained in a two step procedure from a suitably substituted halobenzene, preferably bromo or iodo benzene. For example a bromobenzene compound may be transmetallated with an organometallic reagent such as n-butyllithium in an anhydrous, apolar solvent such as tetrahydrofuran at low temperatures down to −80° C. followed by electrophilic quenching with an aldehyde to give the corresponding secondary alcohol which may be oxidized under standard conditions, for example using Dess Martin periodinane, to give compounds of formula (VII) wherein $R^a$ is selected from H, $C_{1-4}$alkyl, or $C_{0-4}$alkylenephenyl and $R^b=C_{1-4}$alkyl, or $C_{0-4}$alkylenephenyl.

Compounds of formula (VII) may also be formed from the corresponding aryliodide and boronic acids using palladium chemistry in a carbon monoxide atmosphere. Thus, heating aryliodides with carbon monoxide, methylboronic acid and palladium tetrakis triphenylphosphine provides compounds of formula (VII) wherein $R^a$ and $R^b$ are H.

Compounds of formula (VII) may undergo standard chemical reactions and functional group interconversion reactions known to the skilled man to give other compounds of formula (VII). Thus, compounds of formula (VII) may be chlorinated using standard reagents such as Selectafluor™ and sodium chloride. Also, suitably substituted halo compounds of formula (VII) may undergo standard palladium catalysed cross coupling reactions such as Suzuki, Stille, Heck reactions to give a variety of standard products. For example, bromo or iodo compounds of formula (VII) may undergo alkylation and arylation reactions via Suzuki coupling reactions upon treatment with an organoborane e.g. triethyl borane in the presence of [1,1-bis(diphenylphosphino)ferocene]palladium (II) chloride, and potassium carbonate in an aprotic solvent such as N,N-dimethylformamide to give alkyl or aryl substituted compounds of formula (VII).

Compounds of formula (X) may be obtained from the reaction of acid chlorides of formula (XI) and imidazoles of formula (XV) wherein $R^6$ is a suitable protecting group in a suitable aprotic solvent such as toluene or acetonitrile in the presence of a mild base such as triethylamine at temperatures ranging from −10°-130° C.

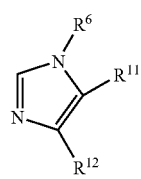

(XV)

Suitably functionalised acid chlorides of formula (XI) may be synthesised from the corresponding acid upon treatment with thionyl chloride at 80° C. for ~1 hour. Alternatively, acid chlorides may be synthesised from carboxylic acids upon treatment with oxalyl chloride in an aprotic solvent such as toluene at room temperature for up to 4 hours. Suitably functionalized acids may be obtained by utilising standard literature procedures available to the skilled man, thus substituents may be introduced via electrophilic or nucleophilic substitution or cross coupling reactions or via functional group interconversion.

Compounds of formula (X) can also be synthesized by oxidation of compounds of formula (XVI) by suitable oxidising agents, wherein $R^6$ is hydrogen or a suitable protecting group.

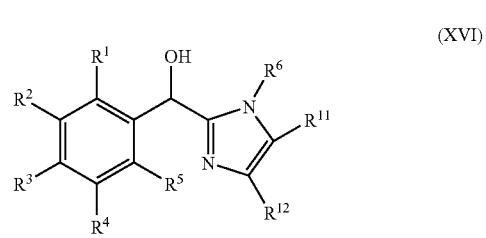

(XVI)

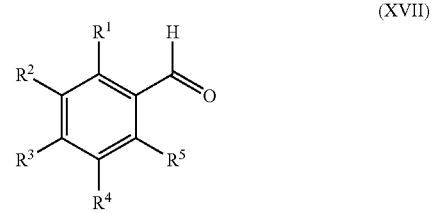

(XVII)

One such oxidation may include Dess Martin oxidation conditions. For example, a compound of formula (X), may be prepared by stirring the corresponding compound of formula (XVI) at room temperature with Dess-Martin Periodinane in a suitable polar solvent such as dichloromethane.

Compounds of formula (XVI) may be formed by the 1,2-addition of a suitably protected organometallic compound to a suitable aldehyde. Thus reaction of an organolithium compound of formula (VI) and a corresponding aldehyde of formula (XVII), in an anhydrous, aprotic solvent such as tetrahydrofuran at temperatures ranging from −80-0° C. provides compounds of formula (XVI).

It is to be understood that precursors to compounds of formula (I) and compounds of formula (I) themselves may undergo functional group interconversion in order to deliver alternative compounds of formula (I). For example compounds of formula (I) wherein $R^6$ is hydrogen may be reacted with alkylating agents of the formula L-$C_{0-2}$alkylene$R^7$, L-$C_{1-2}$alkyleneO$R^7$, L-$C_{1-2}$alkyleneC(O)$R^7$, L-$C_{1-2}$alkyleneOC(O)$R^7$, L-$C_{1-2}$alkyleneOC(O)O$R^7$, L-$C_{1-2}$alkyleneC(O)O$R^7$, L-$C_{1-2}$alkyleneN(H)C(O)$R^7$, L-$C_{1-2}$alkyleneN($R^7$)C(O)$R^7$, L-$C_{1-2}$alkyleneC(O)NH$R^7$, L-$C_{1-2}$alkyleneNHC(O)N$R^{15}R^{16}$, L-$C_{1-2}$alkyleneN$R^7$C(O)N$R^{15}R^{16}$, L-$C_{1-2}$alkyleneC(O)N$R^{15}R^{16}$, L-$C_{1-2}$alkyleneOC(O)NH$R^7$, L-$C_{1-2}$alkyleneOC(O)N$R^{15}R^{16}$, to provide compounds wherein $R^6$ is —$C_{0-2}$alkylene$R^7$, —$C_{1-2}$alkyleneO$R^7$, —$C_{1-2}$alkyleneC(O)$R^7$, —$C_{1-2}$alkyleneOC(O)$R^7$, —$C_{1-2}$alkyleneOC(O)O$R^7$—$C_{1-2}$alkyleneC(O)O$R^7$, —$C_{1-2}$alkyleneN(H)C(O)$R^7$, —$C_{1-2}$alkyleneN($R^7$)C(O)$R^7$, —$C_{1-2}$alkyleneC(O)NH$R^7$, —$C_{1-2}$alkyleneNHC(O)N$R^{15}R^{16}$, —$C_{1-2}$alkyleneN$R^7$C(O)N$R^{15}R^{16}$, —$C_{1-2}$alkyleneC(O)N$R^{15}R^{16}$, —$C_{1-2}$alkyleneOC(O)NH$R^7$, —$C_{1-2}$alkyleneOC(O)N$R^{15}R^{16}$. L is a suitable leaving group such as Cl, Br, I, or a sulfonate such as trifluoromethanesulfonate. For example compounds of formula (I)

wherein $R^6$ is hydrogen may be reacted with alkylating agents in the presence of a mild base such as cesium carbonate, potassium carbonate, triethylamine, or diisopropylethylamine, in an aprotic solvent such as acetone, 1-methyl-2-pyrrolidinone, dichloromethane, tetrahydrofuran, acetonitrile or N,N-dimethylformamide optionally in the presence of a salt such as sodium iodide. Generally the alkylation reaction will proceed for up to 72 h at room temperature, optionally the reaction may be heated to reflux or may be microwaved at 200 W for up to 1 h.

Alkylating agents of the form $Cl-CH_2OC(O)R^7$ may be produced from the reaction of the acid chloride $ClC(O)R^7$ with paraformaldehyde in the presence of a Lewis acid such as zinc chloride at temperatures up to 80° C. for 2-3 hours. Under alkylating conditions such reagents give compounds of formula (I) wherein $R^6$ is $CH_2OC(O)R^7$.

Alkylating agents of the form $L-CH_2OC(O)OR^7$ may be produced from the reaction of the alcohol $HOR^7$ with chloromethyl chloroformate in an aprotic solvent such as dichloromethane at temperatures ranging from 0° C. to room temperature. Under alkylating conditions such reagents give compounds of formula (I) wherein $R^6$ is $CH_2OC(O)OR^7$.

Alkylating agents of the form $L-CH_2OC(O)NHR^7$, may be produced from the reaction of the amine $R^7NH_2$ with chloromethyl chloroformate in an aprotic solvent such as dichloromethane at temperatures ranging from -10° C. to room temperature. Under alkylating conditions such reagents give compounds of formula (I) wherein $R^6$ is $CH_2OC(O)NHR^7$.

Alkylating agents of the form $L-CH_2OC(O)NR^{15}R^{16}$, may be produced from the reaction of the amine $R^{15}R^{16}NH$ with chloromethyl chloroformate in an aprotic solvent such as dichloromethane optionally in the presence of a mild base such as diisopropylethylamine at temperatures ranging from -0° C. to room temperature. Under alkylating conditions such reagents give compounds of formula (I) wherein $R^6$ is $CH_2OC(O)NR^{15}R^{16}$.

Compounds of formula (I) wherein $R^6$ is hydrogen may be reacted with acylating agents of the formula $ClC(O)R^7$, $O[OC(O)R^7]_2$, $ClC(O)OR^7$, $ClC(O)NHR^7$, $ClC(O)NR^{15}R^{16}$, to provide compounds wherein $R^6$ is $-C(O)R^7$, $-OC(O)R^7$, $-C(O)OR^7$, $-C(O)NHR^7$, $-C(O)NR^{15}R^{16}$. For example compounds of formula (I) wherein $R^6$ is hydrogen may be reacted with acylating agents in the presence of a mild base such as triethylamine, or pyridine in an aprotic solvent such as dichloromethane, tetrahdyrofuran or acetonitrile at temperatures ranging from room temperature to 100° C. for between 1 and 36 h.

It is possible to form the acylating agent $ClC(O)OR^7$ in situ. Thus a compound of formula (I) wherein $R^6$ is hydrogen, may be reacted with phosgene or diphosgene in an anhydrous solvent such as dichloromethane or acetonitrile in the presence of a mild base such as pyridine in the presence of an alcohol $R^7OH$ at ambient temperature to give the compound of formula (I) wherein $R^6$ is $C(O)OR^7$.

Compounds of formula (I) wherein $R^6$ is hydrogen may be reacted with phosphorylating agents of the formula $Cl-P(=O)[N(R^7)_2(R^7)_2]$ to give compounds of formula (I) wherein $R^6$ is $P(=O)[N(R^7)_2(R^7)_2]$. For example reaction with a corresponding bis(dialkylamino)phosphoryl chloride e.g. bis(dimethylamino)phosphoryl chloride in an aprotic solvent such as dichloromethane.

Compounds of formula (I) wherein $R^6$ is hydrogen may be reacted with silating agents of the formula $Cl-Si(R^7)$ to give compounds of formula (I) wherein $R^6$ is $Si(R^7)_3$ For example reaction with a corresponding alkylsilane or arylsilane e.g. chlorotrimethylsilane in an aprotic solvent such as dichloromethane or tetrahydrofuran.

Compounds of formula (I) wherein $R^6$ is hydrogen may be reacted with sulphonating agents of the formula $Cl-S(=O)_2 R^{10}$ to give compounds of formula (I) wherein $R^6$ is $S(=O)_2 R^{10}$. For example reaction with a corresponding sulphonyl chloride e.g. methanesulphonyl chloride in an aprotic solvent such as dichloromethane, optionally with a weak base such as triethylamine.

Compounds of formula (I) wherein $R^6$ is hydrogen may be reacted with cyanogen bromide in an aprotic solvent such as dichloromethane, optionally with a weak base such as diisopropylethylamine to give compounds of formula (I) wherein $R^6$ is CN.

Compounds of formula (III) may be alkylated to give compounds of formula (I) wherein $R^9$ is $C_1$-$C_4$ alkoxy. Thus, treatment of compounds of formula (III) with a strong base such as sodium hydride in an aprotic solvent such as tetrahydrofuran followed by addition of an alkylating agent will provide compounds of formula (I) wherein $R^9$ is $C_1$-$C_4$ alkoxy.

Compounds of formula (II) may be cyclopropanated to give compounds of formula (I) wherein $R^8$ and $R^9$ together form a cyclopropyl ring. Compounds of formula (II) may be reacted with a carbenoid species, $CR^dR^e$. For example, when $R^d=R^e=F$, a reactive species such as trimethylsilyl difluoro (fluorosulfonyl)acetate (TFDA) may be reacted with a compound of formula (II), with an optional apolar solvent at elevated temperature in the presence of sodium fluoride to yield a product of formula (I) after deprotection, wherein the cyclopropyl ring is substituted with fluoro.

Other specific methods include treatment of chloroform with base, preferably under phase transfer catalysis conditions, thermolysis of a suitable organometallic precursor such as an aryl trifluoromethyl, trichloromethyl, or phenyl(trifluoromethyl) mercury derivative or treatment with a diazoalkane in the presence of a transition metal catalyst and treatment with a diazoalkane in the absence of a transition metal catalyst followed by thermolysis of the intermediate pyrazoline, or generation from a sulphur ylid.

Moreover, persons skilled in the art will be aware of variations of, and alternatives to, the processes described which allow the compounds defined by formula (I) to be obtained.

It will also be appreciated by persons skilled in the art that, within certain of the processes described, the order of the synthetic steps employed may be varied and will depend inter alia on factors such as the nature of other functional groups present in a particular substrate, the availability of key intermediates, and the protecting group strategy (if any) to be adopted. Clearly, such factors will also influence the choice of reagent for use in the said synthetic steps.

The skilled person will appreciate that the compounds of the invention could be made by methods other than those herein described, by adaptation of the methods herein described and/or adaptation of methods known in the art, for example the art described herein, or using standard textbooks such as "Comprehensive Organic Transformations—A Guide to Functional Group Transformations", R C Larock, Wiley-VCH (1999 or later editions).

It is to be understood that the synthetic transformation methods mentioned herein are exemplary only and they may be carried out in various different sequences in order that the desired compounds can be efficiently assembled. The skilled chemist will exercise his judgement and skill as to the most efficient sequence of reactions for synthesis of a given target compound.

Further examples of replacement groups in accordance with the foregoing examples and examples of other prodrug types may be found in the aforementioned references.

The present invention also relates to intermediates of formula (LX) below:

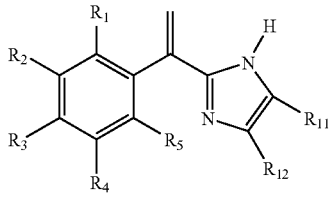

Formula (LX)

where:
$R^1$-$R^{12}$, $R^a$, $R^b$, and n are all as defined for formula (I) above or a pharmaceutical salt or a prodrug thereof. With reference to formula (LX), suitably $R^1$ and $R^2$ are selected from $C_{1-4}$ alkyl and $R^3$, $R^4$ and $R^5$ are hydrogen.

The present invention also relates to intermediates of formula (LXV) below:

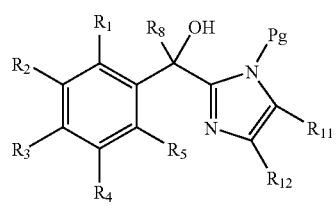

Formula (LXV)

where:
$R^1$-$R^{12}$, $R^a$, $R^b$, and n are all as defined for formula (I) above and where Pg is a chemical protecting group or a pharmaceutical salt or a prodrug thereof. With reference to formula (LXV), suitably $R^1$ and $R^2$ are selected from $C_{1-4}$ alkyl and $R^3$, $R^4$ and $R^5$ are hydrogen.

The present invention also relates to intermediates of formula (LXX) below:

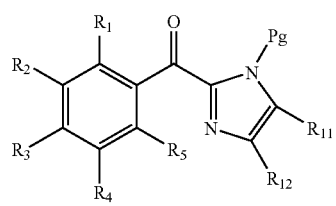

Formula (LXX)

where:
$R^1$-$R^{12}$, $R^a$, $R^b$, and n are all as defined for formula (I) above and where Pg is a chemical protecting group or a pharmaceutical salt or a prodrug thereof. With reference to formula (LXX), suitably $R^1$ and $R^2$ are selected from $C_{1-4}$ alkyl and $R^3$, $R^4$ and $R^5$ are hydrogen.

It will be understood that throughout the application all references to formula (I) apply equally to compounds of the formulas (LX), (LXV) and (LXX) above.

Furthermore, it will be understood that all the suitable groups and preferences applied to $R^1$-$R^{12}$, $R^a$, $R^b$, and n for formula (I) apply equally to compounds of the formulas (LX), (LXV) and (LXX) above.

Finally, certain compounds of formula (I) may themselves act as intermediates in the preparation of other compounds of formula (I).

One of ordinary skill in the art would understand that Pg in the formulas (LX), (LXV) and (LXX) above can represent a wide range of possible protecting group and the specific group required will depend on the final compounds to be made and can be readily selected by one of ordinary skill. Preferred protecting groups include benzyl, para-methoxybenzyl, allyl, trityl, or 1,1-diethoxymethyl, preferably benzyl.

This invention also relates to a pharmaceutical composition comprising a compound of formula (I), or a pharmaceutically acceptable salt thereof, or a pharmaceutically acceptable solvate of either entity, together with a pharmaceutically acceptable diluent or carrier, which may be adapted for oral, parenteral or topical administration.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

The methods by which the compounds may be administered include oral administration by capsule, bolus, tablet, powders, lozenges, chews, multi and nanoparticulates, gels, solid solution, films, sprays, or liquid formulation. Liquid forms include suspensions, solutions, syrups, drenches and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet. Oral drenches are commonly prepared by dissolving or suspending the active ingredient in a suitable medium.

Compounds of the present invention may be administered alone or in combination with one or more other compounds of the invention or in combination with one or more other drugs (or as any combination thereof). The compounds may be administered alone or in a formulation appropriate to the specific use envisaged, the particular species of host mammal being treated and the parasite involved. Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Thus compositions useful for oral administration may be prepared by mixing the active ingredient with a suitable finely divided diluent and/or disintegrating agent and/or binder, and/or lubricant etc. Other possible ingredients include antioxidants, colourants, flavouring agents, preservatives and taste-masking agents.

For oral dosage forms, depending on dose, the drug may make up from 1 wt % to 80 wt % of the dosage form, more typically from 5 wt % to 60 wt % of the dosage form. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Examples of diluents include lactose (monohydrate, spray-dried monohydrate, anhydrous and the like), mannitol, xylitol, dextrose, sucrose, sorbitol, microcrystalline cellulose, starch and dibasic calcium phosphate dihydrate.

Oral formulations may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Lubricants include magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

The formulation of tablets is discussed in "Pharmaceutical Dosage Forms: Tablets, Vol. 1", by H. Lieberman and L. Lachman, Marcel Dekker, N.Y., 1980 (ISBN 0-8247-6918-X).

The compounds may be administered topically to the skin or mucosa, that is dermally or transdermally. This is a preferred method of administration and as such it is desirable to develop active compounds, which are particularly suited to such formulations. Typical formulations for this purpose include pour-on, spot-on, dip, spray, mousse, shampoo, powder formulation, gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999). Pour-on or spot-on formulations may be prepared by dissolving the active ingredient in an acceptable liquid carrier vehicle such as butyl digol, liquid paraffin or a non-volatile ester, optionally with the addition of a volatile component such as propan-2-ol. Alternatively, pour-on, spot-on or spray formulations can be prepared by encapsulation, to leave a residue of active agent on the surface of the animal, this effect may ensure that the compounds of formula (I) have increased persistence of action and are more durable, for example they may be more waterfast.

Agents may be added to the formulations of the present invention to improve the persistence of such formulations on the surface of the animal to which they are applied, for example to improve their persistence on the coat of the animal. It is particularly preferred to include such agents in a formulation which is to be applied as a pour-on or spot-on formulation. Examples of such agents acrylic copolymers and in particular fluorinated acrylic copolymers. A particular suitable reagent is Foraperle™ (Redline Products Inc, Texas, USA).

Certain topical formulations may include unpalatable additives to minimize accidental oral exposure.

Injectable formulations may be prepared in the form of a sterile solution, which may contain other substances, for example enough salts or glucose to make the solution isotonic with blood. Acceptable liquid carriers include vegetable oils such as sesame oil, glycerides such as triacetin, esters such as benzyl benzoate, isopropyl myristate and fatty acid derivatives of propylene glycol, as well as organic solvents such as pyrrolidin-2-one and glycerol formal. The formulations are prepared by dissolving or suspending the active ingredient in the liquid carrier such that the final formulation contains from 0.01 to 10% by weight of the active ingredient.

Alternatively, the compounds can be administered parenterally, or by injection directly into the blood stream, muscle or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques. Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as powdered a dried form to be used in conjunction with a suitable vehicle such as sterile, pyrogen-free water. The preparation of parenteral formulations under sterile conditions, for example, by lyophilisation, may readily be accomplished using standard pharmaceutical techniques well known to those skilled in the art. The solubility of compounds of formula (I) used in the preparation of parenteral solutions may be increased by the use of appropriate formulation techniques, such as the incorporation of solubility-enhancing agents.

Such formulations are prepared in a conventional manner in accordance with standard medicinal or veterinary practice.

These formulations will vary with regard to the weight of active compound contained therein, depending on the species of host animal to be treated, the severity and type of infection and the body weight of the host. For parenteral, topical and oral administration, typical dose ranges of the active ingredient are 0.01 to 100 mg per kg of body weight of the animal. Preferably the range is 0.1 to 10 mg per kg.

Formulations may be immediate and/or modified controlled release. Controlled release formulations include modified release formulations including delayed-, sustained-, pulsed-, controlled, targeted, or programmed release. Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298. Alternatively, compounds of the invention may be formulated as a solid, semi-solid, or thixotropic liquid for administration as an implanted depot providing modified release of the active compound. Examples of such formulations include drug-coated stents and PGLA microspheres.

As an alternative the compounds may be administered to a non-human animal with the feedstuff and for this purpose a concentrated feed additive or premix may be prepared for mixing with the normal animal feed.

All the aforementioned aqueous dispersions or emulsions or spraying mixtures can be applied, for example, to crops by any suitable means, chiefly by spraying, at rates which are generally of the order of about 100 to about 1,200 liters of spraying mixture per hectare, but may be higher or lower (eg. low or ultra-low volume) depending upon the need or application technique. The compounds or compositions according to the invention are conveniently applied to vegetation and in particular to roots or leaves having pests to be eliminated. Another method of application of the compounds or compositions according to the invention is by chemigation, that is to say, the addition of a formulation containing the active ingredient to irrigation water. This irrigation may be sprinkler irrigation for foliar pesticides or it can be ground irrigation or underground irrigation for soil or for systemic pesticides.

The concentrated suspensions, which can for example be applied by spraying, are prepared so as to produce a stable fluid product which does not settle (fine grinding) and usually contain from about 10 to about 75% by weight of active ingredient, from about 0.5 to about 30% of surface-active agents, from about 0.1 to about 10% of thixotropic agents, from about 0 to about 30% of suitable additives, such as anti-foaming agents, corrosion inhibitors, stabilizers, penetrating agents, adhesives and, as the carrier, water or an organic liquid in which the active ingredient is poorly soluble or insoluble. Some organic solids or inorganic salts may be dissolved in the carrier to help prevent settling or as anti-freezes for water.

The wettable powers (or powder for spraying) are usually prepared so that they contain from about 10 to about 80% by weight of active ingredient, from about 20 to about 90% of a solid carrier, from about 0 to about 5% of a wetting agent, from about 3 to about 10% of a dispersing agent and, when necessary, from about 0 to about 80% of one or more stabilizers and/or other additives, such as penetrating agents, adhesives, anti-caking agents, colorants, or the like. To obtain these wettable powders, the active ingredient(s) is(are) thoroughly mixed in a suitable blender with additional substances which may be impregnated on the porous filler and is(are) ground using a mill or other suitable grinder. This produces wettable powders, the wettability and the suspendability of which are advantageous. They may be suspended in water to give any desired concentration and this suspension can be employed very advantageously in particular for application to plant foliage.

The "water dispersible granules (WG)" (granules which are readily dispersible in water) have compositions which are substantially close to that of the wettable powders. They may be prepared by granulation of formulations described for the wettable powders, either by a wet route (contacting finely divided active ingredient with the inert filler and a little water, e.g. 1 to 20% by weight, or with an aqueous solution of a dispersing agent or binder, followed by drying and screening), or by a dry route (compacting followed by grinding and screening).

Depending on the method of application or the nature of the composition or use thereof, the rates and concentrations of the formulated compositions may vary according. Generally speaking, the compositions for application to control arthropod, plant nematode, helminth or protozoan pests usually contain from about 0.00001% to about 95%, more particularly from about 0.0005% to about 50% by weight of one or more compounds of formula (I), or pesticidally acceptable salts thereof, or of total active ingredients (that is to say the compound of formula (I), or a pesticidally acceptable salt thereof, together with: other substances toxic to arthropods or plant nematodes, anthelmintics, anticoccidials, synergists, trace elements or stabilizers). The actual compositions employed and their rate of application will be selected to achieve the desired effect(s) by the farmer, livestock producer, medical or veterinary practitioner, pest control operator or other person skilled in the art.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Compounds of the invention can also be mixed with one or more biologically active compounds or agents including insecticides, acaricides, anthelmintics, fungicides, nematocides, antiprotozoals, bactericides, growth regulators, entomopathogenic bacteria, viruses or fungi to form a multi-component pesticide giving an even broader spectrum of pharmaceutical, veterinary or agricultural utility. Thus, the present invention also pertains to a composition comprising a biologically effective amount of compounds of the invention and an effective amount of at least one additional biologically active compound or agent and can further comprise one or more of surfactant, a solid diluent or a liquid diluent. Specific further active compounds include those described in International Patent Application No WO0 2005/090313, at pages 39 to 44.

It be may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

The compounds of the invention, i.e. those of formula (I), possess parasiticidal activity in humans, animals, insects and plants. They are particularly useful in the treatment of ectoparasites.

This invention also relates to a compound of formula (I), or a pharmaceutically acceptable salt thereof, or a pharmaceutically acceptable solvate of either entity, or a pharmaceutical composition containing any of the foregoing, for use as a medicament.

A further aspect of this invention relates to the use of a compound of formula (I), or a pharmaceutically acceptable salt thereof, or a pharmaceutically acceptable solvate of either entity, for the manufacture of a medicament for the treatment of a parasitic infestation.

In one embodiment this invention is useful for the manufacture of a medicament for the treatment of a parasitic infestation in humans.

In one embodiment this invention is useful for the manufacture of a medicament for the treatment of a parasitic infestation in animals.

In one embodiment this invention is useful for the manufacture of a medicament for the treatment of a parasitic infestation in insects.

In one embodiment this invention is useful for the manufacture of a medicament for the treatment of a parasitic infestation in plants.

An even further aspect of this invention relates to a method of treating a parasitic infestation in a mammal which comprises treating said mammal with an effective amount of a compound of formula (I), or a pharmaceutically acceptable salt thereof, or a pharmaceutically acceptable solvate of either entity, or a pharmaceutical composition containing any of the foregoing.

A yet further aspect of this invention relates to a method of preventing a parasitic infestation in a mammal which comprises treating said mammal with an effective amount of a compound of formula (I), or a pharmaceutically acceptable salt thereof, or a pharmaceutically acceptable solvate of either entity, or a pharmaceutical composition containing any of the foregoing.

In a still further embodiment this invention also relates to a method of controlling disease transmission in a mammal which comprises treating said mammal with an effective amount of a compound of formula (I), or a pharmaceutically acceptable salt thereof, or a pharmaceutically acceptable solvate of either entity, or a pharmaceutical composition containing any of the foregoing.

According to another aspect of the present invention, there is provided a method for the control of arthropod, plant nematode or helminth pests at a locus which comprises the treatment of the locus (e.g. by application or administration) with an effective amount of a compound of general formula (I), or a pesticidally acceptable salt thereof.

For the avoidance of doubt, references herein to "treatment" as used herein includes references to curative, palliative and prophylactic treatment, references to "control" (of parasites and/or pests etc.) include kill, repel, expel, incapacitate, deter, eliminate, alleviate, minimise, eradicate.

The compounds of the invention have utility in the control of arthropod pests. They may, in particular, be used in the fields of veterinary medicine, livestock husbandry and the maintenance of public health: against arthropods which are parasitic internally or externally upon vertebrates, particularly warm-blooded vertebrates, including man and domestic animals such as dogs, cats, cattle, sheep, goats, equines, swine, poultry and fish for example *Acarina*, including ticks (e.g. *Ixodes* spp., *Boophilus* spp. e.g. *Boophilus microplus, Amblyomma* spp., *Hyalomma* spp., *Rhipicephalus* spp. e.g. *Rhipicephalus appendiculatus, Haemaphysalis* spp., *Dermacentor* spp., *Ornithodorus* spp. (e.g. *Ornithodorus moubata*), mites (e.g. *Damalinia* spp., *Dermanyssus gallinae, Sarcoptes* spp. e.g. *Sarcoptes scabiei, Psoroptes* spp., *Chorioptes* spp., *Demodex* spp., *Eutrombicula* spp.), specific further arthropod pests include those described in International Patent Application No WO 2005/090313; *Diptera* (e.g. *Aedes* spp., *Anopheles* spp., *Muscidae* spp. e.g. *Stomoxys calcitrans* and *Haematobia irritans, Hypoderma* spp., *Gastrophilus* spp., *Simulium* spp.); *Hemiptera* (e.g. *Triatoma* spp.); *Phthiraptera* (e.g. *Damalinia* spp., *Linognathus* spp.); *Siphonaptera* (e.g. *Ctenocephalides* spp.); *Dictyoptera* (e.g. *Periplaneta* spp., *Blatella* spp.) and *Hymenoptera* (e.g. *Monomorium pharaonis*). The compounds of the present invention also have utility in the field of control of plant pests, soil inhabiting pests and other environmental pests.

The present invention is particularly useful in the control of arthropod pests in mammals, in particular humans and animals. Preferably this invention is useful in the control of arthropod pests in animals which includes livestock such as cattle, sheep, goats, equines, swine and companion animals such as dogs and cats.

The compounds of the invention are of particular value in the control of arthropods which are injurious to, or spread or act as vectors of diseases in, man and domestic animals, for example those hereinbefore mentioned, and more especially in the control of ticks, mites, lice, fleas, midges and biting, nuisance and myiasis flies. They are particularly useful in controlling arthropods which are present inside domestic host animals or which feed in or on the skin or suck the blood of the animal, for which purpose they may be administered orally, parenterally, percutaneously or topically.

The compounds of the invention are of value for the treatment and control of the various lifecycle stages of parasites including egg, nymph, larvae, juvenile and adult stages.

According to another aspect of the present invention, there is provided a method for the control of arthropod pests of insects which comprises treatment of the insect with an effective amount of a compound of general formula (I), or a pesticidally acceptable salt thereof. Compounds of the present invention may also be used for the treatment of infections caused by mites, and in particular varoaa mites. In particular compounds of the present invention may also be used for the treatment of varoaa mite infection in bees.

According to another aspect of the present invention, there is provided a method for the control of arthropod pests of plants which comprises treatment of the plant with an effective amount of a compound of general formula (I), or a pesticidally acceptable salt thereof. The compounds of the invention also have utility in the control of arthropod pests of plants. The active compound is generally applied to the locus at which the arthropod infestation is to be controlled at a rate of about 0.005 kg to about 25 kg of active compound per hectare (ha) of locus treated, preferably 0.02 to 2 kg/ha. Under ideal conditions, depending on the pest to be controlled, the lower rate may offer adequate protection. On the other hand, adverse weather conditions and other factors may require that the active ingredient be used in higher proportions. For foliar application, a rate of 0.01 to 1 kg/ha may be used. Preferably, the locus is the plant surface, or the soil around the plant to be treated.

According to another aspect of the present invention, there is provided a method for the protection of timber which comprises treatment of the timber with an effective amount of a compound of general formula (I), or a pesticidally acceptable salt thereof. Compounds of the present invention are also valuable in the protection of timber (standing, felled, converted, stored or structural) from attack by sawflies or beetles or termites. They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack. Solid or liquid compositions for application topically to timber, stored products or household goods usually contain from about 0.00005% to about 90%, more particularly from about 0.001% to about 10%, by weight of one or more compounds of formula (I) or pesticidally acceptable salts thereof.

The liquid compositions of this invention may, in addition to normal agricultural use applications be used for example to treat substrates or sites infested or liable to infestation by arthropods (or other pests controlled by compounds of this invention) including premises, outdoor or indoor storage or processing areas, containers or equipment or standing or running water.

The present invention also relates to a method of cleaning animals in good health comprising the application to the animal of compound of formula (I) or a veterinarily acceptable salt. The purpose of such cleaning is to reduce or eliminate the infestation of humans with parasites carried by the animal and to improve the environment in which humans inhabit.

The biological activity of the compounds was tested using one or more of the test methods outlined below.

In Vitro Tick Assay

Application of octopamine agonists to acarids for example, ticks, causes distinct behavioural changes compared to untreated control ticks. Treated ticks become agitated and move constantly, this prevents ticks attaching and feeding on a host animal to which the compound has been applied. Normal behaviour of ticks is to go into stasis when all other external stimuli are removed. Agitation and movement can be measured in vitro in the laboratory to predict efficacy and potency in vivo.

The assay was run using unfed *Rhipicephalus sanguineus* (brown dog tick) and precoated glass vials with an inner surface area of 34.5 cm$^2$. Each compound was tested in duplicate.

Compound (345 μg) was dissolved in isopropyl alcohol (500 μl) and delivered to each vial. The vials were placed on a tilting roller in a fume hood for 2 hours to allow the isopropyl alcohol to evaporate giving a compound concentration for each vial of 10 μg/cm$^2$. Five *R. sanguineus* (male and female) were added to each coated vial and the vial sealed with a firm wad of cotton wool. Vials were then kept, undisturbed, on the bench at room temperature. Observation and recordings of activity were taken at 24, 48 and 72 hours after addition of ticks to the vials. The $ED_{100}$ value was determined as the lowest dose at which all five ticks were seen moving around inside the vial.

Octopamine Activity

One skilled in the art could determine agonist activity of compounds against insect octopamine receptors expressed in CHO cells by adapting the methods described in B. Maqueira, H. Chatwin, P. D. Evans, J. Neurochemistry, 2005, 94, 2, 547. Compound activity can be measured as an increase in cAMP by various methods known to a skilled person and can be recorded as % Vmax (Vmax=maximal octopamine response) and $EC_{50}$.

Adrenergic Activity

Methods from literature procedures were simply adapted, as could be readily performed by one skilled in the art, in order to determine α2 adrenergic activity of the compounds. Suitable procedures include those described in J J. Meana, F. Barturen, J. A. Garcia-Sevilla, Journal of Neurochemistry, 1989, 1210; and D. J. Loftus, J. M. Stolk, D. C. U'Pritchard, Life Sciences, 1984, 35, 610.

EXAMPLES

The following Examples illustrate the preparation of compounds of the formula (I).

In the following Examples, structures are depicted as follows:

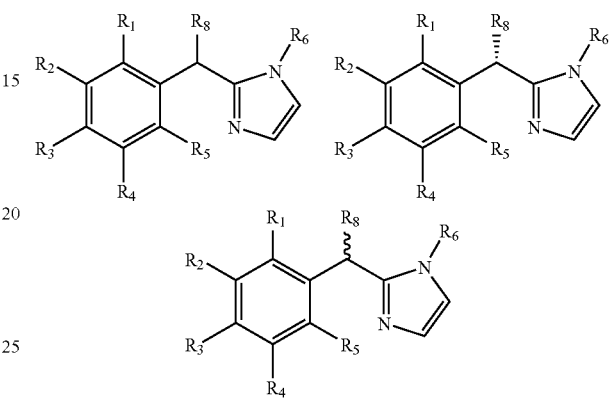

Unless specified otherwise, the wedge and dashed bonds indicate absolute stereochemistry as drawn at this chiral centre, a wiggly bond indicates that the absolute stereochemistry is unknown but the compound is a single stereoisomer at this chiral centre. Straight bonds emanating from a chiral centre indicate that the stereoisomers are not resolved and a mixture of stereoisomers is present.

When the source of a simple precursor is unspecified these compounds may be obtained from commercial suppliers or according to literature procedures. The following is a list of commercial suppliers for such compounds:

Sigma-Aldrich, P O Box 14508, St. Louis, Mo., 63178, USA
Lancaster Synthesis Ltd., Newgate, White Lund, Morecambe, Lancashire, LA3 3BN, UK
Maybridge, Trevillett, Tintagel, Cornwall, PL34 0HW, UK
Fluorochem Ltd., Wesley Street, Old Glossop, Derbyshire, SK13 7RY, UK
ASDI Inc, 601 Interchange Blvd., Newark, Del., 19711, USA
Alfa Aesar, 26 Parkridge Road, Ward Hill, Mass., 01835, USA
Bionet Research Ltd., Highfield Industrial Estate, Camelford, Cornwall, PL32 9QZ, UK
Acros Organics, Janssens Pharmaceuticalaan 3A, Geel, 2440, Belgium
Apin Chemicals Ltd., 3D Milton Park, Abingdon, Oxfordshire, OX14 4RU, UK
Pfaltz & Bauer, Inc., 172 East Aurora Street, Waterbury, Conn. 06708, USA
Trans World Chemicals, Inc., 14674 Southlawn Lane, Rockville, Md. 20850, USA
Peakdale Molecular Ltd., Peakdale Science Park, Sheffield Road, Chapel-en-le-Frith, High Peak, SK23 0PG, UK
TCI America, 9211 N. Harborgate Street, Portland, Oreg. 97203, USA
Fluka Chemie GmbH, Industriestrasse 25, P.O. Box 260, CH-9471 Buchs, Switzerland
JRD Fluorochemicals Ltd., Unit 11, Mole Business Park, Leatherhead, Surrey, KT22 7BA, UK Instruments Used In the following experimental details, nuclear magnetic resonance spectral data were obtained using Varian Inova 300, Varian Inova 400, Varian Mercury 400, Varian Unityplus 400, Bruker AC 300 MHz, Bruker AM 250 MHz or Varian T60 MHz spectrometers, the observed chemical shifts being consistent with the proposed structures. N.m.r chemical shifts are quoted in p.p.m downfield from tetramethylsilane. Mass spectral data were obtained on a Finnigan ThermoQuest Aqa, a Waters micromass ZQ, Bruker APEX II FT-MS or a Hewlett Packard GCMS System Model 5971 spectrometer. The calculated and observed ions quoted refer to the isotopic composition of lowest mass. HPLC means high performance liquid chromatography. Analytical HPLC data was collected on a HP1100 Series HPLC system. Preparative HPLC data was collected using a Gilson Preparative HPCL system.

CHN microanalysis data were collected using Exeter Analytical CE 440 instruments by Warwick Analytical Service, (University of Warwick Science Park, Barclays Venture Centre, Sir William Lyons Road, Coventry, CV4 7EZ).

Optical rotation data was collected using a Perkin Elmer Polarimeter 341 by Warwick analytical Service, (University of Warwick Science Park, Barclays Venture Centre, Sir William Lyons Road, Coventry, CV4 7EZ).

Example 1

2-[1-(2,3-Dimethylphenyl)ethyl]-1H-imidazole

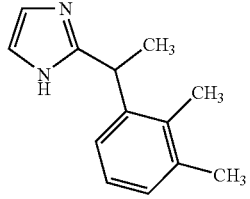

A solution of the compound of Preparation 194 (11.0 g, 38.1 mmol) and palladium(II) hydroxide (1.10 g, 7.83 mmol) in methanol (100 ml) was heated to 60° C. at a pressure of 300 psi under a hydrogen atmosphere for 18 h. The reaction mixture was then filtered and concentrated in vacuo and the residue was re-crystallised from hot acetonitrile (50 ml) to give the title compound (3.27 g).

Experimental MH$^+$ 201.3; expected 201.1 $^1$H-NMR (CD$_3$OD): 1.50-1.55 (3H), 2.15-2.20 (3H), 2.20-2.25 (3H), 4.40-4.50 (1H), 6.80-6.85 (1H), 6.90-6.92 (2H), 6.95-7.00 (2H) Rhip. Funct. ED$_{100}$ mg/cm$^2$=0.1

Alternative Synthesis

A solution of the compound of Preparation 1 (72 mg, 0.36 mmol) in methanol (5 ml) was hydrogenated at 100 psi and 60° C. using palladium (10 wt % on carbon, 10 mg), overnight. The mixture was filtered and the filtrate concentrated in vacuo. The residue was dissolved in methanol (1 ml) and diethylamine (2-3 drops, 1 ml) and purified by automated preparative liquid chromatography (Gilson system, 150 mm×30 mm LUNA C18(2) 10 μm column, 40 ml/min) using an acetonitrile:water gradient [30:70 to 98:2]. The appropriate fractions were concentrated in vacuo to give the title compound (26 mg).

Experimental MH$^+$ 201.2; expected 201.1 $^1$H-NMR (d$_6$-DMSO): 1.65-1.72 (3H), 2.13-2.18 (3H), 2.24-2.31 (3H), 4.43-4.52 (1H), 6.89-6.92 (2H), 7.00-7.03 (1H), 7.03-7.11 (2H)

Alternative Synthesis

To a mixture of the compound of Preparation 1 (1.0 g, 3.26 mmol) and ammonium formate (1.0 g, 15.9 mmol) in formic acid (20 ml) was added palladium (10% wt % on carbon, 1.0 g). The reaction mixture was heated at 100° C. for 72 h, filtered and concentrated in vacuo. The residue was triturated with methanol:ethyl acetate [1:9] to give the title compound (200 mg).

Experimental MH$^+$ 201.3; expected 201.1 $^1$H-NMR (CD$_3$OD): 1.65-1.70 (3H), 2.20-2.25 (3H), 2.25-2.30 (3H), 4.80-4.90 (1H), 6.80-6.85 (1H), 7.00-7.10 (2H), 7.35-7.40 (2H)

Alternative Synthesis

A mixture of the crude compound of Preparation 13 (500 mg, 2.3 mmol) and palladium (10 wt % on carbon, 223 mg) in formic acid (10 ml) was heated at reflux for 36 h. The reaction mixture was filtered and the filtrate was concentrated in vacuo to give the crude title compound Experimental MH$^+$ 201.3; expected 201.1

Example 2

2-{1-[2-Methyl-3-(trifluoromethyl)phenyl]ethyl}-1H-imidazole

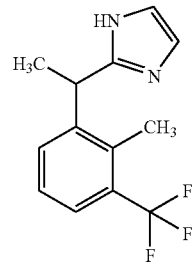

A mixture of the compound of Preparation 148 (2.0 g, 5.8 mmol) and palladium (10 wt % on carbon, 500 mg) in methanol (25 ml) was heated at 60° C. under a hydrogen atmosphere (150 psi) for 24 h. The mixture was filtered through Arbocel® and the filtrate was concentrated in vacuo.

The residue was purified by flash chromatography (silica), eluting with methanol. The appropriate fractions were combined and concentrated to give the title compound (11 mg).

$^1$H-NMR (CD$_3$OD): 1.58-1.62 (3H), 2.40-2.43 (3H), 4.56-4.62 (1H), 6.90-6.94 (2H), 7.21-7.29 (2H), 7.47-7.51 (1H) Experimental MH$^+$ 255.3; expected 255.1 Rhip. Funct. ED$_{100}$ mg/cm$^2$=>1

Example 3

2-[1-(1H-Imidazol-2-yl)ethyl]-6-methylbenzonitrile

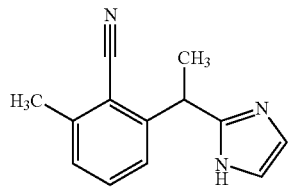

To a solution of the compound of Preparation 167 (50 mg, 0.17 mmol) in 2-propanol (2 ml) was added ammonium formate (105 mg, 1.67 mmol) and palladium (10 wt % on carbon, 36 mg). The reaction mixture was heated at 80° C., under nitrogen, for 2 h and then cooled. The mixture was filtered through Arbocel®, washing through with 2-propanol, and the filtrate was concentrated in vacuo.

The residue was dissolved in acetonitrile:water (9:1, 4 ml) and purified by automated preparative liquid chromatography (Gilson system, 150 mm×30 mm LUNA C18(2) 10 μm column, 40 ml/min) using an acetonitrile:water gradient [30:70 (20 min) to 95:5 (21 min)]. The appropriate fractions were combined and concentrated to give the title compound (8 mg).

Experimental MH$^+$ 212.1; expected 212.1 $^1$H-NMR (d$_6$-Acetone): 1.64-1.66 (3H), 2.50-2.51 (3H), 4.59-4.61 (1H), 6.90-7.05 (2H), 7.19-7.21 (1H), 7.23-7.25 (1H), 7.42-7.45 (1H) Rhip. Funct. ED$_{100}$ mg/cm$^2$=0.3

Similarly Prepared were:

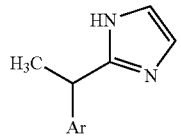

| Ex. No. | Ar | Name | From Prep. | MH$^+$ Found/ Expected | Rhip. Funct. ED$_{100}$ mg/cm$^2$ |
|---|---|---|---|---|---|
| 4 | 3-ethylphenyl | 2-[1-(3-Ethylphenyl)ethyl]-1H-imidazole | 146 | 201.3 201.1 | >1 |
| 5 | 3-cyclopropylphenyl | 2-[1-(3-Cyclopropylphenyl)-ethyl]-1H-imidazole | 138 | 213.2 213.1 | >10 |
| 6 | biphenyl-3-yl | 2-(1-Biphenyl-3-ylethyl)-1H-imidazole | 137 | 249.4 249.1 | <=10 |
| 7 | 2-fluoro-3-methylphenyl | 2-[1-(2-Fluoro-3-methylphenyl)-ethyl]-1H-imidazole | 143 | 205.2 205.1 | 0.1, 0.3, <=0.03 |
| 8 | 4-methyl-3-trifluoromethylphenyl | 2-{1-[2-Methyl-5-(trifluoromethyl)phenyl]-ethyl}-1H-imidazole | 144 | 255.3 255.1 | >1 |
| 9 | 3-ethyl-2-methylphenyl | 2-[1-(3-Ethyl-2-methylphenyl)-ethyl]-1H-imidazole | 176 | 215.4 215.2 | 1 |

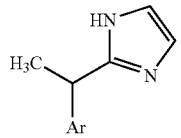

| Ex. No. | Ar | Name | From Prep. | MH+ Found/ Expected | Rhip. Funct. ED$_{100}$ mg/cm$^2$ |
|---|---|---|---|---|---|
| 10 | 3-cyano-5-methylphenyl | 3-[1-(1H-Imidazol-2-yl)ethyl]-5-methylbenzonitrile | 169 | 212.3 / 212.1 | <=10 |
| 11 | 3-cyano-2-methylphenyl | 3-[1-(1H-Imidazol-2-yl)ethyl]-2-methylbenzonitrile | 168 | 212.2 / 212.1 | <=10 |
| 12 | 2-(difluoromethyl)-3-methylphenyl | 2-{1-[2-(Difluoromethyl)-3-methylphenyl]ethyl}-1H-imidazole | 181 | 237.2 / 237.1 | >1 |

Example 4

$^1$H-NMR (CDCl$_3$): 1.14-1.21 (3H), 1.62-1.70 (3H), 2.53-2.62 (2H), 4.15-4.22 (1H), 6.80-6.85 (2H), 6.97-7.02 (2H), 7.02-7.07 (1H), 7.15-7.21 (1H)

Example 5

$^1$H-NMR (d$_6$-DMSO): 0.58-0.62 (2H), 0.83-0.87 (2H), 1.50-1.54 (3H), 1.80-1.84 (1H), 4.03-4.05 (1H), 6.80-6.88 (3H), 6.95-6.98 (3H), 7.10-7.14 (1H)

Example 6

$^1$H-NMR (CD$_3$OD): 1.68-1.74 (3H), 4.25-4.34 (1H), 6.95-6.97 (2H), 7.19-7.21 (1H), 7.27-7.45 (6H), 7.55-7.59 (2H)

Example 7

$^1$H-NMR (d$_6$-DMSO): 1.42-1.50 (3H), 2.15-2.20 (3H), 4.37-4.41 (1H), 6.71-6.75 (1H), 6.89-6.98 (3H), 7.03-7.06 (1H)

Example 8

$^1$H-NMR (CD$_3$OD): 1.61-1.65 (3H), 2.39-2.42 (3H), 4.51-4.58 (1H), 6.94-6.98 (2H), 7.32-7.36 (2H), 7.37-7.41 (1H)

Example 9

$^1$H-NMR (d$_6$-Acetone): 1.11-1.19 (3H), 1.55-1.59 (3H), 2.26-2.28 (3H), 2.60-2.68 (2H), 4.45-4.52 (1H), 6.89-6.93 (2H), 6.97-7.01 (3H)

Example 10

$^1$H-NMR (CDCl$_3$): 1.65-1.71 (3H), 2.35-2.38 (3H), 4.19-4.24 (1H), 6.98-7.00 (2H), 7.28-7.34 (3H)

Example 11

$^1$H-NMR (d$_6$-Acetone): 1.60-1.63 (3H), 2.58-2.59 (3H), 4.55-4.50 (1H), 6.90-6.95 (2H), 7.29-7.33 (1H), 7.50-7.60 (2H)

Example 12

$^1$H-NMR (CDCl$_3$): 1.70-1.75 (3H), 2.32-2.34 (3H), 4.54-4.60 (1H), 6.91-6.93 (2H), 7.21-7.25 (3H)

Example 13

1-Benzyl-2-{1-[3-(difluoromethyl)phenyl]ethyl}-1H-imidazole

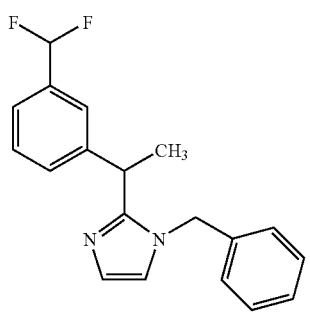

To a solution of the compound of Preparation 142 (100 mg, 0.32 mmol) in 2-propanol (4 ml) was added ammonium formate (406 mg, 6.44 mmol) and palladium (10 wt % on carbon, 137 mg). The reaction mixture was heated at 80° C., under nitrogen, for 18 h and then cooled. The mixture was filtered through Arbocel®, washing through with 2-propanol, and the filtrate was concentrated in vacuo.

The residue was dissolved in acetonitrile:water (9:1, 4 ml) and purified by automated preparative liquid chromatography (Gilson system, 100 mm×30 mm LUNA C18(2) 5 μm column, 40 ml/min) using an acetonitrile:water gradient [40:60 (20 min) to 95:5 (25 min)]. The appropriate fractions were combined and concentrated to give the title compound (8 mg).

Experimental $MH^+$ 313.4; expected 313.2 $^1$H-NMR ($d_6$-Acetone): 1.58-1.61 (3H), 4.25-4.31 (1H), 4.99-5.03 (1H), 5.10-5.14 (1H), 6.80-6.82 (1H), 6.94-6.98 (3H), 7.00-7.02 (1H), 7.20-7.25 (3H), 7.38-7.41 (4H) Rhip. Funct. $ED_{100}$ mg/cm$^2$=>1

Similarly Prepared Was:

mate (1.0 g, 20 mmol) and palladium (10 wt % on carbon, 300 mg). The reaction mixture was heated at 80° C., under nitrogen, for 72 h and then cooled. The mixture was filtered through Arbocel®, washing through with 2-propanol, and the filtrate was concentrated in vacuo.

The residue was dissolved in acetonitrile (2 ml) and diethylamine (2-3 drops) and purified by automated preparative liquid chromatography (Gilson system, 150 mm×50 mm LUNA C18(2) AX 5 μm column, 40 ml/min) using an acetonitrile:water gradient [40:60 (15 min) to 95:5 (15.5 min)]. The appropriate fractions were combined and concentrated to give the title compound (74 mg).

Experimental $MH^+$ 229.3; expected 229.2 $^1$H-NMR ($d_6$-Acetone): 0.95-1.00 (3H), 1.51-1.60 (5H), 2.13-2.15 (3H), 2.58-2.61 (2H), 4.47-4.52 (1H), 6.85-6.90 (2H), 6.96-7.00 (3H) Rhip. Funct. $ED_{100}$ mg/cm$^2$<=10

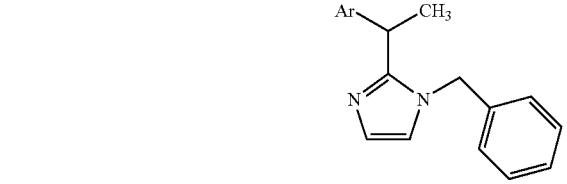

| Ex. No. | Ar | Name | From Prep. | MH+ Found/ Expected | Rhip. Funct. $ED_{100}$ mg/cm$^2$ |
|---|---|---|---|---|---|
| 14 | 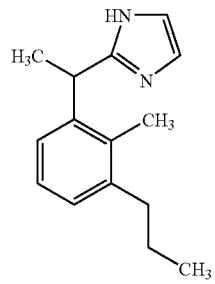 | 1-Benzyl-2-{1-[2-(difluoromethyl)-3-methylphenyl]ethyl}-1H-imidazole | 181 | 327.2 327.2 | >1 |

Example 14

$^1$H-NMR (CD$_3$OD): 1.59-1.62 (3H), 2.30-2.31 (3H), 4.54-4.59 (1H), 6.80-6.83 (3H), 6.88-6.90 (1H), 7.00-7.02 (2H), 7.15-7.17 (1H), 7.18-7.20 (2H), 7.26-7.27 (1H)

Example 15

2-[1-(2-Methyl-3-propylphenyl)ethyl]-1H-imidazole

To a solution of the compound of Preparation 136 (720 mg, 2.3 mmol) in 2-propanol (20 ml) was added ammonium for-

Example 16

2-{1-[2-(Trifluoromethyl)phenyl]ethyl}-1H-imidazole

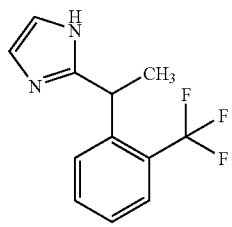

A mixture of the compound of Preparation 51 (212 mg, 0.88 mmol) and palladium (10 wt % on carbon, 500 mg) in methanol (10 ml) was heated at 60° C. under a hydrogen atmosphere (150 psi) for 60 h. The mixture was filtered through Arbocel® and the filtrate was concentrated in vacuo.

The residue was dissolved in methanol (2 ml) diethylamine (2-3 drops) and purified by automated preparative liquid chromatography (Gilson system, 150 mm×50 mm LUNA C18(2) 10 μm column, 40 ml min) using an acetonitrile:water gradient [35:65 to 95:5]. The appropriate fractions were concentrated in vacuo to give the title compound (58 mg).

Experimental $MH^+$ 241.3; expected 241.1 $^1$H-NMR (CD$_3$OD): 1.60-1.66 (3H), 4.53-4.61 (1H), 6.88-6.95 (2H), 7.31-7.39 (2H), 7.48-7.53 (1H), 7.62-7.68 (1H) Rhip. Funct. $ED_{100}$ mg/cm$^2$=3

Similarly Prepared were:

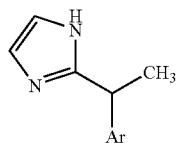

| Ex. No. | Ar | Name | From Prep. | MH+ Found/ Expected | Rhip. Funct. ED100 mg/cm² |
|---|---|---|---|---|---|
| 17 | 2,4-dimethylphenyl | 2-[1-(2,5-Dimethyl-phenyl)ethyl]-1H-imidazole | 49 | 201.4 / 201.1 | >10 |
| 18 | 2,6-dimethylphenyl | 2-[1-(2,6-Dimethyl-phenyl)ethyl]-1H-imidazole | 66 | 201.3 / 201.1 | >1 |
| 19 | 3,5-dimethylphenyl | 2-[1-(3,5-Dimethyl-phenyl)ethyl]-1H-imidazole | 50 | 201.4 / 201.1 | 0.3, 1 |
| 20 | 3-methylphenyl | 2-[1-(3-Methylphenyl)-ethyl]-1H-imidazole | 48 | 187.3 / 187.1 | 0.1 |
| 21 | phenyl | 2-(1-Phenylethyl)-1H-imidazole | 57 | 173.2 / 173.1 | 1 |
| 22 | 4-methylphenyl | 2-[1-(4-Methylphenyl)-ethyl]-1H-imidazole | 58 | 187.3 / 187.1 | >1 |
| 23 | 2,4,6-trimethylphenyl | 2-(1-Mesitylethyl)-1H-imidazole | 59 | 215.4 / 215.2 | >1 |
| 24 | 3-(trifluoromethyl)phenyl | 2-{1-[3-(Trifluoro-methyl)-phenyl]ethyl}-1H-imidazole | 60 | 241.3 / 241.1 | >1 |

-continued

| Ex. No. | Ar | Name | From Prep. | MH+ Found/ Expected | Rhip. Funct. ED₁₀₀ mg/cm² |
|---|---|---|---|---|---|
| 25 | 4-(trifluoromethyl)phenyl | 2-{1-[4-(Trifluoromethyl)phenyl]ethyl}-1H-imidazole | 61 | 241.3 / 241.1 | >1 |
| 26 | 3-methoxy-2-methylphenyl | 2-[1-(3-Methoxy-2-methylphenyl)ethyl]-1H-imidazole | 62 | 217.3 / 217.1 | >1 |
| 27 | 2-ethyl-3-methylphenyl | 2-[1-(2-Ethyl-3-methylphenyl)ethyl]-1H-imidazole | 63 | 215.3 / 215.2 | <=10 |
| 28 | 3-(trifluoromethoxy)phenyl | 2-{1-[3-(Trifluoromethoxy)phenyl]ethyl}-1H-imidazole | 65 | 257.1 / 257.1 | <=10 |
| 29 | 2,6-difluoro-3-methylphenyl | 2-[1-(2,6-Difluoro-3-methylphenyl)ethyl]-1H-imidazole | 73 | 223.2 / 223.1 | >1 |
| 30 | 3,5-difluorophenyl | 2-[1-(3,5-Difluorophenyl)ethyl]-1H-imidazole | 10 | 209.2 / 209.1 | >1 |
| 31 | 2-fluoro-3-(trifluoromethyl)phenyl | 2-{1-[2-Fluoro-3-(trifluoromethyl)phenyl]ethyl}-1H-imidazole | 12 | 259.1 / 259.1 | >1 |

Example 17

$^1$H-NMR (d$_6$-Acetone): 1.60-1.70 (3H), 2.08-2.15 (3H), 2.21-2.30 (3H), 4.40-4.50 (1H), 6.81-6.92 (2H), 6.93-6.99 (1H), 7.00-7.08 (2H)

Example 18

$^1$H-NMR (CDCl$_3$): 1.68-1.72 (3H), 2.04-2.12 (6H), 4.49-4.55 (1H), 6.86-6.91 (2H), 6.95-6.98 (2H), 7.00-7.05 (1H)

Example 19

$^1$H-NMR (CD$_3$OD): 1.55-1.60 (3H), 2.19-2.21 (6H), 4.05-4.15 (1H), 6.75-7.80 (3H), 6.85-6.90 (2H)

Example 20

$^1$H-NMR (CDCl$_3$): 1.67-1.71 (3H), 2.28-2.30 (3H), 4.12-4.18 (1H), 6.90-6.93 (2H), 7.00-7.06 (2H), 7.17-7.23 (2H)

Example 21

$^1$H-NMR (CDCl$_3$): 1.67-1.72 (3H), 4.14-4.21 (1H), 6.89-6.94 (2H), 7.18-7.25 (3H), 7.26-7.33 (2H)

Example 22

$^1$H-NMR (CDCl$_3$): 1.67-1.70 (3H), 2.29-2.31 (3H), 4.12-4.18 (1H), 6.89-6.92 (2H), 7.10-7.12 (4H)

Example 23

$^1$H-NMR (CD$_3$OD): 1.55-1.65 (3H), 2.00-2.10 (3H), 2.14-2.17 (3H), 2.18-2.20 (3H), 4.40-4.50 (1H), 6.80-6.90 (1H), 6.90-6.95 (3H)

Example 24

$^1$H-NMR (CDCl$_3$): 1.69-1.73 (3H), 4.23-4.30 (1H), 6.92-6.97 (2H), 7.31-7.35 (2H), 7.52-7.56 (2H)

Example 25

$^1$H-NMR (CDCl$_3$): 1.69-1.74 (3H), 4.22-4.30 (1H), 6.92-6.97 (2H), 7.31-7.35 (2H), 7.52-7.56 (2H)

Example 26

$^1$H-NMR (CDCl$_3$): 1.64-1.68 (3H), 2.09-2.13 (3H), 3.77-3.81 (3H), 4.38-4.45 (1H), 6.72-6.77 (2H), 6.87-6.89 (2H), 7.09-7.15 (1H)

Example 27

$^1$H-NMR (CD$_3$OD): 1.03-1.09 (3H), 1.58-1.63 (3H), 2.29-2.31 (3H), 2.65-2.75 (2H), 4.42-4.48 (1H), 6.82-6.85 (2H), 6.92-7.00 (3H)

Example 28

$^1$H-NMR (CD$_3$OD): 1.60-1.65 (3H), 4.20-4.26 (1H), 6.90-6.93 (2H), 7.03-7.06 (2H), 7.18-7.20 (1H), 7.33-7.37 (1H)

Example 29

$^1$H-NMR (CDCl$_3$): 1.68-1.72 (3H), 2.17-2.20 (3H), 4.60-4.65 (1H), 6.70-6.75 (1H), 6.90-6.93 (2H), 6.95-7.00 (1H)

Example 32

2-[1-(2,3,5-Trimethylphenyl)ethyl]-1H-imidazole

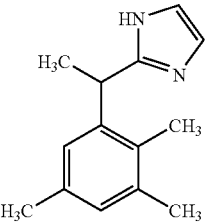

A mixture of the compound of Preparation 64 (150 mg, 0.52 mmol) and palladium (10 wt % on carbon, 15 mg) in 2-propanol (5 ml) was heated at 60° C. under a hydrogen atmosphere (200 psi) for 18 h. The mixture was filtered through Arbocel® and the filtrate was concentrated in vacuo.

The residue was dissolved in acetonitrile (1.22 ml) and diethylamine (2-3 drops) and purified by automated preparative liquid chromatography (Gilson system, 150 mm×50 mm LUNA C18(2) 5 µm column, 40 ml/min) using an acetonitrile:water gradient [32:68 (20 min) to 95:5 (21 min)]. The appropriate fractions were combined and concentrated to give the title compound (30 mg).

Experimental MH$^+$ 215.4; expected 215.2 $^1$H-NMR (CD$_3$OD): 1.57-1.60 (3H), 2.15-2.19 (6H), 2.20-2.22 (3H), 4.35-4.39 (1H), 6.80-6.82 (1H), 6.87-6.90 (3H) Rhip. Funct. ED$_{100}$ mg/cm$^2$=>1

Example 33

2-[1-(2,3-Dimethylphenyl)propyl]-1H-imidazole

A mixture of the compound of Preparation 47 (255 mg, 1.2 mmol) and palladium (10 wt % on carbon, 50 mg) in 2-propanol (50 ml) was heated at 40° C. under a hydrogen atmosphere (200 psi) for 18 h. The mixture was filtered through Arbocel® and the filtrate was concentrated in vacuo. The residue was re-crystallised from warm diethyl ether (5 ml) and the solid was triturated with further diethyl ether (5 ml) to give the title compound (175 mg).

Experimental MH$^+$ 215.3; expected 215.2 $^1$H-NMR (CDCl$_3$): 0.87-0.95 (3H), 1.90-2.03 (1H), 2.11-2.16 (3H), 2.23-2.27 (3H), 2.28-2.38 (1H), 4.19-4.25 (1H), 6.85-6.90 (2H), 7.01-7.07 (3H) Rhip. Funct. ED$_{100}$ mg/cm$^2$=1

Example 34

2-[1-(2-Chloro-3-methylphenyl)ethyl]-1H-imidazole

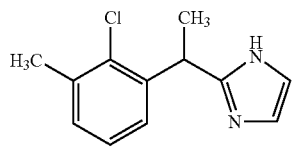

A mixture of the compound of Preparation 67 (1.51 g, 6.8 mmol) and palladium hydroxide (20 wt % Pd on carbon, 500 mg) in 2-propanol (100 ml) was heated at 50° C. under a hydrogen atmosphere (200 psi) for 18 h. The mixture was filtered through Arbocel® and the filtrate was concentrated in vacuo.

The residue was dissolved in acetonitrile (1 ml) and diethylamine (2-3 drops) and purified by automated preparative liquid chromatography (Gilson system, 100 mm×30 mm LUNA C18(2) 10 μm column, 40 ml/min) using an acetonitrile:water gradient [35:65 (15 min) to 95:5 (15.5 min)]. The appropriate fractions were combined and concentrated to give the title compound (21 mg).

Experimental MH$^+$ 221.3; expected 221.1 $^1$H-NMR (d$_6$-DMSO): 1.49-1.53 (3H), 2.34-2.37 (3H), 4.58-4.62 (1H), 6.79-6.81 (1H), 6.95-7.00 (2H), 7.10-7.13 (1H), 7.18-7.20 (1H) Rhip. Funct. ED$_{100}$ mg/cm$^2$=0.1

Similarly Prepared were:

| Ex. No. | Ar | Name | From Prep. | MH$^+$ Found/ Expected | Rhip. Funct. ED$_{100}$ mg/cm$^2$ |
|---|---|---|---|---|---|
| 35 | 2,4-dichlorophenyl | 2-[1-(2,4-Dichlorophenyl)ethyl]-1H-imidazole | 56 | 241.2 / 241.0 | >1 |
| 36 | 4-chloro-3-methylphenyl | 2-[1-(4-Chloro-3-methylphenyl)ethyl]-1H-imidazole | 74 | 221.3 / 221.1 | >10 |
| 37 | 2,3-dichlorophenyl | 2-[1-(2,3-Dichlorophenyl)ethyl]-1H-imidazole | 52 | 241.2 / 241.0 | >1 |
| 38 | 3,4-dichlorophenyl | 2-[1-(3,4-Dichlorophenyl)ethyl]-1H-imidazole | 53 | 241.2 / 241.0 | 3 |
| 39 | 3-chlorophenyl | 2-[1-(3-Chlorophenyl)ethyl]-1H-imidazole | 54 | 201.3 / 201.3 | >1 |

-continued

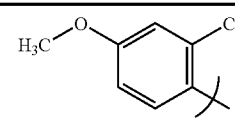

| Ex. No. | Ar | Name | From Prep. | MH+ Found/ Expected | Rhip. Funct. ED$_{100}$ mg/cm$^2$ |
|---|---|---|---|---|---|
| 40 | 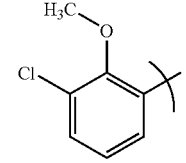 | 2-[1-(2-chloro-4-Methoxyphenyl)ethyl]-1H-imidazole | 75 | 237.3 237.1 | >1 |
| 41 | 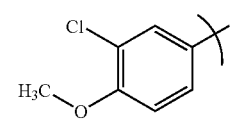 | 2-[1-(3-Chloro-2-methoxyphenyl)ethyl]-1H-imidazole | 77 | 237.3 237.1 | >1 |
| 42 | 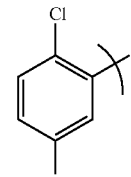 | 2-[1-(3-Chloro-4-methoxyphenyl)ethyl]-1H-imidazole | 76 | 237.3 237.1 | >1 |
| 43 | 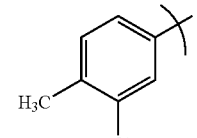 | 2-[1-(2,5-Dichloro-phenyl)ethyl]-1H-imidazole | 55 | 241.2 241.0 | >1 |
| 44 | 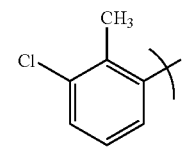 | 2-[1-(3-Chloro-4-methyl-phenyl)ethyl]-1H-imidazole | 68 | 221.3 221.1 | >1 |
| 45 | 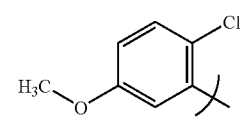 | 2-[1-(3-Chloro-2-methyl-phenyl)ethyl]-1H-imidazole | 69 | 221.3 221.1 | >1 |
| 46 | 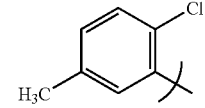 | 2-[1-(2-Chloro-5-methoxyphenyl)ethyl]-1H-imidazole | 70 | 237.2 237.1 | <=10 |
| 47 | | 2-[1-(2-Chloro-5-methyl-phenyl)ethyl]-1H-imidazole | 71 | 221.3 221.1 | — |

Example 36

¹H-NMR (CD₃OD): 1.53-1.62 (3H), 2.20-2.28 (3H), 4.10-4.20 (1H), 6.83-6.92 (2H), 6.92-6.99 (1H), 7.06-7.11 (1H), 7.14-7.21 (1H)

Example 38

¹H-NMR (CD₃OD): 1.60-1.65 (3H), 4.20-4.30 (1H), 6.90-7.00 (2H), 7.10-7.15 (1H), 7.36-7.40 (1H), 7.40-7.44 (1H)

Example 39

¹H-NMR (CD₃OD): 1.60-1.63 (3H), 4.20-4.24 (1H), 6.95-6.97 (2H), 7.14-7.16 (1H), 7.19-7.27 (3H)

Example 40

¹H-NMR (d₆-Acetone): 1.55-1.65 (3H), 3.75-3.81 (3H), 5.18-5.25 (1H), 6.80-6.85 (1H), 6.95-6.98 (1H), 7.10-7.20 (2H), 7.35-7.40 (1H)

Example 43

¹H-NMR (CD₃OD): 1.58-1.61 (3H), 4.60-4.64 (1H), 6.95-6.97 (2H), 7.07-7.08 (1H), 7.18-7.20 (1H), 7.37-7.39 (1H)

Example 44

¹H-NMR (CD₃OD): 1.58-1.61 (3H), 2.24-2.26 (3H), 4.15-4.20 (1H), 6.89-6.91 (2H), 7.00-7.02 (1H), 7.17-7.19 (2H)

Example 46

¹H-NMR (CD₃OD): 1.57-1.60 (3H), 3.62-3.63 (3H), 4.60-4.65 (1H), 6.60-6.61 (1H), 6.72-6.75 (1H), 6.91-6.93 (2H), 7.21-7.24 (1H)

Example 48

2-[1-(2,3-Difluorophenyl)ethyl]-1H-imidazole

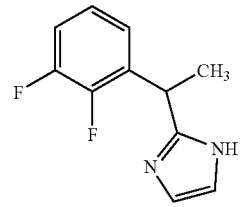

To a solution of the compound of Preparation 2 (320 mg, 1.55 mmol) in 2-propanol (20 ml) was added ammonium formate (1.47 g, 23.3 mmol) and palladium (10 wt % on carbon, 495 mg). The reaction mixture was heated at 80° C. for 18 h and then cooled. The mixture was filtered through Arbocel®, washing through with 2-propanol (10 ml), and the filtrate was concentrated in vacuo.

The residue was dissolved in acetonitrile (2 ml) and purified by automated preparative liquid chromatography (Gilson system, 150 mm×50 mm LUNA C18(2) 10 µm column, 40 ml/min) using an acetonitrile:water gradient [30:70 (20 min) to 95:5 (21 min)]. The appropriate fractions were combined and concentrated to give the title compound (10 mg).

Experimental MH⁺ 209.4; expected 209.1 ¹H-NMR (CD₃OD): 1.62-1.65 (3H), 4.54-4.61 (1H), 6.90-6.96 (2H), 7.02-7.25 (3H) Rhip. Funct. ED₁₀₀ mg/cm²=3

Similarly Prepared were:

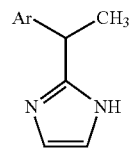

| Ex. No. | Ar | Name | From Prep. | MH⁺ Found/ Expected | Rhip. Funct. ED₁₀₀ mg/cm² |
|---|---|---|---|---|---|
| 49 | 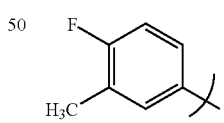 | 2-[1-(5-Methoxy-2,4-dimethylphenyl)ethyl]-1H-imidazole | 11 | 231.2 231.1 | <=10 |
| 50 | | 2-[1-(4-Fluoro-3-methyl-phenyl)ethyl]-1H-imidazole | 4 | 205.2 205.1 | >1 |

-continued

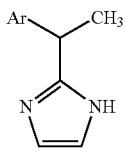

| Ex. No. | Ar | Name | From Prep. | MH+ Found/ Expected | Rhip. Funct. ED$_{100}$ mg/cm$^2$ |
|---|---|---|---|---|---|
| 51 | 2,6-difluorophenyl | 2-[1-(2,6-Difluorophenyl)ethyl]-1H-imidazole | 5 | 209.2 / 209.1 | >1 |
| 52 | 3-fluoro-2-methylphenyl | 2-[1-(3-Fluoro-2-methylphenyl)ethyl]-1H-imidazole | 6 | 205.3 / 205.1 | >1 |
| 53 | 3-fluorophenyl | 2-[1-(3-Fluorophenyl)ethyl]-1H-imidazole | 7 | 191.3 / 191.1 | >1 |
| 54 | 2-chloro-3-(trifluoromethyl)phenyl | 2-{1-[2-Chloro-3-(trifluoromethyl)phenyl]ethyl}-1H-imidazole | 8 | 275.1 / 275.1 | >1 |
| 55 | 3-fluoro-5-methylphenyl | 2-[1-(3-Fluoro-5-methylphenyl)ethyl]-1H-imidazole | 9 | 205.3 / 205.1 | 0.3 |
| 56 | 3-methyl-2-(trifluoromethyl)phenyl | 2-{1-[3-Methyl-2-(trifluoromethyl)phenyl]ethyl}-1H-imidazole | 72 | 255.3 / 255.1 | >1 |

Example 49

$^1$H-NMR (d$_6$-DMSO): 1.45-1.49 (3H), 2.00-2.02 (3H), 2.19-2.21 (3H), 3.60-3.61 (3H), 4.23-4.27 (1H), 6.70-6.72 (1H), 6.77-6.79 (1H), 6.83-6.85 (1H), 6.92-6.95 (1H)

Example 50

$^1$H-NMR (CDCl$_3$): 1.62-1.67 (3H), 2.15-2.20 (3H), 4.19-4.24 (1H), 6.82-6.87 (3H), 6.97-7.01 (2H)

Example 51

$^1$H-NMR (CDCl$_3$): 1.75-1.80 (3H), 4.68-4.73 (1H), 6.82-6.87 (2H), 6.94-6.96 (2H), 7.17-7.21 (1H)

Example 52

$^1$H-NMR (CDCl$_3$): 1.63-1.66 (3H), 2.18-2.20 (3H), 4.39-4.44 (1H), 6.90-7.00 (4H), 7.10-7.15 (1H)

Example 53

$^1$H-NMR (CDCl$_3$): 1.70-1.74 (3H), 4.18-4.23 (1H), 6.90-7.00 (4H), 7.00-7.02 (1H), 7.17-7.20 (1H)

Example 54

$^1$H-NMR (CDCl$_3$): 1.69-1.74 (3H), 4.79-4.85 (1H), 6.94-6.98 (2H), 7.26-7.31 (1H), 7.41-7.44 (1H), 7.55-7.58 (1H)

Example 55

$^1$H-NMR (d$_6$-Acetone): 1.60-1.64 (3H), 2.25-2.27 (3H), 4.19-4.24 (1H), 6.75-6.82 (2H), 6.85-6.98 (3H)

Example 56

$^1$H-NMR (CD$_3$OD): 1.60-1.64 (3H), 2.50-2.54 (3H), 4.63-4.67 (1H), 6.90-6.93 (2H), 7.07-7.10 (1H), 7.18-7.20 (1H), 7.30-7.34 (1H)

Example 57

2-[1-(2-Fluoro-5-methylphenyl)ethyl]-1H-imidazole

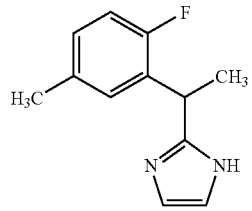

A mixture of the compound of Preparation 3 (74 mg, 0.31 mmol), palladium (10 wt % on carbon, 140 mg) and ammonium formate (394 mg, 6.4 mmol) in 2-propanol (20 ml) was heated at 80° C. for 24 h. The mixture was filtered through Arbocel® and the filtrate was concentrated in vacuo.

The residue was dissolved in acetonitrile:methanol (1 ml) and purified by automated preparative liquid chromatography (Gilson system, 150 mm×30 mm LUNA C18(2) 10 μm column, 40 ml/min) using an acetonitrile:water gradient [50:50 (20 min) to 98:2 (20.5 min)]. The appropriate fractions were combined and concentrated to give the title compound (49 mg).

Experimental MH$^+$ 205.1; expected 205.1 $^1$H-NMR (d$_6$-Acetone): 1.60-1.63 (3H), 2.20-2.22 (3H), 4.43-4.47 (1H), 6.84-6.86 (1H), 6.90-7.00 (2H), 7.00-7.07 (2H) Rhip. Funct. ED$_{100}$ mg/cm$^2$=>1

Example 58

2-[(1S)-1-(2,3-Dimethylphenyl)ethyl]-1H-imidazole

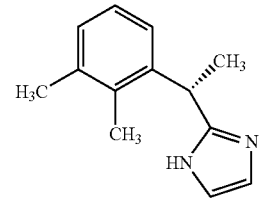

The compound of Example 1 (750 mg, 3.75 mmol) was dissolved in ethanol (4 ml) and the enantiomers were separated by automated preparative liquid chromatography (Gilson system, 50×50 mm ID Chiralcel OD, 20 μm column, 50 ml/min) using ethanol:hexane [10:90] as the mobile phase. The appropriate fractions were combined and concentrated to give the title compound (370 mg).

Retention time=5.79 min Chiralcel OD-H, 250×4.6 mm ID, 5 μm column, ethanol:hexane [10:90], 1 ml/min Experimental MH$^+$ 201.3; expected 201.1 $^1$H-NMR (CD$_3$OD): 1.56-1.60 (3H), 2.18-2.20 (3H), 2.22-2.24 (3H), 4.45-4.50 (1H), 6.80-6.86 (3H), 6.95-6.99 (2H) Optical rotation, (25° C., methanol, 5.035 mg/ml, path length 100 mm): 365 nm=+266.93, 546 nm=+88.43, 589 nm=+73.58 Rhip. Funct. ED$_{100}$ mg/cm$^2$=0.1

Alternative Synthesis

To a solution of the compound of Preparation 1 (600 g, 3 mol) in methanol (6.0 l) was added bis(norbornadiene) rhodium (I) tetrafluoroborate (1.50 g) and S(+)-1-[(R)-2-diphenyl phosphinoferrocenyl]ethylditert.butylphosphine (2.61 g) and the reaction mixture was heated at 25° C., under a hydrogen atmosphere (45-60 psi), for 10 h. The reaction was monitored by HPLC, (upon completion:starting material <0.1%, optical purity 93-94%). To the mixture was added charcoal (60 g) and the solution was stirred for 30 min. The mixture was filtered through Hyflo Super Cel®, washing through with methanol (2×300 ml). To the filtrate was added di-p-toluoyl-L-tartaric acid (1.2 kg, 3.08 mol). The reaction mixture was stirred at room temperature for 1 h and the solid material formed was collected by filtration. To the solid salt was added dichloromethane (6.0 l) and aqueous sodium hydroxide solution (1N, 6.0 l) and the reaction mixture was stirred for 30 min. The organic layer was separated and was washed with aqueous sodium hydroxide solution (1N, 2×3.0 L). The organic layer was extracted with hydrochloric acid (1N, 3×2.0 L). The combined acidic aqueous layer was adjusted to pH 10 by addition of aqueous sodium hydroxide solution (1N) and the resulting precipitate was collected by filtration and dried in vacuo, at 50° C., to give the title compound (optical purity 98.58%). The process of di-p-toluoyl-L-tartaric acid salt formation and generation of free base was repeated once more to give the title compound (0.359 kg, optical purity 99.66%) after second resolution.

Example 59

2-[(1R)-1-(2,3-Dimethylphenyl)ethyl]-1H-imidazole

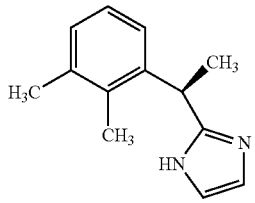

The compound of Example 1 (750 mg, 3.75 mmol) was dissolved in ethanol (4 ml) and the enantiomers were separated by automated preparative liquid chromatography (Gilson system, 50×50 mm ID Chiralcel OD, 20 μm column, 50 ml/min) using ethanol:hexane [10:90] as the mobile phase. The appropriate fractions were combined and concentrated to give the title compound (370 mg).

Retention time=7.84 min Chiralcel OD-H, 250×4.6 mm ID, 5 μm column, ethanol:hexane [10:90], 1 ml/min Experimental $MH^+$ 201.3; expected 201.1 $^1$H-NMR ($CD_3OD$): 1.56-1.60 (3H), 2.18-2.20 (3H), 2.22-2.24 (3H), 4.43-4.48 (1H), 6.80-6.86 (3H), 6.95-6.99 (2H) Optical rotation, (25° C., methanol, 5.24 mg/ml, path length 100 mm): 365 nm=−262.79, 546 nm=−86.26, 589 nm=−72.23 Rhip. Funct. $ED_{100}$ $mg/cm^2$=>10

Example 60

2-[(1R*)-1-(3-Methylphenyl)ethyl]-1H-imidazole

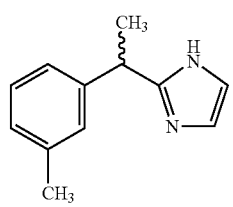

The compound of Example 20 (40 mg, 0.22 mmol) was dissolved in ethanol (1 ml) and the enantiomers were separated by automated preparative liquid chromatography (Gilson system, 250×20 mm ID Chiralpak AD-H, 5 μm column, 15 ml/min) using ethanol:hexane [5:95] as the mobile phase. The appropriate fractions were combined and concentrated to give the title compound (16 mg).

Retention time=7.93 min Chiralpak AD-H, 250×4.6 mm ID, 5 μm column, ethanol:hexane [10:90], 1 ml/min Experimental $MH^+$ 187.2; expected 187.1 $^1$H-NMR ($CD_3OD$): 1.58-1.62 (3H), 2.23-2.27 (3H), 4.12-4.18 (1H), 6.87-6.89 (2H), 6.94-7.01 (3H), 7.09-7.14 (1H) Rhip. Funct. $ED_{100}$ $mg/cm^2$=0.3

Example 61

2-[(1R*)-1-(3-Methylphenyl)ethyl]-1H-imidazole

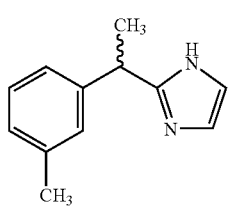

The compound of Example 20 (40 mg, 0.22 mmol) was dissolved in ethanol (1 ml) and the enantiomers were separated by automated preparative liquid chromatography (Gilson system, 250×20 mm ID Chiralpak AD-H, 5 μm column, 15 ml/min) using ethanol:hexane [5:95] as the mobile phase. The appropriate fractions were combined and concentrated to give the title compound (15 mg).

Retention time=6.06 min Chiralpak AD-H, 250×4.6 mm ID, 5 μm column, ethanol:hexane [10:90], 1 ml/min Experimental $MH^+$ 187.2; expected 187.1 $^1$H-NMR ($CD_3OD$): 1.58-1.62 (3H), 2.23-2.27 (3H), 4.12-4.18 (1H), 6.87-6.90 (2H), 6.94-7.00 (3H), 7.09-7.14 (1H) Rhip. Funct. $ED_{100}$ $mg/cm^2$=0.1

Example 62

1-Benzyl-2-[(1R*)-1-(2,3-dimethylphenyl)ethyl]-1H-imidazole

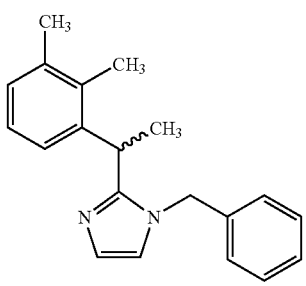

The compound of Example 76 (540 mg, 1.8 mmol) was dissolved in ethanol (2 ml) and hexane (2 ml) and the enantiomers were separated by automated preparative liquid chromatography (Gilson system, 50×50 mm ID Chiralcel OD, 20 μm column, 40 ml/min) using ethanol:hexane [5:95] as the mobile phase. The appropriate fractions were combined and concentrated to give the title compound (240 mg).

Retention time=5.82 min Chiralcel OD-H, 250×4.6 mm ID, 5 μm column, ethanol:hexane [10:90], 1 ml/min Experimental $MH^+$ 291.3; expected 291.1 $^1$H-NMR ($d_6$-Acetone): 1.50-1.53 (3H), 2.19-2.26 (6H), 4.31-4.36 (1H), 4.68-4.72 (1H), 4.90-4.94 (1H), 6.70-6.72 (1H), 6.90-7.00 (6H), 7.20-7.25 (3H) Rhip. Funct. $ED_{100}$ $mg/cm^2$=0.3

Example 63

1-Benzyl-2-[1-(1R*)-(2,3-dimethylphenyl)ethyl]-1H-imidazole

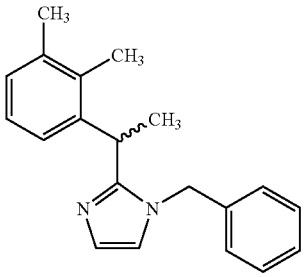

The compound of Example 76 (540 mg, 1.8 mmol) was dissolved in ethanol (2 ml) and hexane (2 ml) and the enantiomers were separated by automated preparative liquid chromatography (Gilson system, 50×50 mm ID Chiralcel OD, 20 μm column, 40 ml/min) using ethanol:hexane [5:95] as the mobile phase. The appropriate fractions were combined and concentrated to give the title compound (260 mg).

Retention time=8.80 min Chiralcel OD-H, 250×4.6 mm ID, 5 μm column, ethanol:hexane [10:90], 1 ml/min Experimental MH$^+$ 291.3; expected 291.1 Rhip. Funct. ED$_{100}$ mg/cm$^2$=>3

Example 64

2-[(1R*)-1-(2-Fluoro-3-methylphenyl)ethyl]-1H-imidazole

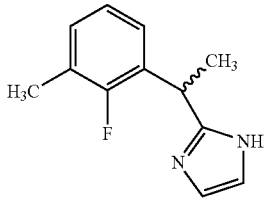

The compound of Example 7 (18 mg, 0.09 mmol) was dissolved in ethanol:hexane (1:1, 2 ml) and the enantiomers were separated by automated preparative liquid chromatography (Gilson system, 250×20 mm ID Chiralcel OD-H, 5 μm column, 15 ml/min) using ethanol:hexane [5:95] as the mobile phase. The appropriate fractions were combined and concentrated to give the title compound (6 mg). Retention time=6.15 min Chiralcel OD-H, 250×4.6 mm ID, 5 μm column, ethanol:hexane [10:90], 1 ml/min Rhip. Funct. ED$_{100}$ mg/cm$^2$=0.3

Example 65

2-[(1R*)-1-(2-Fluoro-3-methylphenyl)ethyl]-1H-imidazole

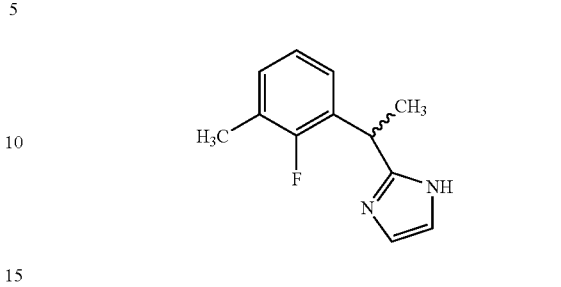

The compound of Example 7 (18 mg, 0.09 mmol) was dissolved in ethanol:hexane (1:1, 2 ml) and the enantiomers were separated by automated preparative liquid chromatography (Gilson system, 250×20 mm ID Chiralcel OD-H, 5 μm column, 15 ml/min) using ethanol:hexane [5:95] as the mobile phase. The appropriate fractions were combined and concentrated to give the title compound (7 mg).

Retention time=6.90 min Chiralcel OD-H, 250×4.6 mm ID 5 μm column, ethanol:hexane [10:90], 1 ml/min Rhip. Funct. ED$_{100}$ mg/cm$^2$=1

Example 66

{2-[(1R*)1-(2,3-Dimethylphenyl)ethyl]-1H-imidazol-1-yl}methyl pivalate

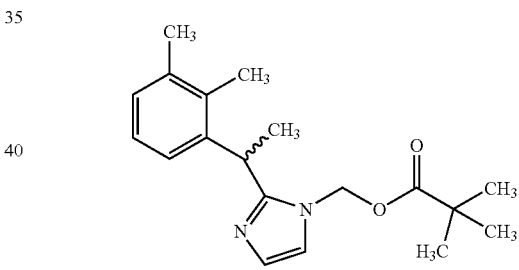

To a suspension of the compound of Example 1 (120 mg, 0.6 mmol) and potassium carbonate (246 mg, 1.8 mmol) in dimethylformamide (4 ml) was added chloromethyl pivalate (215 μl, 1.5 mmol) and the reaction mixture stirred at room temperature overnight. Water (10 ml) was added and the mixture then extracted with ethyl acetate (2×10 ml). The organic layers were combined, washed with water (10 ml) and brine (10 ml), dried (MgSO$_4$) and concentrated in vacuo.

The residue was dissolved in acetonitrile (2 ml) and purified by automated preparative liquid chromatography (Gilson system, 150 mm×21.2 mm LUNA C18(2) 5 μm column) using an acetonitrile:water gradient [50:50 to 95:5]. The appropriate fractions were concentrated in vacuo to give the title compound (136 mg).

Experimental MH$^+$ 315.4; expected 315.2 $^1$H-NMR (CD$_3$OD): 0.96-0.99 (9H), 1.58-1.61 (3H), 2.28-2.30 (3H), 2.35-2.38 (3H), 4.62-4.72 (1H), 5.53-5.66 (2H), 6.60-6.64 (1H), 6.90-7.00 (3H), 7.18-7.19 (1H) Rhip. Funct. ED$_{100}$ mg/cm$^2$=0.03

Example 67

{2-[1-(2,3-Dimethylphenyl)ethyl]-1H-imidazol-1-yl}methyl propionate

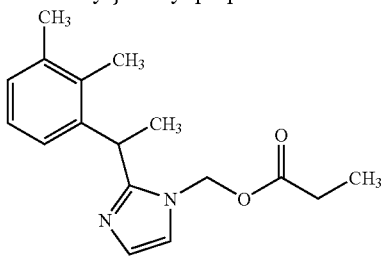

To a suspension of the compound of Example 1 (120 mg, 0.6 mmol) and caesium carbonate (731 mg, 1.8 mmol) in acetone (4 ml), under nitrogen, was added chloromethyl propionate (Eur. J. Pharm. Sci: 24; 5; 2005; 433-440, 183 mg, 1.5 mmol) and the reaction mixture was stirred at room temperature for 18 h. The mixture was filtered and the filtrate was concentrated in vacuo.

The residue was dissolved in acetonitrile (1.5 ml) and purified by automated preparative liquid chromatography (Gilson system, 150 mm×21.2 mm LUNA C18(2) 5 mm column) using an acetonitrile:water gradient [50:50 to 95:5]. The appropriate fractions were concentrated to give the title compound (137 mg).

Experimental $MH^+$ 287.4; expected 287.2 $^1$H-NMR ($CD_3OD$): 0.84-0.11 (3H), 1.53-1.59 (3H), 1.82-2.02 (2H), 2.22-2.30 (3H), 2.31-2.38 (3H), 4.60-4.68 (1H), 5.41-5.48 (1H), 5.64-5.69 (1H), 6.50-6.56 (1H), 6.83-6.99 (3H), 7.13-7.16 (1H) Rhip. Funct. $ED_{100}$ mg/cm$^2$=0.01

Similarly Prepared from Example 1 were:

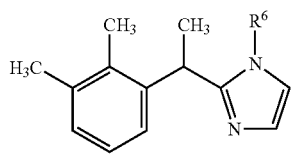

| Ex. No. | R$^6$ | Precursor | From | MH$^+$ Found/Expected | Rhip. Funct. $ED_{100}$ mg/cm$^2$ |
|---|---|---|---|---|---|
| 68 | 2-butanoate) | Chloromethyl 3-methyl-butanoate | Ref. 1 | 315.5 / 315.2 | 0.03 |
| 69 | | Chloromethyl heptanoate | Prep. 117 | 343.5 / 343.2 | 0.03 |
| 70 | | Chloromethyl butyrate | — | 301.5 / 301.2 | 0.01 |
| 71 | | Chloromethyl 3-cyclopentylpropanoate | Prep. 116 | 355.6 / 355.3 | <=0.03 |
| 72 | | Chloromethyl pentanoate | Ref. 2 | 315.4 / 315.2 | 0.03 |
| 73 | | Chloromethyl 3,3-dimethylbutanoate | Prep. 118 | 329.4 / 329.2 | 0.01 |
| 74 | | Chloromethyl 2-methyl-propanoate | Ref. 3 | 301.6 / 301.3 | <0.03 / <=0.1 |

Ref. 1: Acta Chem. Scand. Ser. B; EN; 36; 7; 1982; 467-474.
Ref. 2: J. Am. Chem. Soc.; 43; 1921; 665
Ref. 3: EP-79782, Example 6

Example 68

{2-[1-(2,3-Dimethylphenyl)ethyl]-1H-imidazol-1-yl}methyl 3-methyl butanoate $^1$H-NMR (CD$_3$OD): 0.75-0.80 (6H), 1.54-1.58 (3H), 1.70-1.80 (1H), 1.80-1.84 (2H), 2.23-2.30 (3H), 2.31-2.34 (3H), 4.60-4.68 (1H), 5.48-5.55 (1H), 5.61-5.68 (1H), 6.51-6.58 (1H), 6.83-6.95 (2H), 6.95-6.99 (1H), 7.12-7.18 (1H)

Example 69

{2-[1-(2,3-Dimethylphenyl)ethyl]-1H-imidazol-1-yl}methyl heptanoate $^1$H-NMR (CD$_3$OD): 0.82-0.89 (3H), 1.08-1.3 (6H), 1.3-1.4 (2H), 1.52-1.59 (3H), 1.88-1.98 (2H), 2.24-2.30 (3H), 2.30-2.35 (3H), 4.60-4.69 (1H), 5.42-5.51 (1H), 5.62-5.71 (1H), 6.50-6.56 (1H), 6.86-6.99 (3H), 7.12-7.16 (1H)

Example 70

{2-[1-(2,3-Dimethylphenyl)ethyl]-1H-imidazol-1-yl}methyl butyrate $^1$H-NMR (CD$_3$OD): 0.78-0.83 (3H), 1.35-1.47 (2H), 1.55-1.61 (3H), 1.90-1.98 (2H), 2.28-2.32 (3H), 2.33-2.37 (3H), 2.32-2.36 (2H), 4.61-4.69 (1H), 5.46-5.52 (1H), 5.66-5.72 (1H), 6.52-6.58 (1H), 6.88-7.00 (3H), 7.15-7.17 (1H)

Example 73

{2-[1-(2,3-Dimethylphenyl)ethyl]-1H-imidazol-1-yl}methyl 3,3-dimethylbutanoate $^1$H-NMR (d$_6$-Acetone): 0.89-0.92 (9H), 1.58-1.60 (3H), 1.96-1.97 (2H), 2.29-2.31 (3H), 2.38-2.40 (3H), 4.60-4.64 (1H), 5.50-5.54 (1H), 5.70-5.74 (1H), 6.67-6.69 (1H), 6.90-6.96 (2H), 6.99-7.01 (1H), 7.12-7.14 (1H)

Example 74

{2-[1-(2,3-Dimethylphenyl)ethyl]-1H-imidazol-1-yl}methyl 2-methyl propanoate $^1$H-NMR (d$_6$-Acetone): 0.91-0.94 (6H), 1.58-1.60 (3H), 2.20-2.24 (1H), 2.24-2.26 (3H), 2.36-2.38 (3H), 4.60-4.64 (1H), 5.66-5.70 (1H), 5.68-5.70 (1H), 6.90-6.95 (2H), 6.98-7.00 (1H), 7.12-7.14 (1H)

Similarly Prepared from Example 58 was:

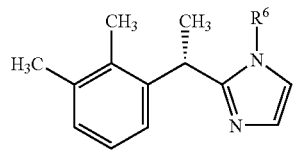

| Ex. No. | R$^6$ | Precursor | From | MH$^+$ Found/ Expected | Rhip. Funct. ED$_{100}$ mg/cm$^2$ |
|---|---|---|---|---|---|
| 75 | (structure) | Chloromethyl propionate | Ref. 4 | 287.2 287.2 | <=0.03, <=0.01, 0.3 |

Ref. 4: J. Am. Chem. Soc.; 43; 1921; 660

4.61-4.70 (1H), 5.48-5.55 (1H), 5.64-5.72 (1H), 6.53-6.59 (1H), 6.90-6.96 (2H), 6.97-7.01 (1H), 7.16-7.20 (1H)

Example 71

{2-[1-(2,3-Dimethylphenyl)ethyl]-1H-imidazol-1-yl}methyl 3-cyclopentylpropanoate $^1$H-NMR (CD$_3$OD): 0.92-1.06 (2H), 1.35-1.45 (2H), 1.47-1.55 (2H), 1.56-1.63 (6H), 1.63-1.73 (2H), 1.91-2.00 (2H), 2.28-2.33 (3H), 2.33-2.38 (3H), 4.62-4.71 (1H), 5.48-5.55 (1H), 5.68-5.73 (1H), 6.52-6.59 (1H), 6.88-7.01 (3H), 7.18-7.19 (1H)

Example 72

{2-[1-(2,3-Dimethylphenyl)ethyl]-1H-imidazol-1-yl}methyl pentanoate $^1$H-NMR (CD$_3$OD): 0.82-0.86 (3H), 1.13-1.24 (2H), 1.31-1.40 (2H), 1.56-1.61 (3H), 1.87-2.00 (2H), 2.26-2.31 (3H),

Example 75

{2-[1-(2,3-Dimethylphenyl)ethyl]-1H-imidazol-1-yl}methyl propionate $^1$H-NMR (d$_6$-Acetone): 0.89-0.95 (3H), 1.57-1.60 (3H), 2.03-2.06 (2H), 2.27-2.29 (3H), 2.32-2.35 (3H), 4.60-4.65 (1H), 5.44-5.50 (1H), 5.71-5.76 (1H), 6.62-6.64 (1H), 6.90-7.00 (3H), 7.14-7.16 (1H)

Example 76

1-Benzyl-2-[1-(2,3-dimethylphenyl)ethyl]-1H-imidazole

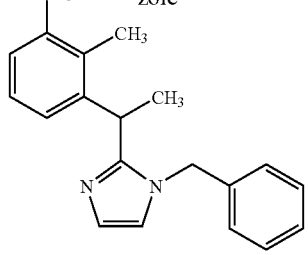

To a suspension of the compound of Example 1 (100 mg, 0.50 mmol) and caesium carbonate (407 mg, 1.25 mmol) in acetone (4 ml) was added benzyl bromide (171 mg, 1.00 mmol). The reaction mixture was stirred at room temperature, under nitrogen, for 18 h and then concentrated in vacuo. The residue was partitioned between water (10 ml) and ethyl acetate (10 ml) and the two layers were separated. The aqueous layer was extracted with ethyl acetate (10 ml) and the combined organic phases were dried (MgSO$_4$) and concentrated in vacuo.

The residue was dissolved in methanol:water (9:1, 2 ml) and purified by automated preparative liquid chromatography (Gilson system, 150 mm×30 mm LUNA C18(2) 10 μm column, 40 ml/min) using an acetonitrile:water gradient [60:40 to 95:5]. The appropriate fractions were concentrated in vacuo to give the title compound (100 mg).

Experimental MH$^+$ 291.0; expected 291.2 $^1$H-NMR (d$_6$-Acetone): 1.45-1.55 (3H), 2.15-2.20 (3H), 2.20-2.24 (3H), 4.26-4.35 (1H), 4.65-4.70 (1H), 4.85-4.93 (1H), 6.66-6.70 (1H), 6.82-7.00 (6H), 7.17-7.28 (3H) Rhip. Funct. ED$_{100}$ mg/cm$^2$=0.01

Similarly Prepared from Example 1 were:

Example 79

1-[4-({2-[(1S)-1-(2,3-Dimethylphenyl)ethyl]-1H-imidazol-1-yl}methyl)phenyl]-1H-1,2,4-triazole

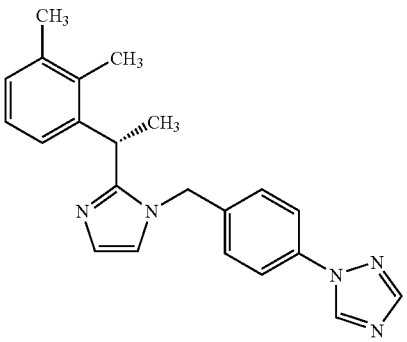

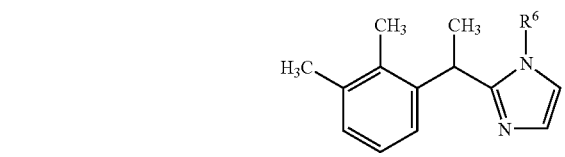

| Ex. No. | R$^6$ | Precursor (all commercially available) | MH$^+$ Found/ Expected | Rhip. Funct. ED$_{100}$ mg/cm$^2$ |
|---|---|---|---|---|
| 77 | (CH$_2$-3-methoxyphenyl group) | 1-(Bromomethyl)-3-methoxybenzene | 321.4 / 321.2 | >1 |
| 78 | (CH(CH$_3$)phenyl group) | (1-Bromoethyl)benzene | 305.4 / 305.2 | >1 |

Example 77

2-[1-(2,3-Dimethylphenyl)ethyl]-1-(3-methoxybenzyl)-1H-imidazole $^1$H-NMR (d$_6$-Acetone): 1.50-1.56 (3H), 2.19-2.28 (6H), 3.66-3.72 (3H), 4.30-4.39 (1H), 4.66-4.71 (1H), 4.86-4.94 (1H), 6.40-6.44 (1H), 6.48-6.52 (1H), 6.71-6.80 (2H), 6.90-6.99 (3H), 7.00-7.02 (1H), 7.14-7.20 (1H)

Example 78

2-[1-(2,3-Dimethylphenyl)ethyl]-1-(1-phenylethyl)-1H-imidazole $^1$H-NMR (d$_6$-Acetone): 1.72-1.79 (3H), 1.80-1.90 (3H), 2.23-2.31 (6H), 5.05-5.11 (1H), 5.48-5.58 (1H), 6.64-6.70 (1H), 6.70-6.80 (2H), 6.88-6.95 (1H), 6.95-7.00 (1H), 7.04-7.20 (4H), 7.66-7.70 (1H)

To a mixture of the compound of Example 58 (90 mg, 0.45 mmol) and caesium carbonate (244 mg, 0.75 mmol) in 1-methyl-2-pyrrolidinone (1 ml) was added 1-[4-(bromomethyl)phenyl]-1H-1,2,4-triazole (83 μl, 0.5 mmol). The reaction mixture was stirred at room temperature for 18 h and then concentrated in vacuo. The residue was dissolved in 1-methyl-2-pyrrolidinone (0.8 ml) and purified by automated preparative liquid chromatography (Gilson system, 150 mm×22.4 mm LUNA C18(2) 5 μm column, 20 ml/min) using an acetonitrile:water gradient [15:85 (3 min) to 98:2 (11 min)]. The appropriate fractions were combined and concentrated to give the title compound (57 mg)

Experimental MH$^+$ 358.5; expected 358.2 $^1$H-NMR (CDCl$_3$): 1.61-1.66 (3H), 2.13-2.21 (6H), 4.20-4.26 (1H), 4.60-4.80 (2H), 6.63-6.66 (1H), 6.80-6.82 (1H), 6.87-6.98 (4H), 7.11-7.13 (1H), 7.47-7.51 (2H), 8.04-8.06 (1H), 8.43-8.45 (1H) Rhip. Funct. ED$_{100}$ mg/cm$^2$<=10.

Example 80

1-[3-(Benzyloxy)benzyl]-2-[(1S)-1-(2,3-dimethylphenyl)ethyl]-1H-imidazole

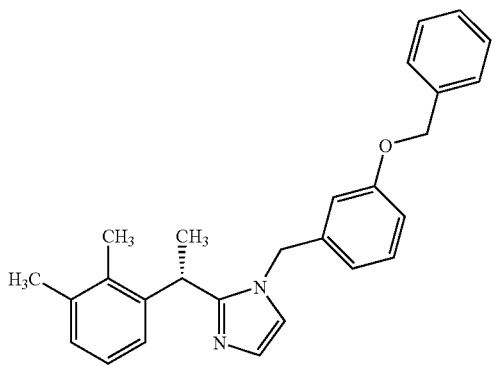

To a mixture of the compound of Example 58 (90 mg, 0.45 mmol) and caesium carbonate (244 mg, 0.75 mmol) in 1-methyl-2-pyrrolidinone (1 ml) was added 1-(benzyloxy)-3-(bromomethyl)benzene (139 mg, 0.50 mmol). The reaction mixture was stirred at room temperature for 48 h and then filtered through a Whatman PTFE filter tube (5 μm).

The filtrate was purified by automated preparative liquid chromatography (Gilson system, 150 mm×22.4 mm LUNA C18(2) 5 μm column, 20 ml/min) using an acetonitrile:water gradient [50:50 (15 min) to 98:2 (20 min)]. The appropriate fractions were combined and concentrated to give the title compound (31 mg).

Experimental MH$^+$ 397.5; expected 397.2 $^1$H-NMR (d$_6$-Acetone): 1.50-1.54 (3H), 2.19-2.25 (6H), 4.33-4.38 (1H), 4.65-4.70 (1H), 4.90-4.95 (1H), 4.98-5.00 (2H), 6.46-6.51 (2H), 6.74-6.76 (1H), 6.84-6.98 (4H), 7.00-7.01 (1H), 7.15-7.20 (1H), 7.31-7.42 (5H) Rhip. Funct. ED$_{100}$ mg/cm$^2$<=10

Similarly Prepared from Example 58 were:

| Ex. No. | R$^6$ | Precursor | MH$^+$ Found/ Expected | Rhip. Funct. ED$_{100}$ mg/cm$^2$ |
|---|---|---|---|---|
| 81 | 4-(methylsulfonyl)benzyl | 1-(Bromomethyl)-4-(methylsulfonyl)benzene | 369.4 / 369.1 | 1 |
| 82 | 4-benzoylbenzyl | [4-(Bromomethyl)phenyl](phenyl)methanone | 395.4 / 395.2 | <=10 |
| 83 | 4-(methoxycarbonyl)benzyl | Methyl 4-(bromomethyl)benzoate | 349.4 / 349.2 | <=10 |
| 84 | pyridin-4-ylmethyl | 4-(Bromomethyl)pyridine | 292.4 / 292.2 | <=10 |
| 85 | 3-cyanobenzyl | 3-(Bromomethyl)benzonitrile | 316.4 / 316.2 | >0.01 |

-continued
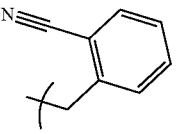
| Ex. No. | R⁶ | Precursor | MH⁺ Found/ Expected | Rhip. Funct. ED$_{100}$ mg/cm² |
|---|---|---|---|---|
| 86 | 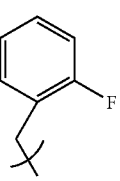 | 2-(Bromomethyl)benzonitrile | 316.4 316.2 | >0.01 |
| 87 | 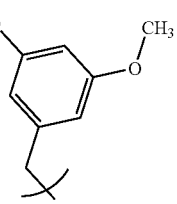 | 3-(Bromomethyl)-4-fluoro-benzonitrile | 334.4 334.2 | >0.01 |
| 88 | 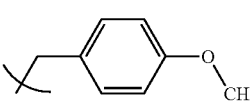 | 1-(Bromomethyl)-3,5-dimethoxy-benzene | 351.5 351.2 | >0.01 |
| 89 | 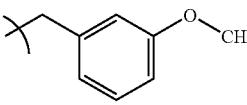 | 1-(Bromomethyl)-4-methoxy-benzene | 321.4 321.2 | >0.01 |
| 90 |  | 1-(Bromomethyl)-3-methoxy-benzene | 321.4 321.2 | >0.01 |
| 91 | 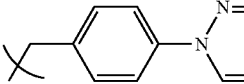 | Methyl 4-(bromomethyl)-3-methoxybenzoate | 379.5 379.2 | >0.01 |
| 92 | 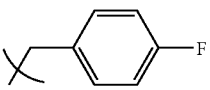 | 1-[4-(Bromomethyl)phenyl]-1H-pyrazole | 357.5 357.2 | >0.01 |
| 93 | | 1-(Bromomethyl)-4-fluoro-benzene | 309.4 309.2 | <=10 |
| 94 | 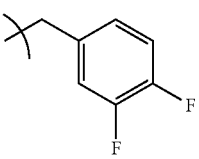 | 4-(Bromomethyl)-1,2-difluoro-benzene | 327.2 327.2 | >0.01 |

-continued

| Ex. No. | R⁶ | Precursor | MH⁺ Found/ Expected | Rhip. Funct. ED$_{100}$ mg/cm² |
|---|---|---|---|---|
| 95 | 2-fluorobenzyl | 1-(Bromomethyl)-2-fluoro-benzene | 309.3 / 309.2 | >0.01 |
| 96 | 3-(difluoromethoxy)benzyl | 1-(Bromomethyl)-3-(difluoromethoxy)benzene | 357.2 / 357.2 | <=10 |
| 97 | 2,3-difluorobenzyl | 1-(Bromomethyl)-2,3-difluoro-benzene | 327.2 / 327.2 | >0.01 |
| 98 | 3-fluorobenzyl | 1-(Bromomethyl)-3-fluoro-benzene | 309.3 / 309.2 | >0.01 |
| 99 | 2,4-difluorobenzyl | 1-(Bromomethyl)-2,4-difluoro-benzene | 327.4 / 327.2 | >0.01 |
| 100 | 3,5-difluorobenzyl | 1-(Bromomethyl)-3,5-difluoro-benzene | 327.4 / 327.2 | >0.01 |
| 101 | 2,6-difluorobenzyl | 2-(Bromomethyl)-1,3-difluoro-benzene | 327.4 / 327.2 | >0.01 |
| 102 | 2-chloro-4-fluoro-6-methylbenzyl | 1-(Bromomethyl)-2-chloro-4-fluorobenzene | 343.4 / 343.1 | >0.01 |

-continued

| Ex. No. | R⁶ | Precursor | MH⁺ Found/Expected | Rhip. Funct. ED₁₀₀ mg/cm² |
|---|---|---|---|---|
| 103 | 2,5-difluorobenzyl | 2-(Bromomethyl)-1,4-difluoro-benzene | 327.4 / 327.2 | >0.01 |
| 104 | 4-chloro-2-fluorobenzyl | 1-(Bromomethyl)-4-chloro-2-fluorobenzene | 343.4 / 343.1 | >0.01 |
| 105 | 2,3,4-trifluorobenzyl | 2-(Bromomethyl)-1,3,4-trifluoro-benzene | 345.4 / 345.2 | >0.01 |
| 106 | 2,4,5-trifluorobenzyl | 1-(Bromomethyl)-2,4,5-trifluoro-benzene | 345.5 / 345.2 | >0.01 |
| 107 | 4-methylbenzyl | 1-(Bromomethyl)-4-methyl-benzene | 305.5 / 305.2 | <=10 |
| 108 | 2,4,6-trifluorobenzyl | 2-(Bromomethyl)-1,3,5-trifluoro-benzene | 345.4 / 345.2 | >0.01 |
| 109 | 2-methylbenzyl | 1-(Bromomethyl)-2-methyl-benzene | 305.4 / 305.2 | <=10 |

-continued

| Ex. No. | R⁶ | Precursor | MH⁺ Found/ Expected | Rhip. Funct. ED₁₀₀ mg/cm² |
|---|---|---|---|---|
| 110 | 2-CF₃, 4-F benzyl | 1-(Bromomethyl)-4-fluoro-2-(trifluoromethyl)benzene | 377.5 / 377.2 | >0.01, >0.03 |
| 111 | 2-F, 3-CH₃ benzyl | 1-(Bromomethyl)-2-fluoro-3-methylbenzene | 323.2 / 323.2 | >0.01, >0.03 |
| 112 | 3-CF₃ benzyl | 1-(Bromomethyl)-3-(trifluoromethyl)benzene | 359.2 / 359.2 | <=10 |
| 113 | 4-Cl benzyl | 1-(Bromomethyl)-4-chlorobenzene | 325.1 / 325.1 | <=10 |
| 114 | 4-CF₃ benzyl | 1-(Bromomethyl)-4-(trifluoromethyl)benzene | 359.2 / 359.2 | <=10 |
| 115 | 3-Cl benzyl | 1-(Bromomethyl)-3-chlorobenzene | 325.1 / 325.1 | >0.01 |
| 116 | 2-CF₃ benzyl | 1-(Bromomethyl)-2-(trifluoromethyl)benzene | 359.2 / 359.2 | >0.01 |
| 117 | 3-F, 4-CF₃ benzyl | 4-(Bromomethyl)-2-fluoro-1-(trifluoromethyl)benzene | 377.2 / 377.2 | <=10 |

-continued

| Ex. No. | R⁶ | Precursor | MH⁺ Found/ Expected | Rhip. Funct. ED$_{100}$ mg/cm² |
|---|---|---|---|---|
| 118 | 2-fluoro-4-(trifluoromethyl)benzyl | 2-(Bromomethyl)-4-fluoro-1-(trifluoromethyl)benzene | 377.2 / 377.2 | <=10 |
| 119 | 3-chloro-2-fluorobenzyl | 1-(Bromomethyl)-3-chloro-2-fluorobenzene | 343.2 / 343.1 | <=10 |
| 120 | 3,5-dimethylbenzyl | 1-(Bromomethyl)-3,5-dimethyl-benzene | 319.4 / 319.2 | <=10 |
| 121 | 2-ethylbenzyl | 1-(Bromomethyl)-2-ethyl-benzene | No mass ion | <=10 |
| 122 | 2-(trifluoromethoxy)benzyl | 1-(Bromomethyl)-2-(trifluoromethoxy)benzene | 375.4 / 375.2 | <=10 |
| 123 | 3-(trifluoromethoxy)benzyl | 1-(Bromomethyl)-3-(trifluoromethoxy)benzene | 375.4 / 375.2 | >0.1 |
| 124 | 2'-cyanobiphenyl-4-ylmethyl | 4'-(Bromomethyl)biphenyl-2-carbonitrile | 392.5 / 392.2 | >0.1 |
| 125 | 4-iodobenzyl | 1-(Bromomethyl)-4-iodobenzene | 417.3 / 417.1 | >0.1 |

-continued

| Ex. No. | R⁶ | Precursor | MH⁺ Found/ Expected | Rhip. Funct. ED$_{100}$ mg/cm² |
|---|---|---|---|---|
| 126 | 4-[(trifluoromethyl)thio]phenylmethyl | 1-(Bromomethyl)-4-[(trifluoromethyl)thio]benzene | 391.4 / 391.1 | <=10 |
| 127 | 3-(4-fluorophenoxy)phenylmethyl | 1-(Bromomethyl)-3-(4-fluorophenoxy)benzene | 401.4 / 401.2 | >0.1 |
| 128 | 4-tert-butylphenylmethyl | 1-(Bromomethyl)-4-tert-butylbenzene | 347.5 / 347.2 | <=10 |
| 129 | 2,5-dichlorophenylmethyl | 2-(Bromomethyl)-1,4-dichlorobenzene | 359.4 / 359.1 | <=10 |
| 130 | 2-chloro-5-(trifluoromethyl)phenylmethyl | 2-(Bromomethyl)-1-chloro-4-(trifluoromethyl)benzene | 393.4 / 393.1 | 1 |
| 131 | 5-chloro-2-methylphenylmethyl | 2-(Bromomethyl)-4-chloro-1-methylbenzene | 339.4 / 339.2 | 1 |
| 132 | 2-naphthylmethyl | 2-(Bromomethyl)naphthalene | 341.4 / 341.2 | <=10 |
| 133 | 3,4-dichlorophenylmethyl | 4-(Bromomethyl)-1,2-dichlorobenzene | 359.4 / 359.1 | <=10 |
| 134 | 2,6-dichlorophenylmethyl | 2-(Bromomethyl)-1,3-dichlorobenzene | 359.4 / 359.1 | >0.1 |

-continued

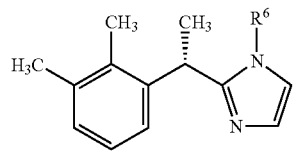

| Ex. No. | R⁶ | Precursor | MH⁺ Found/ Expected | Rhip. Funct. $ED_{100}$ mg/cm² |
|---|---|---|---|---|
| 135 | (4-biphenylmethyl) | 4-(Bromomethyl)biphenyl | 367.4 367.2 | >0.1 |

Example 81

2-[(1S)-1-(2,3-Dimethylphenyl)ethyl]-1-[4-(methylsulfonyl)benzyl]-1H-imidazole $^1$H-NMR (CDCl$_3$): 1.60-1.64 (3H), 2.09-2.11 (3H), 2.18-2.20 (3H), 2.97-3.00 (3H), 4.19-4.23 (1H), 4.70-4.76 (1H), 4.79-4.85 (1H), 6.61-6.65 (1H), 6.80-6.81 (1H), 6.84-6.95 (4H), 7.14-7.17 (1H), 7.72-7.78 (2H)

Example 82

[4-({2-[(1S)-1-(2,3-Dimethylphenyl)ethyl]-1H-imidazol-1-yl}methyl)phenyl](phenyl)methanone $^1$H-NMR (CDCl$_3$): 1.64-1.70 (3H), 2.17-2.19 (3H), 2.22-2.24 (3H), 4.23-4.29 (1H), 4.70-4.77 (1H), 4.80-4.86 (1H), 6.80-6.84 (1H), 6.85-6.92 (3H), 6.94-7.00 (2H), 7.18-7.20 (1H), 7.45-7.52 (2H), 7.59-7.62 (1H), 7.68-7.72 (2H), 7.75-7.79 (2H)

Example 83

Methyl 4-({2-[(1S)-1-(2,3-dimethylphenyl)ethyl]-1H-imidazol-1-yl}methyl)benzoate $^1$H-NMR (d$_6$-Acetone): 1.53-1.61 (3H), 2.15-2.22 (6H), 3.83-3.85 (3H), 4.28-4.35 (1H), 4.80-4.86 (1H), 5.02-5.10 (1H), 6.70-6.74 (1H), 6.86-6.98 (5H), 7.05-7.07 (1H), 7.80-7.84 (2H)

Example 84

4-({2-[(1S)-1-(2,3-Dimethylphenyl)ethyl]-1H-imidazol-1-yl}methyl)pyridine $^1$H-NMR (CDCl$_3$): 1.61-1.64 (3H), 2.10-2.12 (3H), 2.21-2.23 (3H), 4.12-4.20 (1H), 4.60-4.66 (1H), 4.75-4.80 (1H), 6.65-6.71 (3H), 6.82-6.83 (1H), 6.89-6.96 (2H), 7.12-7.13 (1H), 8.40-8.44 (2H)

Example 85

3-({2-[(1S)-1-(2,3-Dimethylphenyl)ethyl]-1H-imidazol-1-yl}methyl)benzonitrile $^1$H-NMR (d$_6$-Acetone): 1.55-1.58 (3H), 2.17-2.20 (6H), 4.38-4.41 (1H), 4.93-4.98 (1H), 5.05-5.09 (1H), 6.63-6.65 (1H), 6.80-6.87 (2H), 6.97-7.00 (2H), 7.12-7.13 (1H), 7.18-7.20 (1H), 7.37-7.40 (1H), 7.52-7.54 (1H)

Example 86

2-({2-[(1S)-1-(2,3-Dimethylphenyl)ethyl]-1H-imidazol-1-yl}methyl)benzonitrile $^1$H-NMR (d$_6$-Acetone): 1.55-1.58 (3H), 2.16-2.20 (6H), 4.29-4.33 (1H), 4.93-4.98 (1H), 5.10-5.14 (1H), 6.66-6.68 (1H), 6.80-6.86 (2H), 6.95-7.00 (3H), 7.10-7.11 (1H), 7.57-7.59 (2H)

Example 87

3-({2-[(1S)-1-(2,3-Dimethylphenyl)ethyl]-1H-imidazol-1-yl}methyl)-4-fluorobenzonitrile $^1$H-NMR (d$_6$-Acetone): 1.57-1.60 (3H), 2.16-2.18 (3H), 2.20-2.22 (3H), 4.42-4.46 (1H), 5.01-5.05 (1H), 5.06-5.11 (1H), 6.60-6.68 (2H), 6.80-6.82 (2H), 7.00-7.01 (1H), 7.15-7.16 (1H), 7.21-7.25 (1H), 7.60-7.62 (1H)

Example 88

1-(3,5-Dimethoxybenzyl)-2-[(1S)-1-(2,3-dimethylphenyl)ethyl]-1H-imidazole $^1$H-NMR (d$_6$-Acetone): 1.50-1.53 (3H), 2.20-2.25 (6H), 3.62-3.66 (6H), 4.33-4.38 (1H), 4.60-4.64 (1H), 4.81-4.85 (1H), 6.02-6.05 (2H), 6.36-6.38 (1H), 6.76-6.79 (1H), 6.90-6.98 (3H), 7.00-7.01 (1H)

Example 89

2-[(1S)-1-(2,3-Dimethylphenyl)ethyl]-1-(4-methoxybenzyl)-1H-imidazole $^1$H-NMR (d$_6$-Acetone): 1.51-1.54 (3H), 2.20-2.25 (6H), 3.76-3.78 (3H), 4.36-4.40 (1H), 4.60-4.64 (1H), 4.80-4.84 (1H), 6.68-6.70 (1H), 6.79-6.85 (4H), 6.90-7.00 (4H)

Example 90

2-[(1S)-1-(2,3-Dimethylphenyl)ethyl]-1-(3-methoxybenzyl)-1H-imidazole $^1$H-NMR (d$_6$-Acetone): 1.51-1.54 (3H), 2.20-2.25 (6H), 3.65-3.67 (3H), 4.36-4.40 (1H), 4.62-4.66 (1H), 4.90-4.94

(1H), 6.40-6.42 (1H), 6.48-6.50 (1H), 6.72-6.74 (1H), 6.79-6.81 (1H), 6.95-7.00 (3H), 7.00-7.01 (1H), 7.17-7.20 (1H)

Example 91

Methyl 4-({2-[(1S)-1-(2,3-dimethylphenyl)ethyl]-1H-imidazol-1-yl}methyl)-3-methoxybenzoate $^1$H-NMR (d$_6$-Acetone): 1.51-1.54 (3H), 2.16-2.18 (3H), 2.20-2.22 (3H), 3.84-3.90 (6H), 4.32-4.36 (1H), 4.81-4.86 (2H), 6.46-6.48 (1H), 6.71-6.73 (1H), 6.85-6.90 (2H), 6.97-6.98 (1H), 7.01-7.02 (1H), 7.39-7.41 (1H), 7.50-7.51 (1H)

Example 92

1-[4-({2-[(1S)-1-(2,3-Dimethylphenyl)ethyl]-1H-imidazol-1-yl}methyl)phenyl]-1H-pyrazole $^1$H-NMR (d$_6$-Acetone): 1.52-1.55 (3H), 2.20-2.24 (6H), 4.36-4.40 (1H), 4.78-4.82 (1H), 4.96-5.00 (1H), 6.44-6.46 (1H), 6.70-6.72 (1H), 6.90-7.00 (5H), 7.04-7.06 (1H), 7.63-7.69 (3H), 8.21-8.23 (1H)

Example 93

2-[(1S)-1-(2,3-Dimethylphenyl)ethyl]-1-(4-fluorobenzyl)-1H-imidazole $^1$H-NMR (d$_6$-Acetone): 1.53-1.56 (3H), 2.19-2.24 (6H), 4.32-4.36 (1H), 4.71-4.75 (1H), 4.90-4.94 (1H), 6.65-6.67 (1H), 6.89-6.95 (3H), 6.95-7.00 (4H), 7.00-7.01 (1H)

Example 94

1-(3,4-Difluorobenzyl)-2-[(1S)-1-(2,3-dimethylphenyl)ethyl]-1H-imidazole $^1$H-NMR (d$_6$-Acetone): 1.55-1.58 (3H), 2.20-2.23 (6H), 4.36-4.40 (1H), 4.80-4.84 (1H), 4.97-5.01 (1H), 6.62-6.70 (3H), 6.82-6.90 (2H), 6.96-6.98 (1H), 7.04-7.05 (1H), 7.06-7.10 (1H)

Example 95

2-[(1S)-1-(2,3-Dimethylphenyl)ethyl]-1-(2-fluorobenzyl)-1H-imidazole $^1$H-NMR (d$_6$-Acetone): 1.56-1.59 (3H), 2.20-2.24 (6H), 4.38-4.42 (1H), 4.80-4.90 (2H), 6.60-6.63 (1H), 6.64-6.66 (1H), 6.88-6.95 (3H), 7.00-7.03 (2H), 7.06-7.09 (1H), 7.25-7.28 (1H)

Example 96

1-[3-(Difluoromethoxy)benzyl]-2-[(1S)-1-(2,3-dimethylphenyl)ethyl]-1H-imidazole $^1$H-NMR (d$_6$-Acetone): 1.51-1.54 (3H), 2.19-2.23 (6H), 4.32-4.38 (1H), 4.79-4.83 (1H), 4.97-5.01 (1H), 6.61-6.63 (1H), 6.70-6.79 (2H), 6.81-6.82 (1H), 6.88-6.99 (2H), 7.00-7.05 (2H), 7.25-7.30 (1H)

Example 97

1-(2,3-Difluorobenzyl)-2-[(1S)-1-(2,3-dimethylphenyl)ethyl]-1H-imidazole $^1$H-NMR (d$_6$-Acetone): 1.56-1.59 (3H), 2.20-2.24 (6H), 4.39-4.43 (1H), 4.89-4.93 (1H), 5.00-5.04 (1H), 6.39-6.41 (1H), 6.61-6.63 (1H), 6.81-6.90 (2H), 6.95-7.00 (2H), 7.06-7.07 (1H), 7.14-7.19 (1H)

Example 98

2-[(1S)-1-(2,3-Dimethylphenyl)ethyl]-1-(3-fluorobenzyl)-1H-imidazole $^1$H-NMR (d$_6$-Acetone): 1.51-1.54 (3H), 2.19-2.23 (6H), 4.32-4.36 (1H), 4.76-4.80 (1H), 4.96-5.00 (1H), 6.53-6.55 (1H), 6.70-6.75 (2H), 6.89-6.99 (4H), 7.02-7.04 (1H), 7.22-7.25 (1H)

Example 99

1-(2,4-Difluorobenzyl)-2-[(1S)-1-(2,3-dimethylphenyl)ethyl]-1H-imidazole $^1$H-NMR (d$_6$-Acetone): 1.56-1.59 (3H), 2.20-2.24 (6H), 4.39-4.43 (1H), 4.81-4.91 (2H), 6.60-6.65 (2H), 6.77-6.80 (1H), 6.83-6.86 (1H), 6.89-6.99 (3H), 7.01-7.03 (1H)

Example 100

1-(3,5-Difluorobenzyl)-2-[(1S)-1-(2,3-dimethylphenyl)ethyl]-1H-imidazole $^1$H-NMR (d$_6$-Acetone): 1.56-1.59 (3H), 2.19-2.23 (6H), 4.36-4.40 (1H), 4.81-4.85 (1H), 5.00-5.04 (1H), 6.40-6.44 (2H), 6.69-6.71 (1H), 6.78-6.82 (1H), 6.83-6.90 (2H), 6.98-6.99 (1H), 7.09-7.10 (1H)

Example 101

1-(2,6-Difluorobenzyl)-2-[(1S)-1-(2,3-dimethylphenyl)ethyl]-1H-imidazole $^1$H-NMR (d$_6$-Acetone): 1.57-1.60 (3H), 2.26-2.28 (3H), 2.37-2.39 (3H), 4.60-4.64 (1H), 4.72-4.77 (1H), 5.05-5.10 (1H), 6.57-6.59 (1H), 6.85-6.84 (3H), 6.97-7.05 (3H), 7.39-7.43 (1H)

Example 102

1-(2-Chloro-4-fluorobenzyl)-2-[(1S)-1-(2,3-dimethylphenyl)ethyl]-1H-imidazole $^1$H-NMR (d$_6$-Acetone): 1.56-1.59 (3H), 2.16-2.20 (6H), 4.32-4.37 (1H), 4.81-4.85 (1H), 4.96-5.00 (1H), 6.29-6.32 (1H), 6.69-6.71 (1H), 6.82-6.88 (3H), 6.99-7.03 (2H), 7.20-7.22 (1H)

Example 103

1-(2,5-Difluorobenzyl)-2-[(1S)-1-(2,3-dimethylphenyl)ethyl]-1H-imidazole $^1$H-NMR (d$_6$-Acetone): 1.57-1.60 (3H), 2.19-2.24 (6H), 4.40-4.44 (1H), 4.87-4.91 (1H), 4.96-5.00 (1H), 6.16-6.20 (1H), 6.67-6.70 (1H), 6.82-6.88 (2H), 6.96-7.00 (2H), 7.06-7.09 (2H)

Example 104

1-(4-Chloro-2-fluorobenzyl)-2-[(1S)-1-(2,3-dimethylphenyl)ethyl]-1H-imidazole $^1$H-NMR (d$_6$-Acetone): 1.56-1.59 (3H), 2.19-2.23 (6H), 4.39-4.44 (1H), 4.82-4.86 (1H), 4.96-5.00 (1H), 6.49-6.53 (1H), 6.65-6.68 (1H), 6.80-6.90 (2H), 6.96-6.99 (2H), 7.07-7.08 (1H), 7.16-7.19 (1H)

Example 105

2-[(1S)-1-(2,3-Dimethylphenyl)ethyl]-1-(2,3,6-trifluorobenzyl)-1H-imidazole $^1$H-NMR (d$_6$-Acetone): 1.57-1.60 (3H), 2.21-2.23 (3H), 2.36-2.38 (3H), 4.57-4.61 (1H), 4.85-4.89 (1H), 4.97-5.01 (1H), 6.47-6.50 (1H), 6.81-6.89 (2H), 6.90-7.01 (3H), 7.23-7.28 (1H)

Example 106

2-[(1S)-1-(2,3-Dimethylphenyl)ethyl]-1-(2,4,5-trifluorobenzyl)-1H-imidazole $^1$H-NMR (d$_6$-Acetone): 1.57-1.60 (3H), 2.18-2.20 (3H), 2.21-2.23 (3H), 4.40-4.45 (1H), 4.90-4.94 (1H), 4.95-5.01 (1H), 6.27-6.32 (1H), 6.61-6.63 (1H), 6.80-6.88 (2H), 6.99-7.00 (1H), 7.10-7.11 (1H), 7.11-7.15 (1H)

Example 107

2-[(1S)-1-(2,3-Dimethylphenyl)ethyl]-1-(4-methylbenzyl)-1H-imidazole $^1$H-NMR (d$_6$-Acetone): 1.51-1.55 (3H), 2.20-2.22 (3H), 2.22-2.26 (6H), 4.30-4.36 (1H), 4.61-4.65 (1H), 4.80-4.85 (1H), 6.70-6.72 (1H), 6.78-6.81 (2H), 6.90-6.99 (4H), 7.03-7.06 (2H)

Example 108

2-[(1S)-1-(2,3-Dimethylphenyl)ethyl]-1-(2,4,6-trifluorobenzyl)-1H-imidazole $^1$H-NMR (d$_6$-Acetone): 1.57-1.60 (3H), 2.21-2.23 (3H), 2.30-2.32 (3H), 4.57-4.61 (1H), 4.76-4.80 (1H), 4.84-4.88 (1H), 6.47-6.49 (1H), 6.81-6.92 (5H), 6.97-6.99 (1H)

Example 109

2-[(1S)-1-(2,3-Dimethylphenyl)ethyl]-1-(2-methylbenzyl)-1H-imidazole $^1$H-NMR (d$_6$-Acetone): 1.55-1.58 (3H), 2.02-2.04 (3H), 2.10-2.12 (3H), 2.21-2.23 (3H), 4.21-4.36 (1H), 4.65-4.69 (1H), 4.78-4.82 (1H), 6.47-6.49 (1H), 6.75-6.77 (1H), 6.80-6.82 (1H), 6.95-7.00 (3H), 7.04-7.07 (1H), 7.18-7.20 (2H)

Example 110

2-[(1S)-1-(2,3-Dimethylphenyl)ethyl]-1-[4-fluoro-2-(trifluoromethyl)benzyl]-1H-imidazole $^1$H-NMR (d$_6$-Acetone): 1.57-1.60 (3H), 2.07-2.09 (3H), 2.15-2.17 (3H), 4.28-4.32 (1H), 5.00-5.04 (1H), 5.16-5.20 (1H), 6.38-6.41 (1H), 6.78-6.80 (1H), 6.85-6.88 (2H), 7.00-7.04 (2H), 7.16-7.19 (1H), 7.41-7.43 (1H)

Example 111

2-[(1S)-1-(2,3-Dimethylphenyl)ethyl]-1-(2-fluoro-3-methylbenzyl)-1H-imidazole $^1$H-NMR (d$_6$-Acetone): 1.57-1.59 (3H), 2.20-2.25 (9H), 4.38-4.42 (1H), 4.80-4.86 (2H), 6.44-6.48 (1H), 6.64-6.66 (1H), 6.87-6.97 (4H), 7.00-7.01 (1H), 7.10-7.14 (1H)

Example 112

2-[(1S)-1-(2,3-Dimethylphenyl)ethyl]-1-[3-(trifluoromethyl)benzyl]-1H-imidazole $^1$H-NMR (d$_6$-Acetone): 1.52-1.56 (3H), 2.18-2.21 (6H), 4.36-4.40 (1H), 4.90-4.95 (1H), 5.08-5.12 (1H), 6.67-6.70 (1H), 6.81-6.90 (2H), 6.98-6.99 (1H), 7.10-7.16 (3H), 7.40-7.44 (1H), 7.50-7.52 (1H)

Example 113

1-(4-Chlorobenzyl)-2-[(1S)-1-(2,3-dimethylphenyl)ethyl]-1H-imidazole $^1$H-NMR (d$_6$-Acetone): 1.51-1.54 (3H), 2.18-2.22 (6H), 4.31-4.38 (1H), 4.86-4.91 (1H), 4.95-4.99 (1H), 6.67-6.70 (1H), 6.81-6.97 (5H), 7.03-7.04 (1H), 7.20-7.23 (1H)

Example 114

2-[(1S)-1-(2,3-Dimethylphenyl)ethyl]-1-[4-(trifluoromethyl)benzyl]-1H-imidazole $^1$H-NMR (d$_6$-Acetone): 1.52-1.56 (3H), 2.17-2.20 (6H), 4.31-4.39 (1H), 4.90-4.96 (1H), 5.07-5.12 (1H), 6.67-6.70 (1H), 6.83-6.89 (2H), 6.99-7.04 (3H), 7.09-7.10 (1H), 7.49-7.53 (2H)

Example 115

1-(3-Chlorobenzyl)-2-[(1S)-1-(2,3-dimethylphenyl)ethyl]-1H-imidazole $^1$H-NMR (d$_6$-Acetone): 1.56-1.58 (3H), 2.00-2.05 (6H), 4.34-4.39 (1H), 4.78-4.82 (1H), 4.98-5.02 (1H), 6.69-6.71 (1H), 6.79-6.83 (2H), 6.87-6.97 (3H), 7.04-7.05 (1H), 7.19-7.23 (2H)

Example 116

2-[(1S)-1-(2,3-Dimethylphenyl)ethyl]-1-[2-(trifluoromethyl)benzyl]-1H-imidazole $^1$H-NMR (d$_6$-Acetone): 1.56-1.58 (3H), 2.01-2.03 (3H), 2.16-2.18 (3H), 4.22-4.28 (1H), 4.99-5.03 (1H), 5.15-5.20 (1H), 6.40-6.42 (1H), 6.78-6.80 (1H), 6.89-6.92 (2H), 7.01-7.04 (2H), 7.40-7.44 (2H), 7.70-7.72 (1H)

Example 117

2-[(1S)-1-(2,3-Dimethylphenyl)ethyl]-1-[3-fluoro-4-(trifluoromethyl)benzyl]-1H-imidazole $^1$H-NMR (d$_6$-Acetone): 1.54-1.58 (3H), 2.10-2.17 (6H), 4.38-4.42 (1H), 5.00-5.05 (1H), 5.12-5.18 (1H), 6.60-6.70 (2H), 6.80-6.85 (3H), 7.00-7.01 (1H), 7.16-7.17 (1H), 7.45-7.52 (1H)

Example 118

2-[(1S)-1-(2,3-Dimethylphenyl)ethyl]-1-[5-fluoro-2-(trifluoromethyl)benzyl]-1H-imidazole $^1$H-NMR (d$_6$-Acetone): 1.57-1.60 (3H), 2.09-2.15 (6H), 4.31-4.38 (1H), 5.02-5.07 (1H), 5.10-5.15 (1H), 5.95-5.98 (1H), 6.78-6.80 (1H), 6.81-6.88 (2H), 7.04-7.05 (1H), 7.10-7.16 (2H), 7.72-7.76 (1H)

Example 119

1-(3-Chloro-2-fluorobenzyl)-2-[(1S)-1-(2,3-dimethylphenyl)ethyl]-1H-imidazole $^1$H-NMR (d$_6$-Acetone): 1.55-1.58 (3H), 2.20-2.23 (6H), 4.39-4.44 (1H), 4.90-4.95 (1H), 5.00-5.05 (1H), 6.50-6.54 (1H), 6.61-6.63 (1H), 6.80-6.90 (2H), 6.95-7.00 (2H), 7.09-7.10 (1H), 7.30-7.35 (1H)

Example 120

1-(3,5-Dimethylbenzyl)-2-[(1S)-1-(2,3-dimethylphenyl)ethyl]-1H-imidazole $^1$H-NMR (d$_6$-Acetone): 1.52-1.55 (3H), 2.17-2.19 (6H), 2.21-2.25 (6H), 4.35-4.40 (1H), 4.60-4.65 (1H), 4.80-4.85 (1H), 6.42-6.45 (2H), 6.71-6.73 (1H), 6.81-6.82 (1H), 6.90-7.00 (4H)

Example 121

2-[(1S)-1-(2,3-Dimethylphenyl)ethyl]-1-(2-ethylbenzyl)-1H-imidazole $^1$H-NMR (d$_6$-Acetone): 0.98-1.02 (3H), 1.56-1.59 (3H), 2.16-2.17 (3H), 2.21-2.22 (3H), 2.30-2.38 (2H), 4.25-4.34 (1H), 4.71-4.77 (1H), 4.80-4.85 (1H), 6.57-6.59 (1H), 6.73-6.80 (2H), 6.94-7.00 (3H), 7.05-7.09 (1H), 7.20-7.23 (2H)

Example 122

2-[(1S)-1-(2,3-Dimethylphenyl)ethyl]-1-[2-(trifluoromethoxy)benzyl]-1H-imidazole $^1$H-NMR (d$_6$-Acetone): 1.55-1.59 (3H), 2.16-2.22 (6H), 4.31-4.38 (1H), 4.82-4.87 (1H), 4.99-5.02 (1H), 6.58-6.60 (1H), 6.67-6.70 (1H), 6.84-6.91 (2H), 6.97-6.99 (1H), 7.01-7.02 (1H), 7.16-7.20 (1H), 7.30-7.40 (2H)

Example 123

2-[(1S)-1-(2,3-Dimethylphenyl)ethyl]-1-[3-(trifluoromethoxy)benzyl]-1H-imidazole $^1$H-NMR (d$_6$-Acetone): 1.56-1.59 (3H), 2.19-2.22 (6H), 4.36-4.40 (1H), 4.80-4.85 (1H), 5.00-5.05 (1H), 6.70-6.72 (1H), 6.78-6.80 (1H), 6.82-6.94 (3H), 6.99-7.00 (1H), 7.06-7.08 (1H), 7.16-7.19 (1H), 7.35-7.38 (1H)

Example 124

4'-({2-[(1S)-1-(2,3-Dimethylphenyl)ethyl]-1H-imidazol-1-yl}methyl)biphenyl-2-carbonitrile $^1$H-NMR (d$_6$-Acetone): 1.57-1.60 (3H), 2.20-2.21 (6H), 4.38-4.42 (1H), 4.81-4.85 (1H), 5.00-5.05 (1H), 6.76-6.78 (1H), 6.90-7.02 (5H), 7.07-7.08 (1H), 7.42-7.45 (2H), 7.58-7.61 (2H), 7.78-7.80 (1H), 7.82-7.84 (1H)

Example 125

2-[(1S)-1-(2,3-Dimethylphenyl)ethyl]-1-(4-iodobenzyl)-1H-imidazole $^1$H-NMR (d$_6$-Acetone): 1.50-1.53 (3H), 1.97-1.99 (3H), 2.00-2.02 (3H), 4.30-4.35 (1H), 4.75-4.80 (1H), 4.96-5.00 (1H), 6.61-6.64 (2H), 6.68-6.70 (1H), 6.86-6.95 (3H), 7.01-7.02 (1H), 7.58-7.60 (2H)

Example 126

2-[(1S)-1-(2,3-Dimethylphenyl)ethyl]-1-{4-[(trifluoromethyl)thio]benzyl}-1H-imidazole $^1$H-NMR (d$_6$-Acetone): 1.53-1.56 (3H), 2.17-2.20 (6H), 4.31-4.38 (1H), 4.83-4.88 (1H), 5.03-5.08 (1H), 6.67-6.69 (1H), 6.82-6.88 (2H), 6.95-7.00 (3H), 7.07-7.08 (1H), 7.50-7.54 (2H)

Example 127

2-[(1S)-1-(2,3-Dimethylphenyl)ethyl]-1-[3-(4-fluorophenoxy)benzyl]-1H-imidazole $^1$H-NMR (d$_6$-Acetone): 1.50-1.53 (3H), 2.19-2.23 (6H), 4.33-4.38 (1H), 4.67-4.71 (1H), 4.89-4.93 (1H), 6.50-6.52 (1H), 6.64-6.68 (2H), 6.80-6.82 (1H), 6.86-7.00 (6H), 7.14-7.19 (2H), 7.22-7.25 (1H)

Example 128

1-(4-tert-Butylbenzyl)-2-[(1S)-1-(2,3-dimethylphenyl)ethyl]-1H-imidazole $^1$H-NMR (d$_6$-Acetone): 1.13-1.15 (9H), 1.51-1.53 (3H), 2.20-2.26 (6H), 4.36-4.40 (1H), 4.66-4.70 (1H), 4.82-4.87 (1H), 6.70-6.73 (1H), 6.80-6.82 (2H), 6.90-7.00 (4H), 7.25-7.28 (2H)

Example 129

1-(2,5-Dichlorobenzyl)-2-[(1S)-1-(2,3-dimethylphenyl)ethyl]-1H-imidazole $^1$H-NMR (d$_6$-Acetone): 1.55-1.59 (3H), 2.11-2.20 (6H), 4.37-4.41 (1H), 4.89-4.93 (1H), 5.02-5.06 (1H), 6.19-6.21 (1H), 6.76-6.79 (1H), 6.80-6.82 (1H), 6.82-6.84 (1H), 7.00-7.01 (1H), 7.09-7.10 (1H), 7.19-7.22 (1H), 7.37-7.39 (1H)

Example 130

1-[2-Chloro-5-(trifluoromethyl)benzyl]-2-[(1S)-1-(2,3-dimethylphenyl)ethyl]-1H-imidazole $^1$H-NMR (d$_6$-Acetone): 1.56-1.60 (3H), 2.10-2.12 (3H), 2.18-2.20 (3H), 4.39-4.44 (1H), 4.99-5.05 (1H), 5.12-5.18 (1H), 6.57-6.59 (1H), 6.71-6.80 (3H), 7.01-7.03 (1H), 7.10-7.12 (1H), 7.50-7.53 (1H), 7.58-7.60 (1H)

Example 131

1-(5-Chloro-2-methylbenzyl)-2-[(1S)-1-(2,3-dimethylphenyl)ethyl]-1H-imidazole $^1$H-NMR (d$_6$-Acetone): 1.56-1.60 (3H), 2.02-2.04 (3H), 2.10-2.12 (3H), 2.20-2.21 (3H), 4.24-4.28 (1H), 4.71-4.78 (1H), 4.88-4.93 (1H), 6.32-6.34 (1H), 6.78-6.80 (1H), 6.90-7.00 (4H), 7.13-7.17 (1H)

Example 132

2-[(1S)-1-(2,3-Dimethylphenyl)ethyl]-1-(2-naphthylmethyl)-1H-imidazole $^1$H-NMR (d$_6$-Acetone): 1.51-1.54 (3H), 2.17-2.21 (6H), 4.38-4.41 (1H), 4.87-4.91 (1H), 5.10-5.14 (1H), 6.74-6.78 (1H), 6.90-6.93 (2H), 6.98-6.99 (1H), 7.01-7.08 (2H), 7.28-7.29 (1H), 7.43-7.46 (2H), 7.70-7.80 (2H), 7.81-7.84 (1H)

Example 133

1-(3,4-Dichlorobenzyl)-2-[(1S)-1-(2,3-dimethylphenyl)ethyl]-1H-imidazole $^1$H-NMR (d$_6$-Acetone): 1.52-1.55 (3H), 2.19-2.22 (6H), 4.35-4.40 (1H), 4.85-4.90 (1H), 5.00-5.06 (1H), 4.98-5.00 (2H), 6.63-6.66 (1H), 6.78-6.80 (1H), 6.81-6.87 (3H), 6.99-7.00 (1H), 7.10-7.11 (1H), 7.30-7.33 (1H)

Example 134

1-(2,6-Dichlorobenzyl)-2-[(1S)-1-(2,3-dimethylphenyl)ethyl]-1H-imidazole $^1$H-NMR (d$_6$-Acetone): 1.60-1.63 (3H), 2.30-2.32 (3H), 2.40-2.42 (3H), 4.66-4.72 (2H), 5.05-5.09 (1H), 6.41-6.43 (1H), 6.67-6.70 (1H), 6.81-6.82 (1H), 6.96-7.01 (2H), 7.40-7.46 (3H)

Example 135

1-(Biphenyl-4-ylmethyl)-2-[(1S)-1-(2,3-dimethylphenyl)ethyl]-1H-imidazole $^1$H-NMR (d$_6$-Acetone): 1.54-1.56 (3H), 2.20-2.22 (6H), 4.36-4.40 (1H), 4.80-4.84 (1H), 4.97-5.00 (1H), 6.71-6.73 (1H), 6.93-6.99 (4H), 7.06-7.07 (1H), 7.36-7.37 (1H), 7.42-7.46 (3H), 7.55-7.58 (2H), 7.60-7.63 (2H)

Example 136

Cyclopropylmethyl {2-[1-(2,3-dimethylphenyl)ethyl]-1H-imidazol-1-yl}methyl carbonate

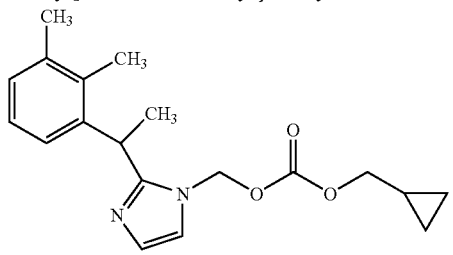

To a mixture of the compound of Example 1 (100 mg, 0.50 mmol) and caesium carbonate (407 mg, 1.25 mmol) in acetone (5 ml) and under nitrogen was added Preparation 119 (205 mg, 1.25 mmol). The reaction mixture was stirred at room temperature for 60 h and then concentrated in vacuo. To the residue was added water (10 ml) and ethyl acetate (20 ml) and the two layers were separated. The organic phase was then dried (MgSO$_4$) and concentrated in vacuo.

The residue was dissolved in acetonitrile (0.8 ml) and purified by automated preparative liquid chromatography (Gilson system, 150 mm×30 mm LUNA C18(2) 10 μm column, 40 ml/min) using an acetonitrile:water gradient [55:45 (20 min) to 98:2 (20.1 min)]. The appropriate fractions were combined and concentrated to give the title compound (74 mg).

Experimental MH$^+$ 329.4; expected 329.2 $^1$H-NMR (d$_6$-Acetone): 0.20-0.30 (2H), 0.50-0.60 (2H), 1.05-1.15 (1H), 1.55-1.60 (3H), 2.30-2.40 (6H), 3.80-3.95 (2H), 4.60-4.70 (1H), 5.40-5.45 (1H), 5.70-5.80 (1H), 6.65-6.70 (1H), 6.90-6.95 (2H), 6.95-7.00 (1H), 7.17-7.20 (1H) Rhip. Funct. ED$_{100}$ mg/cm$^2$=0.01

Similarly Prepared from Example 1 were:

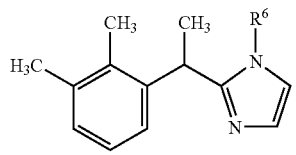

| Ex. No. | R$^6$ | Precursor | From Prep. | MH$^+$ Found/ Expected | Rhip. Funct. ED$_{100}$ mg/cm$^2$ |
|---|---|---|---|---|---|
| 137 | 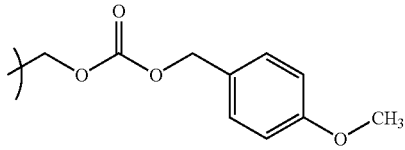 | Chloromethyl 4-methoxybenzyl carbonate | 120 | 395.3, 395.2 | 0.1 |

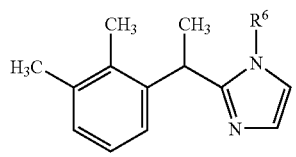

| Ex. No. | R[6] | Precursor | From Prep. | MH+ Found/ Expected | Rhip. Funct. ED$_{100}$ mg/cm$^2$ |
|---|---|---|---|---|---|
| 138 | | Chloromethyl 2,2,2-trifluoroethyl carbonate | 124 | 357.3, 357.1 | 0.03 |
| 139 | | Chloromethyl 3-methylbutyl carbonate | 121 | 345.4, 345.2 | <=0.03 |
| 140 | | Chloromethyl isopropyl carbonate | 122 | 317.3, 317.2 | 0.01 |
| 141 | | Chloromethyl cyclobutyl carbonate | 123 | 329.4, 329.2 | 0.03 |

Example 137

{2-[1-(2,3-Dimethylphenyl)ethyl]-1H-imidazol-1-yl}methyl 4-methoxybenzyl carbonate $^1$H-NMR (d$_6$-Acetone): 1.50-1.60 (3H), 2.25-2.35 (6H), 3.80-3.85 (3H), 4.60-4.65 (1H), 4.95-5.10 (2H), 5.40-5.50 (1H), 5.70-5.80 (1H), 6.60-6.65 (1H), 6.90-7.00 (5H), 7.15-7.18 (1H), 7.25-7.35 (2H)

Example 138

{2-[1-(2,3-Dimethylphenyl)ethyl]-1H-imidazol-1-yl}methyl 2,2,2-trifluoroethyl carbonate $^1$H-NMR (d$_6$-Acetone): 1.50-1.60 (3H), 2.20-2.30 (6H), 4.50-4.70 (3H), 5.50-5.55 (1H), 5.80-5.85 (1H), 6.60-6.64 (1H), 6.85-7.00 (3H), 7.14-7.18 (1H)

Example 139

{2-[1-(2,3-Dimethylphenyl)ethyl]-1H-imidazol-1-yl}methyl 3-methylbutyl carbonate $^1$H-NMR (d$_6$-Acetone): 0.80-0.90 (6H), 1.40-1.50 (2H), 1.55-1.60 (3H), 1.60-1.65 (1H), 2.20-2.30 (6H), 4.00-4.10 (2H), 4.60-4.65 (1H), 5.40-5.45 (1H), 5.70-5.75 (1H), 6.60-6.65 (1H), 6.85-6.90 (2H), 6.95-7.00 (1H), 7.10-7.15 (1H)

Example 140

{2-[1-(2,3-Dimethylphenyl)ethyl]-1H-imidazol-1-yl}methyl isopropyl carbonate $^1$H-NMR (d$_6$-Acetone): 1.10-1.20 (6H), 1.50-1.60 (3H), 2.20-2.30 (6H), 4.60-4.65 (1H), 4.70-4.75 (1H), 5.38-5.42 (1H), 5.65-5.70 (1H), 6.60-6.64 (1H), 6.85-6.90 (2H), 6.95-7.00 (1H), 7.10-7.14 (1H)

Example 141

Cyclobutyl {2-[1-(2,3-dimethylphenyl)ethyl]-1H-imidazol-1-yl}methyl carbonate $^1$H-NMR (d$_6$-Acetone): 1.50-1.60 (3H), 1.60-1.75 (2H), 1.90-2.00 (2H), 2.20-2.24 (2H), 2.25-2.30 (6H), 4.55-4.60 (1H), 4.70-4.80 (1H), 5.38-5.41 (1H), 5.65-5.70 (1H), 6.60-6.64 (1H), 6.85-6.90 (2H), 6.95-7.00 (1H), 7.10-7.13 (1H)

Example 142

{2-[1-(2,3-Dimethylphenyl)ethyl]-1H-imidazol-1-yl}methyl (2,4-dichlorobenzyl)carbamate

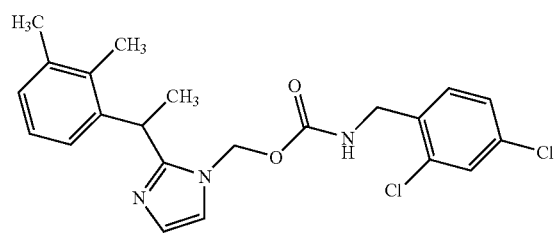

To a mixture of the compound of Example 1 (100 mg, 0.5 mmol) and caesium carbonate (163 mg, 0.5 mmol) in anhydrous acetone (2 ml) was added dropwise the compound of Preparation 125 (134 mg, 0.5 mmol) in anhydrous acetone (1 ml). The reaction mixture was stirred at room temperature for 4 days and then ethyl acetate (5 ml) and water (5 ml) was added. The two layers were separated and the aqueous layer was extracted with ethyl acetate (2×5 ml). The combined organic layers were dried (MgSO$_4$) and concentrated in vacuo.

The residue was dissolved in methanol (1.5 ml) and purified by automated preparative liquid chromatography (Gilson system, 150 mm×30 mm LUNA C18(2) 10 μm column, 40 ml/min) using an acetonitrile:water gradient [55:45 (20 min) to 95:5 (21 min)]. The appropriate fractions were combined and concentrated to give the title compound (106 mg).

Experimental MH$^+$ 432.3; expected 432.1 $^1$H-NMR (d$_6$-Acetone): 1.48-1.55 (3H), 2.23-2.27 (3H), 2.29-2.33 (3H), 4.22-4.30 (2H), 4.60-4.65 (1H), 5.38-5.41 (1H), 5.59-5.62 (1H), 6.60-6.63 (1H), 6.81-6.95 (3H), 7.08-7.10 (1H), 7.20-7.26 (1H), 7.41-7.50 (1H) Rhip. Funct. ED$_{100}$ mg/cm$^2$=1

Example 143

1-{2-[1-(2,3-Dimethylphenyl)ethyl]-1H-imidazol-1-yl}ethyl methyl[2-(methylsulfonyl)ethyl]carbamate

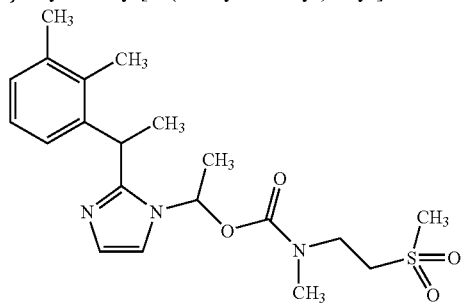

To a mixture of the compound of Example 1 (100 mg, 0.5 mmol) and caesium carbonate (163 mg, 0.5 mmol) in anhydrous acetone (2 ml) was added dropwise Preparation 133 (230 mg, 0.5 mmol) in anhydrous acetone (1 ml). The reaction mixture was stirred at room temperature for 14 days and then dichloromethane (5 ml) and water (5 ml) was added. The two layers were separated and the aqueous layer was extracted with dichloromethane (2×5 ml). The combined organic layers were dried (MgSO$_4$) and concentrated in vacuo.

The residue was dissolved in methanol (1.5 ml) and purified by automated preparative liquid chromatography (Gilson system, 150 mm×21.4 mm LUNA C18(2) 5 μm column, 20 ml/min) using an acetonitrile:water gradient [20:80 (3 min) to 98:2 (16 min)]. The appropriate fractions were combined and concentrated to give the title compound (7 mg).

Experimental MH$^+$ 408.4; expected 408.2 Rhip. Funct. ED$_{100}$ mg/cm$^2$=0.3

Similarly Prepared from Example 1 were:

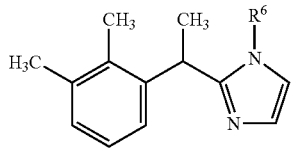

| Ex. No. | R$^6$ | Precursor | From Prep. | MH$^+$ Found/ Expected | Rhip. Funct. ED$_{100}$ mg/cm$^2$ |
|---|---|---|---|---|---|
| 144 | ![structure] | 1-Chloroethyl morpholine-4-carboxylate | 134 | 358.5 358.2 | <=10 |
| 145 | ![structure] | Chloromethyl thiomorpholine-4-carboxylate 1,1-dioxide | 126 | 392.4 392.2 | <=10 |
| 146 | ![structure] | 1-(Chloromethyl) 2-methyl (2S)-pyrrolidine-1,2-dicarboxylate | 127 | 386.4 386.2 | >1 |

-continued

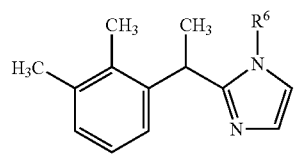

| Ex. No. | R⁶ | Precursor | From Prep. | MH⁺ Found/ Expected | Rhip. Funct. ED$_{100}$ mg/cm² |
|---|---|---|---|---|---|
| 147 | (cyclohexylcarbamate group) | Chloromethyl cyclohexylcarbamate | 128 | 356.4 / 356.2 | <=10 |
| 148 | (2-(2,4-dichlorophenyl)ethylcarbamate group) | Chloromethyl [2-(2,4-dichlorophenyl)ethyl]carbamate | 129 | 446.3 / 446.1 | >1 |
| 149 | (N-methyl-N-cyclohexylcarbamate group) | Chloromethyl cyclohexyl(methyl)-carbamate | 130 | 370.5 / 370.2 | <=10 |
| 150 | (N-methyl-N-benzylcarbamate group) | Chloromethyl benzyl(methyl)-carbamate | 131 | 378.5 / 378.2 | <=10 |
| 151 | (N-methyl-N-(2-phenylethyl)carbamate group) | Chloromethyl methyl(2-phenyl-ethyl)carbamate | 132 | 392.5 / 392.2 | <=10 |
| 152 | (2-methyl pyrrolidine-1,2-dicarboxylate group) | 1-(2-Chloroethyl) 2-methyl (2S)-pyrrolidine-1,2-dicarboxylate | 135 | 400.4 / 400.2 | >1 |

Example 144

1-{2-[1-(2,3-Dimethylphenyl)ethyl]-1H-imidazol-1-yl}ethyl morpholine-4-carboxylate $^1$H-NMR (CD$_3$OD): 1.06-1.09 (3H), 1.58-1.60 (3H), 2.30-2.31 (3H), 2.40-2.41 (2H), 3.39-3.46 (4H), 3.50-3.43 (4H), 4.88-4.92 (1H), 6.17-6.20 (1H), 6.38-6.40 (1H), 6.89-6.92 (1H), 6.99-7.01 (1H), 7.23-7.24 (1H)

Example 145

{2-[1-(2,3-Dimethylphenyl)ethyl]-1H-imidazol-1-yl}methyl thiomorpholine-4-carboxylate 1,1-dioxide $^1$H-NMR (d$_6$-Acetone): 1.52-1.55 (3H), 2.25-2.27 (3H), 2.37-2.39 (3H), 2.75-2.85 (2H), 2.90-3.00 (2H), 3.35-3.42 (2H), 3.76-3.80 (2H), 4.61-4.65 (1H), 5.68-5.69 (2H), 6.62-6.64 (1H), 6.89-6.95 (2H), 6.98-7.01 (1H), 7.09-7.10 (1H)

Example 146

1-({2-[1-(2,3-Dimethylphenyl)ethyl]-1H-imidazol-1-yl}methyl) 2-methyl (2S)-pyrrolidine-1,2-dicarboxylate $^1$H-NMR (d$_6$-Acetone): 1.50-1.55 (3H), 1.78-1.89 (3H), 2.10-2.20 (1H), 2.22-2.27 (3H), 2.34-2.39 (3H), 3.58-3.63 (3H), 4.59-4.64 (1H), 6.59-6.61 (1H), 6.82-6.90 (3H), 7.01-7.06 (1H)

Example 147

{2-[1-(2,3-Dimethylphenyl)ethyl]-1H-imidazol-1-yl}methyl cyclohexylcarbamate $^1$H-NMR (d$_6$-Acetone): 1.02-1.20 (3H), 1.20-1.30 (2H), 1.51-1.54 (3H), 1.54-1.57 (1H), 1.61-1.68 (2H), 1.75-1.82 (2H), 2.22-2.24 (3H), 2.30-2.33 (3H), 3.22-3.30 (1H), 4.60-4.64 (1H), 5.31-5.34 (1H), 5.54-5.57 (1H), 6.60-6.62 (1H), 6.82-6.83 (1H), 6.83-6.87 (1H), 6.95-6.98 (1H), 7.03-7.04 (1H)

Example 148

{2-[1-(2,3-Dimethylphenyl)ethyl]-1H-imidazol-1-yl}methyl [2-(2,4-dichlorophenyl)ethyl]carbamate $^1$H-NMR (d$_6$-Acetone): 1.50-1.56 (3H), 2.22-2.24 (3H), 2.30-2.32 (3H), 2.85-2.90 (2H), 3.30-3.35 (2H), 4.60-4.64 (1H), 5.30-5.33 (1H), 5.55-5.58 (1H), 6.60-6.62 (1H), 6.82-6.90 (2H), 6.96-6.98 (1H), 7.03-7.04 (2H), 7.19-7.24 (2H), 7.40-7.41 (1H)

Example 149

{2-[1-(2,3-Dimethylphenyl)ethyl]-1H-imidazol-1-yl}methyl cyclohexyl(methyl)carbamate $^1$H-NMR (d$_6$-Acetone): 1.00-1.10 (1H), 1.20-1.40 (4H), 1.41-1.60 (6H), 1.70-1.80 (2H), 2.10-2.16 (3H), 2.30-2.42 (6H), 4.61-4.70 (1H), 5.40-5.60 (2H), 6.62-6.65 (1H), 6.81-6.82 (1H), 6.83-6.98 (2H), 7.10-7.15 (1H)

Example 150

{2-[1-(2,3-Dimethylphenyl)ethyl]-1H-imidazol-1-yl}methyl benzyl(methyl)carbamate $^1$H-NMR (d$_6$-Acetone): 1.41-1.59 (3H), 2.18-2.26 (3H), 2.30-2.40 (3H), 2.70-2.80 (3H), 4.00-4.05 (1H), 4.25-4.38 (1H), 4.60-4.73 (1H), 5.59-5.69 (2H), 6.60-6.70 (1H), 6.80-7.00 (3H), 7.01-7.06 (1H), 7.10-7.19 (2H), 7.20-7.33 (3H)

Example 151

{2-[1-(2,3-Dimethylphenyl)ethyl]-1H-imidazol-1-yl}methyl methyl(2-phenylethyl)carbamate $^1$H-NMR (d$_6$-Acetone): 1.33-1.41 (3H), 1.50-1.56 (3H), 2.17-2.20 (1H), 2.20-2.22 (3H), 2.22-2.26 (2H), 2.36-2.39 (3H), 2.45-2.55 (1H), 4.62-4.70 (1H), 5.60-5.70 (2H), 6.67-6.70 (1H), 6.82-6.92 (3H), 7.10-7.18 (2H), 7.18-7.24 (2H), 7.24-7.27 (2H)

Example 152

1-(1-{2-[1-(2,3-Dimethylphenyl)ethyl]-1H-imidazol-1-yl}ethyl) 2-methyl (2S)-pyrrolidine-1,2-dicarboxylate $^1$H-NMR (CD$_3$OD): 1.10-1.13 (3H), 1.56-1.60 (3H), 1.85-1.90 (3H), 2.20-2.24 (1H), 2.30-2.32 (3H), 2.39-2.41 (3H), 3.40-3.50 (2H), 3.60-3.63 (1H), 3.70-3.75 (2H), 4.29-4.33 (1H), 4.79-4.83 (1H), 6.10-6.13 (1H), 6.37-6.40 (1H), 6.90-9.93 (1H), 7.00-7.03 (1H), 7.20-7.23 (1H)

Example 153

2-[(1S)-1-(2,3-Dimethylphenyl)ethyl]-1-methyl-1H-imidazole

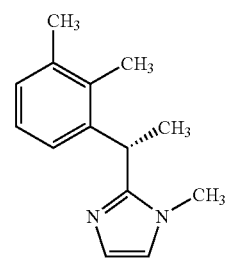

To a mixture of the compound of Example 58 (100 mg, 0.5 mmol) and caesium carbonate (407 mg, 1.25 mmol) in acetone (4 ml) was added iodomethane (78 μl, 1.25 mmol). The reaction mixture was stirred at room temperature, under nitrogen, for 4 h and then concentrated in vacuo. to the residue was added water (10 ml) and the solution was extracted with ethyl acetate (2×10 ml). The combined extracts were dried (MgSO$_4$) and concentrated in vacuo.

The residue was dissolved in methanol (1 ml) and purified by automated preparative liquid chromatography (Gilson system, 150 mm×21.4 mm LUNA C18(2) 5 μm column, 20 ml/min) using an acetonitrile:water gradient [20:80 (3 min) to 98:2 (16 min)]. The appropriate fractions were combined and concentrated to give the title compound (40 mg).

Experimental MH$^+$ 215.3; expected 215.1 $^1$H-NMR (d$_6$-Acetone): 1.45-1.50 (3H), 2.20-2.30 (6H), 3.10-3.15 (3H), 4.35-4.45 (1H), 6.55-6.60 (1H), 6.80-6.85 (1H), 6.85-6.90 (2H), 6.90-6.95 (1H) Rhip. Funct. ED$_{100}$ mg/cm$^2$=0.3

Similarly Prepared from Example 1 was:

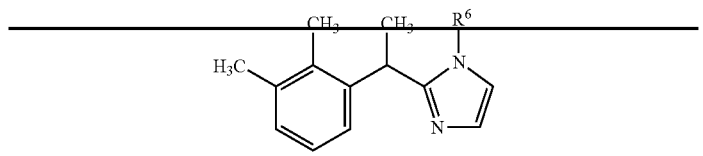

| Ex. No. | R⁶ | Precursor | MH⁺ Found/ Expected | Rhip. Funct. $ED_{100}$ mg/cm² |
|---|---|---|---|---|
| 154 | (cyclopropylmethyl) | (Bromomethyl)cyclopropane | 255.2; 255.2 | 1 |

Example 154

1-(Cyclopropylmethyl)-2-[1-(2,3-dimethylphenyl)ethyl]-1H-imidazole

¹H-NMR (d₆-Acetone): 0.00-0.05 (1H), 0.10-0.20 (1H), 0.30-0.45 (2H), 0.80-0.90 (1H), 1.50-1.60 (3H), 2.20-2.30 (6H), 3.30-3.50 (2H), 4.40-4.50 (1H), 6.60-6.65 (1H), 6.80-6.90 (2H), 6.90-6.95 (1H), 7.05-7.10 (1H)

Similarly Prepared from Example 58 was:

| Ex. No. | R⁶ | Precursor | MH⁺ Found/ Expected | Rhip. Funct. $ED_{100}$ mg/cm² |
|---|---|---|---|---|
| 155 | ethyl | Bromoethane | 229.2; 229.2 | 1 |

Example 155

2-[(1S)-1-(2,3-Dimethylphenyl)ethyl]-1-ethyl-1H-imidazole

¹H-NMR (d₆-Acetone): 0.90-1.00 (3H), 1.50-1.60 (3H), 2.20-2.35 (6H), 3.50-3.70 (2H), 4.40-4.50 (1H), 6.60-6.63 (1H), 6.80-6.90 (2H), 6.90-7.00 (2H)

Example 156

{2-[1-(2,5-Dimethylphenyl)ethyl]-1H-imidazol-1-yl}methyl pivalate

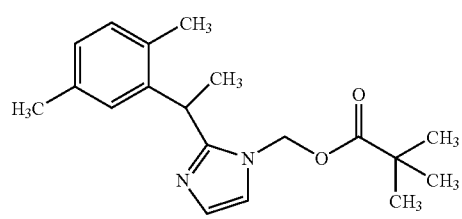

To a mixture of the compound of Example 17 (58 mg, 0.29 mmol) and caesium carbonate (236 mg, 0.72 mmol) in acetone (5 ml) was added chloromethyl pivalate (87 mg, 0.58 mmol). The reaction mixture was stirred at room temperature and under nitrogen for 18 h and then concentrated in vacuo. To the residue was added diethyl ether and the solution was passed through a silica plug (10 g), eluting with diethyl ether. The appropriate fractions were combined and concentrated to give the title compound (78 mg).

¹H-NMR (CDCl₃): 1.01-1.05 (9H), 1.61-1.65 (3H), 2.13-2.16 (3H), 2.35-2.37 (3H), 4.38-4.44 (1H), 5.34-5.38 (1H), 5.47-5.51 (1H), 6.65-6.67 (1H), 6.85-6.89 (1H), 6.96-7.02 (3H) Experimental MH⁺ 315.4; expected 315.2 Rhip. Funct. $ED_{100}$ mg/cm²<=10

Similarly Prepared by Alkylation with Chloromethyl Pivalate were:

| Ex. No. | AR | From Ex. | MH⁺ Found/ Expected | Rhip. Funct. $ED_{100}$ mg/cm² |
|---|---|---|---|---|
| 157 | 2-methyl-3-methoxyphenyl | 26 | 331.3 331.2 | <=10 |
| 158 | 2-(trifluoromethyl)phenyl | 16 | 355.3 355.2 | 0.3, 1 |
| 159 | 3-(trifluoromethyl)phenyl | 24 | 355.3 355.2 | <=10 |

-continued

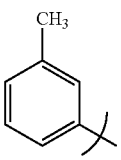

| Ex. No. | AR | From Ex. | MH+ Found/ Expected | Rhip. Funct. ED$_{100}$ mg/cm$^2$ |
|---|---|---|---|---|
| 160 | 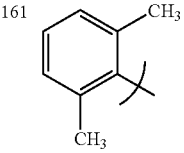 | 20 | 301.2 / 301.2 | 0.1 |
| 161 | 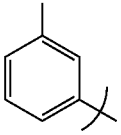 | 18 | 315.2 / 315.2 | >1 |
| 162 | 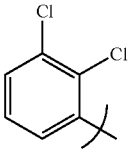 | 39 | 321.1 / 321.1 | 0.3 |
| 163 | 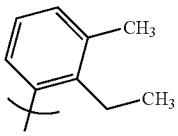 | 37 | 355.2 / 355.1 | <=10 |
| 164 | 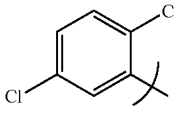 | 27 | 329.4 / 329.2 | <=1, 1 |
| 165 |  | 43 | 355.1 / 355.1 | >1 |
| 166 | 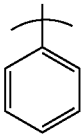 | 54 | 389.2 / 389.1 | 0.3 |
| 167 |  | 21 | 287.3 / 287.2 | 1, 0.3 |

Example 157

{2-[1-(3-Methoxy-2-methylphenyl)ethyl]-1H-imidazol-1-yl}methyl pivalate $^1$H-NMR (CDCl$_3$): 1.01-1.05 (9H), 1.61-1.65 (3H), 2.23-2.25 (3H), 3.79-3.81 (3H), 4.45-4.55 (1H), 5.33-5.36 (1H), 5.42-5.46 (1H), 6.40-6.43 (1H), 6.65-6.68 (1H), 6.96-7.01 (3H)

Example 158

(2-{1-[2-(Trifluoromethyl)phenyl]ethyl}-1H-imidazol-1-yl)methyl pivalate $^1$H-NMR (CDCl$_3$): 0.93-0.96 (9H), 1.69-1.73 (3H), 4.61-4.68 (1H), 5.51-5.60 (2H), 6.98-7.01 (2H), 7.24-7.31 (2H), 7.37-7.42 (1H), 7.61-7.64 (1H)

Example 159

(2-{1-[3-(Trifluoromethyl)phenyl]ethyl}-1H-imidazol-1-yl)methyl pivalate $^1$H-NMR (CDCl$_3$): 0.96-0.99 (9H), 1.68-1.72 (3H), 4.30-4.36 (1H), 5.52-5.56 (1H), 5.65-5.69 (1H), 6.98-7.01 (2H), 7.36-7.38 (2H), 7.42-7.45 (2H)

Example 160

{2-[1-(3-Methylphenyl)ethyl]-1H-imidazol-1-yl}methyl pivalate $^1$H-NMR (CDCl$_3$): 1.02-1.05 (9H), 1.68-1.71 (3H), 2.25-2.27 (3H), 4.19-4.25 (1H), 5.51-5.62 (2H), 6.93-7.01 (4H), 7.11-7.16 (1H)

Example 161

{2-[1-(2,6-Dimethylphenyl)ethyl]-1H-imidazol-1-yl}methyl pivalate $^1$H-NMR (CDCl$_3$): 1.03-1.06 (9H), 1.72-1.76 (3H), 2.00-2.10 (6H), 4.54-4.60 (1H), 5.13-5.17 (1H), 5.32-5.36 (1H), 6.92-7.02 (5H)

Example 162

{2-[1-(3-Chlorophenyl)ethyl]-1H-imidazol-1-yl}methyl pivalate $^1$H-NMR (CDCl$_3$): 1.00-1.03 (9H), 1.66-1.70 (3H), 4.20-4.27 (1H), 5.51-5.66 (2H), 6.97-7.01 (2H), 7.04-7.08 (1H), 7.12-7.20 (3H)

Example 164

{2-[1-(2-Ethyl-3-methylphenyl)ethyl]-1H-imidazol-1-yl}methyl pivalate $^1$H-NMR (CD$_3$OD): 0.98-1.00 (9H), 1.20-1.24 (3H), 1.60-1.63 (3H), 2.37-2.38 (3H), 2.80-2.86 (2H), 4.60-4.65 (1H), 5.53-5.56 (1H), 5.66-5.70 (1H), 6.61-6.63 (1H), 6.90-6.95 (2H), 6.99-7.01 (1H), 7.18-7.19 (1H)

Example 166

(2-{1-[2-Chloro-3-(trifluoromethyl)phenyl]ethyl}-1H-imidazol-1-yl)methyl pivalate $^1$H-NMR (CDCl$_3$): 0.96-0.99 (9H), 1.69-1.72 (3H), 4.94-5.01 (1H), 5.60-5.64 (1H), 5.72-5.76 (1H), 7.03-7.05 (2H), 7.26-7.30 (1H), 7.40-7.43 (1H), 7.55-7.59 (1H)

Example 167

[2-(1-Phenylethyl)-1H-imidazol-1-yl]methyl pivalate

¹H-NMR (CDCl₃): 1.01-1.04 (9H), 1.68-1.72 (3H), 4.22-4.28 (1H), 5.51-5.61 (2H), 6.96-7.00 (2H), 7.13-7.19 (3H), 7.22-7.27 (2H)

Example 168

3-[1-(1H-Imidazol-2-yl)ethyl]benzonitrile

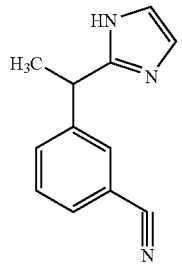

To a solution of the compound of Preparation 196 (264 mg, 1.23 mmol) in anhydrous N,N-dimethyl formamide (3 ml), at −15° C., was added dropwise thionyl chloride (0.20 ml, 2.7 mmol). The reaction mixture was allowed to warm to 0° C. over 4 h and then poured into an ice:water mixture. The mixture was extracted with ethyl acetate and the extracts were dried (MgSO₄) and concentrated in vacuo.

The residue was dissolved in warm methanol (1 ml) and purified by automated preparative liquid chromatography (Gilson system, 150 mm×50 mm Sunfire C18 10 μm column, 120 ml/min) using an acetonitrile:water gradient [20:80 (2 min) to 95:5 (18.5 min)]. The appropriate fractions were combined and concentrated to give the title compound (7 mg).

Experimental MH⁺ 198.1; expected 198.1 ¹H-NMR (CDCl₃): 1.68-1.72 (3H), 4.22-4.26 (1H), 6.97-7.00 (2H), 7.40-7.43 (1H), 7.50-7.55 (3H) Rhip. Funct. ED₁₀₀ mg/cm²=>1

Example 169

1-Benzyl-2-[1-(3-methylphenyl)ethyl]-1H-imidazole

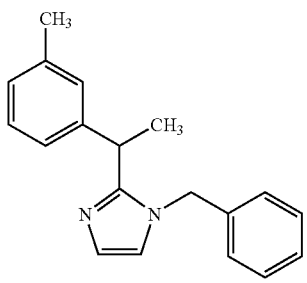

To a mixture of the compound of Example 20 (500 mg, 2.68 mmol) and caesium carbonate (2.19 g, 6.71 mmol) in acetone (20 ml) was added benzyl bromide (0.64 ml, 5.37 mmol). The reaction mixture was stirred at room temperature for 18 h, filtered through Celite® and then concentrated in vacuo.

The residue was dissolved in acetonitrile (2 ml) and purified by automated preparative liquid chromatography (Gilson system, 150 mm×50 mm LUNA C18(2) 10 μm column, 40 ml/min) using an acetonitrile:water gradient [50:50 (20 min) to 95:5 (21 min)]. The appropriate fractions were combined and concentrated to give the title compound (272 mg).

Experimental MH⁺ 277.4; expected 277.2 ¹H-NMR (d₆-Acetone): 1.57-1.60 (3H), 2.11-2.12 (3H), 4.08-4.13 (1H), 4.90-4.95 (1H), 5.01-5.06 (1H), 6.90-6.91 (1H), 6.91-7.00 (6H), 7.10-7.14 (1H), 7.21-7.25 (3H) Rhip. Funct. ED₁₀₀ mg/cm²=>1

Example 170

1-Methyl-2-[1-(3-methylphenyl)ethyl]-1H-imidazole

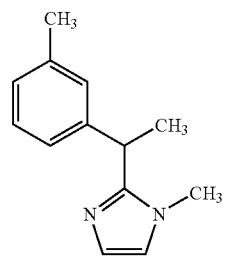

To a mixture of the compound of Example 20 (500 mg, 2.68 mmol) and caesium carbonate (2.19 g, 6.71 mmol) in acetone (20 ml) was added methyl iodide (0.33 ml, 5.37 mmol). The reaction mixture was stirred at room temperature for 2 h, filtered through Celite® and then concentrated in vacuo.

The residue was dissolved in acetonitrile (2 ml) and purified by automated preparative liquid chromatography (Gilson system, 150 mm×50 mm LUNA C18(2) 10 μm column, 40 ml/min) using an acetonitrile:water gradient [50:50 (20 min) to 95:5 (21 min)]. The appropriate fractions were combined and concentrated to give the title compound (230 mg).

Experimental MH⁺ 201.4; expected 201.1 ¹H-NMR (d₆-Acetone): 1.59-1.62 (3H), 2.12-2.14 (3H), 4.17-4.21 (1H), 6.80-6.81 (1H), 6.89-6.90 (1H), 6.96-7.02 (3H), 7.14-7.17 (1H) Rhip. Funct. ED₁₀₀ mg/cm²=>1

Example 171

1-{2-[1-(2,3-Dimethylphenyl)ethyl]-1H-imidazol-1-yl}ethyl morpholine-4-carboxylate

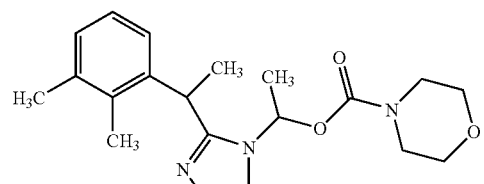

To a mixture of the compound of Example 1 (100 mg, 0.5 mmol) and caesium carbonate (163 mg, 0.5 mmol) in anhydrous acetone (2 ml) was added Preparation 134 (96 mg, 0.50 mmol) in anhydrous acetone (1 ml). The reaction mixture was stirred at room temperature for 14 days and then diluted with water (5 ml) and ethyl acetate (5 ml). The two layers were separated and the aqueous phase was extracted with ethyl acetate (2×5 ml). The combined organic phases were dried (MgSO₄) and concentrated in vacuo.

The residue was dissolved in acetonitrile (1.5 ml) and purified by automated preparative liquid chromatography (Gilson system, 150 mm×21.4 mm LUNA C18(2) 5 µm column, 20 ml/min) using an acetonitrile:water gradient [20:80 (3 min) to 98:2 (16 min)]. The appropriate fractions were combined and concentrated to give the title compound (6 mg).

Retention time 6.13 min (Gilson system, 150 mm×4.6 mm LUNA C18(2) 5 µm column, 15 ml/min) using a 0.1% trifluoroacetic acid:acetonitrile gradient [95:5 (5 min) to 2:98 (9 min)]. Experimental MH$^+$ 358.5; expected 358.2 $^1$H-NMR (CD$_3$OD): 1.55-1.60 (3H), 1.62-1.65 (3H), 2.27-2.30 (3H), 2.30-2.33 (3H), 2.90-3.00 (2H), 3.39-3.49 (2H), 4.61-4.65 (1H), 6.50-6.56 (2H), 6.85-6.89 (1H), 6.99-7.03 (1H), 7.17-7.18 (1H) Rhip. Funct. ED$_{100}$ mg/cm$^2$=1

Example 172

{2-[(1S)-1-(2,3-Dimethylphenyl)ethyl]-1H-imidazol-1-yl}methyl pivalate

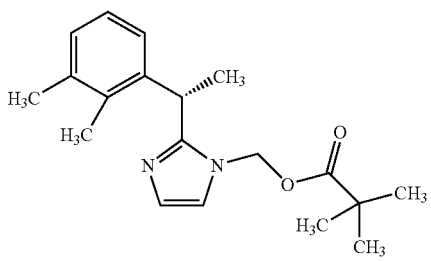

To a mixture of the compound of Example 58 (500 mg, 2.5 mmol) and caesium carbonate (1.79 g, 5.5 mmol) in anhydrous acetone (10 ml) was added chloromethyl pivalate (0.43 ml, 3.0 mmol). The reaction mixture was stirred at room temperature for 18 h. To the mixture was added dichloromethane (10 ml) and water (10 ml) and the two layers were separated. The aqueous phase was extracted with dichloromethane (2×10 ml) and the combined organic phases were dried (MgSO$_4$) and concentrated in vacuo.

The residue was dissolved in acetonitrile (2 ml) and purified by automated preparative liquid chromatography (Gilson system, 250 mm×50 mm LUNA C18(2) 10 µm column, 120 ml/min) using an acetonitrile:water gradient [55:45 (20 min) to 95:5 (20.5 min)]. The appropriate fractions were combined and concentrated to give the title compound (410 mg).

Experimental MH$^+$ 315.2; expected 315.2 $^1$H-NMR (d$_6$-Acetone): 0.97-1.00 (9H), 1.57-1.60 (3H), 2.28-2.30 (3H), 2.37-2.39 (3H), 4.60-4.65 (1H), 5.56-5.60 (1H), 5.65-5.69 (1H), 6.75-6.78 (1H), 6.90-7.00 (3H), 7.12-7.13 (1H)

Example 173

2-[(1S)-1-(2,3-Dimethylphenyl)ethyl]-1-(3,3,3-trifluoropropyl)-1H-imidazole

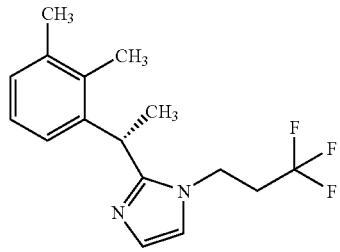

To a mixture of the preparation of Example 58 (50 mg, 0.25 mmol) and caesium carbonate (203 mg, 0.62 mmol) in acetonitrile (2.5 ml) was added 1,1,1-trifluoro-3-iodopropane (73 µl, 0.62 mmol). The reaction mixture was heated at 100° C. in a microwave (200 W) for 45 min and then concentrated in vacuo. To the residue was added water (10 ml) and the mixture was extracted with ethyl acetate (2×10 ml). The combined extracts were dried (MgSO$_4$) and concentrated in vacuo.

The residue was dissolved in acetonitrile (1 ml) and diethylamine (2-3 drops) and purified by automated preparative liquid chromatography (Gilson system, 150 mm×30 mm LUNA C18(2) 10 µm column, 40 ml/min) using an acetonitrile:water gradient [50:50 (20 min) to 98:2 (20.1 min)]. The appropriate fractions were combined and concentrated to give the title compound (20 mg).

Experimental MH$^+$ 297.3; expected 297.2 $^1$H-NMR (d$_6$-Acetone): 1.55-1.60 (3H), 1.79-1.90 (1H), 2.23-2.25 (3H), 2.43-2.62 (4H), 3.81-3.89 (2H), 4.46-4.53 (1H), 6.58-6.61 (1H), 6.85-6.92 (2H), 6.96-6.99 (1H), 7.06-7.08 (1H) Rhip. Funct. ED$_{100}$ mg/cm$^2$<=10

Similarly Prepared from Example 58 was:

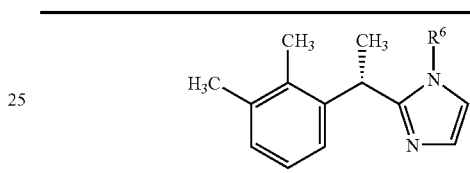

| Ex. No. | R$^6$ | Precursor | MH$^+$ Found/ Expected | Rhip. Funct. ED$_{100}$ mg/cm$^2$ |
|---|---|---|---|---|
| 174 | (isobutyl) | 2-Bromopropane | 243.3 / 243.2 | >1 |

Example 174

2-[(1S)-1-(2,3-Dimethylphenyl)ethyl]-1-isopropyl-1H-imidazole $^1$H-NMR (d$_6$-Acetone): 0.80-0.83 (3H), 1.29-1.32 (3H), 1.57-1.59 (3H), 2.25-2.27 (3H), 2.30-2.32 (3H), 4.00-4.06 (1H), 4.41-4.45 (1H), 6.58-6.60 (1H), 6.85-6.88 (2H), 6.95-6.97 (1H), 7.06-7.07 (1H)

Example 175

2-[1-(2,3-Dimethylphenyl)ethyl]-1-(4-methoxybenzyl)-1H-imidazole

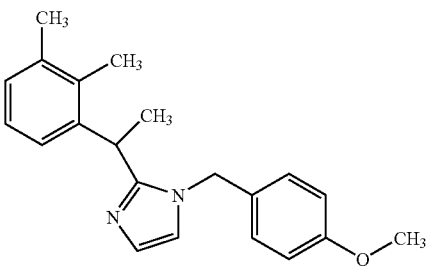

To a solution of the compound of Example 1 (100 mg, 0.5 mmol) and N,N-diisopropylethylamine (77 mg, 0.6 mmol) in dichloromethane, under nitrogen, was added 4-methoxybenzyl bromide (151 mg, 0.75 mmol). The reaction mixture was stirred at room temperature for 90 min and water (10 ml) was added. The layers were separated, and the aqueous layer washed with dichloromethane (15 ml). The combined organics were dried (MgSO$_4$) and concentrated in vacuo.

The residue was dissolved in methanol:water (9:1, 3 ml) and purified by automated preparative liquid chromatography (Gilson system, 150 mm×4.6 mm LUNA C18(2) 10 μm column, 20 ml/min) using an acetonitrile:water gradient [60:40 to 95:5]. The appropriate fractions were concentrated in vacuo to give the title compound (10 mg).

Experimental MH$^+$ 321.5; expected 321.2 $^1$H-NMR (d$_6$-Acetone): 1.48-1.53 (3H), 2.16-2.21 (3H), 2.21-2.24 (3H), 3.70-3.75 (3H), 4.31-4.36 (1H), 4.58-4.64 (1H), 4.74-4.81 (1H), 6.62-6.69 (1H), 6.72-6.82 (4H), 6.85-6.98 (4H) Rhip. Funct. ED$_{100}$ mg/cm$^2$=0.3

Similarly Prepared from Example 1 were:

Example 178

2-[1-(2,3-Dimethylphenyl)ethyl]-1-(2-methoxybenzyl)-1H-imidazole

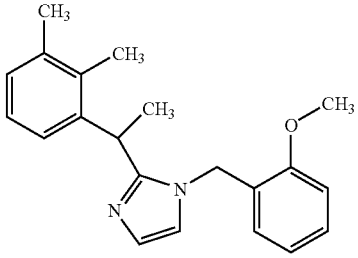

1-(Bromomethyl)-2-methoxybenzene (J. Indian Chem. Soc.; 28, 1951, 277; 150 mg, 0.75 mmol) was added to a

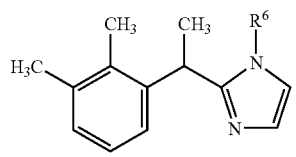

| Ex. No. | R$^6$ | Precursor | MH$^+$ Found/ Expected | Rhip. Funct. ED$_{100}$ mg/cm$^2$ |
|---|---|---|---|---|
| 176 | 4-(trifluoromethyl)benzyl | 1-(Bromomethyl)-4-(trifluoromethyl)benzene | 359.3 359.2 | >1, 1 |
| 177 | methoxymethyl | Bromo(methoxy)methane | 245.4 245.2 | 0.1 |

Example 176

2-[1-(2,3-Dimethylphenyl)ethyl]-1-[4-(trifluoromethyl)benzyl]-1H-imidazole $^1$H-NMR (d$_6$-Acetone): 1.51-1.58 (3H), 2.12-2.21 (6H), 4.32-4.40 (1H), 4.91-4.99 (1H), 5.08-5.16 (1H), 6.68-6.78 (1H), 6.84-6.92 (2H), 6.96-7.06 (3H), 7.07-7.12 (1H), 7.48-7.56 (2H)

Example 177

2-[1-(2,3-Dimethylphenyl)ethyl]-1-(methoxymethyl)-1H-imidazole $^1$H-NMR (d$_6$-Acetone): 1.54-1.60 (3H), 2.28-2.32 (3H), 2.33-2.37 (3H), 3.04-3.09 (3H), 4.54-4.61 (1H), 4.82-4.90 (1H), 4.92-4.99 (1H), 6.72-6.78 (1H), 6.88-7.00 (3H), 7.08-7.12 (1H)

suspension of the compound of Example 1 (100 mg, 0.5 mmol) and caesium carbonate (406 mg, 1.2 mmol) in acetone (4 ml), under a nitrogen atmosphere. The reaction mixture was stirred at room temperature for 18 h. The mixture was filtered and the filtrate was concentrated in vacuo. To the residue was added water (10 ml) and ethyl acetate (10 ml) and the two layers were separated. The aqueous layer was washed with a further portion of ethyl acetate (10 ml) and the combined organic layers were dried (MgSO$_4$) and concentrated in vacuo.

The residue was dissolved in methanol:water (9:1, 2 ml) and purified by automated preparative liquid chromatography (Gilson system, 150 mm×30 mm LUNA C18(2) 10 μm column, 40 ml/min) using an acetonitrile:water gradient [20:80 to 98:2]. The appropriate fractions were concentrated in vacuo to give the title compound (24 mg)

Experimental MH$^+$ 321.5; expected 321.2 $^1$H-NMR (d$_6$-Acetone): 1.48-1.53 (3H), 2.14-2.19 (3H), 2.20-2.26 (3H), 3.78-3.82 (3H), 4.32-4.40 (1H), 4.64-4.78 (2H), 6.49-6.54 (1H), 6.68-6.72 (1H), 6.73-6.80 (1H), 6.86-6.98 (5H), 7.19-7.24 (1H) Rhip. Funct. ED$_{100}$ mg/cm$^2$<=10.

Example 179

1-Benzyl-2-[1-(2-fluoro-3-methylphenyl)ethyl]-1H-imidazole

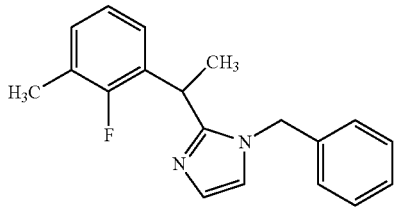

To a solution of the compound of Example 7 (69 mg, 0.34 mmol) and triethylamine (57 μl, 0.41 mmol) in anhydrous tetrahydrofuran (3 ml), under nitrogen, was added benzyl bromide (81 μl, 0.68 mmol). The reaction mixture was stirred at room temperature for 11 days and then concentrated in vacuo. To the residue was added saturated aqueous sodium hydrogen carbonate solution (10 ml) and the mixture was extracted with ethyl acetate (2×10 ml). The combined extracts were dried (MgSO$_4$), filtered through silica and the filtrate was concentrated in vacuo to give the title compound (66 mg).

Experimental MH$^+$ 295.2; expected 295.2 $^1$H-NMR (d$_6$-Acetone): 1.56-1.60 (3H), 2.19-2.22 (3H), 4.43-4.50 (1H), 4.95-5.00 (1H), 5.04-5.10 (1H), 6.90-6.99 (5H), 7.00-7.04 (2H), 7.10-7.17 (3H) Rhip. Funct. ED$_{100}$ mg/cm$^2$=1

Example 180

4-Fluorophenyl 2-[1-(2,3-dimethylphenyl)ethyl]-1H-imidazole-1-carboxylate

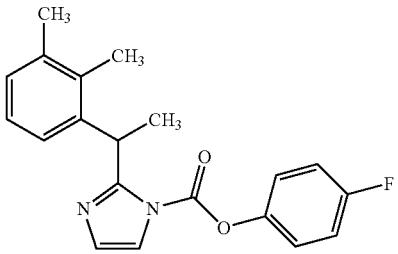

To a solution of the compound of Example 1 (100 mg, 0.5 mmol) in anhydrous tetrahydrofuran (2 ml) was added triethylamine (0.08 ml, 0.6 mmol), followed by 4-fluorophenyl chloroformate (0.26 ml, 2.0 mmol). The reaction mixture was then stirred at room temperature, under nitrogen, for 1 h. To the mixture was added ethyl acetate (10 ml) and water (10 ml) and the two layers were separated. The aqueous layer was washed with ethyl acetate (10 ml) and the combined organic phases were dried (MgSO$_4$) and concentrated in vacuo.

The residue was dissolved in acetonitrile (1 ml) and purified by automated preparative liquid chromatography (Gilson system, 150 mm×30 mm LUNA C18(2) 10 μm column, 40 ml/min) using an acetonitrile:water gradient [55:45 (20 min) to 98:2 (20.1 min)]. The appropriate fractions were concentrated in vacuo to give the title compound (60 mg).

Experimental MH$^+$ 339.3; expected 339.1 $^1$H-NMR (d$_6$-Acetone): 1.50-1.60 (3H), 2.15-2.25 (6H), 4.40-4.50 (1H), 6.80-6.85 (1H), 6.90-7.00 (3H), 7.00-7.05 (1H), 7.15-7.25 (2H), 7.35-7.40 (1H) Rhip. Funct. ED$_{100}$ mg/cm$^2$=0.03

Example 181

Benzyl 2-[(1S)-1-(2,3-dimethylphenyl)ethyl]-1H-imidazole-1-carboxylate

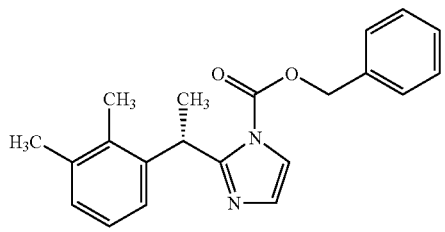

To a solution of the compound of Example 58 (7.50 g, 37.4 mmol) and triethylamine (5.74 ml, 41.2 mmol) in dichloromethane (100 ml), cooled in an ice bath, was added dropwise benzyl chloroformate (21.4 ml, 150 mmol). The reaction mixture was allowed to warm to room temperature and stirred under nitrogen for 3 h. The mixture was cooled, before addition of aqueous sodium hydrogen carbonate solution and dichloromethane and the two layers were separated. The aqueous phase was extracted with dichloromethane and the combined organic phases were dried (MgSO$_4$) and concentrated in vacuo. To the residue was added cyclohexane and the solution was filtered and concentrated in vacuo.

The residue was purified by flash chromatography (silica) with gradient elution, ethyl acetate:cyclohexane [10:90 to 100:0]. The appropriate fractions were combined and concentrated to give the title compound (9.96 g).

Experimental MH$^+$ 335.2; expected 335.2 $^1$H-NMR (d$_6$-Acetone): 1.50-1.53 (3H), 2.22-2.29 (6H), 5.05-5.10 (1H), 5.23-5.25 (2H), 6.50-6.52 (1H), 6.83-6.87 (1H), 6.97-7.00 (2H), 7.28-7.31 (2H), 7.35-7.38 (3H), 7.50-7.51 (1H) Rhip. Funct. ED$_{100}$ mg/cm$^2$=>0.03

Similarly Prepared from Example 1 was:

| Ex. No. | R$^6$ | Precursor | MH$^+$ Found/ Expected | Rhip. Funct. ED$_{100}$ mg/cm$^2$ |
|---|---|---|---|---|
| 182 | 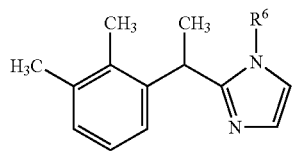 | Isopropyl chlorocarbonate | 287.4 287.2 | 0.03 |

Example 182

Isopropyl 2-[1-(2,3-dimethylphenyl)ethyl]-1H-imidazole-1-carboxylate $^1$H-NMR (d$_6$-Acetone): 1.10-1.20 (6H), 1.45-1.55 (3H), 2.20-2.35 (6H), 4.90-5.00 (1H), 5.00-5.10 (1H), 6.40-6.45 (1H), 6.80-6.85 (1H), 6.90-7.00 (2H), 7.40-7.45 (1H)

Example 183

Isobutyl 2-[(1S)-1-(2,3-dimethylphenyl)ethyl]-1H-imidazole-1-carboxylate

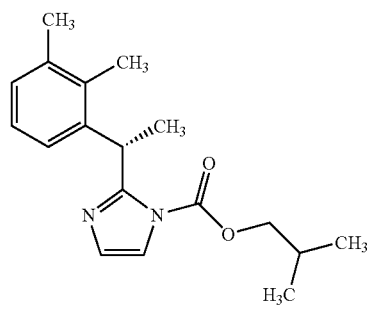

To a solution of the compound of Example 58 (1.00 g, 5.0 mmol) and triethylamine (0.77 ml, 5.5 mmol) in anhydrous dichloromethane (10 ml) was added dropwise isobutyl chloroformate (2.60 ml, 20 mmol). The reaction mixture was stirred at room temperature for 18 h and then concentrated in vacuo. The residue was partitioned between water (10 ml) and ethyl acetate (10 ml) and the two layers were separated. The aqueous layer was extracted with ethyl acetate (10 ml) and the combined organic layers were dried (MgSO$_4$) and concentrated in vacuo.

The residue was dissolved in acetonitrile:water (9:1, 4 ml) and purified by automated preparative liquid chromatography (Gilson system, 150 mm×30 mm LUNA C18(2) 5 μm column, 40 ml/min) using an acetonitrile:water gradient [65:35 to 95:5]. The appropriate fractions were combined and concentrated to give the title compound (150 mg).

Experimental MH$^+$ 301.4; expected 301.2 $^1$H-NMR (CDCl$_3$): 0.89-0.95 (6H), 1.60-1.63 (3H), 1.91-2.00 (1H), 2.28-2.39 (6H), 3.95-4.04 (2H), 5.05-5.11 (1H), 6.62-6.65 1H), 6.90-7.01 (3H), 7.40-7.41 (1H) Rhip. Funct. ED$_{100}$ mg/cm$^2$=0.03

Similarly Prepared by Acylation with Isobutyl Chlorocarbonate were:

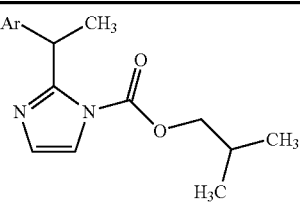

| Ex. No. | Ar | From Ex. | MH$^+$ Found/ Expected | Rhip. Funct. ED$_{100}$ mg/cm$^2$ |
|---|---|---|---|---|
| 184 | 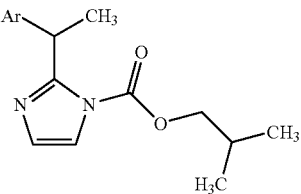 | 52 | 305.4 305.2 | 0.3 |
| 185 | | 29 | 323.6 323.2 | 1 |
| 186 | | 1 | 301.4 301.2 | 0.01 |

Example 184

Isobutyl 2-[1-(3-fluoro-2-methylphenyl)ethyl]-1H-imidazole-1-carboxylate $^1$H-NMR (CDCl$_3$): 0.83-0.95 (6H), 1.60-1.64 (3H), 1.91-1.99 (1H), 2.35-2.38 (3H), 3.97-4.02 (2H), 5.00-5.03 (1H), 6.59-6.61 (1H), 6.80-6.85 (1H), 6.98-7.03 (2H), 7.39-7.40 (1H)

Example 185

Isobutyl 2-[1-(2,6-difluoro-3-methylphenyl)ethyl]-1H-imidazole-1-carboxylate $^1$H-NMR (CDCl$_3$): 0.85-0.96 (6H), 1.74-1.78 (3H), 1.95-2.00 (1H), 2.17-2.20 (3H), 3.98-4.04 (2H), 4.99-5.03 (1H), 6.65-6.71 (1H), 6.90-6.97 (2H), 7.39-7.41 (1H)

Example 186

Isobutyl 2-[1-(2,3-dimethylphenyl)ethyl]-1H-imidazole-1-carboxylate $^1$H-NMR (d$_6$-Acetone): 0.80-0.90 (6H), 1.40-1.50 (3H), 1.80-1.90 (1H), 2.20-2.30 (6H), 3.90-4.00 (2H), 5.00-5.10 (1H), 6.45-6.50 (1H), 6.80-6.85 (1H), 6.90-6.95 (2H), 7.45-7.50 (1H)

Example 187

2-[1-(2,3-Dimethylphenyl)ethyl]-N,N-dimethyl-1H-imidazole-1-sulfonamide

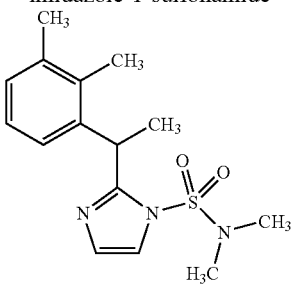

To a solution of the compound of Example 1 (100 mg, 0.5 mmol) and triethylamine (77 μl, 0.55 mmol) in anhydrous tetrahydrofuran (4 ml), was added dimethylsulphamoyl chloride (59 μl, 0.55 mmol). The reaction mixture was stirred at 60° C., under nitrogen, for 36 h and then concentrated in vacuo. The residue was partitioned between water (10 ml) and ethyl acetate (10 ml) and the two layers were separated. The aqueous layer was extracted with ethyl acetate (10 ml) and the combined organic layers were dried (MgSO$_4$) and concentrated in vacuo.

The residue was dissolved in methanol (1.5 ml) and purified by automated preparative liquid chromatography (Gilson system, 150 mm×50 mm LUNA C18(2) 10 μm column, 120 ml/min) using an acetonitrile:water gradient [20:80 to 95:5]. The appropriate fractions were combined and concentrated to give the title compound (49 mg).

Experimental MH$^+$ 308.2; expected 308.1 $^1$H-NMR (d$_6$-Acetone): 1.50-1.56 (3H), 2.22-2.26 (3H), 2.31-2.36 (3H), 2.50-2.57 (6H), 4.95-5.01 (1H), 6.70-6.74 (1H), 6.85-6.95 (2H), 7.00-7.04 (1H), 7.40-7.41 (1H) Rhip. Funct. ED$_{100}$ mg/cm$^2$<=10

Example 188

2-Ethoxy-1-(ethoxymethyl)ethyl 2-[(1S)-1-(2,3-dimethylphenyl)ethyl]-1H-imidazole-1-carboxylate

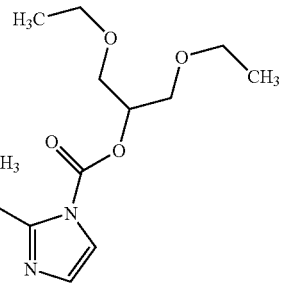

To a mixture of Example 58 (500 mg, 2.5 mmol) and pyridine (0.44 ml, 5.5 mmol) in anhydrous dichloromethane (5 ml), at 0° C. and under nitrogen, was added phosgene (20% in toluene, 1.44 ml, 2.75 mmol). The mixture was stirred at 0° C. for 20 min, before addition of 1,3-diethoxypropan-2-ol (407 mg, 2.75 mmol). The reaction mixture was stirred at room temperature for 30 min and then poured into ice water (10 ml). The mixture was adjusted to pH 7 by addition of solid sodium hydrogen carbonate and the two layers were separated. The aqueous phase was extracted with dichloromethane (2×10 ml) and the combined extracts were dried (MgSO$_4$) and concentrated in vacuo.

The residue was dissolved in methanol (1.5 ml) and purified by automated preparative liquid chromatography (Gilson system, 150 mm×50 mm Sunfire C18 10 μm column, 120 ml/min) using an acetonitrile:water gradient [60:40 (20 min) to 98:2 (20.5 min)]. The appropriate fractions were combined and concentrated to give the title compound (435 mg).

Experimental MH$^+$ 375.2; expected 375.2 $^1$H-NMR (d$_6$-Acetone): 0.97-1.02 (3H), 1.05-1.10 (3H), 1.55-1.59 (3H), 2.25-2.28 (3H), 2.32-2.35 (3H), 3.32-3.50 (5H), 3.52-3.58 (3H), 5.05-5.12 (1H), 6.54-6.57 (1H), 6.84-6.89 (1H), 6.96-6.99 (2H), 7.49-7.50 (1H) Rhip. Funct. ED$_{100}$ mg/cm$^2$=0.03

Example 189

Cyclopropylmethyl 2-[(1S)-1-(2,3-dimethylphenyl)ethyl]-1H-imidazole-1-carboxylate

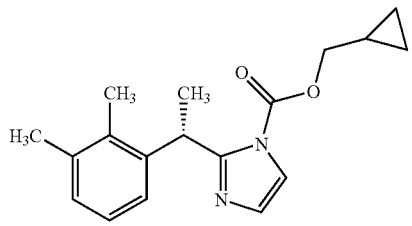

To a mixture of the compound of Example 58 (100 mg, 0.5 mmol) and pyridine (90 μl, 1.1 mmol) in anhydrous acetonitrile (1 ml), at 0° C. and under nitrogen, was added diphosgene (33 μl, 0.28 mmol). The mixture was stirred at 0° C. for 30 min, before addition of cyclopropylmethanol (43 μl, 0.55 mmol). The reaction mixture was stirred at room temperature for 1 h and then filtered.

The filtrate was purified by automated preparative liquid chromatography (Gilson system, 150 mm×22.4 mm LUNA C18(2) 5 μm column, 20 ml/min) using an acetonitrile:water gradient [15:85 (3 min) to 98:2 (16 min)]. The appropriate fractions were combined and concentrated to give the title compound (30 mg).

Experimental MH$^+$ 299.4; expected 299.2 $^1$H-NMR (CDCl$_3$): 0.20-0.30 (2H), 0.50-0.60 (2H), 1.02-1.10 (1H), 1.59-1.65 (3H), 2.30-2.29 (6H), 3.96-4.05 (2H), 5.03-5.10 (1H), 6.62-6.65 (1H), 6.91-7.00 (3H), 7.40-7.41 (1H) Rhip. Funct. ED$_{100}$ mg/cm$^2$=0.03

Similarly Prepared from Example 58 were:

| Ex. No. | R$^6$ | Precursor | MH$^+$ Found/ Expected | Rhip. Funct. ED$_{100}$ mg/cm$^2$ |
|---|---|---|---|---|
| 190 | 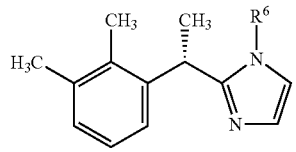 | 2-Isopropoxyethanol | 331.8 331.2 | <=10 |

-continued
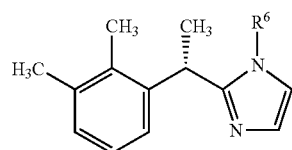
| Ex. No. | R⁶ | Precursor | MH⁺ Found/ Expected | Rhip. Funct. ED$_{100}$ mg/cm² |
|---|---|---|---|---|
| 191 | | 3-(3-Propoxypropoxy)- propan-1-ol | 403.5 403.3 | <=10 |
| 192 | | 2-Ethoxyethanol | 317.2 317.2 | 0.03 |
| 193 | | Cyclobutanol | 300.0 299.2 | <=10 |
| 194 | | 2-Cyclohexylethanol | 355.2 355.2 | 0.03 |
| 195 | | Tetrahydro-2H-pyran- 4-ylmethanol | 343.9 343.2 | <=10 |
| 196 | | 3-(3-Methoxypropoxy)- propan-1-ol | 375.2 375.2 | 0.03 |
| 197 | | (2-Methylcyclopropyl)- methanol | 270.0 269.2 decarboxylates | <=10 |
| 198 | | 3-[3-(3-Butoxy- propoxy)-propoxy]- propan-1-ol | 476.1 475.3 | >0.03 |
| 199 | | 2,2,2-Trifluoroethanol | 327.9 327.1 | <=10 |

-continued
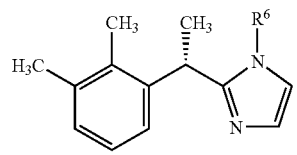
| Ex. No. | R⁶ | Precursor | MH⁺ Found/ Expected | Rhip. Funct. ED$_{100}$ mg/cm² |
|---|---|---|---|---|
| 200 | | Cyclobutylmethanol | 313.2 313.2 | 0.03 |
| 201 | | (1-Methylcyclopropyl)-methanol | 313.9 313.2 | |
| 202 | | 2-Cyclopropylethanol | 313.8 313.2 | <=10 |
| 203 | | 1,3-Dimethoxypropan-2-ol | 348.0 347.2 | >0.03 |
| 204 | | (3-Methyloxetan-3-yl)methanol | 329.9 329.2 | >0.03 |
| 205 | | 5-Methylhexan-1-ol | 300.0 299.2 decarboxyl | >0.03 |
| 206 | | 3-(4-Fluorophenoxy)-propan-1-ol | 397.2 397.2 | 0.03 |
| 207 | | 2,2,3,3,3-Pentafluoro-propan-1-ol | 377.8 377.1 | <=10 |
| 208 | | 2-(Methylthio)ethanol | 319.8 319.1 | <=10 |

-continued

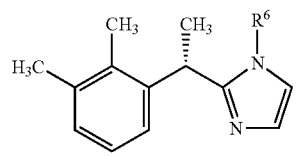

| Ex. No. | R[6] | Precursor | MH+ Found/ Expected | Rhip. Funct. ED$_{100}$ mg/cm$^2$ |
|---|---|---|---|---|
| 209 | (ethyl ester) | Ethanol | 273.7 273.2 | >0.03 |
| 210 | (3-cyclohexylpropyl ester) | 3-Cyclohexylpropan-1-ol | 369.9 369.3 | <=10 |
| 211 | (3-methylbutyl ester) | 3-Methylbutan-1-ol | 315.7 315.2 | >0.03 |
| 212 | (2-isopropylcyclohexyl ester) | 2-Isopropylcyclohexanol | 369.9 369.3 | <=10 |
| 213 | (2-methoxyethyl ester) | 2-Methoxyethanol | 303.2 303.2 | <=0.03, 0.1 |
| 214 | (tetrahydropyran-4-yl ester) | Tetrahydro-2H-pyran-4-ol | 370.8 (MeCN adduct) 370.2 | <=0.03 |
| 215 | (3-cyclopentylpropyl ester) | 3-Cyclopentylpropan-1-ol | 355.9 355.2 | >0.03 |
| 216 | (1-methylpiperidin-4-yl ester) | 1-Methylpiperidin-4-ol | 342.9 342.2 | <=10 |
| 217 | (4,4,4-trifluorobutyl ester) | 4,4,4-Trifluorobutan-1-ol | 355.2 355.2 | 0.03 |
| 218 | (cyclopentyl ester) | Cyclopentanol | 313.8 313.2 | <=10 |

-continued
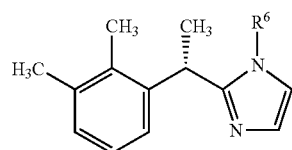
| Ex. No. | R<sup>6</sup> | Precursor | MH+ Found/ Expected | Rhip. Funct. ED$_{100}$ mg/cm$^2$ |
|---|---|---|---|---|
| 219 | | (1-Methylcyclohexyl)-methanol | — | >0.03 |
| 220 | | Cyclopentylmethanol | 328.1 327.2 | <=10 |
| 221 | | 4-Methylpentan-1-ol | 329.8 329.2 | >0.03 |
| 222 | | (1-Propylcyclobutyl)-methanol | 355.9 355.2 | >0.03 |
| 223 | | 2-[(4-Chlorophenyl)-thio]ethanol | 415.9 415.1 | >0.03 |
| 224 | | (2S)-2-Methylbutan-1-ol | 316.0 315.2 | >0.03 |
| 225 | | 3-(Methylthio)propan-1-ol | 333.8 333.2 | >0.03 |
| 226 | | Cyclohexylmethanol | 341.2 341.2 | 0.03 |
| 227 | | 3-Ethoxypropan-1-ol | 332.0 331.2 | >0.03 |

-continued
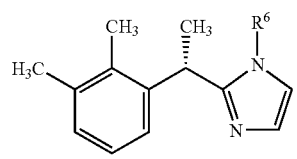
| Ex. No. | R[6] | Precursor | MH+ Found/ Expected | Rhip. Funct. ED$_{100}$ mg/cm$^2$ |
|---|---|---|---|---|
| 228 | | 2-Methylcyclohexanol | — | >0.03 |
| 229 | | 2-(2,6-Dimethyl-morpholin-4-yl)ethanol | 387.1 386.2 | <=10 |
| 230 | | Pentan-1-ol | 315.8 315.2 | <=10 |
| 231 | | trans-4-Methyl-cyclohexanol | 298.1 297.2 decarboxylates | <=10 |
| 232 | | 2-Propylpentan-1-ol | — | >0.03 |
| 233 | | 2-Ethylbutan-1-ol | — | <=10 |
| 234 | | 2,2-Dimethylpropan-1-ol | 315.8 315.2 | <=10 |
| 235 | | Bicyclo[2.2.1]hept-2-yl-methanol | 354.0 353.2 | >0.03 |

-continued
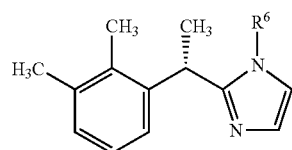
| Ex. No. | R[6] | Precursor | MH+ Found/ Expected | Rhip. Funct. ED$_{100}$ mg/cm$^2$ |
|---|---|---|---|---|
| 236 | | 3,3-Dimethylbutan-1-ol | 330.1 329.2 | >0.03 |
| 237 | | 4-Isopropylcyclo-hexanol | 369.3 369.3 | <=0.03< =0.01 |
| 238 | | 3-(Ethylthio)propan-1-ol | 347.9 347.2 | >0.03 |
| 239 | | Propan-1-ol | 287.7 287.2 | >0.03 |
| 240 | | 3-Methoxy-3-methylbutan-1-ol | 346.0 345.2 | >0.03 |
| 241 | | 3-(Dimethylamino)-2,2-dimethylpropan-1-ol | 359.0 358.2 | <=10 |
| 242 | | 4-Methoxybutan-1-ol | 332.1 331.2 | >0.03 |
| 243 | | 2,2,4-Trimethylpentan-1-ol | 357.3 357.3 | 0.03 |
| 244 | | Butan-1-ol | 301.8 301.2 | >0.03 |
| 245 | | 3-Fluoro-3-methyl-butan-1-ol | 333.8 333.2 | >0.03 |
| 246 | | 2-Isobutoxyethanol | 346.0 345.2 | 0.1 |

-continued
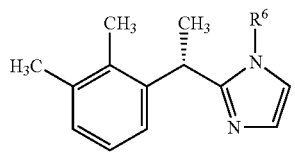
| Ex. No. | R⁶ | Precursor | MH⁺ Found/ Expected | Rhip. Funct. ED$_{100}$ mg/cm² |
|---|---|---|---|---|
| 247 | | 4-Cyclohexylbutan-1-ol | 383.3 383.3 | 0.1 |
| 248 | | 4-Methylpent-3-en-1-ol | 327.9 327.2 | <=10 |
| 249 | | Pentan-3-ol | 315.9 315.2 | >0.03 |
| 250 | | (2S)-Pentan-2-ol | — | >0.03 |
| 251 | | (3S)-3,7-Dimethyl- octan-1-ol | 386.1 385.3 | >0.03 |
| 252 | | 2-Propoxyethanol | 331.8 331.2 | >0.03 |
| 253 | | 2,3-Dimethylpentan-1-ol | 343.2 343.2 | 0.1 |
| 254 | | 2,2-Dimethylbutan-1-ol | — | >0.03 |
| 255 | | Methyl 3-hydroxy-2,2-dimethylpropanoate | 360.0 359.2 | <=10 |

Example 190

2-Isopropoxyethyl 2-[(1S)-1-(2,3-dimethylphenyl)ethyl]-1H-imidazole-1-carboxylate $^1$H-NMR (d$_6$-Acetone): 1.00-1.09 (6H), 1.51-1.55 (3H), 2.25-2.27 (3H), 2.36-2.38 (3H), 3.50-3.63 (3H), 4.32-4.36 (2H), 5.08-5.12 (1H), 6.55-6.58 (1H), 6.82-6.87 (1H), 6.95-6.98 (2H), 7.45-7.47 (1H)

Example 191

3-(3-Propoxypropoxy)propyl 2-[(1S)-1-(2,3-dimethylphenyl)ethyl]-1H-imidazole-1-carboxylate $^1$H-NMR (d$_6$-Acetone): 0.81-0.92 (3H), 0.97-1.13 (6H), 1.42-1.53 (2H), 1.57-1.60 (3H), 2.25-2.40 (6H), 3.21-3.40 (4H), 3.50-3.61 (3H), 5.00-5.15 (2H), 6.50-6.58 (1H), 6.83-6.91 (1H), 6.95-6.98 (2H), 7.47-7.50 (1H)

Example 192

2-Ethoxyethyl 2-[(1S)-1-(2,3-dimethylphenyl)ethyl]-1H-imidazole-1-carboxylate $^1$H-NMR (d$_6$-Acetone): 1.02-1.09 (3H), 1.52-1.57 (3H), 2.24-2.26 (3H), 2.37-2.39 (3H), 3.40-3.48 (2H), 3.59-3.66 (2H), 4.30-4.37 (2H), 5.05-5.11 (1H), 6.55-6.58 (1H), 6.84-6.90 (1H), 6.95-6.99 (2H), 7.48-7.49 (1H)

Example 193

Cyclobutyl 2-[(1S)-1-(2,3-dimethylphenyl)ethyl]-1H-imidazole-1-carboxylate $^1$H-NMR (d$_6$-Acetone): 1.53-1.56 (3H), 1.60-1.65 (1H), 1.70-1.75 (1H), 1.98-2.08 (2H), 2.22-2.30 (5H), 2.36-2.39 (3H), 4.98-5.06 (2H), 6.48-6.50 (1H), 6.84-6.87 (1H), 6.95-6.98 (2H), 7.50-7.52 (1H)

Example 194

2-Cyclohexylethyl 2-[(1S)-1-(2,3-dimethylphenyl)ethyl]-1H-imidazole-1-carboxylate $^1$H-NMR (d$_6$-Acetone): 0.81-0.97 (2H), 1.10-1.30 (4H), 1.42-1.55 (5H), 1.59-1.70 (5H), 2.27-2.29 (3H), 2.36-2.38 (3H), 4.20-4.30 (2H), 5.04-5.09 (1H), 6.50-6.53 (1H), 6.85-6.89 (1H), 6.95-6.99 (2H), 7.46-7.47 (1H)

CHN Analysis Predicted: % C=74.54; % H=8.53; % N=7.90. Observed: % C=74.31; % H=8.50; % N=7.95.

Example 195

Tetrahydro-2H-pyran-4-ylmethyl 2-[(1S)-1-(2,3-dimethylphenyl)ethyl]-1H-imidazole-1-carboxylate $^1$H-NMR (d$_6$-Acetone): 1.17-1.24 (2H), 1.40-1.48 (2H), 1.54-1.57 (3H), 1.80-1.90 (1H), 2.27-2.29 (3H), 2.37-2.39 (3H), 3.20-3.30 (2H), 3.79-3.84 (2H), 4.01-4.15 (2H), 5.02-5.09 (1H), 6.51-6.54 (1H), 6.83-6.86 (1H), 6.95-6.98 (2H), 7.50-7.51 (1H)

Example 196

3-(3-Methoxypropoxy)propyl 2-[(1S)-1-(2,3-dimethylphenyl)ethyl]-1H-imidazole-1-carboxylate $^1$H-NMR (d$_6$-Acetone): 0.95-1.04 (4H), 1.18-1.21 (3H), 1.51-1.56 (3H), 2.27-2.29 (3H), 2.37-2.39 (3H), 3.20-3.23 (2H), 3.24-3.40 (3H), 3.40-3.59 (2H), 5.04-5.10 (2H), 6.49-6.59 (1H), 6.82-6.88 (1H), 6.96-6.99 (2H), 7.46-7.48 (1H)

Example 197

(2-Methylcyclopropyl)methyl 2-[(1S)-1-(2,3-dimethylphenyl)ethyl]-1H-imidazole-1-carboxylate $^1$H-NMR (d$_6$-Acetone): 0.21-0.26 (1H), 0.40-0.48 (1H), 0.62-0.81 (2H), 0.92-0.97 (3H), 1.53-1.56 (3H), 2.26-2.28 (3H), 2.37-2.39 (3H), 4.00-4.12 (2H), 5.05-5.10 (1H), 6.56-6.59 (1H), 6.86-6.89 (1H), 6.95-6.98 (2H), 7.50-7.51 (1H)

Example 198

3-[3-(3-Butoxypropoxy)propoxy]propyl 2-[(1S)-1-(2,3-dimethylphenyl)ethyl]-1H-imidazole-1-carboxylate $^1$H-NMR (d$_6$-Acetone): 1.15-1.20 (3H), 1.30-1.40 (2H), 1.41-1.50 (2H), 1.53-1.56 (3H), 2.25-2.29 (3H), 2.33-2.37 (3H), 3.20-3.25 (1H), 3.30-3.41 (4H), 3.47-3.61 (5H), 5.00-5.05 (1H), 5.10-5.17 (2H), 6.50-6.54 (1H), 6.82-6.86 (1H), 6.95-6.98 (2H), 7.50-7.53 (1H)

Example 199

2,2,2-Trifluoroethyl 2-[(1S)-1-(2,3-dimethylphenyl)ethyl]-1H-imidazole-1-carboxylate $^1$H-NMR (d$_6$-Acetone): 1.53-1.56 (3H), 2.26-2.28 (3H), 2.36-2.38 (3H), 4.80-4.91 (2H), 5.05-5.10 (1H), 6.56-6.59 (1H), 6.86-6.88 (1H), 6.96-6.98 (1H), 7.00-7.01 (1H), 7.50-7.51 (1H)

Example 200

Cyclobutylmethyl 2-[(1S)-1-(2,3-dimethylphenyl)ethyl]-1H-imidazole-1-carboxylate $^1$H-NMR (d$_6$-Acetone): 1.50-1.55 (3H), 1.70-1.80 (2H), 1.80-1.90 (2H), 1.90-2.02 (2H), 2.25-2.27 (3H), 2.35-2.37 (3H), 4.12-4.21 (2H), 5.03-5.09 (1H), 6.53-6.57 (1H), 6.85-6.89 (1H), 6.95-6.98 (2H), 7.46-7.47 (1H)

Example 201

(1-Methylcyclopropyl)methyl 2-[(1S)-1-(2,3-dimethylphenyl)ethyl]-1H-imidazole-1-carboxylate $^1$H-NMR (d$_6$-Acetone): 0.30-0.40 (2H), 0.45-0.55 (2H), 1.02-1.05 (3H), 1.53-1.56 (3H), 2.23-2.25 (3H), 2.34-2.36 (3H), 4.00-4.07 (2H), 5.10-5.15 (1H), 6.57-6.59 (1H), 6.84-6.86 (1H), 6.95-6.98 (2H), 7.51-7.53 (1H)

Example 202

2-Cyclopropylethyl 2-[(1S)-1-(2,3-dimethylphenyl)ethyl]-1H-imidazole-1-carboxylate $^1$H-NMR (d$_6$-Acetone): 0.00-0.05 (2H), 0.35-0.40 (2H), 0.60-0.68 (1H), 1.45-1.56 (5H), 2.24-2.26 (3H), 2.35-2.38 (3H), 4.20-4.35 (2H), 5.05-5.13 (1H), 6.51-6.53 (1H), 6.84-6.88 (1H), 6.92-6.98 (2H), 7.49-7.50 (1H)

Example 203

2-Methoxy-1-(methoxymethyl)ethyl 2-[(1S)-1-(2,3-dimethylphenyl)ethyl]-1H-imidazole-1-carboxylate $^1$H-NMR (d$_6$-Acetone): 1.50-1.53 (3H), 2.29-2.31 (3H), 2.36-2.38 (3H), 3.29-3.35 (6H), 3.41-3.51 (4H), 5.05-5.12 (2H), 6.53-6.55 (1H), 6.85-6.87 (1H), 6.95-6.98 (2H), 7.49-7.51 (1H)

Example 204

(3-Methyloxetan-3-yl)methyl 2-[(1S)-1-(2,3-dimethylphenyl)ethyl]-1H-imidazole-1-carboxylate $^1$H-NMR (d$_6$-Acetone): 1.25-1.26 (3H), 1.55-1.58 (3H), 2.26-2.28 (3H), 2.36-2.38 (3H), 4.23-4.29 (3H), 4.39-4.44 (3H), 5.05-5.10 (1H), 6.58-6.60 (1H), 6.84-6.87 (1H), 6.95-6.98 (2H), 7.50-7.52 (1H)

Example 205

5-Methylhexyl 2-[(1S)-1-(2,3-dimethylphenyl)ethyl]-1H-imidazole-1-carboxylate $^1$H-NMR (d$_6$-Acetone): 0.80-0.84 (6H), 1.15-1.20 (2H), 1.25-1.30 (2H), 1.49-1.61 (5H), 2.26-2.28 (3H), 2.37-2.39 (3H), 4.19-4.25 (2H), 5.05-5.10 (1H), 6.56-6.58 (1H), 6.84-6.86 (1H), 6.95-6.98 (2H), 7.48-7.50 (1H)

Example 206

3-(4-Fluorophenoxy)propyl 2-[(1S)-1-(2,3-dimethylphenyl)ethyl]-1H-imidazole-1-carboxylate $^1$H-NMR (d$_6$-Acetone): 1.50-1.53 (3H), 2.05-2.10 (2H), 2.24-2.26 (3H), 2.34-2.37 (3H), 3.97-4.01 (2H), 4.36-4.40 (1H), 4.01-4.05 (1H), 5.02-5.07 (1H), 6.50-6.53 (1H), 6.82-6.90 (3H), 6.91-6.96 (2H), 7.00-7.05 (2H), 7.51-7.52 (1H)
CHN Analysis
Predicted: % C=69.68; % H=6.36; % N=7.07.
Observed: % C=69.70; % H=6.37; % N=7.07.

Example 207

2,2,3,3,3-Pentafluoropropyl 2-[(1S)-1-(2,3-dimethylphenyl)ethyl]-1H-imidazole-1-carboxylate $^1$H-NMR (d$_6$-Acetone): 1.53-1.57 (3H), 2.25-2.27 (3H), 2.35-2.38 (3H), 4.85-4.99 (2H), 5.03-5.09 (1H), 6.55-6.58 (1H), 6.85-6.99 (2H), 7.00-7.01 (1H), 7.45-7.46 (1H)

Example 208

2-(Methylthio)ethyl 2-[(1S)-1-(2,3-dimethylphenyl)ethyl]-1H-imidazole-1-carboxylate $^1$H-NMR (d$_6$-Acetone): 1.51-1.54 (3H), 2.02-2.05 (3H), 2.24-2.26 (3H), 2.35-2.38 (3H), 2.61-2.72 (2H), 4.30-4.41 (2H), 5.03-5.10 (1H), 6.52-6.56 (1H), 6.85-6.91 (1H), 6.95-6.99 (2H), 7.50-7.51 (1H)

Example 209

Ethyl 2-[(1S)-1-(2,3-dimethylphenyl)ethyl]-1H-imidazole-1-carboxylate $^1$H-NMR (d$_6$-Acetone): 1.17-1.21 (3H), 1.51-1.53 (3H), 2.26-2.28 (3H), 2.36-2.38 (3H), 4.19-4.26 (2H), 5.03-5.08 (1H), 6.51-6.53 (1H), 6.85-6.88 (1H), 6.96-6.99 (2H), 7.47-7.49 (1H)

Example 210

3-Cyclohexylpropyl 2-[(1S)-1-(2,3-dimethylphenyl)ethyl]-1H-imidazole-1-carboxylate $^1$H-NMR (d$_6$-Acetone): 0.79-0.89 (2H), 1.10-1.25 (6H), 1.51-1.54 (3H), 1.58-1.70 (7H), 2.25-2.27 (3H), 2.35-2.38 (3H), 4.12-4.25 (2H), 5.02-5.09 (1H), 6.50-6.53 (1H), 6.84-6.89 (1H), 6.95-6.98 (2H), 7.49-7.54 (1H)

Example 211

3-Methylbutyl 2-[(1S)-1-(2,3-dimethylphenyl)ethyl]-1H-imidazole-1-carboxylate $^1$H-NMR (d$_6$-Acetone): 0.81-0.87 (6H), 1.43-1.60 (6H), 2.27-2.29 (3H), 2.36-2.38 (3H), 4.19-4.27 (2H), 5.03-5.08 (1H), 6.51-6.53 (1H), 6.86-6.88 (1H), 6.96-6.99 (2H), 7.47-7.49 (1H)

Example 212

2-Isopropylcyclohexyl 2-[(1S)-1-(2,3-dimethylphenyl)ethyl]-1H-imidazole-1-carboxylate $^1$H-NMR (d$_6$-Acetone): 0.50-0.54 (3H), 0.70-0.80 (3H), 1.00-1.20 (3H), 1.20-1.45 (3H), 1.50-1.60 (3H), 1.61-1.72 (3H), 1.80-1.89 (1H), 2.24-2.28 (3H), 2.35-2.38 (3H), 4.60-4.65 (1H), 4.70-4.76 (1H), 5.00-5.08 (1H), 6.35-6.45 (1H), 6.82-6.90 (1H), 6.95-6.98 (2H), 7.49-7.54 (1H)

Example 213

2-Methoxyethyl 2-[(1S)-1-(2,3-dimethylphenyl)ethyl]-1H-imidazole-1-carboxylate $^1$H-NMR (d$_6$-Acetone): 1.51-1.54 (3H), 2.25-2.27 (3H), 2.31-2.33 (3H), 3.22-3.23 (3H), 3.45-3.60 (2H), 4.30-4.40 (2H), 5.04-5.11 (1H), 6.56-6.58 (1H), 6.84-6.86 (1H), 6.95-6.99 (2H), 7.44-7.45 (1H)

Example 214

Tetrahydro-2H-pyran-4-yl 2-[(1S)-1-(2,3-dimethylphenyl)ethyl]-1H-imidazole-1-carboxylate $^1$H-NMR (d$_6$-Acetone): 1.50-1.55 (3H), 1.90-1.96 (1H), 2.09-2.11 (1H), 2.24-2.27 (3H), 2.32-2.34 (3H), 3.70-3.83 (4H), 5.02-5.09 (1H), 5.34-5.37 (1H), 6.50-6.53 (1H), 6.83-6.86 (1H), 6.96-6.99 (2H), 7.44-7.45 (1H)

Example 215

3-Cyclopentylpropyl 2-[(1S)-1-(2,3-dimethylphenyl)ethyl]-1H-imidazole-1-carboxylate $^1$H-NMR (d$_6$-Acetone): 0.99-1.05 (2H), 1.22-1.28 (2H), 1.48-1.62 (9H), 1.69-1.74 (3H), 2.26-2.28 (3H), 2.36-2.38 (3H), 4.15-4.22 (2H), 5.03-5.08 (1H), 6.51-6.53 (1H), 6.85-6.87 (1H), 6.95-6.98 (2H), 7.47-7.49 (1H)

Example 216

1-Methylpiperidin-4-yl 2-[(1S)-1-(2,3-dimethylphenyl)ethyl]-1H-imidazole-1-carboxylate $^1$H-NMR (d$_6$-Acetone): 1.50-1.54 (3H), 1.60-1.71 (3H), 1.79-1.88 (2H), 2.10-2.21 (4H), 2.27-2.29 (3H), 2.36-2.38 (3H), 2.50-2.60 (2H), 4.70-4.80 (1H), 5.03-5.10 (1H), 6.52-6.54 (1H), 6.82-6.88 (1H), 6.95-6.98 (2H), 7.49-7.50 (1H)

Example 217

4,4,4-Trifluorobutyl 2-[(1S)-1-(2,3-dimethylphenyl)ethyl]-1H-imidazole-1-carboxylate $^1$H-NMR (d$_6$-Acetone): 1.50-1.55 (3H), 1.89-1.96 (3H), 2.10-2.21 (4H), 2.37-2.39 (3H), 4.21-4.26 (1H), 4.35-4.40 (1H), 5.02-5.09 (1H), 6.50-6.53 (1H), 6.83-6.86 (1H), 6.96-6.99 (2H), 7.47-7.48 (1H)

Example 218

Cyclopentyl 2-[(1S)-1-(2,3-dimethylphenyl)ethyl]-1H-imidazole-1-carboxylate $^1$H-NMR (d$_6$-Acetone): 1.50-1.54 (3H), 1.55-1.75 (6H), 1.80-1.90 (2H), 2.25-2.27 (3H), 2.35-2.37 (3H), 5.05-5.11 (1H), 5.18-5.20 (1H), 6.52-6.54 (1H), 6.83-6.98 (3H), 7.44-7.45 (1H)

Example 219

(1-Methylcyclohexyl)methyl 2-[(1S)-1-(2,3-dimethylphenyl)ethyl]-1H-imidazole-1-carboxylate $^1$H-NMR (d$_6$-Acetone): 0.92-0.93 (3H), 1.20-1.40 (5H), 1.40-1.49 (5H), 1.53-1.56 (3H), 2.26-2.28 (3H), 2.36-2.38 (3H), 3.96-4.02 (2H), 5.10-5.15 (1H), 6.56-6.59 (1H), 6.85-6.87 (1H), 6.95-6.98 (2H), 7.48-7.50 (1H)

Example 220

Cyclopentylmethyl 2-[(1S)-1-(2,3-dimethylphenyl)ethyl]-1H-imidazole-1-carboxylate $^1$H-NMR (d$_6$-Acetone): 1.17-1.25 (2H), 1.45-1.70 (11H), 2.15-2.21 (1H), 2.25-2.26 (3H), 2.35-2.37 (3H), 4.04-4.19 (2H), 5.04-5.10 (1H), 6.52-6.55 (1H), 6.83-6.88 (1H), 6.95-6.98 (2H), 7.47-7.48 (1H)

Example 221

4-Methylpentyl 2-[(1S)-1-(2,3-dimethylphenyl)ethyl]-1H-imidazole-1-carboxylate $^1$H-NMR (d$_6$-Acetone): 0.80-0.85 (6H), 1.12-1.20 (2H), 1.50-1.56 (4H), 1.58-1.61 (2H), 2.27-2.29 (3H), 2.35-2.37 (3H), 4.14-4.19 (1H), 4.20-4.24 (1H), 5.04-5.08 (1H), 6.52-6.55 (1H), 6.85-6.87 (1H), 6.93-6.97 (2H), 7.47-7.49 (1H)

Example 222

(1-Propylcyclobutyl)methyl 2-[(1S)-1-(2,3-dimethylphenyl)ethyl]-1H-imidazole-1-carboxylate $^1$H-NMR (d$_6$-Acetone): 0.81-0.85 (3H), 1.20-1.26 (2H), 1.42-1.46 (2H), 1.52-1.56 (3H), 1.75-1.86 (6H), 2.26-2.28 (3H), 2.35-2.37 (3H), 4.15-4.22 (2H), 5.09-5.13 (1H), 6.58-6.60 (1H), 6.85-6.87 (1H), 6.95-6.98 (2H), 7.43-7.45 (1H)

Example 223

2-[(4-Chlorophenyl)thio]ethyl 2-[(1S)-1-(2,3-dimethylphenyl)ethyl]-1H-imidazole-1-carboxylate $^1$H-NMR (d$_6$-Acetone): 1.54-1.56 (3H), 2.25-2.27 (3H), 2.35-2.37 (3H), 3.20-3.25 (2H), 4.36-4.40 (2H), 5.00-5.05 (1H), 6.51-6.53 (1H), 6.85-6.87 (1H), 6.91-6.95 (2H), 7.30-7.40 (5H)

Example 224

(2S)-2-Methylbutyl 2-[(1S)-1-(2,3-dimethylphenyl)ethyl]-1H-imidazole-1-carboxylate $^1$H-NMR (d$_6$-Acetone): 0.90-0.95 (3H), 1.10-1.20 (1H), 1.32-1.41 (1H), 1.54-1.56 (3H), 1.65-1.71 (1H), 2.25-2.27 (3H), 2.34-2.36 (3H), 4.03-4.05 (2H), 5.04-5.08 (1H), 6.52-6.54 (1H), 6.83-6.86 (1H), 6.96-7.00 (2H), 7.48-7.50 (1H)

Example 225

3-(Methylthio)propyl 2-[(1S)-1-(2,3-dimethylphenyl)ethyl]-1H-imidazole-1-carboxylate $^1$H-NMR (d$_6$-Acetone): 1.52-1.54 (3H), 1.85-1.92 (2H), 2.05-2.07 (3H), 2.27-2.29 (3H), 2.36-2.38 (3H), 2.42-2.46 (2H), 4.22-4.30 (2H), 4.23-4.29 (1H), 4.32-4.38 (1H), 6.51-6.53 (1H), 6.83-6.86 (1H), 6.96-6.99 (2H), 7.51-7.53 (1H)

Example 226

Cyclohexylmethyl 2-[(1S)-1-(2,3-dimethylphenyl)ethyl]-1H-imidazole-1-carboxylate $^1$H-NMR (d$_6$-Acetone): 0.82-0.99 (2H), 1.05-1.23 (3H), 1.50-1.55 (3H), 1.56-1.70 (6H), 2.25-2.27 (3H), 2.37-2.39 (3H), 3.98-4.08 (2H), 5.02-5.09 (1H), 6.49-6.52 (1H), 6.83-6.86 (1H), 6.96-6.99 (2H), 7.48-7.49 (1H)

CHN Analysis
Predicted: % C=74.08; % H=8.29; % N=8.23.
Observed: % C=74.09; % H=8.27; % N=8.27.

Example 227

3-Ethoxypropyl 2-[(1S)-1-(2,3-dimethylphenyl)ethyl]-1H-imidazole-1-carboxylate $^1$H-NMR (d$_6$-Acetone): 1.02-1.06 (3H), 1.54-1.57 (3H), 1.80-1.86 (2H), 2.26-2.28 (3H), 2.36-2.38 (3H), 3.35-3.40 (4H), 4.21-4.30 (2H), 5.03-5.05 (1H), 6.52-6.54 (1H), 6.83-6.86 (1H), 6.96-6.99 (2H), 7.50-7.52 (1H)

Example 228

2-Methylcyclohexyl 2-[(1S)-1-(2,3-dimethylphenyl)ethyl]-1H-imidazole-1-carboxylate $^1$H-NMR (d$_6$-Acetone): 0.70-0.78 (3H), 1.00-1.10 (2H), 1.20-1.30 (2H), 1.40-1.45 (1H), 1.55-1.58 (3H), 1.60-1.64 (1H), 1.65-1.75 (2H), 1.80-1.85 (1H), 2.26-2.28 (3H), 2.36-2.38 (3H), 4.30-4.36 (1H), 5.00-5.05 (1H), 6.40-6.44 (1H), 6.82-6.86 (1H), 6.96-6.99 (2H), 7.50-7.52 (1H)

Example 229

2-(2,6-Dimethylmorpholin-4-yl)ethyl 2-[(1S)-1-(2,3-dimethylphenyl)ethyl]-1H-imidazole-1-carboxylate $^1$H-NMR (d$_6$-Acetone): 0.98-1.03 (3H), 1.53-1.56 (3H), 1.59-1.65 (1H), 2.21-2.24 (1H), 2.27-2.28 (3H), 2.38-2.39 (3H), 2.42-2.58 (2H), 2.60-2.63 (1H), 2.65-2.67 (1H), 3.20-3.29 (1H), 3.35-3.41 (1H), 4.30-4.35 (2H), 5.04-5.09 (1H), 6.54-6.56 (1H), 6.82-6.87 (1H), 6.95-7.00 (2H), 7.49-7.50 (1H)

Example 230

Pentyl 2-[(1S)-1-(2,3-dimethylphenyl)ethyl]-1H-imidazole-1-carboxylate $^1$H-NMR (d$_6$-Acetone): 0.81-0.86 (3H), 1.20-1.33 (4H), 1.53-1.56 (3H), 1.59-1.62 (2H), 2.26-2.27 (3H), 2.35-2.36

(3H), 4.17-4.25 (2H), 5.04-5.10 (1H), 6.52-6.54 (1H), 6.83-6.87 (1H), 6.95-6.97 (2H), 7.49-7.50 (1H)

Example 231 trans-4-Methylcyclohexyl 2-[(1S)-1-(2,3-dimethylphenyl)ethyl]-1H-imidazole-1-carboxylate $^1$H-NMR (d$_6$-Acetone): 0.82-0.90 (3H), 1.00-1.10 (1H), 1.20-1.45 (4H), 1.52-1.55 (3H), 1.65-1.70 (2H), 1.85-1.95 (2H), 2.24-2.30 (6H), 4.60-4.66 (1H), 5.02-5.10 (1H), 6.52-6.55 (1H), 6.82-6.98 (3H), 7.46-7.49 (1H)

Example 232

2-Propylpentyl 2-[(1S)-1-(2,3-dimethylphenyl)ethyl]-1H-imidazole-1-carboxylate $^1$H-NMR (d$_6$-Acetone): 0.90-0.97 (6H), 1.20-1.38 (8H), 1.54-1.58 (3H), 1.65-1.72 (1H), 2.27-2.29 (3H), 2.36-2.38 (3H), 4.10-4.19 (2H), 5.10-5.15 (1H), 6.55-6.58 (1H), 6.85-6.88 (1H), 6.96-6.99 (2H), 7.44-7.46 (1H)

Example 233

2-Ethylbutyl 2-[(1S)-1-(2,3-dimethylphenyl)ethyl]-1H-imidazole-1-carboxylate $^1$H-NMR (d$_6$-Acetone): 0.90-0.96 (6H), 1.24-1.36 (4H), 1.54-1.58 (4H), 2.27-2.29 (3H), 2.36-2.38 (3H), 4.10-4.15 (1H), 4.16-4.20 (1H), 5.07-5.11 (1H), 5.57-5.59 (1H), 6.83-6.87 (1H), 6.95-6.98 (2H), 7.46-7.48 (1H)

Example 234

2,2-Dimethylpropyl 2-[(1S)-1-(2,3-dimethylphenyl)ethyl]-1H-imidazole-1-carboxylate $^1$H-NMR (d$_6$-Acetone): 0.95-0.98 (9H), 1.54-1.57 (3H), 2.26-2.28 (3H), 2.32-2.34 (3H), 3.90-3.94 (1H), 3.96-4.00 (1H), 5.09-5.13 (1H), 6.57-6.59 (1H), 6.84-6.88 (1H), 6.94-6.98 (2H), 7.55-7.57 (1H)

Example 235

Bicyclo[2.2.1]hept-2-ylmethyl 2-[(1S)-1-(2,3-dimethylphenyl)ethyl]-1H-imidazole-1-carboxylate $^1$H-NMR (d$_6$-Acetone): 0.62-0.70 (1H), 1.10-1.16 (2H), 1.25-1.35 (3H), 1.40-1.48 (2H), 1.52-1.57 (3H), 1.61-1.66 (1H), 2.12-2.19 (2H), 2.28-2.30 (3H), 2.37-2.39 (3H), 4.19-4.27 (2H), 5.03-5.08 (1H), 6.51-6.53 (1H), 6.84-6.88 (1H), 6.96-6.99 (2H), 7.46-7.48 (1H)

Example 236

3,3-Dimethylbutyl 2-[(1S)-1-(2,3-dimethylphenyl)ethyl]-1H-imidazole-1-carboxylate $^1$H-NMR (d$_6$-Acetone): 0.89-0.92 (3H), 1.48-1.57 (5H), 2.28-2.30 (3H), 2.37-2.39 (3H), 4.20-4.25 (1H), 4.30-4.35 (1H), 5.02-5.08 (1H), 6.51-6.53 (1H), 6.84-6.87 (1H), 6.96-6.99 (2H), 7.45-7.47 (1H)

Example 237

4-Isopropylcyclohexyl 2-[(1S)-1-(2,3-dimethylphenyl)ethyl]-1H-imidazole-1-carboxylate $^1$H-NMR (d$_6$-Acetone): 0.81-0.86 (6H), 1.03-1.20 (2H), 1.20-1.29 (2H), 1.38-1.48 (2H), 1.54-1.57 (3H), 1.75-1.81 (2H), 1.90-2.00 (2H), 2.27-2.29 (3H), 2.37-2.39 (3H), 4.60-4.67 (1H), 5.02-5.08 (1H), 6.49-6.52 (1H), 6.84-6.87 (1H), 6.96-6.99 (2H), 7.46-7.48 (1H)

CHN Analysis
Predicted: % C=74.96; % H=8.75; % N=7.60.
Observed: % C=74.98; % H=8.78; % N=7.58.

Example 238

3-(Ethylthio)propyl 2-[(1S)-1-(2,3-dimethylphenyl)ethyl]-1H-imidazole-1-carboxylate $^1$H-NMR (d$_6$-Acetone): 1.15-1.20 (3H), 1.55-1.58 (3H), 1.83-1.89 (2H), 2.28-2.30 (3H), 2.36-2.38 (3H), 2.42-2.50 (4H), 4.25-4.30 (1H), 4.33-4.38 (1H), 5.04-5.08 (1H), 6.53-6.55 (1H), 6.85-6.88 (1H), 6.96-6.99 (2H), 7.50-7.52 (1H)

Example 239

Propyl 2-[(1S)-1-(2,3-dimethylphenyl)ethyl]-1H-imidazole-1-carboxylate $^1$H-NMR (d$_6$-Acetone): 0.82-0.86 (3H), 1.55-1.58 (3H), 1.60-1.66 (2H), 2.27-2.29 (3H), 2.36-2.38 (3H), 4.10-4.20 (2H), 5.04-5.10 (1H), 6.53-6.55 (1H), 6.85-6.88 (1H), 6.96-6.99 (2H), 7.49-7.51 (1H)

Example 240

3-Methoxy-3-methylbutyl 2-[(1S)-1-(2,3-dimethylphenyl)ethyl]-1H-imidazole-1-carboxylate $^1$H-NMR (d$_6$-Acetone): 1.10-1.12 (6H), 1.53-1.55 (3H), 1.70-1.80 (2H), 2.26-2.28 (3H), 2.37-2.38 (3H), 3.09-3.10 (3H), 4.21-4.31 (2H), 5.03-5.07 (1H), 6.51-6.53 (1H), 6.85-6.88 (1H), 6.97-6.99 (2H), 7.46-7.47 (1H)

Example 241

3-(Dimethylamino)-2,2-dimethylpropyl 2-[(1S)-1-(2,3-dimethylphenyl)ethyl]-1H-imidazole-1-carboxylate $^1$H-NMR (d$_6$-Acetone): 0.83-0.90 (6H), 1.52-1.55 (3H), 2.15-2.20 (6H), 2.23-2.24 (3H), 2.35-2.36 (3H), 4.00-4.08 (2H), 5.10-5.16 (1H), 6.52-6.55 (1H), 6.83-6.87 (1H), 6.95-6.99 (2H), 7.49-7.50 (1H)

Example 242

4-Methoxybutyl 2-[(1S)-1-(2,3-dimethylphenyl)ethyl]-1H-imidazole-1-carboxylate $^1$H-NMR (d$_6$-Acetone): 1.47-1.55 (5H), 1.61-1.66 (2H), 2.28-2.30 (3H), 2.37-2.39 (3H), 3.21-3.22 (3H), 3.30-3.34 (2H), 4.20-4.26 (2H), 5.04-5.08 (1H), 6.52-6.54 (1H), 6.83-6.86 (1H), 6.97-7.00 (2H), 7.48-7.49 (1H)

Example 243

2,2,4-Trimethylpentyl 2-[(1S)-1-(2,3-dimethylphenyl)ethyl]-1H-imidazole-1-carboxylate $^1$H-NMR (d$_6$-Acetone): 0.82-0.90 (6H), 0.95-0.97 (6H), 1.20-1.22 (2H), 1.53-1.57 (3H), 1.61-1.71 (1H), 2.25-2.27 (3H), 2.35-2.37 (3H), 3.95-4.01 (2H), 5.10-5.15 (1H), 6.55-6.58 (1H), 6.84-6.87 (1H), 6.95-7.00 (2H), 7.49-7.50 (1H)

CHN Analysis
Predicted: % C=74.12; % H=9.05; % N=7.86.
Observed: % C=74.22; % H=9.05; % N=7.91.

Example 244

Butyl 2-[(1S)-1-(2,3-dimethylphenyl)ethyl]-1H-imidazole-1-carboxylate $^1$H-NMR (d$_6$-Acetone): 0.82-0.88 (3H), 1.21-1.28 (2H), 1.54-1.60 (5H), 2.28-2.30 (3H), 2.37-2.39 (3H), 4.17-4.25 (2H), 5.03-5.07 (1H), 6.52-6.54 (1H), 6.82-6.85 (1H), 6.97-7.00 (2H), 7.47-7.49 (1H)

Example 245

3-Fluoro-3-methylbutyl 2-[(1S)-1-(2,3-dimethylphenyl)ethyl]-1H-imidazole-1-carboxylate $^1$H-NMR (d$_6$-Acetone): 1.30-1.33 (3H), 1.37-1.39 (3H), 1.53-1.56 (3H), 1.85-1.95 (2H), 2.29-2.31 (3H), 2.36-2.38 (3H), 4.30-4.34 (1H), 4.39-5.02 (1H), 5.03-5.07 (1H), 6.52-6.54 (1H), 6.85-6.88 (1H), 6.96-6.99 (2H), 7.45-7.46 (1H)

Example 246

2-Isobutoxyethyl 2-[(1S)-1-(2,3-dimethylphenyl)ethyl]-1H-imidazole-1-carboxylate $^1$H-NMR (d$_6$-Acetone): 0.80-0.85 (6H), 1.53-1.57 (3H), 1.65-1.79 (1H), 2.26-2.28 (3H), 2.35-2.37 (3H), 3.15-3.20 (2H), 3.57-3.64 (1H), 4.31-4.40 (2H), 5.06-5.15 (1H), 6.57-6.60 (1H), 6.84-6.87 (1H), 6.95-6.99 (2H), 7.47-7.48 (1H)

Example 247

4-Cyclohexylbutyl 2-[(1S)-1-(2,3-dimethylphenyl)ethyl]-1H-imidazole-1-carboxylate $^1$H-NMR (d$_6$-Acetone): 0.80-0.90 (2H), 1.10-1.25 (8H), 1.50-1.70 (10H), 2.27-2.29 (3H), 2.37-2.39 (3H), 4.15-4.26 (2H), 5.02-5.10 (1H), 6.50-6.52 (1H), 6.84-6.87 (1H), 6.96-7.00 (2H), 7.47-7.48 (1H)

Example 248

4-Methylpent-3-en-1-yl 2-[(1S)-1-(2,3-dimethylphenyl)ethyl]-1H-imidazole-1-carboxylate $^1$H-NMR (d$_6$-Acetone): 1.50-1.60 (6H), 1.62-1.64 (3H), 2.28-2.30 (3H), 2.25-2.35 (2H), 2.37-2.39 (3H), 4.11-4.21 (2H), 5.02-5.10 (2H), 6.53-6.57 (1H), 6.84-6.89 (1H), 6.96-6.99 (2H), 7.42-7.43 (1H)

Example 249

1-Ethylpropyl 2-[(1S)-1-(2,3-dimethylphenyl)ethyl]-1H-imidazole-1-carboxylate $^1$H-NMR (d$_6$-Acetone): 0.72-0.78 (3H), 1.44-1.53 (7H), 2.25-2.28 (3H), 2.32-2.35 (3H), 4.74-4.79 (1H), 5.01-5.06 (1H), 6.42-6.44 (1H), 6.82-6.86 (1H), 6.96-6.99 (2H), 7.50-7.52 (1H)

Example 250

(1S)-1-Methylbutyl 2-[(1S)-1-(2,3-dimethylphenyl)ethyl]-1H-imidazole-1-carboxylate $^1$H-NMR (d$_6$-Acetone): 0.89-0.93 (3H), 1.10-1.22 (5H), 1.41-1.52 (5H), 2.25-2.28 (3H), 2.36-2.39 (3H), 4.89-4.95 (1H), 5.01-5.06 (1H), 6.41-6.46 (1H), 6.85-6.90 (1H), 6.96-6.99 (2H), 7.47-7.49 (1H)

Example 251

(3S)-3,7-Dimethyloctyl 2-[(1S)-1-(2,3-dimethylphenyl)ethyl]-1H-imidazole-1-carboxylate $^1$H-NMR (d$_6$-Acetone): 0.91-0.96 (3H), 1.10-1.16 (3H), 1.20-1.30 (3H), 1.38-1.43 (1H), 1.45-1.55 (5H), 1.60-1.65 (1H), 2.29-2.31 (3H), 2.36-2.38 (3H), 4.20-4.30 (2H), 5.05-5.10 (1H), 6.51-6.53 (1H), 6.83-6.85 (1H), 6.96-6.98 (2H), 7.46-7.48 (1H)

Example 252

2-Propoxyethyl 2-[(1S)-1-(2,3-dimethylphenyl)ethyl]-1H-imidazole-1-carboxylate $^1$H-NMR (d$_6$-Acetone): 0.90-0.95 (3H), 1.42-1.52 (5H), 2.27-2.29 (3H), 2.36-2.38 (3H), 3.31-3.37 (2H), 3.59-3.64 (2H), 4.30-4.36 (2H), 5.07-5.12 (1H), 6.57-6.59 (1H), 6.83-6.85 (1H), 6.95-6.98 (2H), 7.46-7.48 (1H)

Example 253

2,3-Dimethylpentyl 2-[(1S)-1-(2,3-dimethylphenyl)ethyl]-1H-imidazole-1-carboxylate $^1$H-NMR (d$_6$-Acetone): 0.75-0.88 (6H), 1.10-1.21 (1H), 1.30-1.43 (2H), 1.52-1.55 (3H), 1.79-1.88 (1H), 2.25-2.27 (3H), 2.34-2.36 (3H), 4.00-4.25 (2H), 5.02-5.11 (1H), 6.50-6.52 (1H), 6.84-6.87 (1H), 6.96-6.99 (2H), 7.44-7.46 (1H)

Example 254

2,2-Dimethylbutyl 2-[(1S)-1-(2,3-dimethylphenyl)ethyl]-1H-imidazole-1-carboxylate $^1$H-NMR (d$_6$-Acetone): 0.79-0.83 (3H), 0.90-0.92 (6H), 1.25-1.33 (2H), 1.52-1.55 (3H), 2.24-2.26 (3H), 2.33-2.35 (3H), 3.90-3.95 (1H), 4.00-4.04 (1H), 5.10-5.15 (1H), 6.57-6.59 (1H), 6.85-6.88 (1H), 6.94-6.97 (2H), 7.49-7.50 (1H)

Example 255

3-Methoxy-2,2-dimethyl-3-oxopropyl 2-[(1S)-1-(2,3-dimethylphenyl)ethyl]-1H-imidazole-1-carboxylate $^1$H-NMR (d$_6$-Acetone): 1.19-1.24 (6H), 1.51-1.54 (3H), 2.23-2.26 (3H), 2.31-2.34 (3H), 3.59-3.60 (3H), 4.20-4.30 (2H), 5.05-5.11 (1H), 6.57-6.60 (1H), 6.82-6.86 (1H), 6.95-6.99 (2H), 7.19-7.20 (1H)

Example 256

4-Butoxybenzyl 2-[(1S)-1-(2,3-dimethylphenyl)ethyl]-1H-imidazole-1-carboxylate

To a mixture of the compound of Example 58 (200 mg, 1.0 mmol) and pyridine (177 μl, 2.2 mmol) in anhydrous acetonitrile (3 ml), at 0° C. and under nitrogen, was added diphosgene (132 μl, 1.1 mmol). The mixture was allowed to warm to room temperature and stirred for 10 min, before addition to (4-butoxyphenyl)methanol (198 mg, 1.1 mmol) via syringe. The reaction mixture was stirred at room temperature for 30 min and filtered.

The filtrate was purified by automated preparative liquid chromatography (Gilson system, 150 mm×22.4 mm LUNA C18(2) 10 μm column, 24 ml/min) using an acetonitrile:water gradient [15:85 (3 min) to 98:2 (16 min)]. The appropriate fractions were combined and concentrated to give the title compound (6 mg).

Experimental MH$^+$ 364.0; expected 363.2 (compound decarboxylates) $^1$H-NMR (d$_6$-Acetone): 0.92-0.98 (3H), 1.43-1.55 (5H), 1.69-1.78 (2H), 2.24-2.30 (6H), 3.97-4.01 (2H), 5.04-5.09 (1H), 5.17-5.18 (2H), 6.48-6.50 (1H), 6.83-6.88 (3H), 6.95-6.98 (2H), 7.10-7.13 (2H), 7.44-7.45 (1H) Rhip. Funct. ED$_{100}$ mg/cm$^2$=0.03

Similarly Prepared from Example 58 were:

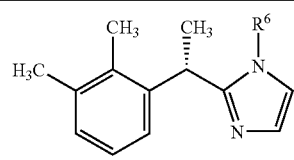

| Ex. No. | R$^6$ | Precursor | MH$^+$ Found/ Expected | Rhip. Funct. ED$_{100}$ mg/cm$^2$ |
|---|---|---|---|---|
| 257 | | Biphenyl-4-ylmethanol | 412.1 411.2 | <=10 |
| 258 | | 2,2-Diphenylethanol | 426.0 425.0 | <=10 |
| 259 | | (3,5-Difluorophenyl)methanol | 371.2 371.2 | 0.1 |
| 260 | | (4-Chlorophenyl)methanol | 369.8 369.1 | >0.03 |
| 261 | | {4-[(4-Fluorobenzyl)oxy]-phenyl}methanol | 460.0 459.2 | <=10 |
| 262 | | (2,4,5-Trimethylphenyl)-methanol | 334.0 333.2 decarboxylates | >0.03 |

-continued
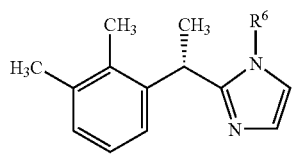
| Ex. No. | R⁶ | Precursor | MH⁺ Found/ Expected | Rhip. Funct. ED₁₀₀ mg/cm² |
|---|---|---|---|---|
| 263 | | (2,4-Dimethylphenyl)-methanol | 363.9 363.2 | >0.03 |
| 264 | | 1-Naphthylmethanol | 342.1 341.2 decarboxylates | 0.03 |
| 265 | | Mesitylmethanol | 334.0 333.2 decarboxylates | <=10 |
| 266 | | [4-(1H-1,2,4-Triazol-1-yl)-phenyl]methanol | — | >0.03 |
| 267 | | (4-tert-Butylphenyl)methanol | 348.1 347.2 decarboxylates | <=10 |
| 268 | | (2-Fluorophenyl)methanol | 310.0 309.2 decarboxylates | 0.01 |
| 269 | | [4-(Benzyloxy)phenyl]-methanol | — | <=10 |
| 270 | | (Pentafluorophenyl)-methanol | 423.0 423.1 | <=10 |

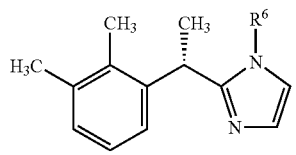
| Ex. No. | R$^6$ | Precursor | MH$^+$ Found/ Expected | Rhip. Funct. ED$_{100}$ mg/cm$^2$ |
|---|---|---|---|---|
| 271 | | Biphenyl-2-ylmethanol | — | <=10 |
| 272 | | (3-Phenoxyphenyl)methanol | 384.0 383.2 decarboxylates | <=10 |
| 273 | | (2,3,5-Trifluorophenyl)-methanol | 389.9 389.1 | >0.03 |
| 274 | | (2-Chloro-4-fluorophenyl)-methanol | — | >0.03 |
| 275 | | (4-Fluoro-3-methoxyphenyl)-methanol | 383.9 383.2 | >0.03 |
| 276 | | (2,6-Dichlorophenyl)-methanol | 403.9 403.1 | >0.03 |

-continued
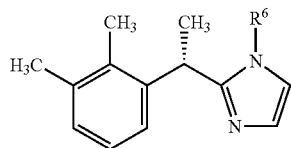
| Ex. No. | R⁶ | Precursor | MH⁺ Found/ Expected | Rhip. Funct. $ED_{100}$ mg/cm² |
|---|---|---|---|---|
| 277 | | 2-(4-tert-Butylphenyl)ethanol | 406.0 405.3 | >0.03 |
| 278 | | (2R)-2-Phenylpropan-1-ol | 363.9 363.2 | |
| 279 | | 2-Mesitylethanol | 392.0 391.2 | >0.03 |
| 280 | | 2-(4-Chlorophenyl)ethanol | 383.9 383.2 | 0.03 |
| 281 | | 2-(4-Isopropyl-2-methyl-phenyl)ethanol | 406.0 405.3 | <=10 |
| 282 | | 2-(4-Methylphenyl)ethanol | 364.0 363.2 | <=10 |
| 283 | | (1S)-1-Phenylpropan-1-ol | 363.9 363.2 | <=10 |
| 284 | | 2-(2,5-Dimethylphenyl)-ethanol | 377.2 377.2 | 0.1 |

-continued
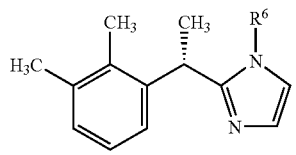
| Ex. No. | R⁶ | Precursor | MH⁺ Found/ Expected | Rhip. Funct. ED$_{100}$ mg/cm² |
|---|---|---|---|---|
| 285 | | 3-Phenylpropan-1-ol | 363.9 363.2 | >0.03 |
| 286 | | (2S)-2-Phenylpropan-1-ol | 363.2 363.2 | 0.03 |
| 287 | | 2-(3-Methylphenyl)ethanol | 363.9 363.2 | >0.03 |
| 288 | | 2-Phenylethanol | 349.9 349.2 | <=10 |
| 289 | | 2-(2-Methylphenyl)ethanol | 363.2 363.2 | 0.03 |
| 290 | | 2-[2-(2-Chloropyrimidin-4-yl)phenyl]ethanol | — | <=10 |
| 291 | | (2,3,4-Trifluorophenyl)-methanol | 389.1 389.1 | 0.03 |

-continued
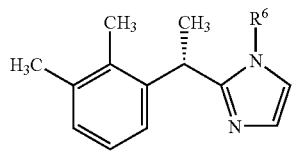
| Ex. No. | R[6] | Precursor | MH+ Found/ Expected | Rhip. Funct. ED$_{100}$ mg/cm$^2$ |
| --- | --- | --- | --- | --- |
| 292 | | [2-(2-Phenylethyl)phenyl]-methanol | 396.1 395.2 decarboxylates | >0.03 |
| 293 | | (5-Fluoro-2-methylphenyl)-methanol | 324.1 323.2 decarboxylates | >0.03 |
| 294 | | (Pentamethylphenyl)-methanol | — | >0.03 |
| 295 | | [4-(Benzyloxy)-3-methoxy-phenyl]methanol | 428.1 427.2 decarboxylates | >0.03 |
| 296 | | (2-Chlorophenyl)methanol | 326.0 325.1 decarboxylates | >0.03 |
| 297 | | (2-Methoxy-5-methylphenyl)-methanol | 336.1 335.2 decarboxylates | <=10 |

-continued

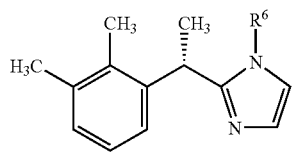

| Ex. No. | R⁶ | Precursor | MH⁺ Found/Expected | Rhip. Funct. ED$_{100}$ mg/cm$^2$ |
|---|---|---|---|---|
| 298 | (3-fluorobenzyl pivalate ester) | (3-Fluorophenyl)methanol | 310.0 309.2 decarboxylates | >0.03 |
| 299 | (4-ethoxybenzyl pivalate ester) | (4-Ethoxyphenyl)methanol | 336.0 335.2 decarboxylates | <=10 |
| 300 | (2,4-difluorobenzyl pivalate ester) | (2,4-Difluorophenyl)methanol | — | >0.03 |
| 301 | (2,4-dimethoxy-3-methylbenzyl pivalate ester) | (2,4-Dimethoxy-3-methyl-phenyl)methanol | 366.0 365.2 decarboxylates | <=10 |
| 302 | (2-fluoro-5-methoxybenzyl pivalate ester) | (2-Fluoro-5-methoxyphenyl)-methanol | 339.9 339.2 decarboxylates | >0.03 |
| 303 | (4-fluoro-2-methoxybenzyl pivalate ester) | (4-Fluoro-2-methoxyphenyl)-methanol | 340.0 339.2 decarboxylates | >0.03 |
| 304 | (4-chloro-2-fluorobenzyl pivalate ester) | (4-Chloro-2-fluorophenyl)-methanol | — | <=10 |

-continued

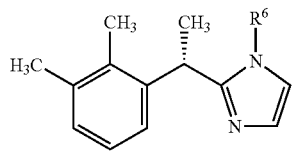

| Ex. No. | R⁶ | Precursor | MH⁺ Found/ Expected | Rhip. Funct. $ED_{100}$ mg/cm² |
|---|---|---|---|---|
| 305 | (2,5-dimethoxybenzyl pivaloate structure) | (2,5-Dimethoxyphenyl)-methanol | — | <=10 |
| 306 | (3-ethoxybenzyl pivaloate structure) | (3-Ethoxyphenyl)methanol | 335.9 335.2 decarboxylates | >0.03 |
| 307 | (2,5-dichlorobenzyl pivaloate structure) | (2,5-Dichlorophenyl)-methanol | 359.9 359.1 decarboxylates | >0.03 |
| 308 | (2,6-difluorobenzyl pivaloate structure) | (2,6-Difluorophenyl)methanol | 328.0 327.2 decarboxylates | >0.03 |
| 309 | (3,5-dichlorobenzyl pivaloate structure) | (3,5-Dichlorophenyl)-methanol | 359.9 359.1 decarboxylates | >0.03 |
| 310 | (5-chloro-2-methoxybenzyl pivaloate structure) | (5-Chloro-2-methoxyphenyl)-methanol | 355.9 355.1 decarboxylates | >0.03 |
| 311 | (3,4-dimethylbenzyl pivaloate structure) | (3,4-Dimethylphenyl)-methanol | 319.9 319.2 decarboxylates | >0.03 |

-continued

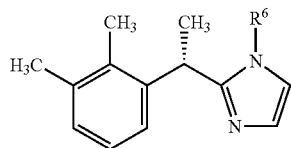

| Ex. No. | R[6] | Precursor | MH[+] Found/ Expected | Rhip. Funct. ED$_{100}$ mg/cm$^2$ |
|---|---|---|---|---|
| 312 | (4-bromobenzyl ester) | (4-Bromophenyl)methanol | 369.9 369.1 decarboxylates | <=10 |
| 313 | (4-cyclopentyloxy-3-methoxybenzyl ester) | [4-(Cyclopentyloxy)-3-methoxyphenyl]methanol | 406.1 405.2 decarboxylates | <=10 |
| 314 | (2,3,5,6-tetrafluorobenzyl ester) | (2,3,5,6-Tetrafluorophenyl)-methanol | 408.0 407.1 decarboxylates | >0.03 |
| 315 | (3-methoxy-4-methylbenzyl ester) | (3-Methoxy-4-methylphenyl)-methanol | 380.0 379.2 | <=10 |
| 316 | (4-methylbenzyl ester) | (4-Methylphenyl)methanol | 305.8 305.2 decarboxylates | >0.03 |
| 317 | (4-cyanobenzyl ester) | 4-(Hydroxymethyl)-benzonitrile | 361.0 360.2 | <=10 |
| 318 | (2-ethoxybenzyl ester) | (2-Ethoxyphenyl)methanol | 380.1 379.2 | <=10 |

-continued

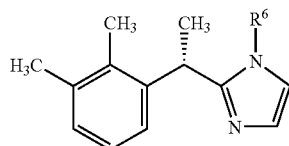

| Ex. No. | R⁶ | Precursor | MH⁺ Found/ Expected | Rhip. Funct. ED₁₀₀ mg/cm² |
|---|---|---|---|---|
| 319 | (2-fluoro-5-methylphenyl ester group) | (2-Fluoro-5-methylphenyl)-methanol | 324.0<br>323.2<br>decarboxylates | <=10 |
| 320 | (2,5-difluoro-4-methylphenyl ester group) | (2,5-Difluoro-4-methyl-phenyl)methanol | 385.2<br>385.2 | <=0.03 |
| 321 | (2,3,6-trifluorophenyl ester group) | (2,3,6-Trifluorophenyl)-methanol | 389.9<br>389.1 | >0.03 |
| 322 | (2-methylbiphenyl-3-yl ester group) | (2-Methylbiphenyl-3-yl)-methanol | 426.0<br>425.2 | <=10 |
| 323 | (2-methoxyphenyl ester group) | (2-Methoxyphenyl)methanol | 322.0<br>321.2<br>decarboxylates | <=0.03 |
| 324 | (4-bromo-2-fluorophenyl ester group) | (4-Bromo-2-fluorophenyl)-methanol | 431.9<br>431.1 | >0.03 |
| 325 | (2,3-dimethoxyphenyl ester group) | (2,3-Dimethoxyphenyl)-methanol | 396.0<br>395.2 | >0.03 |

-continued

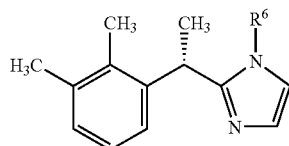

| Ex. No. | R[6] | Precursor | MH+ Found/ Expected | Rhip. Funct. ED$_{100}$ mg/cm$^2$ |
|---|---|---|---|---|
| 326 | (2,3-dichlorobenzyl pivalate ester) | (2,3-Dichlorophenyl)-methanol | 403.9 403.1 | >0.03 |
| 327 | (4-butylbenzyl pivalate ester) | (4-Butylphenyl)methanol | 392.1 391.2 | <=10 |
| 328 | (3-methoxybenzyl pivalate ester) | (3-Methoxyphenyl)methanol | 365.9 365.2 | <=10 |
| 329 | (3,4-dichlorobenzyl pivalate ester) | (3,4-Dichlorophenyl)-methanol | 403.9 403.1 | >0.03 |
| 330 | (3,4-diethoxybenzyl pivalate ester) | (3,4-Diethoxyphenyl)-methanol | 380.1 379.2 decarboxylates | <=10 |
| 331 | (3-methylbenzyl pivalate ester) | (3-Methylphenyl)methanol | 350.1 349.2 | >0.03 |
| 332 | (4-isopropylbenzyl pivalate ester) | (4-Isopropylphenyl)methanol | 378.0 377.2 | >0.03 |

-continued

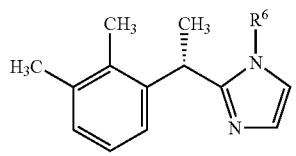

| Ex. No. | R⁶ | Precursor | MH⁺ Found/ Expected | Rhip. Funct. ED₁₀₀ mg/cm² |
|---|---|---|---|---|
| 333 | (3-chlorobenzyl ester structure) | (3-Chlorophenyl)methanol | 369.9 369.1 | >0.03 |
| 334 | (3,4-difluorobenzyl ester structure) | (3,4-Difluorophenyl)methanol | 327.8 327.2 decarboxylates | >0.03 |
| 335 | (2-chloro-3,4-dimethoxybenzyl ester structure) | (2-Chloro-3,4-dimethoxy-phenyl)methanol | 385.9 485.2 decarboxylates | >0.03 |
| 336 | (2-methylbenzyl ester structure) | (2-Methylphenyl)methanol | 349.9 349.1 | >0.03 |
| 337 | (2-chloro-6-fluorobenzyl ester structure) | (2-Chloro-6-fluorophenyl)-methanol | 387.1 387.1 | <=0.03 |
| 338 | (4-methoxybenzyl ester structure) | (4-Methoxyphenyl)methanol | 321.9 321.2 decarboxylates | <=10 |
| 339 | (2,3,5,6-tetramethylbenzyl ester structure) | (2,3,5,6-Tetramethylphenyl)-methanol | 391.1 391.2 | <=10 |

-continued

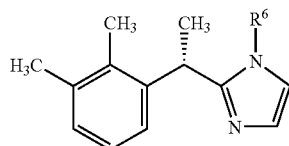

| Ex. No. | R⁶ | Precursor | MH⁺ Found/ Expected | Rhip. Funct. ED$_{100}$ mg/cm² |
|---|---|---|---|---|
| 340 | | (3,4,5-Trifluorophenyl)-methanol | 345.1 345.1 decarboxylates | >0.03 |
| 341 | | (2,5-Difluorophenyl)methanol | 327.1 327.2 decarboxylates | >0.03 |
| 342 | | (3,5-Dimethylphenyl)-methanol | 319.1 319.2 decarboxylates | >0.03 |
| 343 | | [4-(1H-Pyrazol-1-yl)phenyl]-methanol | — | <=10 |
| 344 | | (3-Chloro-4-methylphenyl)-methanol | 340.0 339.2 decarboxylates | >0.03 |
| 345 | | (4-Ethoxy-3-methoxyphenyl)-methanol | 365.1 365.2 decarboxylates | >0.03 |
| 346 | | 3-(Hydroxymethyl)-benzonitrile | 360.1 360.2 | <=10 |

-continued

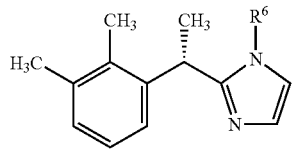

| Ex. No. | R⁶ | Precursor | MH⁺ Found/ Expected | Rhip. Funct. $ED_{100}$ mg/cm² |
|---|---|---|---|---|
| 347 | ![structure with pivalate ester, 2-methoxy-4-methylbenzyl] | (2-Methoxy-4-methylphenyl)-methanol | 335.2 335.2 decarboxylates | >0.03 |
| 348 | ![structure with pivalate ester, 4-fluorobenzyl] | (4-Fluorophenyl)methanol | 309.1 309.2 decarboxylates | <=0.03 |

Example 257

Biphenyl-4-ylmethyl 2-[(1S)-1-(2,3-dimethylphenyl)ethyl]-1H-imidazole-1-carboxylate ¹H-NMR ($d_6$-Acetone): 1.52-1.55 (3H), 2.23-2.30 (6H), 5.09-5.13 (1H), 5.29-5.32 (2H), 6.50-6.52 (1H), 6.84-6.86 (1H), 6.96-6.99 (2H), 7.35-7.39 (3H), 7.42-7.46 (2H), 7.57-7.58 (1H), 7.60-7.68 (4H)

Example 258

2,2-Diphenylethyl 2-[(1S)-1-(2,3-dimethylphenyl)ethyl]-1H-imidazole-1-carboxylate ¹H-NMR ($d_6$-Acetone): 1.48-1.56 (3H), 2.25-2.35 (6H), 4.40-4.47 (1H), 4.79-4.87 (2H), 5.00-5.05 (1H), 6.55-6.58 (1H), 6.82-6.88 (2H), 6.95-6.99 (1H), 7.19-7.21 (1H), 7.21-7.24 (2H), 7.29-7.39 (8H)

Example 259

3,5-Difluorobenzyl 2-[(1S)-1-(2,3-dimethylphenyl)ethyl]-1H-imidazole-1-carboxylate ¹H-NMR ($d_6$-Acetone): 1.52-1.56 (3H), 2.22-2.24 (3H), 2.28-2.30 (3H), 5.02-5.10 (1H), 5.22-5.25 (1H), 5.32-5.37 (1H), 6.48-6.50 (1H), 6.84-7.00 (6H), 7.59-7.60 (1H)

Example 260

4-Chlorobenzyl 2-[(1S)-1-(2,3-dimethylphenyl)ethyl]-1H-imidazole-1-carboxylate

¹H-NMR ($d_6$-Acetone): 1.53-1.56 (3H), 2.22-2.28 (6H), 5.02-5.07 (1H), 5.21-5.28 (2H), 6.48-6.51 (1H), 6.84-6.87 (1H), 6.97-6.99 (2H), 7.25-7.28 (2H), 7.36-7.39 (2H), 7.50-7.51 (1H)

Example 261

4-[(4-Fluorobenzyl)oxy]benzyl 2-[(1S)-1-(2,3-dimethylphenyl)ethyl]-1H-imidazole-1-carboxylate ¹H-NMR ($d_6$-Acetone): 1.52-1.55 (3H), 2.22-2.30 (6H), 5.04-5.13 (3H), 5.19-5.20 (2H), 6.51-6.53 (1H), 6.82-6.86 (1H), 6.95-7.00 (4H), 7.11-7.20 (2H), 7.22-7.25 (2H), 7.45-7.46 (1H), 7.50-7.56 (2H)

Example 262

2,4,5-Trimethylbenzyl 2-[(1S)-1-(2,3-dimethylphenyl)ethyl]-1H-imidazole-1-carboxylate ¹H-NMR ($d_6$-Acetone): 1.51-1.54 (3H), 2.15-2.17 (3H), 2.19-2.23 (6H), 2.23-2.25 (3H), 5.02-5.06 (1H), 5.17-5.20 (1H), 5.21-5.24 (1H), 6.48-6.51 (1H), 6.84-6.86 (1H), 6.96-6.99 (3H), 7.00-7.01 (1H), 7.46-7.48 (1H)

Example 263

2,4-dimethylbenzyl 2-[(1S)-1-(2,3-dimethylphenyl)ethyl]-1H-imidazole-1-carboxylate

Example 264

1-Naphthylmethyl 2-[(1S)-1-(2,3-dimethylphenyl)ethyl]-1H-imidazole-1-carboxylate ¹H-NMR ($d_6$-Acetone): 1.46-1.51 (3H), 2.19-2.26 (6H), 5.04-5.10 (1H), 5.75-5.79 (2H), 6.52-6.55 (1H), 6.83-6.87 (1H), 6.90-6.96 (2H), 7.42-7.50 (3H), 7.53-7.58 (2H), 7.95-7.99 (2H), 8.00-8.03 (1H)

Example 265

Mesitylmethyl 2-[(1S)-1-(2,3-dimethylphenyl)ethyl]-1H-imidazole-1-carboxylate

Example 266

4-(1H-1,2,4-Triazol-1-yl)benzyl 2-[(1S)-1-(2,3-dimethylphenyl)ethyl]-1H-imidazole-1-carboxylate ¹H-NMR ($d_6$-Acetone): 1.53-1.56 (3H), 2.22-2.24 (3H), 2.30-2.32 (3H), 5.03-5.08 (1H), 5.31-5.39 (2H), 6.49-6.52

(1H), 6.84-6.86 (1H), 6.97-7.00 (2H), 7.41-7.44 (2H), 7.56-7.58 (1H), 7.80-7.83 (2H), 8.13-8.14 (1H), 9.02-9.04 (1H)

Example 267

4-tert-Butylbenzyl 2-[(1S)-1-(2,3-dimethylphenyl)ethyl]-1H-imidazole-1-carboxylate $^1$H-NMR (d$_6$-Acetone): 1.28-1.33 (9H), 1.52-1.55 (3H), 2.22-2.28 (6H), 5.02-5.07 (1H), 5.20-5.22 (2H), 6.51-6.53 (1H), 6.84-6.86 (1H), 6.95-6.98 (2H), 7.20-7.23 (2H), 7.38-7.41 (2H), 7.50-7.51 (1H)

Example 268

2-Fluorobenzyl 2-[(1S)-1-(2,3-dimethylphenyl)ethyl]-1H-imidazole-1-carboxylate $^1$H-NMR (d$_6$-Acetone): 1.50-1.54 (3H), 2.22-2.28 (6H), 5.02-5.07 (1H), 5.28-5.31 (1H), 5.37-5.40 (1H), 6.51-6.53 (1H), 6.83-6.85 (1H), 6.95-6.98 (2H), 7.16-7.20 (2H), 7.30-7.33 (1H), 7.40-7.43 (1H), 7.46-7.47 (1H)

Example 269

4-(Benzyloxy)benzyl 2-[(1S)-1-(2,3-dimethylphenyl)ethyl]-1H-imidazole-1-carboxylate $^1$H-NMR (d$_6$-Acetone): 1.50-1.53 (3H), 2.24-2.29 (6H), 5.02-5.07 (1H), 5.11-5.13 (2H), 5.18-5.20 (2H), 6.48-6.50 (1H), 6.81-6.84 (1H), 6.94-7.00 (4H), 7.20-7.24 (2H), 7.33-7.41 (3H), 7.42-7.45 (3H)

Example 270

Pentafluorobenzyl 2-[(1S)-1-(2,3-dimethylphenyl)ethyl]-1H-imidazole-1-carboxylate $^1$H-NMR (d$_6$-Acetone): 1.50-1.53 (3H), 2.25-2.27 (3H), 2.29-2.31 (3H), 4.99-5.02 (1H), 5.38-5.41 (1H), 5.42-5.45 (1H), 6.40-6.42 (1H), 6.80-6.83 (1H), 6.90-6.92 (1H), 6.97-6.98 (1H), 7.46-7.47 (1H)

Example 271

Biphenyl-2-ylmethyl 2-[(1S)-1-(2,3-dimethylphenyl)ethyl]-1H-imidazole-1-carboxylate $^1$H-NMR (d$_6$-Acetone): 1.50-1.53 (3H), 2.15-2.17 (3H), 2.19-2.21 (3H), 4.98-5.02 (1H), 5.19-5.21 (2H), 6.48-6.50 (1H), 6.85-6.95 (3H), 7.20-7.24 (2H), 7.30-7.38 (5H), 7.39-7.41 (2H), 7.41-7.44 (1H)

Example 272

3-Phenoxybenzyl 2-[(1S)-1-(2,3-dimethylphenyl)ethyl]-1H-imidazole-1-carboxylate $^1$H-NMR (d$_6$-Acetone): 1.54-1.57 (3H), 2.23-2.25 (3H), 2.28-2.30 (3H), 5.02-5.10 (1H), 5.20-5.27 (2H), 6.51-6.54 (1H), 6.83-6.85 (1H), 6.91-7.04 (7H), 7.13-7.17 (1H), 7.30-7.41 (3H), 7.49-7.50 (1H)

Example 273

2,3,5-Trifluorobenzyl 2-[(1S)-1-(2,3-dimethylphenyl)ethyl]-1H-imidazole-1-carboxylate $^1$H-NMR (d$_6$-Acetone): 1.53-1.56 (3H), 2.22-2.25 (3H), 2.29-2.32 (3H), 5.00-5.05 (1H), 5.30-5.33 (1H), 5.40-5.43 (1H), 6.48-6.50 (1H), 6.82-6.85 (1H), 6.93-6.98 (3H), 7.25-7.29 (1H), 7.57-7.59 (1H)

Example 274

2-Chloro-4-fluorobenzyl 2-[(1S)-1-(2,3-dimethylphenyl)ethyl]-1H-imidazole-1-carboxylate $^1$H-NMR (d$_6$-Acetone): 1.50-1.53 (3H), 2.21-2.27 (6H), 5.02-5.06 (1H), 5.30-5.34 (1H), 5.36-5.40 (1H), 6.49-6.51 (1H), 6.84-6.86 (1H), 6.95-6.98 (2H), 7.09-7.12 (1H), 7.32-7.34 (1H), 7.39-7.41 (1H), 7.49-7.51 (1H)

Example 275

4-Fluoro-3-methoxybenzyl 2-[(1S)-1-(2,3-dimethylphenyl)ethyl]-1H-imidazole-1-carboxylate $^1$H-NMR (d$_6$-Acetone): 1.50-1.53 (3H), 2.01-2.03 (3H), 2.21-2.26 (6H), 3.80-3.81 (3H), 5.05-5.10 (1H), 5.20-5.23 (2H), 6.47-6.49 (1H), 6.84-6.87 (2H), 6.95-6.98 (2H), 7.09-7.16 (2H), 7.49-7.51 (1H)

Example 276

2,6-Dichlorobenzyl 2-[(1S)-1-(2,3-dimethylphenyl)ethyl]-1H-imidazole-1-carboxylate $^1$H-NMR (d$_6$-Acetone): 1.50-1.53 (3H), 2.20-2.26 (6H), 5.00-5.05 (1H), 5.70-5.72 (1H), 5.77-5.79 (1H), 6.47-6.49 (1H), 6.81-6.83 (1H), 6.95-6.98 (2H), 7.42-7.43 (1H), 7.49-7.52 (3H)

Example 277

2-(4-tert-Butylphenyl)ethyl 2-[(1S)-1-(2,3-dimethylphenyl)ethyl]-1H-imidazole-1-carboxylate $^1$H-NMR (d$_6$-Acetone): 1.23-1.27 (9H), 1.50-1.53 (3H), 2.23-2.30 (6H), 2.85-2.93 (2H), 4.38-4.42 (2H), 5.00-5.05 (1H), 6.54-6.56 (1H), 6.85-6.88 (1H), 6.91-6.95 (2H), 7.16-7.19 (2H), 7.35-7.38 (2H), 7.42-7.43 (1H)

Example 278

(2R)-2-Phenylpropyl 2-[(1S)-1-(2,3-dimethylphenyl)ethyl]-1H-imidazole-1-carboxylate $^1$H-NMR (d$_6$-Acetone): 1.22-1.26 (3H), 1.50-1.53 (3H), 2.25-2.27 (3H), 2.30-2.32 (3H), 3.12-3.18 (1H), 4.24-4.30 (2H), 5.00-5.06 (1H), 6.52-6.54 (1H), 6.85-6.90 (2H), 6.90-6.94 (1H), 7.20-7.25 (3H), 7.29-7.32 (2H), 7.37-7.39 (1H)

Example 279

2-Mesitylethyl 2-[(1S)-1-(2,3-dimethylphenyl)ethyl]-1H-imidazole-1-carboxylate $^1$H-NMR (d$_6$-Acetone): 1.53-1.55 (3H), 2.20-2.21 (3H), 2.24-2.26 (6H), 2.27-2.29 (3H), 2.36-2.38 (3H), 4.20-4.25 (2H), 5.01-5.06 (1H), 6.51-6.53 (1H), 6.80-6.81 (2H), 6.85-6.87 (1H), 6.95-6.99 (2H), 7.46-7.48 (1H)

Example 280

2-(4-Chlorophenyl)ethyl 2-[(1S)-1-(2,3-dimethylphenyl)ethyl]-1H-imidazole-1-carboxylate $^1$H-NMR (d$_6$-Acetone): 1.50-1.53 (3H), 2.24-2.26 (3H), 2.26-2.28 (3H), 2.90-2.96 (2H), 4.40-4.50 (2H), 5.01-5.06 (1H), 6.52-6.54 (1H), 6.83-6.96 (3H), 7.20-7.23 (2H), 7.25-7.27 (2H), 7.39-7.40 (1H)

Example 281

2-(4-Isopropyl-2-methylphenyl)ethyl 2-[(1S)-1-(2,3-dimethylphenyl)ethyl]-1H-imidazole-1-carboxylate $^1$H-NMR (d$_6$-Acetone): 1.19-1.26 (9H), 1.50-1.55 (3H), 2.25-2.29 (6H), 2.85-2.92 (1H), 3.04-3.15 (1H), 4.22-4.31 (2H), 5.00-5.10 (1H), 6.52-6.55 (1H), 6.82-6.96 (3H), 7.15-7.21 (4H), 7.38-7.39 (1H)

Example 282

2-(4-Methylphenyl)ethyl 2-[(1S)-1-(2,3-dimethylphenyl)ethyl]-1H-imidazole-1-carboxylate $^1$H-NMR (d$_6$-Acetone): 1.52-1.55 (3H), 2.25-2.28 (6H), 2.30-2.31 (3H), 2.84-2.89 (2H), 4.35-4.42 (2H), 5.01-5.09 (1H), 6.53-6.55 (1H), 6.82-6.87 (1H), 6.95-6.98 (2H), 7.08-7.09 (4H), 7.40-7.41 (1H)

Example 283

1-Phenylpropyl 2-[(1S)-1-(2,3-dimethylphenyl)ethyl]-1H-imidazole-1-carboxylate $^1$H-NMR (d$_6$-Acetone): 0.89-0.93 (3H), 1.54-1.57 (3H), 1.79-1.84 (1H), 1.90-2.00 (1H), 2.30-2.36 (6H), 5.00-5.05 (1H), 5.60-5.64 (1H), 6.47-6.49 (1H), 6.89-6.93 (1H), 6.98-7.02 (2H), 7.19-7.21 (2H), 7.29-7.33 (3H), 7.60-7.61 (1H)

Example 284

2-(2,5-Dimethylphenyl)ethyl 2-[(1S)-1-(2,3-dimethylphenyl)ethyl]-1H-imidazole-1-carboxylate $^1$H-NMR (d$_6$-Acetone): 1.52-1.56 (3H), 2.20-2.25 (6H), 2.29-2.36 (6H), 2.81-2.94 (2H), 4.31-4.41 (2H), 5.00-5.05 (1H), 6.50-6.52 (1H), 6.84-6.98 (5H), 7.00-7.02 (1H), 7.42-7.43 (1H)

Example 285

3-Phenylpropyl 2-[(1S)-1-(2,3-dimethylphenyl)ethyl]-1H-imidazole-1-carboxylate $^1$H-NMR (d$_6$-Acetone): 1.50-1.53 (3H), 1.90-1.98 (2H), 2.23-2.25 (3H), 2.36-2.38 (3H), 2.60-2.64 (2H), 4.20-4.26 (2H), 5.04-5.08 (1H), 6.51-6.53 (1H), 6.85-6.88 (1H), 6.96-6.98 (2H), 7.16-7.19 (3H), 7.22-7.25 (2H), 7.46-7.48 (1H)

Example 286

2-Phenylpropyl 2-[(1S)-1-(2,3-dimethylphenyl)ethyl]-1H-imidazole-1-carboxylate $^1$H-NMR (d$_6$-Acetone): 1.20-1.24 (3H), 1.51-1.55 (3H), 2.25-2.27 (3H), 2.32-2.34 (3H), 3.05-3.09 (1H), 4.25-4.39 (2H), 5.02-5.10 (1H), 6.51-6.53 (1H), 6.81-6.95 (3H), 7.19-7.22 (1H), 7.27-7.30 (4H), 7.37-7.38 (1H)
CHN Analysis
Predicted: % C=76.21; % H=7.23; % N=7.73.
Observed: % C=76.07; % H=7.24; % N=7.63.

Example 287

2-(3-Methylphenyl)ethyl 2-[(1S)-1-(2,3-dimethylphenyl)ethyl]-1H-imidazole-1-carboxylate $^1$H-NMR (d$_6$-Acetone): 1.50-1.53 (3H), 2.22-2.25 (6H), 2.32-2.35 (3H), 4.38-4.42 (2H), 5.01-5.05 (1H), 6.55-6.57 (1H), 6.85-6.88 (1H), 6.92-7.00 (3H), 7.00-7.05 (2H), 7.14-7.18 (1H), 7.40-7.41 (1H)

Example 288

2-Phenylethyl 2-[(1S)-1-(2,3-dimethylphenyl)ethyl]-1H-imidazole-1-carboxylate $^1$H-NMR (d$_6$-Acetone): 1.51-1.54 (3H), 2.26-2.28 (3H), 2.31-2.33 (3H), 2.90-2.96 (2H), 4.39-4.44 (2H), 5.02-5.06 (1H), 6.52-6.55 (1H), 6.85-6.95 (3H), 7.20-7.30 (5H), 7.39-7.40 (1H)

Example 289

2-(2-Methylphenyl)ethyl 2-[(1S)-1-(2,3-dimethylphenyl)ethyl]-1H-imidazole-1-carboxylate $^1$H-NMR (d$_6$-Acetone): 1.50-1.53 (3H), 2.27-2.30 (6H), 2.33-2.35 (3H), 2.85-2.99 (2H), 4.35-4.42 (2H), 5.02-5.09 (1H), 6.50-6.52 (1H), 6.84-6.87 (1H), 6.96-6.99 (2H), 7.10-7.19 (4H), 7.41-7.42 (1H)
CHN Analysis
Predicted: % C=76.21; % H=7.23; % N=7.73.
Observed: % C=76.22; % H=7.22; % N=7.66.

Example 290

2-[2-(2-Chloropyrimidin-4-yl)phenyl]ethyl 2-[(1S)-1-(2,3-dimethylphenyl)ethyl]-1H-imidazole-1-carboxylate $^1$H-NMR (d$_6$-Acetone): 1.50-1.54 (3H), 2.21-2.29 (6H), 3.10-3.20 (1H), 3.20-3.28 (1H), 4.40-4.50 (2H), 4.97-5.03 (1H), 6.50-6.52 (1H), 6.83-6.91 (3H), 7.18-7.29 (4H), 7.35-7.38 (1H), 7.40-7.42 (1H), 8.75-8.77 (1H)

Example 291

2,3,4-Trifluorobenzyl 2-[(1S)-1-(2,3-dimethylphenyl)ethyl]-1H-imidazole-1-carboxylate $^1$H-NMR (d$_6$-Acetone): 1.50-1.53 (3H), 2.22-2.30 (6H), 5.01-5.07 (1H), 5.25-5.30 (1H), 5.39-5.41 (1H), 6.42-6.44 (1H), 6.81-6.85 (1H), 6.92-6.97 (2H), 7.16-7.20 (2H), 7.44-7.46 (1H)
CHN Analysis
Predicted: % C=64.94; % H=4.93; % N=7.21.
Observed: % C=64.90; % H=4.93; % N=7.21.

Example 292

2-(2-Phenylethyl)benzyl 2-[(1S)-1-(2,3-dimethylphenyl)ethyl]-1H-imidazole-1-carboxylate $^1$H-NMR (d$_6$-Acetone): 1.50-1.53 (3H), 2.21-2.25 (6H), 2.80-2.85 (2H), 2.90-2.95 (2H), 5.01-5.06 (1H), 5.20-5.24 (1H), 5.31-5.35 (1H), 6.49-6.52 (1H), 6.82-6.85 (1H), 6.94-6.97 (2H), 7.12-7.20 (4H), 7.20-7.26 (3H), 7.30-7.34 (2H), 7.46-7.47 (1H)

Example 293

5-Fluoro-2-methylbenzyl 2-[(1S)-1-(2,3-dimethylphenyl)ethyl]-1H-imidazole-1-carboxylate $^1$H-NMR (d$_6$-Acetone): 1.50-1.53 (3H), 2.20-2.29 (9H), 5.01-5.06 (1H), 5.20-5.25 (1H), 5.31-5.35 (1H), 6.48-6.51 (1H), 6.82-6.85 (1H), 6.92-7.00 (2H), 7.00-7.05 (2H), 7.20-7.24 (1H), 7.56-7.58 (1H)

Example 294

Pentamethylbenzyl 2-[(1S)-1-(2,3-dimethylphenyl)ethyl]-1H-imidazole-1-carboxylate $^1$H-NMR (d$_6$-Acetone): 1.45-1.49 (3H), 2.00-2.02 (3H), 2.11-2.13 (6H), 2.18-2.22 (9H), 2.22-2.23 (3H), 4.98-5.02 (1H), 5.31-5.35 (1H), 5.40-5.43 (1H), 6.40-6.43 (1H), 6.81-6.84 (1H), 6.90-6.94 (2H), 7.43-7.45 (1H)

Example 295

4-(Benzyloxy)-3-methoxybenzyl 2-[(1S)-1-(2,3-dimethylphenyl)ethyl]-1H-imidazole-1-carboxylate $^1$H-NMR (d$_6$-Acetone): 1.51-1.54 (3H), 2.21-2.27 (6H), 3.78-3.80 (3H), 5.04-5.11 (3H), 5.18-5.20 (2H), 6.50-6.53 (1H), 6.80-6.90 (2H), 6.90-7.00 (4H), 7.30-7.40 (3H), 7.43-7.46 (2H)

Example 296

2-Chlorobenzyl 2-[(1S)-1-(2,3-dimethylphenyl)ethyl]-1H-imidazole-1-carboxylate $^1$H-NMR (d$_6$-Acetone): 1.51-1.54 (3H), 2.20-2.26 (6H), 5.04-5.09 (1H), 5.30-5.40 (2H), 6.50-6.53 (1H), 6.83-6.85 (1H), 6.96-7.00 (2H), 7.30-7.33 (2H), 7.39-7.41 (1H), 7.43-7.45 (1H), 7.54-7.55 (1H)

Example 297

2-Methoxy-5-methylbenzyl 2-[(1S)-1-(2,3-dimethylphenyl)ethyl]-1H-imidazole-1-carboxylate $^1$H-NMR (d$_6$-Acetone): 1.50-1.53 (3H), 2.20-2.30 (9H), 3.78-3.80 (3H), 5.04-5.12 (1H), 5.20-5.27 (2H), 6.52-6.54 (1H), 6.85-6.90 (2H), 6.95-7.00 (2H), 7.00-7.02 (1H), 7.15-7.18 (1H), 7.42-7.44 (1H)

Example 298

3-Fluorobenzyl 2-[(1S)-1-(2,3-dimethylphenyl)ethyl]-1H-imidazole-1-carboxylate $^1$H-NMR (d$_6$-Acetone): 1.51-1.54 (3H), 2.22-2.28 (6H), 5.02-5.07 (1H), 5.12-5.19 (2H), 6.49-6.51 (1H), 6.82-6.84 (1H), 6.96-7.00 (2H), 7.02-7.10 (3H), 7.36-7.40 (1H), 7.57-7.58 (1H)

Example 299

4-Ethoxybenzyl 2-[(1S)-1-(2,3-dimethylphenyl)ethyl]-1H-imidazole-1-carboxylate $^1$H-NMR (d$_6$-Acetone): 1.37-1.40 (3H), 1.50-1.53 (3H), 2.23-2.28 (6H), 4.00-4.05 (2H), 5.03-5.07 (1H), 5.17-5.20 (2H), 6.49-6.51 (1H), 6.82-6.90 (3H), 6.95-6.99 (2H), 7.10-7.14 (2H), 7.44-7.46 (1H)

Example 300

2,4-Difluorobenzyl 2-[(1S)-1-(2,3-dimethylphenyl)ethyl]-1H-imidazole-1-carboxylate $^1$H-NMR (d$_6$-Acetone): 1.50-1.53 (3H), 2.22-2.27 (6H), 5.01-5.05 (1H), 5.21-5.24 (1H), 5.35-5.39 (1H), 6.43-6.45 (1H), 6.91-6.93 (1H), 6.95-7.00 (2H), 7.00-7.09 (2H), 7.37-7.40 (1H), 7.44-7.46 (1H)

Example 301

2,4-Dimethoxy-3-methylbenzyl 2-[(1S)-1-(2,3-dimethylphenyl)ethyl]-1H-imidazole-1-carboxylate $^1$H-NMR (d$_6$-Acetone): 1.57-1.60 (3H), 2.09-2.11 (3H), 2.22-2.27 (6H), 3.71-3.73 (3H), 3.79-3.81 (3H), 4.45-4.54 (3H), 6.69-6.72 (1H), 6.89-6.91 (2H), 6.95-7.00 (3H), 7.10-7.12 (1H)

Example 302

2-Fluoro-5-methoxybenzyl 2-[(1S)-1-(2,3-dimethylphenyl)ethyl]-1H-imidazole-1-carboxylate $^1$H-NMR (d$_6$-Acetone): 1.51-1.54 (3H), 2.22-2.27 (6H), 3.79-3.81 (3H), 5.02-5.07 (1H), 5.21-5.24 (1H), 5.26-5.29 (1H), 6.51-6.54 (1H), 6.83-6.86 (1H), 6.90-6.96 (4H), 7.03-7.06 (1H), 7.49-7.51 (1H

Example 303

4-Fluoro-2-methoxybenzyl 2-[(1S)-1-(2,3-dimethylphenyl)ethyl]-1H-imidazole-1-carboxylate $^1$H-NMR (d$_6$-Acetone): 1.51-1.54 (3H), 2.22-2.26 (6H), 3.80-3.81 (3H), 5.02-5.07 (1H), 5.19-5.22 (1H), 5.23-5.26 (1H), 6.49-6.52 (1H), 6.62-6.66 (1H), 6.80-6.90 (2H), 6.95-6.98 (2H), 7.21-7.24 (1H), 7.42-7.44 (1H)

Example 304

4-Chloro-2-fluorobenzyl 2-[(1S)-1-(2,3-dimethylphenyl)ethyl]-1H-imidazole-1-carboxylate $^1$H-NMR (d$_6$-Acetone): 1.51-1.54 (3H), 2.21-2.27 (6H), 5.01-5.05 (1H), 5.21-5.25 (1H), 5.35-5.39 (1H), 6.47-6.50 (1H), 6.82-6.86 (1H), 6.92-6.96 (2H), 7.20-7.22 (1H), 7.25-7.35 (2H), 7.47-7.49 (1H)

Example 305

2,5-Dimethoxybenzyl 2-[(1S)-1-(2,3-dimethylphenyl)ethyl]-1H-imidazole-1-carboxylate $^1$H-NMR (d$_6$-Acetone): 1.50-1.53 (3H), 2.21-2.25 (6H), 3.72-3.76 (6H), 5.05-5.09 (1H), 5.20-5.24 (2H), 6.54-6.57 (1H), 6.82-6.93 (6H), 7.47-7.49 (1H)

Example 306

3-Ethoxybenzyl 2-[(1S)-1-(2,3-dimethylphenyl)ethyl]-1H-imidazole-1-carboxylate $^1$H-NMR (d$_6$-Acetone): 1.35-1.39 (3H), 1.52-1.55 (3H), 2.22-2.27 (6H), 4.00-4.04 (2H), 5.03-5.07 (1H), 5.20-5.24 (2H), 6.51-6.53 (1H), 6.80-6.89 (4H), 6.95-6.98 (2H), 7.20-7.24 (1H), 7.50-7.52 (1H)

Example 307

2,5-Dichlorobenzyl 2-[(1S)-1-(2,3-dimethylphenyl)ethyl]-1H-imidazole-1-carboxylate $^1$H-NMR (d$_6$-Acetone): 1.51-1.54 (3H), 2.21-2.27 (6H), 5.01-5.06 (1H), 5.30-5.34 (1H), 5.39-5.43 (1H), 6.50-6.53 (1H), 6.84-6.87 (1H), 6.92-6.97 (2H), 7.40-7.47 (3H), 7.48-7.50 (1H

Example 308

2,6-Difluorobenzyl 2-[(1S)-1-(2,3-dimethylphenyl)ethyl]-1H-imidazole-1-carboxylate ¹H-NMR (d₆-Acetone): 1.51-1.54 (3H), 2.21-2.27 (6H), 5.01-5.06 (1H), 5.32-5.36 (1H), 5.40-5.44 (1H), 6.50-6.53 (1H), 6.82-6.85 (1H), 6.90-6.95 (2H), 7.42-7.44 (1H), 7.50-7.55 (1H)

Example 309

3,5-Dichlorobenzyl 2-[(1S)-1-(2,3-dimethylphenyl)ethyl]-1H-imidazole-1-carboxylate ¹H-NMR (d₆-Acetone): 1.51-1.54 (3H), 2.22-2.24 (3H), 2.27-2.30 (3H), 5.01-5.06 (1H), 5.20-5.24 (1H), 5.31-5.35 (1H), 6.50-6.53 (1H), 6.85-6.88 (1H), 6.95-6.99 (2H), 7.29-7.31 (1H), 7.42-7.44 (1H), 7.57-7.59 (1H)

Example 310

5-Chloro-2-methoxybenzyl 2-[(1S)-1-(2,3-dimethylphenyl)ethyl]-1H-imidazole-1-carboxylate ¹H-NMR (d₆-Acetone): 1.51-1.54 (3H), 2.21-2.27 (6H), 3.79-3.81 (3H), 5.03-5.09 (1H), 5.20-5.23 (1H), 5.27-5.30 (1H), 6.51-6.53 (1H), 6.84-6.86 (1H), 6.90-6.94 (2H), 7.00-7.03 (1H), 7.21-7.23 (1H), 7.35-7.38 (1H), 7.50-7.51 (1H)

Example 311

3,4-Dimethylbenzyl 2-[(1S)-1-(2,3-dimethylphenyl)ethyl]-1H-imidazole-1-carboxylate ¹H-NMR (d₆-Acetone): 1.51-1.54 (3H), 2.20-2.25 (6H), 2.26-2.30 (6H), 5.05-5.10 (1H), 5.17-5.21 (2H), 6.50-6.53 (1H), 6.83-6.85 (1H), 6.95-6.97 (2H), 6.98-7.03 (2H), 7.05-7.08 (1H), 7.44-7.46 (1H)

Example 312

4-Bromobenzyl 2-[(1S)-1-(2,3-dimethylphenyl)ethyl]-1H-imidazole-1-carboxylate

¹H-NMR (d₆-Acetone): 1.50-1.53 (3H), 2.22-2.29 (6H), 5.01-5.06 (1H), 5.20-5.29 (2H), 6.43-6.45 (1H), 6.83-6.86 (1H), 6.95-6.99 (2H), 7.09-7.11 (2H), 7.49-7.53 (3H)

Example 313

4-(Cyclopentyloxy)-3-methoxybenzyl 2-[(1S)-1-(2,3-dimethylphenyl)ethyl]-1H-imidazole-1-carboxylate ¹H-NMR (d₆-Acetone): 1.51-1.54 (3H), 1.58-1.62 (2H), 1.70-1.81 (4H), 1.82-1.89 (2H), 2.22-2.28 (6H), 3.75-3.77 (3H), 4.80-4.83 (1H), 5.06-5.10 (1H), 5.17-5.19 (2H), 6.50-6.53 (1H), 6.80-6.90 (3H), 6.93-6.98 (3H), 7.47-7.48 (1H)

Example 314

2,3,5,6-Tetrafluorobenzyl 2-[(1S)-1-(2,3-dimethylphenyl)ethyl]-1H-imidazole-1-carboxylate ¹H-NMR (d₆-Acetone): 1.51-1.54 (3H), 2.22-2.28 (6H), 5.00-5.05 (1H), 5.39-5.43 (1H), 5.45-5.48 (1H), 6.42-6.45 (1H), 6.80-6.83 (1H), 6.89-6.91 (1H), 6.95-6.97 (1H), 7.47-7.48 (1H), 7.59-7.63 (1H)

Example 315

3-Methoxy-4-methylbenzyl 2-[(1S)-1-(2,3-dimethylphenyl)ethyl]-1H-imidazole-1-carboxylate ¹H-NMR (d₆-Acetone): 1.51-1.54 (3H), 2.07-2.09 (3H), 2.22-2.28 (6H), 3.78-3.80 (3H), 5.04-5.09 (1H), 5.20-5.22 (2H), 6.50-6.53 (1H), 6.78-6.80 (1H), 6.82-6.88 (2H), 6.95-6.98 (2H), 7.18-7.20 (1H), 7.50-7.51 (1H)

Example 316

4-Methylbenzyl 2-[(1S)-1-(2,3-dimethylphenyl)ethyl]-1H-imidazole-1-carboxylate

¹H-NMR (d₆-Acetone): 1.51-1.55 (3H), 2.22-2.30 (9H), 5.02-5.06 (1H), 5.20-5.23 (2H), 6.50-6.53 (1H), 6.83-6.86 (1H), 6.95-6.98 (2H), 7.15-7.19 (3H), 7.45-7.46 (1H)

Example 317

4-Cyanobenzyl 2-[(1S)-1-(2,3-dimethylphenyl)ethyl]-1H-imidazole-1-carboxylate

¹H-NMR (d₆-Acetone): 1.50-1.53 (3H), 2.21-2.28 (6H), 5.02-5.08 (1H), 5.35-5.42 (2H), 6.49-6.52 (1H), 6.88-6.92 (1H), 6.97-7.00 (2H), 7.40-7.43 (2H), 7.58-7.59 (1H), 7.70-7.73 (2H)

Example 318

2-Ethoxybenzyl 2-[(1S)-1-(2,3-dimethylphenyl)ethyl]-1H-imidazole-1-carboxylate

¹H-NMR (d₆-Acetone): 1.20-1.26 (3H), 1.50-1.53 (3H), 2.20-2.24 (6H), 3.97-4.03 (2H), 5.05-5.13 (1H), 5.21-5.24 (1H), 5.33-5.36 (1H), 6.53-6.55 (1H), 6.82-6.89 (2H), 6.92-6.98 (3H), 7.19-7.21 (1H), 7.30-7.33 (1H), 7.46-7.47 (1H)

Example 319

2-Fluoro-5-methylbenzyl 2-[(1S)-1-(2,3-dimethylphenyl)ethyl]-1H-imidazole-1-carboxylate ¹H-NMR (d₆-Acetone): 1.50-1.54 (3H), 2.22-2.31 (9H), 5.02-5.10 (1H), 5.20-5.23 (1H), 5.31-5.34 (1H), 6.50-6.52 (1H), 6.82-6.86 (1H), 6.94-6.98 (2H), 7.00-7.04 (1H), 7.10-7.13 (1H), 7.20-7.24 (1H), 7.45-7.46 (1H)

Example 320

2,5-Difluoro-4-methylbenzyl 2-[(1S)-1-(2,3-dimethylphenyl)ethyl]-1H-imidazole-1-carboxylate ¹H-NMR (d₆-Acetone): 1.50-1.54 (3H), 2.22-2.31 (9H), 5.01-5.06 (1H), 5.20-5.24 (1H), 5.30-5.33 (1H), 6.46-6.48 (1H), 6.82-6.99 (3H), 7.00-7.10 (2H), 7.49-7.53 (1H)

Example 321

2,3,6-Trifluorobenzyl 2-[(1S)-1-(2,3-dimethylphenyl)ethyl]-1H-imidazole-1-carboxylate ¹H-NMR (d₆-Acetone): 1.51-1.54 (3H), 2.21-2.28 (6H), 5.01-5.06 (1H), 5.35-5.39 (1H), 5.41-5.45 (1H), 6.44-6.46 (1H), 6.81-6.85 (1H), 6.93-6.98 (2H), 7.05-7.08 (1H), 7.40-7.45 (2H)

Example 322

(2-Methyl biphenyl-3-yl)methyl 2-[(1S)-1-(2,3-dimethylphenyl)ethyl]-1H-imidazole-1-carboxylate $^1$H-NMR (d$_6$-Acetone): 1.50-1.54 (3H), 2.17-2.18 (3H), 2.21-2.26 (6H), 5.05-5.11 (1H), 5.36-5.41 (2H), 6.50-6.52 (1H), 6.85-6.88 (1H), 6.93-6.98 (2H), 7.20-7.32 (5H), 7.38-7.40 (1H), 7.41-7.45 (2H), 7.56-7.57 (1H)

Example 323

2-Methoxybenzyl 2-[(1S)-1-(2,3-dimethylphenyl)ethyl]-1H-imidazole-1-carboxylate $^1$H-NMR (d$_6$-Acetone): 1.50-1.54 (3H), 2.22-2.29 (6H), 3.79-3.80 (3H), 5.03-5.11 (1H), 5.20-5.30 (2H), 6.51-6.53 (1H), 6.82-6.99 (4H), 7.00-7.02 (1H), 7.18-7.20 (1H), 7.33-7.36 (1H), 7.45-7.46 (1H)

Example 324

4-Bromo-2-fluorobenzyl 2-[(1S)-1-(2,3-dimethylphenyl)ethyl]-1H-imidazole-1-carboxylate $^1$H-NMR (d$_6$-Acetone): 1.51-1.55 (3H), 2.21-2.27 (6H), 5.01-5.06 (1H), 5.22-5.26 (1H), 5.32-5.36 (1H), 6.45-6.47 (1H), 6.82-6.85 (1H), 6.95-6.98 (2H), 7.20-7.23 (1H), 7.35-7.38 (1H), 7.40-7.43 (1H), 7.51-7.53 (1H)

Example 325

2,3-Dimethoxybenzyl 2-[(1S)-1-(2,3-dimethylphenyl)ethyl]-1H-imidazole-1-carboxylate $^1$H-NMR (d$_6$-Acetone): 1.52-1.55 (3H), 2.22-2.27 (6H), 3.69-3.70 (3H), 3.83-3.84 (3H), 5.04-5.09 (1H), 5.24-5.27 (2H), 6.51-6.53 (1H), 6.79-6.81 (1H), 6.84-6.87 (1H), 6.95-6.98 (2H), 7.00-7.06 (2H), 7.45-7.46 (1H)

Example 326

2,3-Dichlorobenzyl 2-[(1S)-1-(2,3-dimethylphenyl)ethyl]-1H-imidazole-1-carboxylate $^1$H-NMR (d$_6$-Acetone): 1.54-1.57 (3H), 2.21-2.26 (6H), 5.02-5.08 (1H), 5.35-5.40 (1H), 5.41-5.45 (1H), 6.47-6.49 (1H), 6.84-6.87 (1H), 6.97-7.00 (2H), 7.21-7.23 (1H), 7.30-7.33 (1H), 7.57-7.58 (1H), 7.58-7.59 (1H)

Example 327

4-Butylbenzyl 2-[(1S)-1-(2,3-dimethylphenyl)ethyl]-1H-imidazole-1-carboxylate $^1$H-NMR (d$_6$-Acetone): 0.88-0.94 (3H), 1.30-1.40 (2H), 1.50-1.61 (5H), 2.23-2.26 (6H), 2.80-2.83 (2H), 5.02-5.10 (1H), 5.20-5.21 (2H), 6.50-6.52 (1H), 6.83-6.86 (1H), 6.95-6.99 (2H), 7.17-7.20 (4H), 7.47-7.48 (1H)

Example 328

3-Methoxybenzyl 2-[(1S)-1-(2,3-dimethylphenyl)ethyl]-1H-imidazole-1-carboxylate $^1$H-NMR (d$_6$-Acetone): 1.50-1.54 (3H), 2.22-2.27 (6H), 3.88-4.00 (3H), 5.04-5.09 (1H), 5.21-5.23 (2H), 6.52-6.54 (1H), 6.81-6.90 (4H), 6.95-6.99 (2H), 7.21-7.25 (1H), 7.46-7.47 (1H)

Example 329

3,4-Dichlorobenzyl 2-[(1S)-1-(2,3-dimethylphenyl)ethyl]-1H-imidazole-1-carboxylate $^1$H-NMR (d$_6$-Acetone): 1.53-1.56 (3H), 2.23-2.28 (6H), 5.02-5.08 (1H), 5.20-5.24 (1H), 5.27-5.31 (1H), 6.44-6.46 (1H), 6.84-6.87 (1H), 6.96-6.99 (2H), 7.20-7.22 (1H), 7.50-7.56 (3H)

Example 330

3,4-Diethoxybenzyl 2-[(1S)-1-(2,3-dimethylphenyl)ethyl]-1H-imidazole-1-carboxylate $^1$H-NMR (d$_6$-Acetone): 1.31-1.39 (6H), 1.50-1.55 (3H), 2.22-2.28 (6H), 3.96-4.07 (4H), 5.03-5.09 (1H), 5.17-5.18 (2H), 6.52-6.54 (1H), 6.80-6.90 (3H), 6.95-7.00 (3H), 7.45-7.46 (1H)

Example 331

3-Methylbenzyl 2-[(1S)-1-(2,3-dimethylphenyl)ethyl]-1H-imidazole-1-carboxylate $^1$H-NMR (d$_6$-Acetone): 1.53-1.56 (3H), 2.23-2.30 (9H), 5.04-5.09 (1H), 5.20-5.24 (2H), 6.49-6.51 (1H), 6.84-6.87 (1H), 6.95-6.98 (2H), 7.05-7.10 (2H), 7.15-7.18 (1H), 7.20-7.23 (1H), 7.48-7.49 (1H)

Example 332

4-Isopropylbenzyl 2-[(1S)-1-(2,3-dimethylphenyl)ethyl]-1H-imidazole-1-carboxylate $^1$H-NMR (d$_6$-Acetone): 1.20-1.24 (6H), 1.52-1.55 (3H), 2.23-2.28 (6H), 5.03-5.08 (1H), 5.20-5.22 (2H), 6.49-6.51 (1H), 6.83-6.86 (1H), 6.96-6.99 (2H), 7.20-7.24 (4H), 7.50-7.51 (1H)

Example 333

3-Chlorobenzyl 2-[(1S)-1-(2,3-dimethylphenyl)ethyl]-1H-imidazole-1-carboxylate $^1$H-NMR (d$_6$-Acetone): 1.52-1.55 (3H), 2.22-2.24 (3H), 2.27-2.29 (3H), 5.02-5.07 (1H), 5.21-5.30 (2H), 6.49-6.51 (1H), 6.85-6.88 (1H), 6.95-6.99 (2H), 7.20-7.22 (1H), 7.35-7.39 (3H), 7.57-7.58 (1H)

Example 334

3,4-Difluorobenzyl 2-[(1S)-1-(2,3-dimethylphenyl)ethyl]-1H-imidazole-1-carboxylate $^1$H-NMR (d$_6$-Acetone): 1.52-1.55 (3H), 2.22-2.24 (3H), 2.28-2.30 (3H), 5.02-5.07 (1H), 5.20-5.24 (1H), 5.25-5.29 (1H), 6.44-6.46 (1H), 6.83-6.86 (1H), 6.95-6.99 (2H), 7.09-7.12 (1H), 7.21-7.28 (2H), 7.56-7.57 (1H)

Example 335

2-Chloro-3,4-dimethoxybenzyl 2-[(1S)-1-(2,3-dimethylphenyl)ethyl]-1H-imidazole-1-carboxylate $^1$H-NMR (d$_6$-Acetone): 1.52-1.55 (3H), 2.22-2.26 (6H), 3.80-3.81 (3H), 3.90-3.92 (3H), 5.02-5.06 (1H), 5.21-5.29 (2H), 6.49-6.51 (1H), 6.85-6.89 (1H), 6.94-7.00 (3H), 7.09-7.12 (1H), 7.44-7.46 (1H)

Example 336

2-Methylbenzyl 2-[(1S)-1-(2,3-dimethylphenyl)ethyl]-1H-imidazole-1-carboxylate

¹H-NMR (d₆-Acetone): 1.51-1.54 (3H), 2.20-2.29 (9H), 5.02-5.07 (1H), 5.21-5.25 (1H), 5.29-5.34 (1H), 6.48-6.51 (1H), 6.84-6.89 (2H), 6.90-6.96 (2H), 7.16-7.25 (3H), 7.50-7.51 (1H)

Example 337

2-Chloro-6-fluorobenzyl 2-[(1S)-1-(2,3-dimethylphenyl)ethyl]-1H-imidazole-1-carboxylate ¹H-NMR (d₆-Acetone): 1.50-1.54 (3H), 2.21-2.25 (6H), 5.01-5.06 (1H), 5.39-5.67 (2H), 6.49-6.52 (1H), 6.82-6.87 (1H), 6.90-6.95 (2H), 7.19-7.24 (1H), 7.35-7.38 (1H), 7.43-7.44 (1H), 7.50-7.56 (1H)

Example 338

4-Methoxybenzyl 2-[(1S)-1-(2,3-dimethylphenyl)ethyl]-1H-imidazole-1-carboxylate

¹H-NMR (d₆-Acetone): 1.50-1.54 (3H), 2.24-2.29 (6H), 3.80-3.81 (3H), 5.02-5.10 (1H), 5.19-5.20 (2H), 6.50-6.53 (1H), 6.83-6.90 (3H), 6.95-6.99 (2H), 7.20-7.23 (2H), 7.43-7.44 (1H)

Example 339

2,3,5,6-Tetramethylbenzyl 2-[(1S)-1-(2,3-dimethylphenyl)ethyl]-1H-imidazole-1-carboxylate ¹H-NMR (d₆-Acetone): 1.44-1.47 (3H), 2.02-2.06 (3H), 2.09-2.12 (6H), 2.19-2.23 (9H), 4.98-5.03 (1H), 5.33-5.35 (1H), 5.30-5.03 (1H), 6.40-6.42 (1H), 6.80-6.84 (1H), 6.90-6.94 (2H), 7.00-7.01 (1H), 7.43-7.44 (1H)

Example 340

3,4,5-Trifluorobenzyl 2-[(1S)-1-(2,3-dimethylphenyl)ethyl]-1H-imidazole-1-carboxylate ¹H-NMR (d₆-Acetone): 1.52-1.54 (3H), 2.22-2.24 (3H), 2.29-2.31 (3H), 5.02-5.08 (1H), 5.20-5.24 (1H), 5.30-5.34 (1H), 6.45-6.47 (1H), 6.83-6.86 (1H), 6.93-6.97 (2H), 7.10-7.16 (2H), 7.57-7.58 (1H)

Example 341

2,5-Difluorobenzyl 2-[(1S)-1-(2,3-dimethylphenyl)ethyl]-1H-imidazole-1-carboxylate ¹H-NMR (d₆-Acetone): 1.52-1.55 (3H), 2.22-2.28 (6H), 5.02-5.09 (1H), 5.23-5.26 (1H), 5.36-5.40 (1H), 6.50-6.52 (1H), 6.82-6.86 (1H), 6.92-6.96 (2H), 7.05-7.10 (1H), 7.19-7.23 (2H), 7.51-7.52 (1H)

Example 342

3,5-Dimethylbenzyl 2-[(1S)-1-(2,3-dimethylphenyl)ethyl]-1H-imidazole-1-carboxylate ¹H-NMR (d₆-Acetone): 1.50-1.53 (3H), 2.22-2.31 (12H), 5.05-5.15 (1H), 5.18-5.20 (2H), 6.52-6.54 (1H), 6.87-6.90 (3H), 6.95-6.98 (3H), 7.50-7.51 (1H)

Example 343

4-(1H-Pyrazol-1-yl)benzyl 2-[(1S)-1-(2,3-dimethylphenyl)ethyl]-1H-imidazole-1-carboxylate ¹H-NMR (d₆-Acetone): 1.51-1.54 (3H), 2.22-2.28 (6H), 5.05-5.14 (1H), 5.25-5.31 (2H), 6.43-6.45 (2H), 6.83-6.86 (1H), 6.96-6.99 (2H), 7.39-7.42 (2H), 7.53-7.54 (1H), 7.69-7.70 (1H), 7.80-7.83 (2H), 8.35-8.36 (1H)

Example 344

3-Chloro-4-methylbenzyl 2-[(1S)-1-(2,3-dimethylphenyl)ethyl]-1H-imidazole-1-carboxylate ¹H-NMR (d₆-Acetone): 1.50-1.53 (3H), 2.21-2.33 (9H), 5.02-5.10 (1H), 5.20-5.27 (2H), 6.47-6.49 (1H), 6.83-6.86 (1H), 6.94-6.97 (2H), 7.10-7.21 (2H), 7.33-7.36 (1H), 7.51-7.53 (1H)

Example 345

4-Ethoxy-3-methoxybenzyl 2-[(1S)-1-(2,3-dimethylphenyl)ethyl]-1H-imidazole-1-carboxylate

Example 346

3-Cyanobenzyl 2-[(1S)-1-(2,3-dimethylphenyl)ethyl]-1H-imidazole-1-carboxylate

¹H-NMR (d₆-Acetone): 1.51-1.54 (3H), 2.22-2.28 (6H), 5.02-5.09 (1H), 5.28-5.31 (1H), 5.38-5.41 (1H), 6.43-6.45 (1H), 6.84-6.86 (1H), 6.95-6.98 (2H), 7.55-7.60 (3H), 7.61-7.63 (1H), 7.85-7.88 (1H)

Example 347

2-Methoxy-4-methylbenzyl 2-[(1S)-1-(2,3-dimethylphenyl)ethyl]-1H-imidazole-1-carboxylate ¹H-NMR (d₆-Acetone): 1.50-1.53 (3H), 2.21-2.25 (6H), 2.32-2.34 (3H), 3.78-3.79 (3H), 5.06-5.11 (1H), 5.19-5.25 (2H), 6.50-6.53 (1H), 6.72-6.74 (1H), 6.81-6.90 (2H), 6.93-6.97 (2H), 7.05-6.08 (1H), 7.42-7.43 (1H)

Example 348

4-Fluorobenzyl 2-[(1S)-1-(2,3-dimethylphenyl)ethyl]-1H-imidazole-1-carboxylate

¹H-NMR (d₆-Acetone): 1.50-1.54 (3H), 2.23-2.27 (6H), 5.01-5.06 (1H), 5.21-5.29 (2H), 6.47-6.49 (1H), 6.82-6.85 (1H), 6.95-6.98 (2H), 7.05-7.11 (2H), 7.32-7.38 (2H), 7.48-7.50 (1H)

Example 349

(7-Methoxy-1,3-benzodioxol-5-yl)methyl 2-[(1S)-1-(2,3-dimethylphenyl)ethyl]-1H-imidazole-1-carboxylate

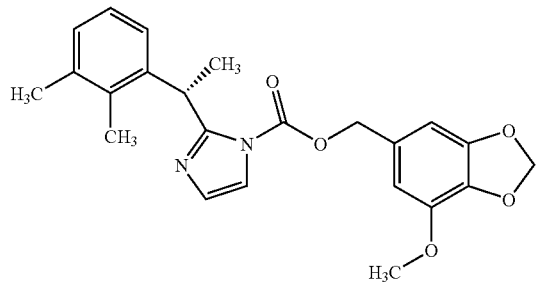

To a mixture of the compound of Example 1 (180 mg, 0.90 mmol) and pyridine (146 µl, 1.80 mmol) in anhydrous acetonitrile (3 ml), at 0° C. and under nitrogen, was added diphosgene (54 µl, 89 mg, 0.45 mmol). The mixture was allowed to warm to room temperature and stirred for 10 min, before addition of (7-methoxy-1,3-benzodioxol-5-yl)methanol (137 mg, 0.75 mmol) in acetonitrile (1 ml), via syringe. The reaction mixture was stirred at room temperature for 30 min and then filtered.

The filtrate was purified by automated preparative liquid chromatography (Gilson system, 150 mm×22.4 mm LUNA C18(2)$_5$ μm column, 20 ml/min) using an acetonitrile:water gradient [15:85 to 98:2]. The appropriate fractions were combined and concentrated to give the title compound (20 mg).

Experimental MH$^+$ 365.9 (minus 44); expected 409.2 or 365.2 $^1$H-NMR (d$_6$-Acetone): 1.50-1.54 (3H), 2.24-2.32 (6H), 3.80-3.81 (3H), 5.05-5.12 (1H), 5.15-5.18 (2H), 6.00-6.01 (2H), 6.50-6.53 (2H), 6.63-6.64 (1H), 6.82-6.86 (1H), 6.95-6.97 (2H), 7.49-7.50 (1H) Rhip. Funct. ED$_{100}$ mg/cm$^2$=0.03

Similarly Prepared from Example 58 were:

| Ex. No. | R$^6$ | Precursor | MH$^+$ Found/ Expected | Rhip. Funct. ED$_{100}$ mg/cm$^2$ |
|---|---|---|---|---|
| 350 | | 2-Naphthylmethanol | 385.9 / 385.2 | <=10 |
| 351 | | (4-Phenyl-2-furyl)-methanol | — | >0.03 |
| 352 | | (6-Phenoxypyridin-3-yl)-methanol | 428.9 / 428.2 | <=10 |
| 353 | | 5-(6-Fluoro-1H-indol-1-yl)pentan-1-ol | 449.0 / 448.2 | >0.03 |
| 354 | | 2-(6-Methoxy-1,5-naphthyridin-4-yl)-ethanol | 432.0 / 431.2 | <=10 |
| 355 | | 2-(2-Naphthyl)ethanol | 399.9 / 399.2 | <=10 |

-continued

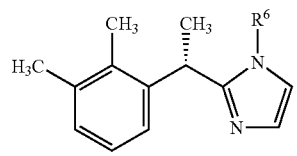

| Ex. No. | R⁶ | Precursor | MH⁺ Found/ Expected | Rhip. Funct. ED$_{100}$ mg/cm² |
|---|---|---|---|---|
| 356 | | 1-Benzofuran-2-ylmethanol | 331.8 331.2 decarboxylates | 0.1 |
| 357 | | 2,3-Dihydro-1,4-benzodioxin-6-yl-methanol | 350.0 349.2 decarboxylates | >0.03 |
| 358 | | (2-Phenyl-1,3-benzothiazol-5-yl)-methanol | 469.0 468.2 | <=10 |
| 359 | | (3-Ethyl-5,5,8,8-tetramethyl-5,6,7,8-tetrahydronaphthalen-2-yl)methanol | 430.1 429.3 decarboxylates | <=10 |

Example 350

2-Naphthylmethyl 2-[(1S)-1-(2,3-dimethylphenyl)ethyl]-1H-imidazole-1-carboxylate ¹H-NMR (d$_6$-Acetone): 1.53-1.56 (3H), 2.20-2.22 (3H), 2.26-2.28 (3H), 5.05-5.12 (1H), 5.40-5.45 (2H), 6.51-6.53 (1H), 6.85-6.96 (3H), 7.18-7.21 (1H), 7.51-7.56 (3H), 7.80-7.81 (1H), 7.83-7.95 (3H)

Example 351

(4-Phenyl-2-furyl)methyl 2-[(1S)-1-(2,3-dimethylphenyl)ethyl]-1H-imidazole-1-carboxylate ¹H-NMR (d$_6$-Acetone): 1.48-1.56 (3H), 2.20-2.30 (6H), 4.42-4.51 (1H), 4.80-4.86 (2H), 6.49-6.53 (2H), 6.85-7.01 (10H) h

Example 352

(6-Phenoxypyridin-3-yl)methyl 2-[(1S)-1-(2,3-dimethylphenyl)ethyl]-1H-imidazole-1-carboxylate ¹H-NMR (d$_6$-Acetone): 1.51-1.54 (3H), 2.23-2.29 (6H), 5.01-5.10 (1H), 5.20-5.30 (2H), 6.44-6.47 (1H), 6.84-6.88 (1H), 6.90-6.98 (3H), 7.12-7.15 (2H), 7.20-7.24 (1H), 7.40-7.46 (2H), 7.50-7.51 (1H), 7.65-7.67 (1H), 8.10-8.12 (1H)

Example 353

5-(6-Fluoro-1H-indol-1-yl)pentyl 2-[(1S)-1-(2,3-dimethylphenyl)ethyl]-1H-imidazole-1-carboxylate ¹H-NMR (d$_6$-Acetone): 1.22-1.28 (2H), 1.52-1.55 (3H), 1.60-1.66 (2H), 1.80-1.85 (2H), 2.24-2.26 (3H), 2.35-2.37 (3H), 4.16-4.26 (4H), 5.01-5.06 (1H), 6.40-6.42 (1H), 6.51-6.53 (1H), 6.80-6.90 (2H), 6.96-6.99 (2H), 7.19-7.21 (1H), 7.22-7.23 (1H), 7.40-7.41 (1H), 7.49-7.52 (1H)

Example 354

2-(6-Methoxy-1,5-naphthyridin-4-yl)ethyl 2-[(1S)-1-(2,3-dimethylphenyl)ethyl]-1H-imidazole-1-carboxylate ¹H-NMR (d$_6$-Acetone): 1.43-1.46 (3H), 2.21-2.26 (6H), 3.42-3.60 (2H), 4.00-4.01 (3H), 4.61-4.75 (2H), 4.92-4.97 (1H), 6.51-6.53 (1H), 6.82-6.95 (3H), 7.08-7.10 (1H), 7.29-7.30 (1H), 7.42-7.44 (1H), 8.20-8.23 (1H), 8.61-8.63 (1H)

Example 355

2-(2-Naphthyl)ethyl 2-[(1S)-1-(2,3-dimethylphenyl)ethyl]-1H-imidazole-1-carboxylate ¹H-NMR (d$_6$-Acetone): 1.52-1.55 (3H), 2.24-2.30 (6H), 3.10-3.15 (2H), 4.45-4.60 (2H), 5.00-5.07 (1H), 6.52-6.55 (1H), 6.82-6.95 (3H), 7.39-7.49 (4H), 7.71-7.72 (1H), 7.80-7.87 (3H)

Example 356

1-Benzofuran-2-ylmethyl 2-[(1S)-1-(2,3-dimethylphenyl)ethyl]-1H-imidazole-1-carboxylate $^1$H-NMR (d$_6$-Acetone): 1.52-1.56 (3H), 2.21-2.23 (3H), 2.30-2.32 (3H), 5.03-5.10 (1H), 5.39-5.42 (2H), 6.45-6.47 (1H), 6.81-6.98 (4H), 7.21-7.24 (1H), 7.30-7.34 (1H), 7.45-7.51 (2H), 7.62-7.64 (1H)

Example 357

2,3-Dihydro-1,4-benzodioxin-6-ylmethyl 2-[(1S)-1-(2,3-dimethylphenyl)ethyl]-1H-imidazole-1-carboxylate $^1$H-NMR (d$_6$-Acetone): 1.51-1.54 (3H), 2.24-2.29 (6H), 4.21-4.24 (4H), 5.03-5.11 (3H), 6.50-6.53 (1H), 6.78-6.80 (2H), 6.82-6.88 (2H), 6.96-6.99 (2H), 7.46-7.48 (1H)

Example 358

(2-Phenyl-1,3-benzothiazol-5-yl)methyl 2-[(1S)-1-(2,3-dimethylphenyl)ethyl]-1H-imidazole-1-carboxylate $^1$H-NMR (d$_6$-Acetone): 1.51-1.54 (3H), 2.21-2.22 (3H), 2.27-2.28 (3H), 5.02-5.09 (1H), 5.20-5.28 (2H), 6.50-6.52 (1H), 6.82-6.98 (3H), 7.36-7.39 (1H), 7.58-7.61 (4H), 8.00-8.05 (2H), 8.14-8.18 (2H)

Example 359

(3-Ethyl-5,5,8,8-tetramethyl-5,6,7,8-tetrahydronaphthalen-2-yl)methyl 2-[(1S)-1-(2,3-dimethylphenyl)ethyl]-1H-imidazole-1-carboxylate $^1$H-NMR (d$_6$-Acetone): 1.09-1.15 (3H), 1.20-1.30 (12H), 1.50-1.54 (3H), 1.64-1.66 (4H), 2.20-2.29 (6H), 2.50-2.60 (2H), 5.04-5.10 (1H), 5.22-5.24 (2H), 6.52-6.55 (1H), 6.81-6.84 (1H), 6.92-6.95 (2H), 7.20-7.21 (1H), 7.37-7.38 (1H), 7.44-7.45 (1H)

Preparations

Preparation 1

2-[1-(2,3-Dimethylphenyl)vinyl]-1H-imidazole

The compound of Preparation 13 (80 mg, 0.37 mmol) was stirred at 50° C. in thionyl chloride (2 ml) for 1 h. The reaction was quenched into iced water (5 ml) and then basified with dilute aqueous sodium hydroxide solution. The aqueous phase was then extracted with dichloromethane (2×10 ml). The combined extracts were dried (MgSO$_4$) and concentrated in vacuo to give the title compound (72 mg).

Alternative Synthesis

A solution of thionyl chloride (37 ml, 498 mmol) in acetonitrile (200 ml) was added to the compound of Preparation 13 (48.90 g, 226 mmol). The resulting solution was stirred at room temperature for 2 h, then poured into ice/water (600 ml), during which time the internal temperature was maintained at <25° C. The reaction mixture was then neutralised by the addition of aqueous sodium hydroxide solution (4N) while maintaining the temperature at <35° C. The mixture was adjusted to pH 6, and the suspension obtained was filtered at room temperature. The light beige crystalline solid obtained was washed with water (100 ml) and dried in vacuo at 60° C. to give the title compound (30.6 g).

Experimental MH$^+$ 199.2; expected 199.1

Alternative Synthesis

To a solution of the compound of Preparation 195 (1.0 kg, 3.25 mol) in 2-propanol (10 L) was added palladium (10 wt. % on carbon, 100.0 g) and the reaction mixture was heated at 60° C. under a hydrogen atmosphere (45-60 psi) for 24 h. The mixture was cooled and filtered through Hyflo Super Cel®, washing through with 2-propanol (2×250 ml). The filtrate was concentrated in vacuo and diluted with acetonitrile (1300 ml) and stirred to get a solution. To this solution, was then added dropwise sulphuric acid (conc., 1.2 L). The reaction mixture was stirred at 55° C. for 18 h. The mixture was cooled to −5° C., quenched with water (12.5 l), and adjusted to pH 10 by addition of aqueous sodium hydroxide solution (50%). The resulting solid was collected by filtration, reslurried with water (15.0 L) filtered, washed with water (2.5 L) and dried in vacuo at 50° C. to give the title compound (0.413 kg, purity by HPLC 99.80%).

Preparation 2

2-[1-(2,3-Difluorophenyl)vinyl]-1H-imidazole

A solution of the compound of Preparation 14 (240 mg, 1.1 mmol) and thionyl chloride (1.56 ml, 21.4 mmol) in acetonitrile (5 ml) was heated at 70° C. for 10 h and then stirred at room temperature for 18 h. The mixture was concentrated in vacuo and to the residue was added toluene. This solution was concentrated in vacuo and the process was repeated. The residue was then partitioned between ethyl acetate (50 ml) and saturated aqueous sodium hydrogen carbonate solution (30 ml). The two layers were separated and the aqueous layer was extracted with ethyl acetate (2×40 ml). The combined organic phases were dried (MgSO$_4$) and stirred with activated charcoal, before being filtered and concentrated in vacuo to give the title compound (325 mg).

Experimental MH$^+$ 207.1; expected 207.1

Similarly Prepared were:

| Prep. No | Name | MH$^+$ Found/ Expected | From Prep. | From |
|---|---|---|---|---|
| 3 | 2-[1-(2-Chloro-6-fluoro-3-methylphenyl)vinyl]-1H-imidazole | 237.1 / 237.1 | 88 | 1-(2-Chloro-6-fluoro-3-methylphenyl)-1-(1H-imidazol-2-yl)ethanol |
| 4 | 2-[1-(4-Fluoro-3-methylphenyl)vinyl]-1H-imidazole | 203.1 / 203.1 | 15 | 1-(4-Fluoro-3-methylphenyl)-1-(1H-imidazol-2-yl)ethanol |
| 5 | 2-[1-(2,6-Difluorophenyl)vinyl]-1H-imidazole | 207.3 / 207.1 | 16 | 1-(2,6-Difluorophenyl)-1-(1H-imidazol-2-yl)ethanol |

| Prep. No | Name | MH+ Found/ Expected | From Prep. | From |
|---|---|---|---|---|
| 6 | 2-[1-(3-Fluoro-2-methylphenyl)vinyl]-1H-imidazole | 203.3 203.1 | 17 | 1-(3-Fluoro-2-methylphenyl)-1-(1H-imidazol-2-yl)ethanol |
| 7 | 2-[1-(3-Fluorophenyl)vinyl]-1H-imidazole | 189.3 189.1 | 18 | 1-(3-Fluorophenyl)-1-(1H-imidazol-2-yl)ethanol |
| 8 | 2-{1-[2-Chloro-3-(trifluoromethyl)phenyl]vinyl}-1H-imidazole | 273.1 273.0 | 21 | 1-[2-Chloro-3-(trifluoromethyl)phenyl]-1-(1H-imidazol-2-yl)ethanol |
| 9 | 2-[1-(3-Fluoro-5-methylphenyl)vinyl]-1H-imidazole | — | 19 | 1-(3-Fluoro-5-methylphenyl)-1-(1H-imidazol-2-yl)ethanol |
| 10 | 2-[1-(3,5-Difluorophenyl)vinyl]-1H-imidazole | — | 22 | 1-(3,5-Difluorophenyl)-1-(1H-imidazol-2-yl)ethanol |
| 11 | 2-[1-(5-Methoxy-2,4-dimethylphenyl)vinyl]-1H-imidazole | 229.3 229.1 | 20 | 1-(1H-Imidazol-2-yl)-1-(5-methoxy-2,4-dimethylphenyl)ethanol |
| 12 | 2-{1-[2-Fluoro-3-(trifluoromethyl)phenyl]vinyl}-1H-imidazole | 257.4 257.1 | 23 | 1-[2-Fluoro-3-(trifluoromethyl)phenyl]-1-(1H-imidazol-2-yl)ethanol |

Preparation 13

1-(2,3-Dimethylphenyl)-1-(1H-imidazol-2-yl)ethanol 1-(Diethoxymethyl)imidazole (76.0 g, 446 mmol) and N,N,N,N-tetramethylethylene diamine (67.6 mL, 446 mmol) were dissolved in 2-methyltetrahydrofuran (400 ml) and cooled to −40° C., under nitrogen. n-Butyl lithium (2.5M in hexane, 180 ml, 446 mmol) was added slowly maintaining the reaction temperature at <−25° C. throughout. The reaction mixture was stirred for an hour and allowed to warm to 0° C., after which 2,3-dimethylacetophenone (44.00 g, 297.00 mmol) was added whilst maintaining the reaction temperature at <15° C. throughout. The reaction was stirred at room temperature overnight and then quenched with aqueous hydrochloric acid (2N, 1 l). The mixture was extracted with ethyl acetate (500 ml) and to the aqueous layer was added sodium carbonate. The aqueous layer was further extracted with ethyl acetate (800 ml) and the combined extracts were washed with water (500 ml), dried (MgSO$_4$) and concentrated in vacuo to give the title compound (48.9 g).

Experimental MH+ 217.2; expected 217.1

Alternative Synthesis

To a solution of methylmagnesium bromide (0.63 ml, 0.88 mmol) was added a stirred solution of the compound of Preparation 24 (80 mg, 0.4 mmol) in anhydrous tetrahydrofuran at 0° C. The reaction mixture was stirred for 30 min, quenched with saturated ammonium chloride solution, basified with saturated sodium hydrogen carbonate solution and extracted with dichloromethane (2×3 ml). The organic layers were dried (MgSO$_4$) and concentrated in vacuo to give the title compound (85 mg)

Experimental MH+ 217.2; expected 217.1

Preparation 14

1-(2,3-Difluorophenyl)-1-(1H-imidazol-2-yl)ethanol

To a solution of the compound of Preparation 25 (450 mg, 2.2 mmol) in tetrahydrofuran (5 ml), at 0° C., was added methylmagnesium bromide (3M in diethyl ether, 2.16 ml, 6.5 mmol) and the reaction mixture was stirred at room temperature for 1 h. To the mixture was added hydrochloric acid (0.1M, 15 ml) and the mixture basified by addition of saturated aqueous sodium hydrogen carbonate solution. The mixture was extracted with ethyl acetate (3×20 ml) and the combined organics were dried (MgSO$_4$) and concentrated in vacuo to give the title compound (240 mg)

Experimental MH+ 225.1; expected 225.1

Similarly Prepared were:

| Prep. No | Name | MH+ Found/ Expected | From Prep. | From |
|---|---|---|---|---|
| 15 | 1-(4-Fluoro-3-methylphenyl)-1-(1H-imidazol-2-yl)ethanol | 221.1 221.1 | 26 | (4-Fluoro-3-methylphenyl)(1H-imidazol-2-yl)methanone |
| 16 | 1-(2,6-Difluorophenyl)-1-(1H-imidazol-2-yl)ethanol | — | 27 | (2,6-Difluorophenyl)(1H-imidazol-2-yl)methanone |
| 17 | 1-(3-Fluoro-2-methylphenyl)-1-(1H-imidazol-2-yl)ethanol | — | 28 | (3-Fluoro-2-methylphenyl)(1H-imidazol-2-yl)methanone |
| 18 | 1-(3-Fluorophenyl)-1-(1H-imidazol-2-yl)ethanol | — | 29 | (3-Fluorophenyl)(1H-imidazol-2-yl)methanone |
| 19 | 1-(3-Fluoro-5-methylphenyl)-1-(1H-imidazol-2-yl)ethanol | — | 31 | (3-Fluoro-5-methylphenyl)(1H-imidazol-2-yl)methanone |
| 20 | 1-(1H-Imidazol-2-yl)-1-(5-methoxy-2,4-dimethylphenyl)ethanol | 247.4 247.1 | 34 | 1H-Imidazol-2-yl(5-methoxy-2,4-dimethylphenyl)methanone |

Preparation 16

¹H-NMR (CD₃OD): 2.00-2.05 (3H), 6.84-6.95 (4H), 7.26-7.34 (1H)

Preparation 18

¹H-NMR (CD₃OD): 1.89-1.92 (3H), 6.89-6.96 (3H), 7.18-7.23 (2H), 7.25-7.31 (1H)

Preparation 19

¹H-NMR (CDCl₃): 1.20-1.25 (3H), 2.21-2.27 (3H), 6.62-6.66 (1H), 6.80-7.00 (3H), 7.41-7.49 (1H)

Preparation 21

1-[2-Chloro-3-(trifluoromethyl)phenyl]-1-(1H-imidazol-2-yl)ethanol

To a solution of the compound of Preparation 30 (1.1 g, 4.0 mmol) in tetrahydrofuran (10 ml), at −78° C., was added dropwise methyllithium (1.6M in diethyl ether, 3 ml, 4.8 mmol). After stirring for 2 h, cold hydrochloric acid (0.1M) was added and the mixture was adjusted to pH 7 by addition of potassium carbonate. The mixture was extracted with ethyl acetate and the combined extracts were dried (MgSO₄) and concentrated in vacuo to give the title compound (600 mg).

Similarly Prepared were:

(15% in dichloromethane, 3 ml) and the reaction mixture was stirred at room temperature for 30 min. The mixture filtered through silica, eluting with diethyl ether and the filtrate was concentrated in vacuo. The residue was purified by flash chromatography (silica), with gradient elution, diethyl ether:dichloromethane [0:1 to 1:1]. The appropriate fractions were combined and concentrated to give the title compound (100 mg).

Experimental MH⁺ 201.2; expected 201.1

Preparation 25

(2,3-difluorophenyl)(1H-imidazol-2-yl)methanone

To a solution of the compound of Preparation 37 (350 mg, 1.67 mmol) in dichloromethane (20 ml) was added Dess-Martin Periodinane (780 mg, 1.80 mmol) and the reaction mixture was stirred at room temperature for 1 h. The mixture was filtered through silica, washing through with dichloromethane and ethyl acetate and the filtrate was concentrated in vacuo. To the residue as added ethyl acetate (100 ml) and the solution was washed with aqueous sodium metabisulphite solution (10%, 40 ml). The aqueous phase was extracted with

| Prep. No | Name | MH⁺ Found/ Expected | From Prep. | From |
|---|---|---|---|---|
| 22 | 1-(3,5-Difluorophenyl)-1-(1H-imidazol-2-yl)ethanol | 225.4 225.1 | 32 | (3,5-Difluorophenyl)(1H-imidazol-2-yl)methanone |
| 23 | 1-[2-Fluoro-3-(trifluoromethyl)-phenyl]-1-(1H-imidazol-2-yl)ethanol | 275.5 275.1 | 33 | [2-Fluoro-3-(trifluoromethyl)-phenyl](1H-imidazol-2-yl)-methanone |

Preparation 24

(2,3-Dimethylphenyl)(1H-imidazol-2-yl)methanone

To the compound of Preparation 201 (200 mg, 1.0 mmol) in dichloromethane (10 ml) was added Dess Martin Periodinane ethyl acetate (100 ml) and the combined organic phases were dried (MgSO₄) and concentrated in vacuo to give the title compound (450 mg)

Experimental MH⁺ 209.1; expected 209.1

Similarly Prepared were:

| Prep. No | Name | MH⁺ Found/ Expected | From Prep. | From |
|---|---|---|---|---|
| 26 | (4-Fluoro-3-methylphenyl)(1H-imidazol-2-yl)methanone | 205.3 205.1 | 38 | (4-Fluoro-3-methylphenyl)(1H-imidazol-2-yl)methanol |
| 27 | (2,6-Difluorophenyl)(1H-imidazol-2-yl)methanone | 209.1 209.1 | 39 | (2,6-Difluorophenyl)(1H-imidazol-2-yl)methanol |
| 28 | (3-Fluoro-2-methylphenyl)(1H-imidazol-2-yl)methanone | 205.3 205.1 | 40 | (3-Fluoro-2-methylphenyl)(1H-imidazol-2-yl)methanol |
| 29 | (3-Fluorophenyl)(1H-imidazol-2-yl)methanone | 191.1 191.1 | 41 | (3-Fluorophenyl)(1H-imidazol-2-yl)methanol |
| 30 | [2-Chloro-3-(trifluoromethyl)-phenyl](1H-imidazol-2-yl)methanone | No data | 42 | [2-Chloro-3-(trifluoromethyl)-phenyl](1H-imidazol-2-yl)methanol |
| 31 | (3-Fluoro-5-methylphenyl)(1H-imidazol-2-yl)methanone | 205.3 205.1 | 43 | (3-Fluoro-5-methylphenyl)(1H-imidazol-2-yl)methanol |
| 32 | (3,5-Difluorophenyl)(1H-imidazol-2-yl)methanone | 209.3 209.1 | 44 | (3,5-Difluorophenyl)(1H-imidazol-2-yl)methanol |
| 33 | [2-Fluoro-3-(trifluoromethyl)phenyl]-(1H-imidazol-2-yl)methanone | 259.4 259.1 | 46 | [2-Fluoro-3-(trifluoromethyl)phenyl]-(1H-imidazol-2-yl)methanol |

Preparation 34

1H-Imidazol-2-yl(5-methoxy-2,4-dimethylphenyl)methanone

To a solution of the compound of Preparation 45 (433 mg, 1.8 mmol) in ethyl acetate (10 ml) was added manganese (IV) oxide (810 mg, 9.3 mmol) and the reaction mixture was stirred at room temperature for 3 h. The mixture was filtered through Arbocel®, washing through with ethyl acetate, and the filtrate was concentrated in vacuo to give the title compound (440 mg).

Experimental MH$^+$ 231.3; expected 231.1

Preparation 35

1-(2,3-Dimethylphenyl)propan-1-one

A mixture of the compound of Preparation 192 (1.0 g, 6.1 mmol) and Dess-Martin Periodinane (2.58 g, 6.1 mmol) in dichloromethane (20 ml) was stirred at room temperature for 1 h. The mixture was then purified by column chromatography (silica), eluting with dichloromethane:cyclohexane [1:1]. The appropriate fractions were combined and concentrated to give the title compound (0.95 g).

$^1$H-NMR (CDCl$_3$): 1.11-1.19 (3H), 2.23-2.29 (6H), 2.79-2.87 (2H), 7.07-7.12 (1H), 7.17-7.27 (3H)

Preparation 36

(1-Benzyl-1H-imidazol-2-yl)(2,3-dimethylphenyl)methanone

A solution of 2,3-dimethylbenzoic acid (100 g, 666 mmol) in thionyl chloride (350 ml) was heated at 80° C. for 1 h, before cooling to room temperature and concentrating in vacuo. To the residue was added toluene (100 ml) and the solution was again concentrated in vacuo. The intermediate acid chloride was added to a mixture of 1-benzylimidazole (100 g, 632 mmol) and triethylamine (100 ml) in acetonitrile (1 l) and the reaction mixture was heated at reflux for 18 h. The reaction mixture was concentrated in vacuo and to the residue was added diethyl ether (500 ml) and ethyl acetate (50 ml). This solution was washed with water (500 ml) and saturated aqueous sodium hydrogen carbonate solution (500 ml), filtered through silica gel (100 g) and concentrated in vacuo to give the title compound (182 g).

Experimental MH$^+$ 291.4; expected 291.1

Alternative Synthesis

To a solution of 2,3-dimethylbenzoic acid (2.0 kg, 13.2 mol) in toluene (20 L) was added N,N-dimethylformamide (20 ml), followed by oxalyl chloride (2.0 kg, 15.6 mol) at room temperature. The reaction mixture was stirred at room temperature for 4 h and monitored by thin layer chromatography. If necessary, excess oxalyl chloride (25 g) was added until no starting material was observed. Excess toluene and oxalyl chloride were removed by distillation under vacuum at temperatures below 70° C. To the residue was added toluene (150 ml) and the mixture was again concentrated in vacuo to give 2,3-dimethylbenzoyl chloride (2.0 kg).

To a solution of 1-benzyl-1H-imidazole (1.69 Kg, 10.56 mol) in dichloromethane (14.0 L), at −7° C., was added triethylamine (1.61 kg, 10.56 mol). A solution of 2,3-dimethylbenzoyl chloride (2.0 kg, 11.99 mol) in dichloromethane (6.0 L) was then added dropwise and the reaction mixture was stirred at room temperature for 16 h. The reaction was monitored by Thin layer Chromatography. After completion of the reaction, the reaction mixture was diluted with water (5.0 L) and the mixture was stirred for a further 15 min. The two layers were separated and the organic phase was concentrated in vacuo. To the residue was added toluene (8.0 L) and the solution was cooled to −5° C., before addition of hydrochloric acid (5N, 8.0 L). The two layers were separated and the aqueous layer was adjusted to pH 9-12, by addition of aqueous sodium hydroxide solution (50%), and extracted with toluene (4.0 L and then 8.0 L). The combined organic phases were concentrated in vacuo to give the title compound (2.8 kg).

Preparation 37

(2,3-Difluorophenyl)(1H-imidazol-2-yl)methanol

To a solution of 1-(diethoxymethyl)-1H-imidazole (1.65 ml, 10.1 mmol) in tetrahydrofuran (15 ml), at −60° C. and under nitrogen, was added n-butyllithium (2.5 M in hexanes, 4.03 ml, 10.1 mmol). The reaction mixture was stirred at −60° C. for 1 h, before addition of 2,3-difluorobenzaldehyde (1.00 ml, 9.2 mmol), and then allowed to warm to room temperature over 18 h. The mixture was concentrated in vacuo and to the residue was added ethyl acetate (50 ml) and hydrochloric acid (3M, 50 ml). The two layers were separated and the aqueous phase was basified with aqueous sodium hydroxide solution (20%) and extracted with ethyl acetate (3×100 ml). The combined organic phases were dried (MgSO$_4$) and concentrated in vacuo and the residue was re-crystallised from 2-propanol to give the title compound (1.25 g)

Experimental MH$^+$ 211.1; expected 211.1

Similarly Prepared were:

| Prep. No | Name | MH+ Found/ Expected | From | From |
|---|---|---|---|---|
| 38 | (4-Fluoro-3-methylphenyl)(1H-imidazol-2-yl)methanol | 207.2 / 207.1 | — | 4-Fluoro-3-methyl-benzaldehyde |
| 39 | (2,6-Difluorophenyl)(1H-imidazol-2-yl)methanol | 211.1 / 211.1 | — | 2,6-Difluoro-benzaldehyde |
| 40 | (3-Fluoro-2-methylphenyl)(1H-imidazol-2-yl)methanol | 207.3 / 207.1 | — | 3-Fluoro-2-methyl-benzaldehyde |
| 41 | (3-Fluorophenyl)(1H-imidazol-2-yl)methanol | 193.1 / 193.1 | — | 3-Fluoro-benzaldehyde |
| 42 | [2-Chloro-3-(trifluoromethyl)-phenyl](1H-imidazol-2-yl)methanol | — | — | 2-Chloro-3-(trifluoromethyl)-benzaldehyde |
| 43 | (3-Fluoro-5-methylphenyl)(1H-imidazol-2-yl)methanol | 207.3 / 207.1 | — | 3-Fluoro-5-methyl-benzaldehyde |

-continued

| Prep. No | Name | MH+ Found/ Expected | From | From |
|---|---|---|---|---|
| 44 | (3,5-Difluorophenyl)(1H-imidazol-2-yl)methanol | 211.3 / 211.1 | — | 3,5-Difluoro-benzaldehyde |
| 45 | 1H-Imidazol-2-yl(5-methoxy-2,4-dimethylphenyl)methanol | 233.3 / 233.1 | Prep. 190 | 5-Methoxy-2,4-dimethyl-benzaldehyde |
| 46 | [2-Fluoro-3-(trifluoromethyl)-phenyl](1H-imidazol-2-yl)methanol | 261.4 / 261.1 | — | 2-Fluoro-3-(trifluoromethyl)-benzaldehyde |

Preparation 47

2-[1-(2,3-Dimethylphenyl)prop-1-en-1-yl]-1H-imidazole

A solution of the compound of Preparation 83 (350 mg, 1.52 mmol) in hydrochloric acid (2N, 50 ml) was heated at reflux for 18 h. The reaction mixture was concentrated in vacuo and the residue was partitioned between dichloromethane (20 ml) and aqueous sodium hydrogen carbonate solution (20 ml). The two layers were separated and the aqueous phase was extracted with dichloromethane (2×20 ml). The combined organic phases were dried (MgSO$_4$) and concentrated in vacuo to give the title compound (255 mg).

Experimental MH+ 213.2; expected 213.1

Preparation 48

2-[1-(3-Methylphenyl)vinyl]-1H-imidazole

A solution of the compound of Preparation 78 (850 mg, 4.2 mmol) in hydrochloric acid (6N, 20 ml) was heated at reflux for 18 h. The reaction mixture was concentrated in vacuo and the residue was partitioned between dichloromethane (20 ml) and water (10 ml). The mixture was adjusted to pH 7 by addition of saturated aqueous sodium hydrogen carbonate solution and the two layers were separated. The organic phase was dried (MgSO$_4$) and concentrated in vacuo to give the title compound (800 mg).

Experimental MH+ 185.3; expected 185.1

Similarly Prepared were:

| Prep. No | Name | MH+ Found/ Expected | From Prep. | From |
|---|---|---|---|---|
| 49 | 2-[1-(2,5-Dimethylphenyl)vinyl]-1H-imidazole | 217.0 / 217.3 | 80 | 1-(2,5-Dimethylphenyl)-1-(1H-imidazol-2-yl)ethanol |
| 50 | 2-[1-(3,5-Dimethylphenyl)vinyl]-1H-imidazole | 199.3 / 199.1 | 82 | 1-(3,5-Dimethylphenyl)-1-(1H-imidazol-2-yl)ethanol |
| 51 | 2-{1-[2-(Trifluoromethyl)phenyl]vinyl}-1H-imidazole | 239.4 / 239.1 | 79 | 1-(1H-imidazol-2-yl)-1-[2-(trifluoromethyl)phenyl]ethanol |
| 52 | 2-[1-(2,3-Dichlorophenyl)vinyl]-1H-imidazole | 239.2 / 239.0 | 84 | 1-(2,3-Dichlorophenyl)-1-(1H-imidazol-2-yl)ethanol |
| 53 | 2-[1-(3,4-Dichlorophenyl)vinyl]-1H-imidazole | 239.2 / 239.0 | 85 | 1-(3,4-Dichlorophenyl)-1-(1H-imidazol-2-yl)ethanol |
| 54 | 2-[1-(3-Chlorophenyl)vinyl]-1H-imidazole | 205.1 / 205.3 | 86 | 1-(3-Chlorophenyl)-1-(1H-imidazol-2-yl)ethanol |
| 55 | 2-[1-(2,5-Dichlorophenyl)vinyl]-1H-imidazole | 239.2 / 239.0 | 87 | 1-(2,5-Dichlorophenyl)-1-(1H-imidazol-2-yl)ethanol |
| 56 | 2-[1-(2,4-Dichlorophenyl)vinyl]-1H-imidazole | 239.2 / 239.0 | 98 | 1-(2,4-Dichlorophenyl)-1-(1H-imidazol-2-yl)ethanol |
| 57 | 2-(1-Phenylvinyl)-1H-imidazole | 171.2 / 171.1 | 99 | 1-(1H-Imidazol-2-yl)-1-phenylethanol |
| 58 | 2-[1-(4-Methylphenyl)vinyl]-1H-imidazole | 185.3 / 185.1 | 100 | 1-(1H-Imidazol-2-yl)-1-(4-methylphenyl)ethanol |
| 59 | 2-(1-Mesitylvinyl)-1H-imidazole | 213.4 / 213.1 | 101 | 1-(1H-Imidazol-2-yl)-1-mesitylethanol |
| 60 | 2-{1-[3-(Trifluoromethyl)phenyl]vinyl}-1H-imidazole | 239.3 / 239.1 | 102 | 1-(1H-Imidazol-2-yl)-1-[3-(trifluoromethyl)phenyl]-ethanol |
| 61 | 2-{1-[4-(Trifluoromethyl)phenyl]vinyl}-1H-imidazole | 239.3 / 239.1 | 103 | 1-(1H-imidazol-2-yl)-1-[4-(trifluoromethyl)phenyl]-ethanol |
| 62 | 2-[1-(3-Methoxy-2-methylphenyl)vinyl]-1H-imidazole | 215.3 / 215.1 | 104 | 1-(1H-Imidazol-2-yl)-1-(3-methoxy-2-methylphenyl)ethanol |
| 63 | 2-[1-(2-Ethyl-3-methylphenyl)-vinyl]-1H-imidazole | 213.3 / 213.1 | 105 | 1-(2-Ethyl-3-methylphenyl)-1-(1H-imidazol-2-yl)ethanol |
| 64 | 2-[1-(2-Bromo-3,5,6-trimethylphenyl)vinyl]-1H-imidazole | 291.3 / 291.0 | 106 | 1-(2-Bromo-3,5,6-trimethylphenyl)-1-(1H-imidazol-2-yl)ethanol |
| 65 | 2-{1-[3-(Trifluoromethoxy)phenyl]vinyl}-1H-imidazole | 255.1 / 255.1 | 107 | 1-(1H-Imidazol-2-yl)-1-[3-(trifluoromethoxy)phenyl]ethanol |

-continued

| Prep. No | Name | MH+ Found/ Expected | From Prep. | From |
|---|---|---|---|---|
| 66 | 2-[1-(2,6-Dimethylphenyl)vinyl]-1H-imidazole | 199.3 199.1 | 109 | 1-(2,6-Dimethylphenyl)-1-(1H-imidazol-2-yl)ethanol |

Preparation 67

2-[1-(2-Chloro-3-methylphenyl)vinyl]-1H-imidazole

A solution of the compound of Preparation 97 (1.22 g, 5.2 mmol) in Eaton's Reagent (15 ml) was stirred at room temperature for 18 h. To the mixture was added ethyl acetate and saturated aqueous sodium hydrogen carbonate solution and the two layers were separated. The organic phase was washed with brine, dried (MgSO$_4$) and concentrated in vacuo to give the title compound (1.00 g).

Experimental MH$^+$ 219.3; expected 219.1

Similarly Prepared were:

| Prep. No | Name | MH+ Found/ Expected | From Prep. | From |
|---|---|---|---|---|
| 68 | 2-[1-(3-Chloro-4-methylphenyl)-vinyl]-1H-imidazole | 219.3 219.1 | 93 | 1-(3-Chloro-4-methylphenyl)-1-(1H-imidazol-2-yl)ethanol |
| 69 | 2-[1-(3-Chloro-2-methylphenyl)vinyl]-1H-imidazole | 219.3 219.1 | 94 | 1-(3-Chloro-2-methylphenyl)-1-(1H-imidazol-2-yl)ethanol |
| 70 | 2-[1-(2-Chloro-5-methoxyphenyl)vinyl]-1H-imidazole | 235.3 235.1 | 95 | 1-(2-Chloro-5-methoxyphenyl)-1-(1H-imidazol-2-yl)ethanol |
| 71 | 2-[1-(2-Chloro-5-methylphenyl)vinyl]-1H-imidazole | 219.3 219.1 | 96 | 1-(2-Chloro-5-methylphenyl)-1-(1H-imidazol-2-yl)ethanol |
| 72 | 2-{1-[3-Methyl-2-(trifluoromethyl)-phenyl]vinyl}-1H-imidazole | 253.3 253.1 | 89 | 1-(1H-Imidazol-2-yl)-1-[3-methyl-2-(trifluoromethyl)phenyl]ethanol |
| 73 | 2-[1-(2,6-Difluoro-3-methylphenyl)vinyl]-1H-imidazole | 221.3 221.1 | 108 | 1-(2,6-Difluoro-3-methylphenyl)-1-(1H-imidazol-2-yl)ethanol |
| 74 | 2-[1-(4-Chloro-3-methylphenyl)-vinyl]-1H-imidazole | 219.1 219.3 | 81 | 1-(4-Chloro-3-methylphenyl)-1-(1H-imidazol-2-yl)ethanol |

Preparation 75

2-[1-(2-Chloro-4-methoxyphenyl)vinyl]-1H-imidazole

A solution of the compound of Preparation 90 (703 mg, 2.7 mmol) in trifluoroacetic acid (15 ml) was heated at 50° C. for 18 h. The reaction mixture was concentrated in vacuo and the residue was neutralised by addition of aqueous sodium hydrogen carbonate solution. The mixture was extracted with ethyl acetate and the combined extracts were concentrated in vacuo to give the title compound (469 mg).

Experimental MH$^+$ 235.3; expected 235.1

Similarly Prepared were:

| Prep. No | Name | MH+ Found/ Expected | From Prep. | From |
|---|---|---|---|---|
| 76** | 2-[1-(3-Chloro-4-methoxyphenyl)vinyl]-1H-imidazole | 235.3 235.1 | 92 | 1-(3-Chloro-4-methoxyphenyl)-1-(1H-imidazol-2-yl)ethanol |
| 77** | 2-[1-(3-Chloro-2-methoxyphenyl)vinyl]-1H-imidazole | 235.3 235.1 | 91 | 1-(3-Chloro-2-methoxyphenyl)-1-(1H-imidazol-2-yl)ethanol |

**The reaction to yield Preparation 76 gave some of Preparation 77 since Preparation 92 contained some Preparation 91 and vice versa.

Preparation 78

1-(1H-Imidazol-2-yl)-1-(3-methyl phenyl)ethanol

To a solution of 1-(diethoxymethyl)-1H-imidazole (935 mg, 5.5 mmol) in anhydrous tetrahydrofuran (6 ml), at −78° C., was added n-butyllithium (2.5M in hexanes, 2.2 ml, 5.5 mmol). The mixture was allowed to warm to 0° C. and then added to a solution of 1-(3-methylphenyl)ethanone (670 mg, 5.0 mmol) in anhydrous tetrahydrofuran (5 ml), also at 0° C. The reaction mixture was stirred at 0° C. for 30 min and then at room temperature for 1 h. The mixture was poured into cold hydrochloric acid (4N, 10 ml) and stirred for 20 min. The mixture was adjusted to pH 7 by addition of sodium hydrogen carbonate and then extracted with dichloromethane. The combined extracts were dried (MgSO$_4$) and concentrated in vacuo to give the title compound (850 mg).

Experimental MH$^+$ 203.3; expected 203.1

Similarly Prepared were:

| Prep. No | Name | MH$^+$ Found/ Expected | From | From |
|---|---|---|---|---|
| 79 | 1-(1H-Imidazol-2-yl)-1-[2-(trifluoromethyl)phenyl]ethanol | 257.3 / 257.1 | — | 1-[2-(Trifluoromethyl)phenyl]-ethanone |
| 80 | 1-(2,5-Dimethylphenyl)-1-(1H-imidazol-2-yl)ethanol | 217.3 / 217.1 | — | 1-(2,5-Dimethylphenyl)-ethanone |
| 81 | 1-(4-Chloro-3-methylphenyl)-1-(1H-imidazol-2-yl)ethanol | 237.3 / 237.1 | — | 1-(4-Chloro-3-methylphenyl)-ethanone |
| 82 | 1-(3,5-Dimethylphenyl)-1-(1H-imidazol-2-yl)ethanol | 217.3 / 217.1 | Prep. 113 | 1-(3,5-Dimethylphenyl)-ethanone |
| 83 | 1-(2,3-Dimethylphenyl)-1-(1H-imidazol-2-yl)propan-1-ol | 231.1 / 231.1 | Prep. 35 | 1-(2,3-Dimethylphenyl)propan-1-one |
| 84 | 1-(2,3-Dichlorophenyl)-1-(1H-imidazol-2-yl)ethanol | 257.2 / 257.0 | — | 1-(2,3-Dichlorophenyl)ethanone |
| 85 | 1-(3,4-Dichlorophenyl)-1-(1H-imidazol-2-yl)ethanol | 257.3 / 257.0 | — | 1-(3,4-Dichlorophenyl)ethanone |
| 86 | 1-(3-Chlorophenyl)-1-(1H-imidazol-2-yl)ethanol | 3223.3 / 223.1 | — | 1-(3-Chlorophenyl)ethanone |
| 87 | 1-(2,5-Dichlorophenyl)-1-(1H-imidazol-2-yl)ethanol | 257.2 / 257.0 | — | 1-(2,5-Dichlorophenyl)ethanone |
| 88 | 1-(2-Chloro-6-fluoro-3-methylphenyl)-1-(1H-imidazol-2-yl)ethanol | 255.2 / 255.1 | — | 1-(2-Chloro-6-fluoro-3-methylphenyl)ethanone |
| 89 | 1-(1H-Imidazol-2-yl)-1[3-methyl-2-(trifluoromethyl)-phenyl]ethanol | 271.4 / 271.1 | Prep. 170 | 1-[3-Methyl-2-(trifluoromethyl)-phenyl]-ethanone |
| 90 | 1-(2-Chloro-4-methoxyphenyl)-1-(1H-imidazol-2-yl)ethanol | 253.3 / 253.1 | J. Org. Chem., 2002, 67, 23, 8043 | 1-(2-Chloro-4-methoxyphenyl)-ethanone |
| 91* | 1-(3-Chloro-2-methoxyphenyl)-1-(1H-imidazol-2-yl)ethanol | 235.3 / 235.1 | Prep. 173 | 1-(3-Chloro-2-methoxyphenyl)-ethanone |
| 92* | 1-(3-Chloro-4-methoxyphenyl)-1-(1H-imidazol-2-yl)ethanol | 235.3 / 235.1 | Prep. 174 | 1-(3-Chloro-4-methoxyphenyl)-ethanone |
| 93 | 1-(3-Chloro-4-methylphenyl)-1-(1H-imidazol-2-yl)ethanol | 237.3 / 237.1 | Prep. 114 | 1-(3-Chloro-4-methylphenyl)-ethanone |
| 94 | 1-(3-Chloro-2-methylphenyl)-1-(1H-imidazol-2-yl)ethanol | 237.3 / 237.1 | Prep. 111 | 1-(3-Chloro-2-methylphenyl)-ethanone |
| 95 | 1-(2-Chloro-5-methoxyphenyl)-1-(1H-imidazol-2-yl)ethanol | 253.2 / 253.1 | Prep. 175 | 1-(2-Chloro-5-methoxyphenyl)-ethanone |
| 96 | 1-(2-Chloro-5-methylphenyl)-1-(1H-imidazol-2-yl)ethanol | 237.3 / 237.1 | Prep. 112 | 1-(2-Chloro-5-methylphenyl)-ethanone |
| 97 | 1-(2-Chloro-3-methylphenyl)-1-(1H-imidazol-2-yl)ethanol | 237.3 / 237.1 | Prep. 110 | 1-(2-Chloro-3-methylphenyl)-ethanone |
| 98 | 1-(2,4-Dichlorophenyl)-1-(1H-imidazol-2-yl)ethanol | 257.2 / 257.0 | — | 1-(2,4-Dichlorophenyl)ethanone |
| 99 | 1-(1H-Imidazol-2-yl)-1-phenylethanol | 189.3 / 189.1 | — | 1-Phenylethanone |
| 100 | 1-(1H-Imidazol-2-yl)-1-(4-methylphenyl)ethanol | 203.3 / 203.1 | — | 1-(4-Methylphenyl)ethanone |
| 101 | 1-(1H-Imidazol-2-yl)-1-mesitylethanol | 231.4 / 231.1 | — | 1-Mesitylethanone |
| 102 | 1-(1H-Imidazol-2-yl)-1-[3-(trifluoromethyl)phenyl]ethanol | 257.3 / 257.1 | — | 1-[3-(Trifluoromethyl)phenyl]-ethanone |
| 103 | 1-(1H-Imidazol-2-yl)-1-[4-(trifluoromethyl)phenyl]ethanol | 257.3 / 257.1 | — | 1-[4-(Trifluoromethyl)phenyl]-ethanone |
| 104 | 1-(1H-Imidazol-2-yl)-1-(3-methoxy-2-methylphenyl)-ethanol | 233.3 / 233.1 | Prep. 115 | 1-(3-Methoxy-2-methylphenyl)-ethanone |
| 105 | 1-(2-Ethyl-3-methylphenyl)-1-(1H-imidazol-2-yl)ethanol | 231.3 / 231.1 | Prep. 178 | 1-(2-Ethyl-3-methylphenyl)-ethanone |
| 106 | 1-(2-Bromo-3,5,6-trimethylphenyl)-1-(1H-imidazol-2-yl)ethanol | — | Prep. 180 | 1-(2-Bromo-3,5,6-trimethylphenyl)ethanone |

-continued

| Prep. No | Name | MH+ Found/ Expected | From | From |
|---|---|---|---|---|
| 107 | 1-(1H-Imidazol-2-yl)-1-[3-(trifluoromethoxy)phenyl]ethanol | — | — | 1-[3-(Trifluoromethoxy)phenyl]ethanone |
| 108 | 1-(2,6-Difluoro-3-methylphenyl)-1-(1H-imidazol-2-yl)ethanol | 239.2 239.1 | — | 1-(2,6-Difluoro-3-methylphenyl)ethanone |
| 109 | 1-(2,6-Dimethylphenyl)-1-(1H-imidazol-2-yl)ethanol | 216.4 216.1 | — | 1-(2,6-Dimethylphenyl)ethanone |

*The reaction to yield Preparation 91 gave some of Preparation 92 since Preparation 173 contained some Preparation 174 and vice versa.

Preparation 107

$^1$H-NMR (CD$_3$OD): 1.89-1.94 (3H), 6.93-6.97 (2H), 7.08-7.13 (1H), 7.33-7.41 (3H)

Preparation 110

1-(2-Chloro-3-methylphenyl)ethanone

To a solution of 2-chloro-3-methylbenzoic acid (1.71 g, 10.0 mmol) in anhydrous tetrahydrofuran (10 ml), at 0° C. and under nitrogen, was added methyllithium (1.6M in diethyl ether, 13.1 ml, 21.0 mmol), via syringe. The reaction mixture was stirred at 0° C. for 30 min and then allowed to warm to room temperature over 1 h. To the reaction mixture was added cold hydrochloric acid (1M, 100 ml) and dichloromethane (110 ml). The mixture was adjusted to pH 7 by addition of saturated aqueous sodium hydrogen carbonate solution and the two layers were separated. The aqueous layer was extracted with further dichloromethane and the combined extracts were dried (MgSO$_4$) and concentrated in vacuo to give the title compound (1.19 g).

$^1$H-NMR (CDCl$_3$): 2.37-2.39 (3H), 2.57-2.60 (3H), 7.15-7.20 (1H), 7.23-7.31 (2H)

Similarly Prepared were:

romethane. The combined extracts were washed with saturated aqueous sodium hydrogen carbonate solution, dried (MgSO$_4$) and concentrated in vacuo.

The residue was purified by flash chromatography (silica), eluting with pentane:dichloromethane [1:1]. The appropriate fractions were combined and concentrated to give the title compound (7.60 g).

$^1$H-NMR (CDCl$_3$): 2.27-2.29 (3H), 2.50-2.53 (3H), 3.79-3.83 (3H), 6.90-6.94 (1H), 7.10-7.14 (1H), 7.16-7.21 (1H)

Preparation 116

Chloromethyl 3-cyclopentylpropanoate

Cyclopentylpropionyl chloride (2.0 g, 12.4 mmol) was added to a mixture of paraformaldehyde (377 mg, 13.0 mmol) and zinc chloride at room temperature under nitrogen. The reaction mixture was heated to 75° C. for 3 hours, cooled and the mixture distilled (90°-100° C.) to give the title compound (1.10 g)

$^1$H-NMR (CDCl$_3$): 1.00-1.10 (2H), 1.45-1.75 (9H), 2.35-2.40 (2H), 5.70-5.75 (2H)

| Prep. No | Name | $^1$H-NMR (CDCl$_3$) | From |
|---|---|---|---|
| 111 | 1-(3-Chloro-2-methylphenyl)ethanone | 2.44-2.46(3H), 2.52-2.54(3H), 7.13-7.18(1H), 7.40-7.45(1H) | 3-Chloro-2-methylbenzoic acid |
| 112 | 1-(2-Chloro-5-methylphenyl)ethanone | 1.67-1.69(3H), 2.29-2.30(3H), 7.13-7.18(1H), 7.22-7.25(1H), 7.30-7.32(1H) | 2-Chloro-5-methylbenzoic acid |
| 113 | 1-(3,5-Dimethylphenyl)ethanone | 2.32-2.35(6H), 2.53-2.55(3H), 7.16-7.18(1H), 7.52-7.54(2H) | 3,5-Dimethylbenzoic acid |
| 114 | 1-(3-chloro-4-Methylphenyl)ethanone | 2.38-2.41(3H), 2.53-2.55(3H), 7.27-7.30(1H), 7.69-7.72(1H), 7.88-7.90(1H) | 3-Chloro-4-methylbenzoic acid |

Preparation 115

1-(3-Methoxy-2-methylphenyl)ethanone

A solution of 2-methyl-3-methoxybenzoic acid (10.0 g, 60.2 mmol) in thionyl chloride (50 ml) was heated at reflux for 1 h and then cooled and concentrated in vacuo. To the residue was added tetrahydrofuran (100 ml) and iron (III) acetylacetonate (638 mg, 1.8 mmol) and the solution was cooled to –20° C., before addition of methylmagnesium bromide (3M in diethyl ether, 22.1 ml, 66.2 mmol). After stirring for 15 min, the mixture was poured into saturated aqueous ammonium chloride solution and extracted with dichlo- Similarly Prepared were:

| Prep. No | Name | $^1$H-NMR (CDCl$_3$): | From |
|---|---|---|---|
| 117 | Chloromethyl heptanoate | 0.90-0.95(3H), 1.20-1.40(6H), 1.60-1.70(2H), 2.30-2.40(2H, 5.70-5.75(2H) | Heptanoyl chloride |
| 118 | Chloromethyl 3,3-dimethylbutanoate | — | 3,3-Dimethylbutanoyl chloride |

Preparation 119

Chloromethyl cyclopropylmethyl carbonate

To a solution of cyclopropylmethanol (0.39 ml, 5.0 mmol) and pyridine (0.40 ml, 5.0 mmol) in dichloromethane (4 ml), at 0° C. and under nitrogen, was added dropwise chloromethyl chlorocarbonate (0.40 ml, 4.5 mmol). The reaction mixture was stirred at 0° C. for 30 min and then at room temperature for 2 h. To the mixture was added diethyl ether (15 ml) and the solid material was collected by filtration and washed with diethyl ether (10 ml). The combined organic phases were dried ($MgSO_4$) and concentrated in vacuo to give the title compound (285 mg).

$^1$H-NMR ($CDCl_3$): 4.35-4.39 (2H), 5.76-5.79 (2H), 7.11-7.15 (1H), 7.37-7.44 (2H)

Similarly Prepared were:

| Prep. No | Name | $^1$H-NMR ($CDCl_3$): | From |
|---|---|---|---|
| 126 | Chloromethyl thiomorpholine-4-carboxylate 1,1-dioxide | 2.99-3.14(4H), 3.98-4.08(4H), 5.78-5.81(2H) | Thiomorpholine 1,1-dioxide |
| 127 | 1-(Chloromethyl) 2-methyl (2S)-pyrrolidine-1,2-dicarboxylate | 1.90-2.00(3H), 2.20-2.30(2H), 3.45-3.55(2H), 3.76-3.79(3H), 4.35-4.42(2H), 5.70-5.73(2H) | Methyl L-prolinate hydrochloride |
| 128 | Chloromethyl cyclohexyl-carbamate | 1.04-1.16(4H), 1.23-1.35(3H), 1.83-1.93(3H), 3.42-3.52(1H), 5.66-5.69(2H) | Cyclohexanamine |
| 129 | Chloromethyl[2-(2,4-dichlorophenyl)ethyl]-carbamate | 2.93-3.00(2H), 3.45-3.51(2H), 5.72-5.75(2H), 7.13-7.22(2H), 7.36-7.41(1H) | 2-(2,4-Dichlorophenyl)-ethanamine |
| 130 | Chloromethyl cyclohexyl-(methyl)-carbamate | 1.00-1.13(1H), 1.26-1.48(4H), 1.62-1.86(5H), 2.76-2.88(3H), 3.77-4.04(1H), 5.76-5.84(2H) | N-Methylcyclohexan-amine |
| 131 | Chloromethyl benzyl-(methyl)-carbamate | 2.86-2.94(3H), 4.48-4.54(2H), 5.83-5.85(2H), 7.19-7.39(5H) | N-Methyl-1-phenyl-methanamine |
| 132 | Chloromethyl methyl(2-phenylethyl)carbamate | 1.50-1.67(5H), 2.61-2.71(2H), 5.75-5.90(2H), 7.23-7.40(5H) | N-Methyl-2-phenylethanamine |

Similarly Prepared were:

| Prep. No | Name | MH$^+$ Found/Expected | From |
|---|---|---|---|
| 120 | Chloromethyl 4-methoxybenzyl carbonate | 345.4 / 345.4 | (4-Methoxy-phenyl)methanol |
| 121 | Chloromethyl 3-methylbutyl carbonate | — | 3-Methylbutan-1-ol |
| 122 | Chloromethyl isopropyl carbonate | — | Propan-2-ol |
| 123 | Chloromethyl cyclobutyl carbonate | — | Cyclobutanol |
| 124 | Chloromethyl 2,2,2-trifluoroethyl carbonate | — | 2,2,2-Trifluoroethanol |

Preparation 125

Chloromethyl (2,4-Dichlorobenzyl)carbamate

To a solution of the compound of 1-(2,4-dichlorophenyl)methanamine (0.15 ml, 1.1 mmol) in anhydrous dichloromethane (2 ml), at −10° C. and under nitrogen, was added dropwise 3-chloropropanoyl chloride (0.12 ml, 1.1 mmol). The reaction mixture was allowed to warm to room temperature and stirred for 18 h. To the mixture was added dichloromethane (5 ml) and water (5 ml) and the two layers were separated. The aqueous layer was extracted with dichloromethane (10 ml) and the combined organic layers were dried ($MgSO_4$) and concentrated in vacuo to give the title compound (725 mg) which was used directly.

Preparation 133

1-Chloroethyl [2-(methylsulfonyl)ethyl]carbamate

To a solution of 2-(methylsulfonyl)ethanamine (176 mg, 1.1 mmol) and N,N-diisopropylethylamine (0.38 ml, 2.2 mmol) in anhydrous dichloromethane (2 ml), at 0° C., was added dropwise 3-chloropropanoyl chloride (0.12 ml, 1.1 mmol). The reaction mixture was allowed to warm to room temperature and stirred for 62 h. To the mixture was added water (5 ml) and the two layers were separated. The aqueous layer was extracted with dichloromethane (2×5 ml) and the combined organic layers were dried ($MgSO_4$) and concentrated in vacuo to give the title compound (260 mg).

Similarly Prepared were:

| Prep. No | Name | From |
|---|---|---|
| 134 | 1-Chloroethyl morpholine-4-carboxylate | Morpholine |
| 135 | 1-(1-Chloroethyl) 2-methyl (2S)-pyrrolidine-1,2-dicarboxylate | 2-methyl (2S)-pyrrolidine-2-carboxylate |

Preparation 136

1-Benzyl-2-[1-(3-cyclopropyl-2-methylphenyl)vinyl]-1H-imidazole

To a solution of the compound of Preparation 140 (1.04 g, 3.0 mmol) in toluene (30 ml) was added potassium phosphate (1.88 g, 8.9 mmol) and cyclopropyl boronic acid (304 mg, 3.5 mmol). The mixture was de-gassed and tricyclohexylphosphine (83 mg, 0.3 mmol) was added. The mixture was de-gassed again, before addition of palladium (II) acetate (33 mg). The reaction mixture was then heated at reflux for 18 h. The mixture was poured into ethyl acetate and water and the two layers were separated. The organic phase was washed with brine, dried ($MgSO_4$) and concentrated in vacuo. The residue was filtered through silica, eluting with ethyl acetate: cyclohexane [1:1] and the filtrate was concentrated in vacuo to give the title compound (720 mg).

$^1$H-NMR (d$_6$-DMSO): 0.44-0.47 (2H), 0.80-0.83 (2H), 1.20-1.25 (1H), 1.70-1.80 (2H), 1.89-1.91 (3H) 5.22-5.24 (1H), 5.61-5.63 (1H), 6.80-6.84 (2H), 6.84-6.86 (1H), 6.86-6.89 (2H), 7.00-7.02 (1H), 7.17-7.23 (3H), 7.40-7.45 (1H)

Similarly Prepared were:

| Prep. No | Name | MH$^+$ Found/ Expected | From Prep. | From |
|---|---|---|---|---|
| 137 | 1-Benzyl-2-(1-biphenyl-3-yl-vinyl)-1H-imidazole | 337.2 337.2 | 147 and phenyl boronic acid | 1-Benzyl-2-[1-(3-bromophenyl)vinyl]-1H-imidazole |
| 138 | 1-Benzyl-2-[1-(3-cyclopropyl-phenyl)vinyl]-1H-imidazole | 301.3 301.2 | 147 | 1-Benzyl-2-[1-(3-bromophenyl)vinyl]-1H-imidazole |

Preparation 139

1-Benzyl-2-[1-(2-bromo-3-methylphenyl)vinyl]-1H-imidazole

To a suspension of the compound of Preparation 149 (3.1 g, 8.3 mmol) in acetonitrile (30 ml) was added thionyl chloride (12.2 ml, 167 mmol) and the reaction mixture was heated at 60° C., under nitrogen, for 11 h. The mixture was concentrated in vacuo and to the residue was added acetonitrile. This solution was concentrated in vacuo and the process was repeated. To the final residue was added 2-propanol (40 ml) and activated charcoal and the mixture was heated at 60° C. for 1 h. The mixture was concentrated in vacuo to give the title compound (3.1 g).

Experimental MH$^+$ 353.3; expected 353.1

Similarly Prepared were:

Preparation 148

1-Benzyl-2-{1-[2-methyl-3-(trifluoromethyl)phenyl]vinyl}-1H-imidazole

A solution of the compound of Preparation 157 (4.90 g, 13.6 mmol) in Eaton's Reagent (50 ml) was stirred at room temperature for 40 h. The mixture was poured into ice/water (200 ml) and adjusted to pH 7 by addition of saturated aqueous sodium hydrogen carbonate solution. The mixture was extracted with ethyl acetate (2×100 ml) and the combined extracts were dried (MgSO$_4$) and concentrated in vacuo to give the title compound (3.1 g).

Experimental MH$^+$ 343.3; expected 343.1

Preparation 149

1-(1-Benzyl-1H-imidazol-2-yl)-1-(2-bromo-3-methylphenyl)ethanol

To a solution of the compound of Preparation 158 (3.38 g, 9.5 mmol) in tetrahydrofuran (30 ml), at 0° C. and under nitrogen, was added dropwise methylmagnesium bromide (3M, 6.34 ml, 19 mmol). The reaction mixture was allowed to warm to room temperature and stirred for 18 h. To the mixture

| Prep. No | Name | MH$^+$ Found/ Expected | From Prep. | From |
|---|---|---|---|---|
| 140 | 1-Benzyl-2-[1-(3-bromo-2-methylphenyl)vinyl]-1H-imidazole | 353.0 353.1 | 151 | 1-(1-Benzyl-1H-imidazol-2-yl)-1-(3-bromo-2-methylphenyl)ethanol |
| 141 | 1-Benzyl-2-{1-[3-bromo-2-(difluoromethyl)phenyl]vinyl}-1H-imidazole | 389.4 389.1 | 152 | 1-(1-Benzyl-1H-imidazol-2-yl)-1-[3-bromo-2-(difluoromethyl)phenyl]ethanol |
| 142 | 1-Benzyl-2-{1-[3-(difluoromethyl)phenyl]vinyl}-1H-imidazole | 311.2 311.1 | 153 | 1-(1-Benzyl-1H-imidazol-2-yl)-1-[3-(difluoromethyl)phenyl]ethanol |
| 143 | 1-Benzyl-2-[1-(2-fluoro-3-methylphenyl)vinyl]-1H-imidazole | 293.3 293.1 | 154 | 1-(1-Benzyl-1H-imidazol-2-yl)-1-(2-fluoro-3-methylphenyl)ethanol |
| 144 | 1-Benzyl-2-{1-[2-methyl-5-(trifluoromethyl)phenyl]vinyl}-1H-imidazole | — | 155 | 1-(1-Benzyl-1H-imidazol-2-yl)-1-[2-methyl-5-(trifluoromethyl)phenyl]ethanol |
| 145 | 1-Benzyl-2-[1-(3-bromo-5-methylphenyl)vinyl]-1H-imidazole | — | 156 | 1-(1-Benzyl-1H-imidazol-2-yl)-1-(3-bromo-5-methylphenyl)ethanol |
| 146 | 1-Benzyl-2-[1-(3-ethylphenyl)-vinyl]-1H-imidazole | 289.2 289.2 | 177 | 1-(1-Benzyl-1H-imidazol-2-yl)-1-(3-ethylphenyl)ethanol |
| 147 | 1-Benzyl-2-[1-(3-bromophenyl)vinyl]-1H-imidazole | 339.0 339.0 | 150 | 1-(1-Benzyl-1H-imidazol-2-yl)-1-(3-bromophenyl)ethanol |

Preparation 145

$^1$H-NMR (CDCl$_3$): 2.20-2.25 (3H), 4.80-4.84 (2H), 5.66-5.70 (1H), 5.81-5.84 (1H), 6.88-6.95 (4H), 7.10-7.14 (1H), 7.21-7.29 (5H)

was added hydrochloric acid (0.1M, 25 ml), and the solution was basified by addition of saturated aqueous sodium hydrogen carbonate solution, and the mixture was extracted with ethyl acetate (4×30 ml). The combined extracts were washed with brine (20 ml), dried (MgSO$_4$) and concentrated in vacuo to give the title compound (3.10 g).

Experimental MH$^+$ 371.3; expected 371.1

Similarly Prepared were:

| Prep. No | Name | MH$^+$ Found/Expected | From Prep. | From |
|---|---|---|---|---|
| 150 | 1-(1-Benzyl-1H-imidazol-2-yl)-1-(3-bromophenyl)ethanol | — | 159 | (1-Benzyl-1H-imidazol-2-yl)(3-bromophenyl)methanone |
| 151 | 1-(1-Benzyl-1H-imidazol-2-yl)-1-(3-bromo-2-methylphenyl)ethanol | 371.2 / 371.1 | 160 | (1-Benzyl-1H-imidazol-2-yl)(3-bromo-2-methylphenyl)methanone |
| 152 | 1-(1-Benzyl-1H-imidazol-2-yl)-1-[3-bromo-2-(difluoromethyl)-phenyl]ethanol | 407.4 / 407.1 | 161 | (1-Benzyl-1H-imidazol-2-yl)[3-bromo-2-(difluoromethyl)phenyl]-methanone |
| 153 | 1-(1-Benzyl-1H-imidazol-2-yl)-1-[3-(difluoromethyl)phenyl]ethanol | 329.3 / 329.1 | 162 | (1-Benzyl-1H-imidazol-2-yl)[3-(difluoromethyl)phenyl]-methanone |
| 154 | 1-(1-Benzyl-1H-imidazol-2-yl)-1-(2-fluoro-3-methylphenyl)ethanol | 311.5 / 311.2 | 163 | (1-Benzyl-1H-imidazol-2-yl)(2-fluoro-3-methylphenyl)methanone |
| 155 | 1-(1-Benzyl-1H-imidazol-2-yl)-1-[2-methyl-5-(trifluoromethyl)-phenyl]ethanol | 361.0 / 361.2 | 164 | (1-Benzyl-1H-imidazol-2-yl)[2-methyl-5-(trifluoromethyl)phenyl]-methanone |
| 156 | 1-(1-Benzyl-1H-imidazol-2-yl)-1-(3-bromo-5-methylphenyl)ethanol | — | 165 | (1-Benzyl-1H-imidazol-2-yl)(3-bromo-5-methylphenyl)methanone |
| 157 | 1-(1-Benzyl-1H-imidazol-2-yl)-1-[2-methyl-3-(trifluoromethyl)-phenyl]ethanol | 361.3 / 361.2 | 166 | (1-Benzyl-1H-imidazol-2-yl)[2-methyl-3-(trifluoromethyl)phenyl]-methanone |

Preparation 156

$^1$H-NMR (CDCl$_3$): 2.07-2.15 (3H), 2.42-2.48 (3H), 4.93-5.00 (2H), 6.75-6.93 (5H), 7.05-7.16 (5H)

Preparation 158

(1-Benzyl-1H-imidazol-2-yl)(2-bromo-3-methylphenyl)methanone

A solution of 2-bromo-3-methylbenzoic acid (2.0 g, 9.3 mmol) in thionyl chloride (4.75 ml, 65.1 mmol) was heated at 65° C., under nitrogen, for 3 h. The mixture was concentrated in vacuo and to the residue was added acetonitrile (25 ml). This solution was concentrated in vacuo and the process was repeated. To the final residue was added acetonitrile (25 ml), 1-benzylimidazole (1.62 g, 10.2 mmol) and triethylamine (1.44 ml, 10.2 mmol) and the reaction mixture was heated at 60° C., under nitrogen, for 18 h. The mixture was concentrated in vacuo and to the residue was added ethyl acetate (80 ml). The solution was washed with water (40 ml) and saturated aqueous sodium hydrogen carbonate solution (40 ml), dried (MgSO$_4$) and concentrated in vacuo to give the title compound (3.38 g).

Similarly Prepared were:

| Prep. No | Name | MH$^+$ Found/Expected | From Prep. | From |
|---|---|---|---|---|
| 159 | (1-Benzyl-1H-imidazol-2-yl)(3-bromophenyl)methanone | 341.1 / 341.0 | — | 3-Bromobenzoic acid |
| 160 | (1-Benzyl-1H-imidazol-2-yl)(3-bromo-2-methylphenyl)-methanone | 355.1 / 355.0 | — | 3-Bromo-2-methylbenzoic acid |
| 161 | (1-Benzyl-1H-imidazol-2-yl)[3-bromo-2-(difluoromethyl)-phenyl]methanone | 391.2 / 391.0 | 182 | 3-Bromo-2-(difluoromethyl)-benzoic acid |
| 162 | (1-Benzyl-1H-imidazol-2-yl)[3-(difluoromethyl)phenyl]-methanone | — | 187 | 3-(Difluoromethyl)benzoic acid |
| 163 | (1-Benzyl-1H-imidazol-2-yl)(2-fluoro-3-methylphenyl)methanone | 295.3 / 295.1 | — | 2-Fluoro-3-methylbenzoic acid |
| 164 | (1-Benzyl-1H-imidazol-2-yl)[2-methyl-5-(trifluoromethyl)phenyl]-methanone | 345.3 / 345.1 | — | 2-Methyl-5-(trifluoromethyl)-benzoic acid |
| 165 | (1-Benzyl-1H-imidazol-2-yl)(3-bromo-5-methylphenyl)methanone | — | 188 | 3-Bromo-5-methylbenzoic acid |
| 166 | (1-Benzyl-1H-imidazol-2-yl)[2-methyl-3-(trifluoromethyl)-phenyl]methanone | 345.2 / 345.1 | — | 2-Methyl-3-(trifluoromethyl)-benzoic acid |

Preparation 162

¹H-NMR (CDCl₃): 5.69-5.71 (2H), 6.81-6.85 (1H), 7.17-7.20 (2H), 7.21-7.24 (2H), 7.30-7.40 (3H), 7.71-7.73 (1H), 8.39-8.42 (2H)

Preparation 165

¹H-NMR (CDCl₃): 2.35-2.38 (3H), 5.61-5.65 (2H), 7.15-7.37 (8H), 7.46-7.50 (1H), 7.92-7.97 (1H)

Preparation 167

2-[1-(1-benzyl-1H-imidazol-2-yl)vinyl]-6-methylbenzonitrile

A mixture of the compound of Preparation 139 (150 mg, 0.43 mmol), potassium hexacyanoferrate(II) (dried in vacuo at 85° C., 36 mg, 0.08 mmol), copper(I) iodide (8 mg), potassium iodide (7 mg), 1-methyl-2-pyrrolidinone (2 ml) and dimethylethylenediamine (49 μl) was placed in a pressure tube and degassed with nitrogen (×3). The tube was sealed and heated at 140° C. for 100 h. To the mixture was added ethyl acetate (10 ml) and water (10 ml) and the two layers were separated. The organic phase was dried (MgSO₄) and concentrated in vacuo to give the title compound (160 mg)

Experimental MH⁺ 300.3; expected 300.2

Preparation 168

3-[1-(1-Benzyl-1H-imidazol-2-yl)vinyl]-2-methylbenzonitrile

To a solution of the compound of Preparation 140 (100 mg, 0.28 mmol) in 1-methyl-2-pyrrolidinone (3 ml) was added sodium cyanide (28 mg, 0.57 mmol) and nickel (II) bromide (62 mg, 0.28 mmol). The reaction mixture was sealed and heated in a microwave (150 W) at 150° C. for 5 min. To the mixture was added water (10 ml) and the solution was extracted with diethyl ether (4×10 ml). The combined extracts were washed with water (10 ml) and brine (10 ml), dried (MgSO₄) and concentrated in vacuo. To the residue was added 2-propanol (15 ml) and activated charcoal and the solution was heated at 60° C. for 1 h. The mixture was then filtered through Arbocel® and the filtrate was concentrated in vacuo to give the title compound (40 mg).

Experimental MH⁺ 300.4; expected 300.2

Preparation 169

3-[1-(1-Benzyl-1H-imidazol-2-yl)vinyl]-5-methylbenzonitrile

To a solution of the compound of Preparation 145 (1.1 g, 3.1 mmol) in N,N-dimethylacetamide (30 ml) was added copper (I) cyanide (641 mg, 7.1 mmol) and the reaction mixture was heated at 150° C. for 3 days. The reaction mixture was poured into ethyl acetate and the mixture was washed with water and brine. The aqueous phase was filtered and the solid material was collected by filtration and dissolved in ethyl acetate, water and N,N,N',N'-tetramethylethylenediamine. The two layers were separated and the organic phase was washed with brine, dried (MgSO₄) and concentrated in vacuo. The residue was filtered through charcoal and silica, eluting with ethyl acetate and the filtrate was concentrated in vacuo to give the title compound (210 mg).

¹H-NMR (CDCl₃): 2.24-2.28 (3H), 4.80-4.92 (2H), 5.56-5.60 (1H), 5.78-5.82 (1H), 6.88-6.97 (3H), 7.10-7.14 (1H), 7.19-7.33 (6H)

Preparation 170

1-[3-Methyl-2-(trifluoromethyl)phenyl]ethanone

To a solution of the compound of Preparation 171 (427 mg, 2.1 mmol) in dichloromethane (20 ml) was added Dess-Martin periodinane (25%, 3.83 ml, 2.3 mmol) and the reaction mixture was stirred at room temperature for 18 h. The reaction mixture was filtered through silica, eluting with dichloromethane, followed by diethyl ether. The filtrate was washed with saturated aqueous sodium hydrogen carbonate solution, dried (MgSO₄) and concentrated in vacuo. To the residue was added dichloromethane and the solution was filtered through silica. The filtrate was dried (MgSO₄) and concentrated in vacuo. The residue was dissolved in tetrahydrofuran and re-concentrated to give the title compound (332 mg).

¹H-NMR (CDCl₃): 1.80-1.85 (3H), 3.75-3.79 (3H), 7.04-7.07 (1H), 7.31-7.33 (1H), 7.40-7.43 (1H)

Preparation 171

1-[3-Methyl-2-(trifluoromethyl)phenyl]ethanol

To a solution of the compound of Preparation 172 (500 mg, 2.1 mmol) in tetrahydrofuran (22 ml), at −78° C., was added n-butyllithium (2.5M in hexanes, 0.92 ml, 2.3 mmol). After stirring for 45 min, acetaldehyde (0.14 ml, 2.5 mmol) was added and the reaction mixture was allowed to warm to room temperature over 18 h. To the mixture was added saturated aqueous ammonium chloride solution and the mixture was extracted with ethyl acetate. The combined extracts were washed with brine, dried (MgSO₄) and concentrated in vacuo to give the title compound (600 mg).

¹H-NMR (CDCl₃): 1.42-1.45 (3H), 2.49-2.53 (3H), 5.38-5.42 (1H), 7.16-7.19 (1H), 7.40-7.43 (1H), 7.65-7.68 (1H)

Preparation 172

1-Bromo-3-methyl-2-(trifluoromethyl)benzene

A mixture of 2-bromo-6-methylbenzoic acid (10.0 g, 47.0 mmol) and sulphur tetrafluoride (5.02 g, 46.5 mmol) was heated in hydrofluoric acid (930 mg, 46.5 mmol) at 110° C. To the reaction mixture was added ethyl acetate and water and the two layers were separated. The organic phase was dried (MgSO₄) and concentrated in vacuo. The residue was distilled under reduced pressure (bp 30-33° C. at 1 mmHg) to give the title compound (1.83 g).

Preparation 173

1-(3-Chloro-2-methoxyphenyl)ethanone

To the compound of Preparation 193 (697 mg, 4.1 mmol) in acetone (30 ml) was added potassium carbonate (1.13 g, 8.2 mmol), followed by methyl iodide (2.0 ml, 4.66 g, 32.8 mmol). The reaction mixture was heated at 40° C. for 18 h, cooled and concentrated in vacuo. The residue was partitioned between ethyl acetate and water and the organic phase was separated, washed with brine, dried (MgSO₄) and concentrated in vacuo to give the title compound (450 mg) as a mixture of regioisomers.

¹H-NMR (CDCl₃): 2.58-2.62 (3H), 3.92-3.95 (3H), 7.47-7.51 (1H), 7.82-7.86 (1H), 7.94-7.97 (1H)

Similarly Prepared was:

| Prep. No | Name | From Prep. | From |
|---|---|---|---|
| 174*** | 1-(3-chloro-4-methoxyphenyl)-ethanone | 193 | 1-(3-chloro-4-hydroxyphenyl)ethanone |

***The reaction to yield Preparation 174 gave some of Preparation 173 since Preparation 193 contained a mixture of 1-(3-chloro-2-hydroxyphenyl) ethanone and 1-(3-chloro-4-hydroxyphenyl)ethanone Preparation 174

$^1$H-NMR (CDCl$_3$): 2.58-2.62 (3H), 3.92-3.95 (3H), 7.47-7.51 (1H), 7.82-7.86 (1H), 7.94-7.97 (1H)

Preparation 175

1-(2-Chloro-5-methoxyphenyl)ethanone

To a solution of SELECTFLUOR™ (5.0 g, 14.1 mmol) and sodium chloride (825 mg, 14.1 mmol) in acetonitrile (200 ml), under nitrogen, was added 1-(3-methoxyphenyl)ethanone (1.94 ml, 14.1 mmol) and the reaction mixture was stirred at room temperature for 5 days. To the mixture was added distilled water (200 ml) and the solution was extracted with dichloromethane (2×100 ml). The combined extracts were dried (MgSO$_4$) and concentrated in vacuo. The residue was purified by column chromatography (silica) with gradient elution, ethyl acetate:cyclohexane [5:95 to 10:90]. The appropriate fractions were combined and concentrated to give the title compound (1.12 g).

$^1$H-NMR (CDCl$_3$): 2.59-2.65 (3H), 3.76-3.80 (3H), 6.88-6.91 (1H), 7.01-7.04 (1H), 7.25-7.28 (1H)

Preparation 176

1-Benzyl-2-[1-(3-ethyl-2-methylphenyl)vinyl]-1H-imidazole

To a solution of the compound of Preparation 140 (207 mg, 0.3 mmol) in N,N-dimethylformamide (28 ml) was added potassium carbonate (1.17 g, 8.5 mmol), [1,1'-bis(diphenylphosphino)ferrocene]palladium (II) chloride (550 mg) and triethylborane (1M, 6.79 ml, 6.8 mmol). The reaction mixture was heated at reflux for 60 h, cooled and concentrated in vacuo. To the residue was added ethyl acetate and water and the two layers were separated. The organic phase was washed with water and brine, dried (MgSO$_4$) and concentrated in vacuo to give the title compound (110 mg).

Experimental MH$^+$ 303.2; expected 303.2

Preparation 177

1-(1-Benzyl-1H-imidazol-2-yl)-1-(3-ethylphenyl) ethanol

To a solution of the compound of Preparation 150 (500 mg, 1.4 mmol) in N,N-dimethylformamide (14 ml) was added potassium carbonate (193 mg, 1.4 mmol) and triethylborane (1M, 3.36 ml, 3.4 mmol). The mixture was de-oxygenated and [1,1'-bis(diphenylphosphino)ferrocene]palladium (II) chloride (114 mg) was added. The reaction mixture was heated at 50° C. for 18 h, cooled and concentrated in vacuo. To the residue was added ethyl acetate and water and the two layers were separated. The organic phase was washed with water and brine, dried (MgSO$_4$) and concentrated in vacuo to give the title compound (500 mg).

Experimental MH$^+$ 307.3; expected 307.2

Preparation 178

1-(2-Ethyl-3-methylphenyl)ethanone

To a solution of the compound of Preparation 179 (367 mg, 1.7 mmol) in anhydrous N,N-dimethylformamide (10 ml), under nitrogen, was added potassium carbonate (4.52 g, 32.7 mmol), followed by [1,1'-bis(diphenylphosphino)ferrocene] palladium (II) chloride (141 mg) and triethylborane (1M in tetrahydrofuran, 4.13 ml, 4.13 mmol). The reaction mixture was heated at 50° C. for 18 h, filtered and concentrated in vacuo. The residue was purified by flash chromatography (Biotage™ 40M cartridge), eluting with ethyl acetate:pentane [5:95]. The appropriate fractions were combined and concentrated to give the title compound (160 mg).

$^1$H-NMR (CDCl$_3$): 1.15-1.20 (3H), 2.35-2.38 (3H), 2.55-2.58 (3H), 2.74-2.81 (2H), 7.12-7.17 (1H), 7.23-7.27 (1H), 7.36-7.40 (1H)

Preparation 179

1-(2-Bromo-3-methylphenyl)ethanone

To a solution of 1-(2-amino-3-methylphenyl)ethanone (Helv. Chim. Acta; EN; 62, 1979, 271-303,) (850 mg, 5.7 mmol) in hydrobromic acid (9 ml, 5.7 mmol) and water (6 ml), at 0° C., was added aqueous sodium nitrite solution (503 mg, 7.3 mmol) and the mixture was stirred for 15 min. This mixture was added to copper (I) bromide (899 mg, 6.3 mmol) in hydrobromic acid (9 ml, 5.7 mmol) at 60° C. and the reaction mixture was heated at 95° C. for a further 30 min. After cooling, the mixture was poured into an ice/water slurry and extracted with ethyl acetate. The combined extracts were dried (MgSO$_4$) and concentrated in vacuo. To the residue was added ethyl acetate:cyclohexane [1:4] and the solution was filtered through silica. The filtrate was concentrated in vacuo to give the title compound (1.06 g).

Preparation 180

1-(2-Bromo-3,5,6-trimethylphenyl)ethanone

To a mixture of 1-bromo-2,4,5-trimethylbenzene (5.0 g, 25.0 mmol) and acetyl chloride (2.45 ml, 34.5 mmol) in dichloromethane (50 ml) was added aluminium chloride (4.42 g, 33.1 mmol) in dichloromethane (50 ml) and the reaction mixture was stirred at room temperature for 18 h. The mixture was poured into water and the two layers were separated. The organic phase was washed with saturated aqueous sodium hydrogen carbonate solution, dried (MgSO$_4$) and filtered through silica. The filtrate was concentrated in vacuo to give the title compound (5.50 g).

$^1$H-NMR (CDCl$_3$): 2.13-2.17 (3H), 2.22-2.27 (3H), 2.28-2.34 (3H), 2.48-2.54 (3H), 6.89-6.92 (1H)

Preparation 181

1-Benzyl-2-{1-[2-(difluoromethyl)-3-methylphenyl] vinyl}-1H-imidazole

To a solution of the compound of Preparation 141 (140 mg, 0.36 mmol) in 1,4-dioxane:water (9:1, 10 ml) was added trimethylboroxine (50 µl, 0.36 mmol) and sodium carbonate (114 mg, 1.08 mmol). The mixture was degassed, before addition of [1,1'-bis(diphenylphosphino)ferrocene]palladium (II) chloride (30 mg). The reaction mixture was heated at 100° C. for 18 h, cooled and concentrated in vacuo. To the residue was added ethyl acetate and the solution was washed with water, dried (MgSO$_4$) and filtered through silica. The filtrate was concentrated in vacuo to give the title compound (110 mg).

Experimental MH$^+$ 325.3; expected 325.2

Preparation 182

3-Bromo-2-(difluoromethyl)benzoic acid

To a solution of the compound of Preparation 183 (4.05 g, 11.9 mmol) in tetrahydrofuran (120 ml) was added aqueous sodium hydroxide solution (1M, 24.30 ml, 24.3 mmol) and the reaction mixture was stirred at room temperature for 18 h. The mixture was partitioned between diethyl ether and water and the two layers were separated. The aqueous layer was acidified with hydrochloric acid (2M) and extracted with ethyl acetate. The combined extracts were dried (MgSO$_4$) and concentrated in vacuo to give the title compound (3.06 g).

Experimental MH$^+$ 251.1; expected 251.0

Preparation 183

Benzyl 3-bromo-2-(difluoromethyl)benzoate

To a solution of the compound of Preparation 185 (4.1 g, 12.9 mmol) in dichloromethane (130 ml) was added (diethylamino)sulphur trifluoride (5.06 ml, 38.6 mmol) and the reaction mixture was stirred at room temperature for 18 h. To the mixture was added additional dichloromethane and saturated aqueous sodium hydrogen carbonate solution and the two layers were separated. The organic phase was concentrated in vacuo and the residue was filtered through silica, eluting with dichloromethane. The filtrate was concentrated in vacuo to give the title compound (4.05 g).

$^1$H-NMR (CDCl$_3$): 5.23-5.25 (1H), 5.33-5.35 (2H), 7.30-7.41 (4H), 7.59-7.64 (2H), 7.85-7.90 (1H)

Similarly Prepared was:

| Prep. No. | Name | $^1$H-NMR (CDCl$_3$) | From |
|---|---|---|---|
| 184 | Methyl 3-(difluoromethyl)-benzoate | 3.85-3.88(3H), 6.47-6.76(1H), 7.44-7.50(1H), 7.61-7.66(1H), 8.05-8.13(2H) | Methyl 3-formyl-benzoate |

Preparation 185

Benzyl 3-bromo-2-formylbenzoate

To a solution of the compound of Preparation 186 (4.77 g, 14.9 mmol) in ethyl acetate (150 ml) was added manganese (IV) oxide (12.95 g, 148.9 mmol) and the reaction mixture was stirred at room temperature for 1 h. The mixture was filtered and the filtrate was concentrated in vacuo to give the title compound (4.11 g).

Experimental MH$^+$ 319.1; expected 319.0

Preparation 186

Benzyl 3-bromo-2-(hydroxymethyl)benzoate

A solution of 4-bromo-2-benzofuran-1(3H)-one (4.02 g, 18.9 mmol) in aqueous sodium hydroxide solution (1M, 18.9 ml) was heated at 100° C. for 1 h. The solution was concentrated in vacuo and the residue was dissolved in toluene and re-concentrated. To a solution of the residue in N,N-dimethylformamide (20 ml) was added benzyl bromide (2.26 ml, 18.90 mmol) and the reaction mixture was stirred at room temperature for 14 days. The mixture was poured into water and the resulting precipitate was collected by filtration, washed with water and pentane and dried to give the title compound (4.77 g).

Experimental MH$^+$ 321.1; expected 321.0

Preparation 187

3-(Difluoromethyl)benzoic acid

To a solution of the compound of Preparation 184 (188 mg, 1.0 mmol) in tetrahydrofuran (5 ml) was added lithium hydroxide monohydrate (85 mg, 2.0 mmol). The reaction mixture was stirred at room temperature for 18 h and then acidified by addition of hydrochloric acid (1M). To the mixture was added water (5 ml) and brine (5 ml) and the solution was extracted with ethyl acetate (3×10 ml). The combined extracts were dried (MgSO$_4$) and concentrated in vacuo to give the title compound (290 mg).

$^1$H-NMR (CDCl$_3$): 6.50-6.80 (1H), 7.50-7.57 (1H), 7.69-7.74 (1H), 8.14-8.21 (2H)

Preparation 188

3-Bromo-5-methylbenzoic acid

To a solution of the compound of Preparation 189 (10.0 g, 43.5 mmol) in acetic acid (45 ml) was added hydrochloric acid (12M, 14.1 ml) and the reaction mixture was heated at 70° C. for 1 h. The solution was cooled to 0° C. and aqueous sodium nitrite solution (5M, 3.0 g, 43.5 mmol) was added. After 1 h, the mixture was cooled to −15° C. and aqueous hypophosphorous acid (50%, 23 ml, 170 mmol) was added dropwise. The reaction mixture was allowed to warm to 10° C. over 2 h and filtered. The solid material was washed with water and cyclohexane and the product was dried to give the title compound (8.6 g).

$^1$H-NMR (CDCl$_3$): 2.32-2.36 (3H), 7.64-7.66 (1H), 7.71-7.74 (1H), 7.79-7.82 (1H)

Preparation 189

2-Amino-3-bromo-5-methylbenzoic acid

To a solution of 2-amino-5-methylbenzoic acid (25.0 g, 170 mmol) in acetic acid (250 ml) was added bromine (10 ml, 195 mmol) and the reaction mixture was stirred at room temperature for 2 h. The mixture was filtered and the solid material was washed with water and cyclohexane and dried to give the title compound (33.4 g).

$^1$H-NMR (CDCl$_3$): 2.08-2.13 (3H), 7.42-7.45 (1H), 7.53-7.56 (1H)

Preparation 190

5-Methoxy-2,4-dimethylbenzaldehyde

To a solution of the compound of Preparation 191 (4.12 g, 14 mmol) in 1,4-dioxane (30 ml) was added aqueous sodium carbonate solution (15M, 2.80 ml, 42 mmol). After purging with nitrogen, trimethylboroxine (1.95 ml, 14 mmol) was added, followed by [1,1'-bis(diphenylphosphino)ferrocene]dichloropalladium(II) (1.03 g). The reaction mixture was heated at 100° C. for 18 h, cooled and filtered through Arbocel®. The filtrate was concentrated in vacuo and to the residue was added dichloromethane. The solution was filtered through silica and the filtrate was concentrated in vacuo to give the title compound (988 mg).

¹H-NMR (CDCl₃): 2.19-2.23 (3H), 2.53-2.57 (3H), 3.80-3.85 (3H), 7.21-7.24 (2H), 10.23-10.25 (1H)

Preparation 191

2,4-Dibromo-5-methoxybenzaldehyde

To a solution of 3-methoxybenzaldehyde (5.00 g, 4.47 ml, 36.7 mmol) in methanol (245 ml) was added aqueous sodium bromide solution (5M, 36.7 ml, 184 mmol) and aqueous OXONE® solution (45.00 g, 73.4 mmol). The reaction mixture was stirred at room temperature for 18 h, before addition of aqueous sodium thiosulphate solution (1M, 200 ml) and ethyl acetate (400 ml). The two layers were separated and the organic phase was washed with water and brine, dried (MgSO₄) and concentrated in vacuo. The residue was purified by flash chromatography (Biotage) eluting with ethyl acetate:cyclohexane [10:90]. The appropriate fractions were combined and concentrated to give the title compound (4.12 g).

¹H-NMR (CDCl₃): 3.89-3.93 (3H), 7.37-7.39 (1H), 7.79-7.82 (1H), 10.20-10.23 (1H)

Preparation 192

1-(2,3-Dimethylphenyl)propan-1-ol

To a solution of 2,3-dimethylbenzaldehyde (1.0 g, 7.5 mmol) in anhydrous tetrahydrofuran (50 ml), at −78° C. and under nitrogen, was added ethyllithium (0.5M in benzene:cyclohexane 9:1, 14.9 ml, 7.5 mmol), dropwise via syringe. The reaction mixture was stirred at −78° C. for 30 min and then poured into ice cold hydrochloric acid (2N, 20 ml). The mixture was extracted with ethyl acetate (2×50 ml) and the combined extracts were dried (MgSO₄) and concentrated in vacuo to give the title compound (1.22 g).

¹H-NMR (CDCl₃): 0.93-0.99 (3H), 1.68-1.76 (2H), 2.18-2.22 (3H), 2.25-2.28 (3H), 4.87-4.92 (1H), 7.03-7.13 (2H), 7.28-7.38 (1H)

Preparation 193

1-(3-Chloro-2-hydroxyphenyl)ethanone and 1-(3-chloro-4-hydroxyphenyl)ethanone

A solution of 2-chlorophenyl acetate (1.98 g, 11.6 mmol) in 1,2-dichlorobenzene (10 ml) was added dropwise to a solution of aluminium chloride (1.90 g, 13.9 mmol) in 1,2-dichlorobenzene (10 ml). The reaction mixture was heated at 100° C. for 24 h and then cooled, before addition of dichloromethane (10 ml). The mixture was poured into hydrochloric acid (10%, 12 ml), at 0° C., and the two layers were separated. The aqueous phase was extracted with dichloromethane and the combined organic phases were washed with water, dried (MgSO₄) and concentrated in vacuo. The residue was purified by column chromatography (silica), eluting with cyclohexane. The appropriate fractions were combined and concentrated to give the title compound as a 1:1 mixture of regioisomers (1.0 g).

Preparation 194

1-Benzyl-2-[1-(2,3-dimethylphenyl)vinyl]-1H-imidazole

To a suspension of the compound of Preparation 195 (500 mg, 1.63 mmol) in acetonitrile (10 ml) was added thionyl chloride (0.2 mmol, 2.74 mmol) and the reaction mixture was stirred at room temperature for 18 h. The reaction mixture was concentrated in vacuo and the residue was triturated with ethyl acetate to give the title compound (450 mg).

Experimental MH⁺ 289.3; expected 289.2

Alternative Synthesis

A solution of the compound of Preparation 195 (82.00 g, 267.6 mmol) in Eaton's Reagent (380 ml) was stirred at room temperature for 18 h. The reaction mixture was poured onto ice and the solution was washed with diethyl ether and adjusted to pH 7 by addition sodium carbonate. The aqueous layer was extracted with ethyl acetate and the combined organic extracts were concentrated in vacuo to give the title compound (79.0 g).

Experimental MH⁺ 289.4; expected 289.2

Preparation 195

1-(1-Benzyl-1H-imidazol-2-yl)-1-(2,3-dimethylphenyl)ethanol

To a solution of the compound of Preparation 36 (182 g, 626.8 mmol) in tetrahydrofuran (1 l), at 0° C., was added methylmagnesium chloride (3M in tetrahydrofuran, 271 ml, 814 mmol). The reaction mixture was stirred at room temperature for 18 h and then poured into hydrochloric acid (2M, 500 ml). To the mixture was added diethyl ether (500 ml) and saturated aqueous sodium chloride solution (100 ml) and the two layers were separated. To the aqueous layer was added ethyl acetate (500 ml) and sodium carbonate (50 g) and the organic layer was separated. The resulting solid material was collected by filtration and triturated with diethyl ether (300 ml) to give the title compound (82 g).

Experimental MH⁺ 307.4; expected 307.2

Alternative Synthesis

To a solution of methylmagnesium chloride (3M in tetrahydrofuran, 5.0 L, 15.2 mol), under nitrogen, was added a solution of the compound of Preparation 36 (2.8 kg, 9.6 mol) in toluene (6.0 L), at −10° C. The reaction mixture was stirred at −10° C. for 4 h and then quenched by the dropwise addition of aqueous ammonium chloride solution (20%, 14.0 L). The resulting solid was collected by filtration and then was slurried with water (2×10 L) and filtered. The residue obtained is further slurried in acetonitrile (14 L) and filtered. The solid material collected by filtration was washed with acetonitrile (2×4 L) and dried in vacuo at 50° C. to give the title compound (2.63 kg, 99.75% pure by HPLC).

Preparation 196

3-[1-(1H-Imidazol-2-yl)ethyl]benzamide

A solution of the compound of Preparation 197 (311 mg, 1.35 mmol) in ammonium hydroxide (28% in water, 15 ml) was heated at 85° C. for 2 h. The mixture was then cooled and concentrated in vacuo to give the title compound (364 mg).

Experimental MH⁺ 216.2; expected 216.1

Preparation 197

Methyl 3-[1-(1H-imidazol-2-yl)ethyl]benzoate

To a solution of the compound of Preparation 198 (477 mg, 1.5 mmol) in 2-propanol (10 ml) was added ammonium formate (945 mg, 15.0 mmol) and palladium (10 wt. % on carbon, 168 mg) and the reaction mixture was heated at 80° C. for 18 h. The mixture was filtered through Arbocel® and the filtrate was concentrated in vacuo to give the title compound (270 mg).

Experimental MH⁺ 231.4; expected 231.1

Preparation 198

Methyl 3-[1-(1-benzyl-1H-imidazol-2-yl)vinyl]benzoate

A mixture of the compound of Preparation 199 (2.55 g, 7.3 mmol) and thionyl chloride (2.12 ml, 29.1 mmol) in acetonitrile (20 ml) was stirred at room temperature for 18 h. The mixture was concentrated in vacuo and the residue was partitioned between ethyl acetate and aqueous sodium hydrogen carbonate solution. The two layers were separated and the organic phase was filtered through silica and charcoal and concentrated in vacuo. The residue was purified by column chromatography (silica), with gradient elution, ethyl acetate:cyclohexane [1:1 to 4:1 to 1:0]. The appropriate fractions were combined and concentrated to give the title compound (2.32 g).

Experimental MH$^+$ 319.3; expected 319.1

Preparation 199

Methyl 3-[1-(1-benzyl-1H-imidazol-2-yl)-1-hydroxyethyl]benzoate

To a solution of the compound of Preparation 200 (3.82 g, 11.9 mmol) in tetrahydrofuran (25 ml), at 0° C., was added methylmagnesium chloride (3M in tetrahydrofuran, 5.17 ml, 15.5 mmol) and the reaction mixture was stirred at room temperature for 18 h. The mixture was poured into a mixture of ice, hydrochloric acid (2M) and diethyl ether and the two layers were separated. The aqueous layer was adjusted to pH 7 by addition of solid sodium hydrogen carbonate and then extracted with ethyl acetate. The combined extracts were dried (MgSO$_4$) and concentrated in vacuo to give the title compound (2.55 g).

Experimental MH$^+$ 337.4; expected 337.1

Preparation 200

Methyl 3-[(1-benzyl-1H-imidazol-2-yl)carbonyl]benzoate

A solution of 3-(methoxycarbonyl)benzoic acid (2.53 g, 14.0 mmol) in thionyl chloride (7.17 ml, 98.30 mmol) was heated at reflux for 1 h. The mixture was cooled and concentrated in vacuo and to the residue was added toluene. This solution was concentrated in vacuo and to the residue was added anhydrous acetonitrile (24 ml), 1-benzyl-1H-imidazole (2.22 g, 14.0 mmol) and triethylamine (2.35 ml, 16.9 mmol). The reaction mixture was heated at reflux for 18 h and then cooled and concentrated in vacuo. To the residue was added ethyl acetate and the solution was washed with water and saturated aqueous sodium hydrogen carbonate solution. The organic phase was filtered through silica, eluting with ethyl acetate, and the filtrate was concentrated in vacuo to give the title compound (3.82 g).

Experimental MH$^+$ 321.3; expected 321.1

Preparation 201

(2,3-Dimethylphenyl)(1H-imidazol-2-yl)methanol

To a solution of 1-(diethoxymethyl)-1H-imidazole (698 mg, 4.10 mmol) in anhydrous tetrahydrofuran (7 ml), at −78° C., was added n-butyllithium (2.5 M in hexane, 1.64 ml, 4.1 mmol). The reaction mixture was stirred at −78° C. for 1 h, before addition of a solution of 2,3-dimethylbenzaldehyde (500 mg, 3.73 mmol) in tetrahydrofuran (3 ml). The reaction mixture was stirred at −78° C. for 2 h, warmed to room temperature and quenched with ice cold hydrochloric acid (4M, 20 ml). The reaction mixture was concentrated in vacuo and to the residue was added water (20 ml). The solution was extracted with diethyl ether (2×20 ml) and the aqueous layer was basified by addition of solid sodium hydrogen carbonate. This solution was extracted with ethyl acetate (3×20 ml) and the combined organic phases were dried (MgSO$_4$) and concentrated in vacuo to give the title compound (543 mg)

Experimental MH$^+$ 203.1; expected 203.1

The invention claimed is:

1. Compound 2-[(1S)-1-(2,3-dimethylphenyl)ethyl]-1H-imidazole; or a pharmaceutically acceptable salt thereof, which has the formula

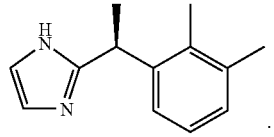

2. A pharmaceutical, veterinary or agricultural composition comprising the compound of claim 1 or a pharmaceutically acceptable salt thereof, and a suitable excipient or carrier.

3. The compound of claim 1 wherein the compound is a free base.

* * * * *

UNITED STATES PATENT AND TRADEMARK OFFICE
CERTIFICATE OF CORRECTION

PATENT NO. : 7,592,362 B2  Page 1 of 1
APPLICATION NO. : 11/619735
DATED : September 22, 2009
INVENTOR(S) : Chubb et al.

It is certified that error appears in the above-identified patent and that said Letters Patent is hereby corrected as shown below:

Title Page, Item (75) Inventors: should read

Nathan Anthony Logan Chubb, Sandwich (GB); Christelle Lauret, Sandwich (GB)

Signed and Sealed this

Twenty-fourth Day of November, 2009

David J. Kappos
*Director of the United States Patent and Trademark Office*